US012312383B2

(12) United States Patent
Urnov et al.

(10) Patent No.: US 12,312,383 B2
(45) Date of Patent: May 27, 2025

(54) ANIMAL PATHOGEN-DERIVED POLYPEPTIDES AND USES THEREOF FOR GENETIC ENGINEERING

(71) Applicant: ALTIUS INSTITUTE FOR BIOMEDICAL SCIENCES, Seattle, WA (US)

(72) Inventors: Fyodor Urnov, Seattle, WA (US); John A. Stamatoyannopoulos, Seattle, WA (US); Alister P W Funnell, Seattle, WA (US)

(73) Assignee: Altius Institute for Biomedical Sciences, Seattle, WA (US)

( * ) Notice: Subject to any disclaimer, the term of this patent is extended or adjusted under 35 U.S.C. 154(b) by 1062 days.

(21) Appl. No.: 17/047,373

(22) PCT Filed: Apr. 18, 2019

(86) PCT No.: PCT/US2019/028174
§ 371 (c)(1),
(2) Date: Oct. 13, 2020

(87) PCT Pub. No.: WO2019/204643
PCT Pub. Date: Oct. 24, 2019

(65) Prior Publication Data
US 2021/0115093 A1    Apr. 22, 2021

Related U.S. Application Data

(60) Provisional application No. 62/819,237, filed on Mar. 15, 2019, provisional application No. 62/738,825, filed on Sep. 28, 2018, provisional application No. 62/716,223, filed on Aug. 8, 2018, provisional application No. 62/690,905, filed on Jun. 27, 2018, provisional application No. 62/659,656, filed on Apr. 18, 2018.

(51) Int. Cl.
C07K 19/00      (2006.01)
C07K 14/195    (2006.01)

(52) U.S. Cl.
CPC ........ C07K 14/195 (2013.01); *C07K 2319/80* (2013.01)

(58) Field of Classification Search
CPC ............ C07K 2319/80; C07K 2319/00; C07K 2319/09; C07K 2319/60; C07K 2319/04; C07K 2319/81; C12N 2740/10022; C12N 9/22; C12N 15/113; C12N 15/01; C12N 15/62
USPC ...................................................... 435/440
See application file for complete search history.

(56) References Cited

U.S. PATENT DOCUMENTS

| | | |
|---|---|---|
| 8,110,653 B2 | 2/2012 | Stumpp et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,107 B1 | 5/2013 | Zhang et al. |
| 8,450,471 B2 | 5/2013 | Voytas et al. |
| 8,470,973 B2 | 6/2013 | Bonas et al. |
| 8,481,309 B2 | 7/2013 | Zhang et al. |
| 8,507,272 B2 | 8/2013 | Zhang et al. |
| 8,586,526 B2 | 11/2013 | Gregory et al. |
| 8,614,092 B2 | 12/2013 | Zhang et al. |
| 8,912,138 B2 | 12/2014 | Gregory et al. |
| 9,005,973 B2 | 4/2015 | Cost et al. |
| 9,181,535 B2 | 11/2015 | Liu et al. |
| 9,234,016 B2 | 1/2016 | Gregory et al. |
| 9,255,259 B2 | 2/2016 | Cost et al. |
| 9,322,005 B2 | 4/2016 | Gregory et al. |
| 9,353,378 B2 | 5/2016 | Bonas et al. |
| 9,394,545 B2 | 7/2016 | Rebar |
| 9,453,054 B2 | 9/2016 | Bonas et al. |
| 9,458,205 B2 | 10/2016 | Gregory et al. |
| 9,464,285 B2 | 10/2016 | Angel et al. |
| 9,499,592 B2 | 11/2016 | Zhang et al. |
| 9,522,936 B2 | 12/2016 | Miller et al. |
| 9,758,775 B2 | 9/2017 | Voytas et al. |
| 9,758,797 B2 | 9/2017 | Angel et al. |
| 9,777,281 B2 | 10/2017 | Rebar |
| 9,809,628 B2 | 11/2017 | Bonas et al. |

(Continued)

FOREIGN PATENT DOCUMENTS

| | | |
|---|---|---|
| EP | 3187587 | 1/2010 |
| EP | 2379583 | 12/2010 |

(Continued)

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Burstein et al. (2016) "Genomic analysis of 38 Legionella species identifies large and diverse effector repertoires" Nature Genetics 48:2 167-175.

(Continued)

*Primary Examiner* — Robert B Mondesi
*Assistant Examiner* — Mohammad Y Meah
(74) *Attorney, Agent, or Firm* — Shweta Chandra; Bozicevic, Field & Francis LLP

(57) ABSTRACT

Provided herein are polypeptides, compositions, and methods for use thereof for genetic and epigenomic engineering, including, genome editing and gene regulation. These polypeptides and compositions include nucleic acid binding domains that bind to a target nucleic acid of interest. The nucleic acid binding domains include repeat units derived from repeat units identified in proteins from animal pathogens such as bacterium of the order Legionellales and the species *Legionella* and *Francisella*.

20 Claims, 10 Drawing Sheets

Figure 4A:
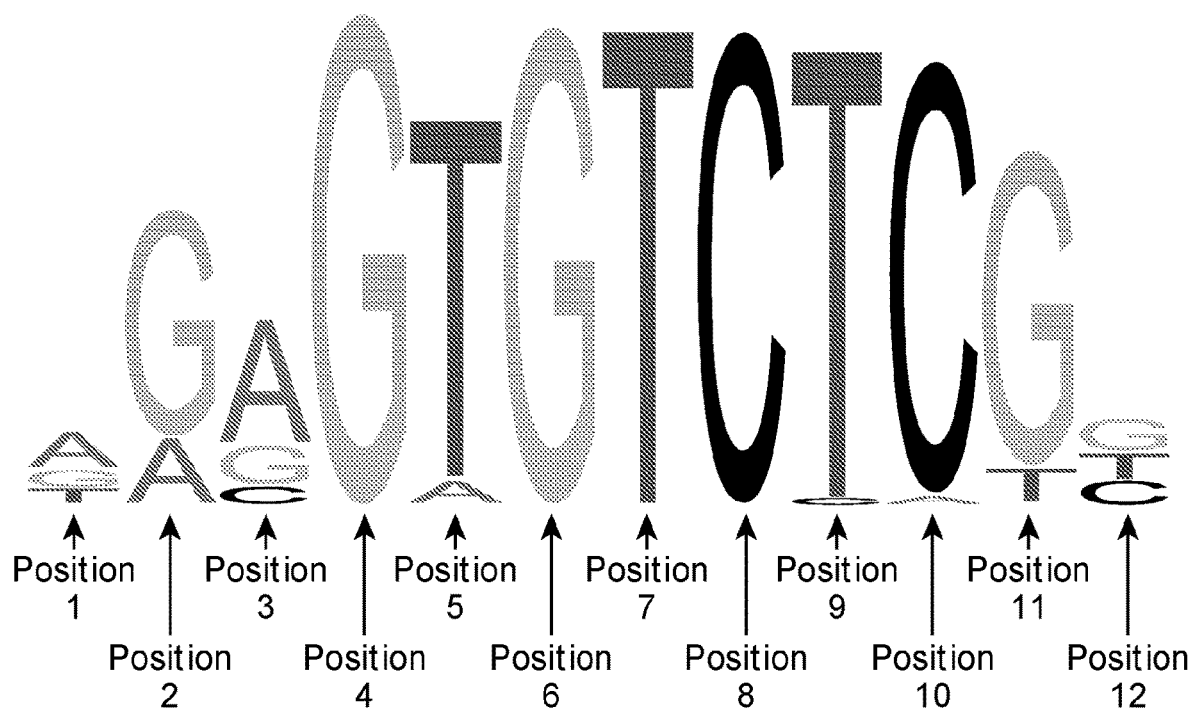

Specification includes a Sequence Listing.

(56) References Cited

U.S. PATENT DOCUMENTS

| | | | |
|---|---|---|---|
| 9,850,497 | B2 | 12/2017 | Perlingeiro et al. |
| 9,902,962 | B2 | 2/2018 | Barbas, III et al. |
| 9,970,028 | B2 | 5/2018 | Cost et al. |
| 2011/0301073 | A1 | 12/2011 | Gregory et al. |
| 2012/0270273 | A1 | 10/2012 | Zhang et al. |
| 2014/0134741 | A1 | 5/2014 | Sangamo |
| 2014/0193915 | A1 | 7/2014 | Lamb et al. |
| 2018/0010152 | A1 | 1/2018 | Gregory |
| 2018/0087072 | A1 | 3/2018 | Sangamo |
| 2018/0237758 | A1 | 8/2018 | Liu et al. |

FOREIGN PATENT DOCUMENTS

| | | |
|---|---|---|
| EP | 2816112 | 12/2010 |
| EP | 2785831 | 11/2012 |
| EP | 2821413 | 11/2012 |
| EP | 2914728 | 11/2013 |
| EP | 2920319 | 11/2013 |
| EP | 2951295 | 1/2014 |
| EP | 2510096 | 10/2014 |
| EP | 3060658 | 10/2014 |
| EP | 2534163 | 11/2015 |
| EP | 2703492 | 12/2015 |
| EP | 3141259 | 3/2017 |
| EP | 3156062 | 4/2017 |
| EP | 2571512 | 8/2017 |
| EP | 2732038 | 9/2018 |
| EP | 2780460 | 11/2018 |
| EP | 2758529 | 3/2019 |
| EP | 2893022 | 5/2020 |
| EP | 2821505 | 1/2021 |
| WO | WO2010079430 | 7/2010 |
| WO | WO2011146121 | 11/2011 |
| WO | WO 2012/168304 | 12/2012 |
| WO | WO 2013/136175 | 9/2013 |
| WO | WO 2013/015220 | 10/2013 |
| WO | WO 2014/018601 | 1/2014 |
| WO | WO 2014/078819 | 5/2014 |
| WO | WO 2018/017774 | 1/2018 |
| WO | WO 2018/035387 | 2/2018 |
| WO | WO 2018/152325 | 8/2018 |
| WO | 2020/006126 | 1/2020 |
| WO | 2020/006131 | 1/2020 |

OTHER PUBLICATIONS

DATABASE UniProt [Online] (Sep. 7, 2016), "SubName: Full=Avrbs3 family type III effector protein {ECO 0000313 EMBL: OAI59848.1;". XP55890219, retrieved from EBI accession No. UNIPROT:A0A177RHNS8.

Database UniProt [Online] Mar. 15, 2017 (Mar. 15, 2017), "SubName: Full=Type—2 restriction enzyme D3 domain-containing protein {EC0:0|EMBOL: 0SHOM4436511.13};", XP55890125, retrieved from EBI accession No. UNIPROT :AQOA1M7IV76.

Jankele et al. (2014) "TAL effectors: tools for DNA targeting", Briefings in Functional Genomics, 13(5):409-419.

U.S. Appl. No. 10/000,746, filed Nov. 30, 2001, Daniel T. Colbert.

U.S. Appl. No. 13/554,922, filed Jul. 20, 2012, Feng Zhang.

U.S. Appl. No. 14/384,957, filed Sep. 12, 2014, Philippe Duchateau.

U.S. Appl. No. 14/443,361, filed May 15, 2015, Poseida Therapeutics, Inc.

U.S. Appl. No. 15/031,995, filed Apr. 25, 2016, Kyocera Document Solutions Inc.

U.S. Appl. No. 15/748,053, filed Jan. 26, 2018, President and Fellows of Harvard College.

U.S. Appl. No. 15/881,721, filed Jan. 26, 2018, Factor Bioscience Inc.

Bogdanove et al., (2018) "Engineering altered protein-DNA recognition specificity," Nucleic Acids Research, 46(10):4845-4871.

Chimeric nuclease and Apoptosis from Wikipedia. Printed on Jun. 10, 2022. 2 pages.

Fu et al., (2014) "Promises and Pitfalls of Intracellular Delivery of Proteins." Bioconjugate Chemistry, vol. 25, pp. 1602-1608.

Kotterman et al., (2014) "Engineering adeno-associated viruses for clinical gene therapy." Nature Reviews, vol. 15, pp. 445-451.

Lenzi et al., (2014) NCBI Bookshelf, A service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.

Miller et al., (2011) "A Tale nuclease architecture for efficient genome editing", Nature Biotechnology, 29:143-148.

Namdev et al., (2016) "Challenges and approaches for Oral protein and peptide drug delivery." Research J. Pharm and Tech., vol. 9, No. 3, pp. 305-312.

Rehman et al., (2016) "Delivery of Therapeutic Proteins: Challenges and Strategies." Current Drug Targets, vol. 17, pp. 1172-1188.

Shim et al., (2018) "Nonviral Delivery Systems for Cancer Gene Therapy: Strategies and Challenges." Current Gene Therapy, vol. 18, pp. 3-20.

"Everything You Ever Wanted to Know About Type II Restriction Enzymes". Printed on Aug. 13, 2023.

"Non-homologous end joining" from Wikipedia. Printed on Jul. 29, 2023.

IcmE/DotB protein A0A0W0Y1Y4, Mar. 28, 2018, Retrieved from URL: https://rest.uniprot.org/unisave/A0A0W0Y1V4?format=txt&versions=11>.

Avirulence Protein AvrBs3 A0A0W0WDL4, Mar. 28, 2018, Retrieved from URL: https://rest.uniprot.org/unisave/A0A0W0WDL4?format=txt&versions=9>.

Uncharacterized Protein A0A1G0X562, Jun. 7, 2017, Retrieved from URL: https://rest.uniprot.org/unisave/A0A1G0X562?format=txt&versions=4>.

Jim Yeadon (2014) "Pros and cons of ZNFs, TALENs, and CRISPR/Cas", Jax Blog, 1-7.

Uniparc, UPI007D81D59, Apr. 6, 2016, 1-3.

Qi et al., (2013) "Repurposing CRISPR as an RNA-Guided Platform for Sequence-Specific Control of Gene Expression", Resource, 152(5):1173-1183.

Koonin and Novozhilov (2009) "Origin and evolution of the genetic code: the universal enigma.", IUBMB life, 61(2):99-111.

Bork P, Koonin EV. Protein sequence motifs. Curr Opin Struct Biol. 1996;6(3):366-376.

Joung JK, Sander JD. TALENs: a widely applicable technology for targeted genome editing. Nat Rev Mol Cell Biol. 2013;14(1):49-55.

Miller, J., Zhang, L., Xia, D. et al. Improved specificity of TALE-based genome editing using an expanded RVD repertoire. Nat Methods 12, 465-471 (2015).

\* cited by examiner

FIG. 1

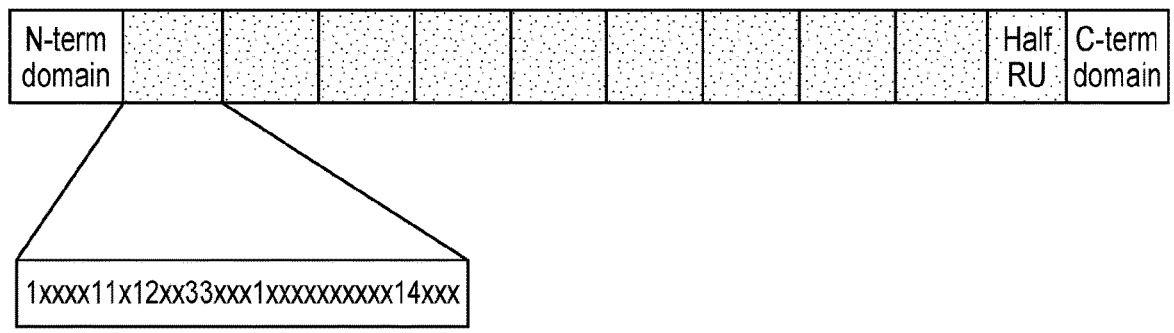

Repeat Units (RUs)

| N-term domain | | | | | | | | | | Half RU | C-term domain |

1xxxx11x12xx33xxx1xxxxxxxxxx14xxx

FIG. 2

```
1         11        21        31        41        51        61        71
MP DLELNFAI PLHLFD DETVFT HBATNDNSQASS SYSSKS SPAS ANARKRTS RKEMSGPP SKEPANTKSR RANSQNNKLS 81        91        101       111       121       131       141       151
LABRLTKYNI DEEFYQTRSB SLLS LNYT KKQI ERLI LYKGRT SAVQQLLC KHEELLNLIS PDGLGHKELI KIAARNGGGN
                                                                       SEQID NO:89

161       171       181       191       201       211       221       231
NLIAVLSCYAKLKEMG FSSQQI IRMVSHAGGANN LKAVTANHDDLQNMGFNVEQ IVRMVS HNGGSKNLKAVT DNHDDLKN
                      SEQID NO:2                                   SEQID NO:3

241       251       261       271       281       291       301       311
MGFNAEQIVRMVS HGGGSKNLKAVT DNHDDLKNMG FNAEQIVSMVSNNGGGSKNLKAVT DNHDDLKNMGFNAEQIVSMVSN
              SEQIDNO:4                              SEQ ID NO:5

321       331       341       351       361       371       381       391
GGGSLNLKAVKKKYHDALKDRGFNTEQIVRMVS HDGGSLNLKAVKKYHDALR ERKFNVEQIVSIVSHGGG SLNLKAVKKYH
  SEQ ID NO:6                      SEQ ID NO:7                       SEQ ID NO:8

401       411       421       431       441       451       461       471
DVLKDREFNAEQIVRMVSHDGGSLNLKAVTDNHDDLKNMGFNAEQIVRMVSHKGGSKNLALVKEYFPVFSSFHFTADQIV
              SEQ ID NO:9                SEQ ID NO:10

481       491       501       511       521       531       541       551
ALICQSKQCFRNLKKNHQCWKNKGLSAEQIVDLI LQET PPKPNFNNTS SSTP SPSAPS FFQGPSTP IPTP VLDN SPAPIF 561       571       581       591       601       611       621       631
SNPVCFFS SRSENNTEQYLQDSTLDLDS QLGD PTKN FNVNNFWS LFPFDDVGYHPHSN DVGYHLHS DEES PFFDF
```

FIG. 3A

| Repeat motif | Spacer | Repeat motif | |
|---|---|---|---|
| 1xxx211x1xxx33x2x1xxxxxxx1 | xxxx | 1xxx211x1xxx33x2x1xxxxxxxx1 | (SEQ ID NO: 14) |
| 1xxx211x1xxx33x2x1xxxxxxxx1 | xxxxx | 1xxx211x1xxx33x2x1xxxxxxxx1 | (SEQ ID NO: 15) |
| 1xxx211x1xxx33x2x1xxxxxxxxx1 | xxxxxx | 1xxx211x1xxx33x2x1xxxxxxxxx1 | (SEQ ID NO: 16) |
| 1xxx211x1xxx33x2x1xxxxxxxxx1 | xxxxxxx | 1xxx211x1xxx33x2x1xxxxxxxxx1 | (SEQ ID NO: 17) |
| 1xxx211x1xxx33x2x1xxxxxxxxx1 | xxxxxxxx | 1xxx211x1xxx33x2x1xxxxxxxxx1 | (SEQ ID NO: 18) |

```
A    A    A    D    A
F    F    F    E    F
I    I    I    K    I
L    L    L    N    L
M    M    M    M    M
T    T    T    S    T
V    V    V    R    V
               Q
```

FIG. 3B

1

FIG. 5
RN-HA-HN-HG-NN-NG-HD-HG-HD-HK
G - A - G - T - G - T - C - T - C - G
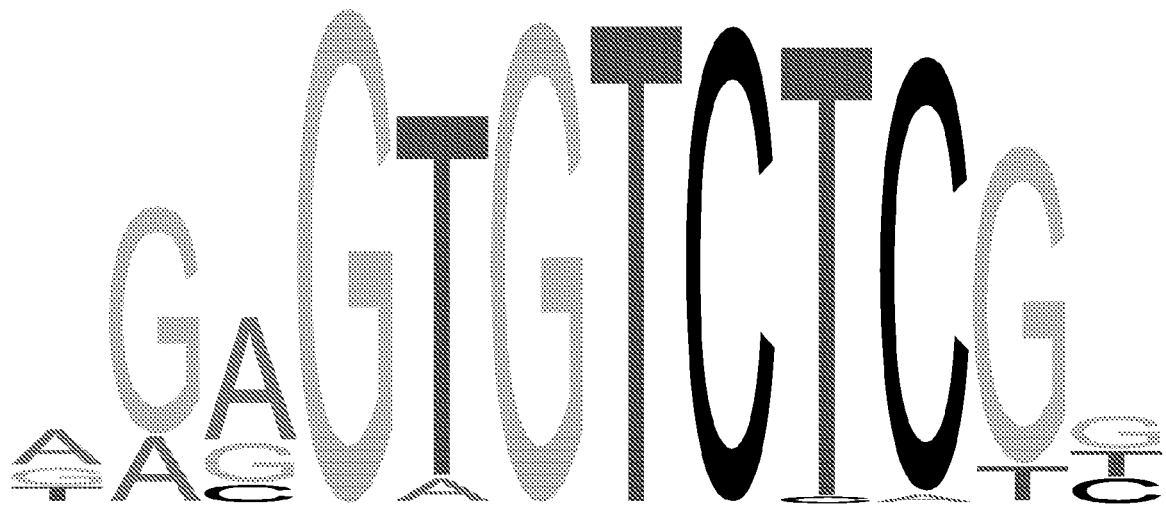
FIG. 6
RN-<u>HA</u>-HN-HG-NN-NG-HD-HG-HD-HK
↓ ↓ ↓ ↓ ↓ ↓ ↓ ↓ ↓ ↓
SELEX   G - <u>A</u> - G - T - G - T - C - T - C - G
MILLER  G - <u>T</u> - G - T - G - T - C - T - C - G

FIG. 7

1   MPKTKITTVSHGYDLDLMSSLPNGDPNQAKQGKIYLSGNGVYVVRDVAGIVHRGQLEFAINLEQLEQKINEPAFKAVILE

81  KTSRAVGYTISNECFNVELNALAKAGFNNLDIDKLIFRSSSRGTVQTVLNSYNILLEKPYNLDRQQILRIASHDGGSKNI
                                                                                  SEQ ID NO:25

161 AAVQKFLPKLMWFGFNADQVIKIVGHDGGSNNIDVVQQFFPELKAFGFSADQVVKIAGHSGGSNNIAVMLAVFPRLRDFG
                                SEQ ID NO:132                                     SEQ ID NO:138

241 FKADDAVRIACRTGGSHNLKAVHKNYERLRARGYDNKKIISIAASNCGTETINTIMSTDEVEESDFLYFVTTVSTPVASQ
    SEQ ID NO:131

321 NLSSASNTNINYSNRFMTARKKTSDDNTDEVEEDQHRDKRRSNGR

FIG. 8A (Cont.)

DNA recognition by each protein domain

| Motif position | Protein domain | DNA base recognized |
|---|---|---|
|  | LEGq N-terminus | none |
| 1 | LEG.RN.001 | G/A |
| 2 | LEG.HA.001 | A |
| 3 | LEG.HN.001 | G |
| 4 | LEG.HG.002 | T |
| 5 | LEG.NN.001 | G |
| 6 | LEG.NG.001 | T |
| 7 | LEG.HD.006 | C |
| 8 | LEG.HG.004 | T |
| 9 | LEG.HD.001 | C |
| 10 | LEG.HK.001 | G |
|  | LEGq C-terminus | none |

FIG. 8B (Cont.)

DNA recognition by each protein domain

| Motif position | Protein domain | DNA base recognized |
|---|---|---|
| 1-2 | LEGm N-terminus | G or GG |
| 3 | LEG.HG.003 | T |
| 4 | LEG.HD.005 | C |
| 5 | LEG.HI.003 | A |
| 6 | LEG.HK.003 | G |
| 7 | LEG.HI.001 | G |
| 8 | LEG.HI.002 | A/C |
| 9 | LEG.HD.002 | C |
| 10 | LEG.HG.005 | T |
| 11 | LEG.HD.003 | C |
| 12 | LEG.HG.001 | T |
| 13 | LEG.HV.001 | G/A/T |
| 14 | LEG.HI.004 | A/G/T |
| 15-17 | LEGm C-terminus | Possible T preference |

SEQUENCE LISTING

```
<160> NUMBER OF SEQ ID NOS: 159

<210> SEQ ID NO 1
<211> LENGTH: 635
<212> TYPE: PRT
<213> ORGANISM: Legionella quateirensis

<400> SEQUENCE: 1

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
    130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
        195                 200                 205

Gly Phe Asn Val Glu Gln Ile Val Arg Met Val Ser His Asn Gly Gly
```

```
                210                 215                 220
Ser Lys Asn Leu Lys Ala Val Thr Asp Asn His Asp Leu Lys Asn
225                 230                 235                 240

Met Gly Phe Asn Ala Glu Gln Ile Val Arg Met Val Ser His Gly Gly
                245                 250                 255

Gly Ser Lys Asn Leu Lys Ala Val Thr Asp Asn His Asp Asp Leu Lys
                260                 265                 270

Asn Met Gly Phe Asn Ala Glu Gln Ile Val Ser Met Val Ser Asn Asn
            275                 280                 285

Gly Gly Ser Lys Asn Leu Lys Ala Val Thr Asp Asn His Asp Asp Leu
            290                 295                 300

Lys Asn Met Gly Phe Asn Ala Glu Gln Ile Val Ser Met Val Ser Asn
305                 310                 315                 320

Gly Gly Gly Ser Leu Asn Leu Lys Ala Val Lys Lys Tyr His Asp Ala
                325                 330                 335

Leu Lys Asp Arg Gly Phe Asn Thr Glu Gln Ile Val Arg Met Val Ser
                340                 345                 350

His Asp Gly Gly Ser Leu Asn Leu Lys Ala Val Lys Lys Tyr His Asp
            355                 360                 365

Ala Leu Arg Glu Arg Lys Phe Asn Val Glu Gln Ile Val Ser Ile Val
370                 375                 380

Ser His Gly Gly Gly Ser Leu Asn Leu Lys Ala Val Lys Lys Tyr His
385                 390                 395                 400

Asp Val Leu Lys Asp Arg Glu Phe Asn Ala Glu Gln Ile Val Arg Met
                405                 410                 415

Val Ser His Asp Gly Gly Ser Leu Asn Leu Lys Ala Val Thr Asp Asn
                420                 425                 430

His Asp Asp Leu Lys Asn Met Gly Phe Asn Ala Glu Gln Ile Val Arg
            435                 440                 445

Met Val Ser His Lys Gly Gly Ser Lys Asn Leu Ala Leu Val Lys Glu
450                 455                 460

Tyr Phe Pro Val Phe Ser Ser Phe His Phe Thr Ala Asp Gln Ile Val
465                 470                 475                 480

Ala Leu Ile Cys Gln Ser Lys Gln Cys Phe Arg Asn Leu Lys Lys Asn
                485                 490                 495

His Gln Gln Trp Lys Asn Lys Gly Leu Ser Ala Glu Gln Ile Val Asp
            500                 505                 510

Leu Ile Leu Gln Glu Thr Pro Pro Lys Pro Asn Phe Asn Asn Thr Ser
            515                 520                 525

Ser Ser Thr Pro Ser Pro Ser Ala Pro Ser Phe Phe Gln Gly Pro Ser
530                 535                 540

Thr Pro Ile Pro Thr Pro Val Leu Asp Asn Ser Pro Ala Pro Ile Phe
545                 550                 555                 560

Ser Asn Pro Val Cys Phe Phe Ser Ser Arg Ser Glu Asn Asn Thr Glu
                565                 570                 575

Gln Tyr Leu Gln Asp Ser Thr Leu Asp Leu Asp Ser Gln Leu Gly Asp
            580                 585                 590

Pro Thr Lys Asn Phe Asn Val Asn Asn Phe Trp Ser Leu Phe Pro Phe
            595                 600                 605

Asp Asp Val Gly Tyr His Pro His Ser Asn Asp Val Gly Tyr His Leu
            610                 615                 620

His Ser Asp Glu Glu Ser Pro Phe Phe Asp Phe
625                 630                 635
```

<210> SEQ ID NO 2
<211> LENGTH: 33
<212> TYPE: PRT
<213> ORGANISM: Legionella quateirensis

<400> SEQUENCE: 2

Phe Ser Ser Gln Gln Ile Ile Arg Met Val Ser His Ala Gly Gly Ala
1               5                   10                  15

Asn Asn Leu Lys Ala Val Thr Ala Asn His Asp Asp Leu Gln Asn Met
            20                  25                  30

Gly

<210> SEQ ID NO 3
<211> LENGTH: 33
<212> TYPE: PRT
<213> ORGANISM: Legionella quateirensis

<400> SEQUENCE: 3

Phe Asn Val Glu Gln Ile Val Arg Met Val Ser His Asn Gly Gly Ser
1               5                   10                  15

Lys Asn Leu Lys Ala Val Thr Asp Asn His Asp Asp Leu Lys Asn Met
            20                  25                  30

Gly

<210> SEQ ID NO 4
<211> LENGTH: 33
<212> TYPE: PRT
<213> ORGANISM: Legionella quateirensis

<400> SEQUENCE: 4

Phe Asn Ala Glu Gln Ile Val Arg Met Val Ser His Gly Gly Gly Ser
1               5                   10                  15

Lys Asn Leu Lys Ala Val Thr Asp Asn His Asp Asp Leu Lys Asn Met
            20                  25                  30

Gly

<210> SEQ ID NO 5
<211> LENGTH: 33
<212> TYPE: PRT
<213> ORGANISM: Legionella quateirensis

<400> SEQUENCE: 5

Phe Asn Ala Glu Gln Ile Val Ser Met Val Ser Asn Asn Gly Gly Ser
1               5                   10                  15

Lys Asn Leu Lys Ala Val Thr Asp Asn His Asp Asp Leu Lys Asn Met
            20                  25                  30

Gly

<210> SEQ ID NO 6
<211> LENGTH: 33
<212> TYPE: PRT
<213> ORGANISM: Legionella quateirensis

<400> SEQUENCE: 6

Phe Asn Ala Glu Gln Ile Val Ser Met Val Ser Asn Gly Gly Gly Ser
1               5                   10                  15

Leu Asn Leu Lys Ala Val Lys Lys Tyr His Asp Ala Leu Lys Asp Arg
            20                  25                  30

Gly

<210> SEQ ID NO 7
<211> LENGTH: 33
<212> TYPE: PRT
<213> ORGANISM: Legionella quateirensis

<400> SEQUENCE: 7

Phe Asn Thr Glu Gln Ile Val Arg Met Val Ser His Asp Gly Gly Ser
1               5                   10                  15

Leu Asn Leu Lys Ala Val Lys Lys Tyr His Asp Ala Leu Arg Glu Arg
            20                  25                  30

Lys

<210> SEQ ID NO 8
<211> LENGTH: 33
<212> TYPE: PRT
<213> ORGANISM: Legionella quateirensis

<400> SEQUENCE: 8

Phe Asn Val Glu Gln Ile Val Ser Ile Val Ser His Gly Gly Gly Ser
1               5                   10                  15

Leu Asn Leu Lys Ala Val Lys Lys Tyr His Asp Val Leu Lys Asp Arg
            20                  25                  30

Glu

<210> SEQ ID NO 9
<211> LENGTH: 33
<212> TYPE: PRT
<213> ORGANISM: Legionella quateirensis

<400> SEQUENCE: 9

Phe Asn Ala Glu Gln Ile Val Arg Met Val Ser His Asp Gly Gly Ser
1               5                   10                  15

Leu Asn Leu Lys Ala Val Thr Asp Asn His Asp Asp Leu Lys Asn Met
            20                  25                  30

Gly

<210> SEQ ID NO 10
<211> LENGTH: 19
<212> TYPE: PRT
<213> ORGANISM: Legionella quateirensis

<400> SEQUENCE: 10

Phe Asn Ala Glu Gln Ile Val Arg Met Val Ser His Lys Gly Gly Ser
1               5                   10                  15

Lys Asn Leu

<210> SEQ ID NO 11
<211> LENGTH: 196
<212> TYPE: PRT
<213> ORGANISM: Flavobacterium okeanokoites

<400> SEQUENCE: 11

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Asp Glu Met Gln Arg Tyr Val Glu Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Leu Leu Ile Gly Gly Glu Met Ile Lys
                165                 170                 175

Ala Gly Thr Leu Thr Leu Glu Val Arg Arg Lys Phe Asn Asn Gly
                180                 185                 190

Glu Ile Asn Phe
        195

<210> SEQ ID NO 12
<211> LENGTH: 176
<212> TYPE: PRT
<213> ORGANISM: Artificial sequence
<220> FEATURE:
<223> OTHER INFORMATION: synthetic sequence

<400> SEQUENCE: 12

Ala Leu Val Lys Glu Tyr Phe Pro Val Phe Ser Ser Phe His Phe Thr
 1                   5                  10                  15

Ala Asp Gln Ile Val Ala Leu Ile Cys Gln Ser Lys Gln Cys Phe Arg
                 20                  25                  30

Asn Leu Lys Lys Asn His Gln Gln Trp Lys Asn Lys Gly Leu Ser Ala
             35                  40                  45

Glu Gln Ile Val Asp Leu Ile Leu Gln Glu Thr Pro Pro Lys Pro Asn
 50                  55                  60

Phe Asn Asn Thr Ser Ser Ser Thr Pro Ser Pro Ser Ala Pro Ser Phe
 65                  70                  75                  80

Phe Gln Gly Pro Ser Thr Pro Ile Pro Thr Pro Val Leu Asp Asn Ser
                 85                  90                  95

Pro Ala Pro Ile Phe Ser Asn Pro Val Cys Phe Phe Ser Ser Arg Ser
                100                 105                 110

Glu Asn Asn Thr Glu Gln Tyr Leu Gln Asp Ser Thr Leu Asp Leu Asp
            115                 120                 125

Ser Gln Leu Gly Asp Pro Thr Lys Asn Phe Asn Val Asn Asn Phe Trp
130                 135                 140

Ser Leu Phe Pro Phe Asp Asp Val Gly Tyr His Pro His Ser Asn Asp
145                 150                 155                 160

Val Gly Tyr His Leu His Ser Asp Glu Glu Ser Pro Phe Phe Asp Phe
                165                 170                 175

<210> SEQ ID NO 13
<211> LENGTH: 143
<212> TYPE: PRT
<213> ORGANISM: Artificial sequence
<220> FEATURE:
<223> OTHER INFORMATION: synthetic sequence

<400> SEQUENCE: 13

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly
        130                 135                 140

<210> SEQ ID NO 14
<211> LENGTH: 60
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, or V.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: The amino acid may be D, E, K, N, M, S, R, or
    Q.
<220> FEATURE:
<221> NAME/KEY: MISC_FEATURE
<222> LOCATION: (6)..(7)
<223> OTHER INFORMATION: The amino acids may be A, F, I, L, M, T, or V.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, or V.
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: The amino acids may be A, G, N, or S.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)

<223> OTHER INFORMATION: The amino acid may be D, E, K, N, M, S, R, or
      Q.
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: The amino acid may be A, F, I, L, M, T, or V.
<220> FEATURE:
<221> NAME/KEY: misc_feature
<222> LOCATION: (19)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: The amino acid may be A, F, I, L, M, T, or V.
<220> FEATURE:
<221> NAME/KEY: misc_feature
<222> LOCATION: (29)..(32)
<223> OTHER INFORMATION: Xaa can be any naturally occurring amino acid
<220> FEATURE:
<221> NAME/KEY: MISC_FEATURE
<222> LOCATION: (33)..(33)
<223> OTHER INFORMATION: The amino acid may be A, F, I, L, M, T, or V.
<220> FEATURE:
<221> NAME/KEY: misc_feature
<222> LOCATION: (34)..(36)
<223> OTHER INFORMATION: Xaa can be any naturally occurring amino acid
<220> FEATURE:
<221> NAME/KEY: MISC_FEATURE
<222> LOCATION: (37)..(37)
<223> OTHER INFORMATION: The amino acid may be D, E, K, N, M, S, R, or
      Q.
<220> FEATURE:
<221> NAME/KEY: MISC_FEATURE
<222> LOCATION: (38)..(39)
<223> OTHER INFORMATION: The amino acids may be A, F, I, L, M, T, or V.
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: MISC_FEATURE
<222> LOCATION: (41)..(41)
<223> OTHER INFORMATION: The amino acid may be A, F, I, L, M, T, or V.
<220> FEATURE:
<221> NAME/KEY: misc_feature
<222> LOCATION: (42)..(44)
<223> OTHER INFORMATION: Xaa can be any naturally occurring amino acid
<220> FEATURE:
<221> NAME/KEY: MISC_FEATURE
<222> LOCATION: (45)..(46)
<223> OTHER INFORMATION: The amino acids may be A, G, N, or S.
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: MISC_FEATURE
<222> LOCATION: (48)..(48)
<223> OTHER INFORMATION: The amino acid may be D, E, K, N, M, S, R, or
      Q.
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: MISC_FEATURE
<222> LOCATION: (50)..(50)
<223> OTHER INFORMATION: The amino acid may be A, F, I, L, M, T, or V.
<220> FEATURE:
<221> NAME/KEY: misc_feature
<222> LOCATION: (51)..(59)
<223> OTHER INFORMATION: Xaa can be any naturally occurring amino acid
<220> FEATURE:
<221> NAME/KEY: MISC_FEATURE
<222> LOCATION: (60)..(60)

<223> OTHER INFORMATION: The amino acid may be A, F, I, L, M, T, or V.

<400> SEQUENCE: 14

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 15
<211> LENGTH: 61
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, or V.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: The amino acid may be D, E, K, N, M, S, R, or
      Q.
<220> FEATURE:
<221> NAME/KEY: MISC_FEATURE
<222> LOCATION: (6)..(7)
<223> OTHER INFORMATION: The amino acids may be A, F, I, L, M, T, or V.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, or V.
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: The amino acids may be A, G, N, or S.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: The amino acid may be D, E, K, N, M, S, R, or
      Q.
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: The amino acid may be A, F, I, L, M, T, or V.
<220> FEATURE:
<221> NAME/KEY: misc_feature
<222> LOCATION: (19)..(27)
<223> OTHER INFORMATION: Xaa can be any naturally occurring amino acid
<220> FEATURE:
<221> NAME/KEY: MISC_FEATURE

```
<222> LOCATION: (28)..(28)
<223> OTHER INFORMATION: The amino acid may be A, F, I, L, M, T, or V.
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: The amino acid may be A, F, I, L, M, T, or V.
<220> FEATURE:
<221> NAME/KEY: misc_feature
<222> LOCATION: (35)..(37)
<223> OTHER INFORMATION: Xaa can be any naturally occurring amino acid
<220> FEATURE:
<221> NAME/KEY: MISC_FEATURE
<222> LOCATION: (38)..(38)
<223> OTHER INFORMATION: The amino acid may be D, E, K, N, M, S, R, or
      Q.
<220> FEATURE:
<221> NAME/KEY: MISC_FEATURE
<222> LOCATION: (39)..(40)
<223> OTHER INFORMATION: The amino acids may be A, F, I, L, M, T, or V.
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: MISC_FEATURE
<222> LOCATION: (42)..(42)
<223> OTHER INFORMATION: The amino acid may be A, F, I, L, M, T, or V.
<220> FEATURE:
<221> NAME/KEY: misc_feature
<222> LOCATION: (43)..(45)
<223> OTHER INFORMATION: Xaa can be any naturally occurring amino acid
<220> FEATURE:
<221> NAME/KEY: MISC_FEATURE
<222> LOCATION: (46)..(47)
<223> OTHER INFORMATION: The amino acids may be A, G, N, or S.
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: MISC_FEATURE
<222> LOCATION: (49)..(49)
<223> OTHER INFORMATION: The amino acid may be D, E, K, N, M, S, R, or
      Q.
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: MISC_FEATURE
<222> LOCATION: (51)..(51)
<223> OTHER INFORMATION: The amino acid may be A, F, I, L, M, T, or V.
<220> FEATURE:
<221> NAME/KEY: misc_feature
<222> LOCATION: (52)..(60)
<223> OTHER INFORMATION: Xaa can be any naturally occurring amino acid
<220> FEATURE:
<221> NAME/KEY: MISC_FEATURE
<222> LOCATION: (61)..(61)
<223> OTHER INFORMATION: The amino acid may be A, F, I, L, M, T, or V.

<400> SEQUENCE: 15

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60
```

```
<210> SEQ ID NO 16
<211> LENGTH: 62
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, or V.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: The amino acid may be D, E, K, N, M, S, R, or
      Q.
<220> FEATURE:
<221> NAME/KEY: MISC_FEATURE
<222> LOCATION: (6)..(7)
<223> OTHER INFORMATION: The amino acids may be A, F, I, L, M, T, or V.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, or V.
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: The amino acids may be A, G, N, or S.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: The amino acid may be D, E, K, N, M, S, R, or
      Q.
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: The amino acid may be A, F, I, L, M, T, or V.
<220> FEATURE:
<221> NAME/KEY: misc_feature
<222> LOCATION: (19)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: The amino acid may be A, F, I, L, M, T, or V.
<220> FEATURE:
<221> NAME/KEY: misc_feature
<222> LOCATION: (29)..(34)
<223> OTHER INFORMATION: Xaa can be any naturally occurring amino acid
<220> FEATURE:
<221> NAME/KEY: MISC_FEATURE
<222> LOCATION: (35)..(35)
<223> OTHER INFORMATION: The amino acid may be A, F, I, L, M, T, or V.
<220> FEATURE:
<221> NAME/KEY: misc_feature
<222> LOCATION: (36)..(38)
<223> OTHER INFORMATION: Xaa can be any naturally occurring amino acid
<220> FEATURE:
<221> NAME/KEY: MISC_FEATURE
```

```
<222> LOCATION: (39)..(39)
<223> OTHER INFORMATION: The amino acid may be D, E, K, N, M, S, R, or
      Q.
<220> FEATURE:
<221> NAME/KEY: MISC_FEATURE
<222> LOCATION: (40)..(41)
<223> OTHER INFORMATION: The amino acids may be A, F, I, L, M, T, or V.
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: MISC_FEATURE
<222> LOCATION: (43)..(43)
<223> OTHER INFORMATION: The amino acid may be A, F, I, L, M, T, or V.
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: MISC_FEATURE
<222> LOCATION: (47)..(48)
<223> OTHER INFORMATION: The amino acids may be A, G, N, or S.
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: MISC_FEATURE
<222> LOCATION: (50)..(50)
<223> OTHER INFORMATION: The amino acid may be D, E, K, N, M, S, R, or
      Q.
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: MISC_FEATURE
<222> LOCATION: (52)..(52)
<223> OTHER INFORMATION: The amino acid may be A, F, I, L, M, T, or V.
<220> FEATURE:
<221> NAME/KEY: misc_feature
<222> LOCATION: (53)..(61)
<223> OTHER INFORMATION: Xaa can be any naturally occurring amino acid
<220> FEATURE:
<221> NAME/KEY: MISC_FEATURE
<222> LOCATION: (62)..(62)
<223> OTHER INFORMATION: The amino acid may be A, F, I, L, M, T, or V.

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa
    50                  55                  60

<210> SEQ ID NO 17
<211> LENGTH: 63
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, or V.
<220> FEATURE:
<221> NAME/KEY: misc_feature
<222> LOCATION: (2)..(4)
<223> OTHER INFORMATION: Xaa can be any naturally occurring amino acid
<220> FEATURE:
```

-continued

```
<221> NAME/KEY: MISC_FEATURE
<222> LOCATION: (5)..(5)
<223> OTHER INFORMATION: The amino acid may be D, E, K, N, M, S, R, or
      Q.
<220> FEATURE:
<221> NAME/KEY: MISC_FEATURE
<222> LOCATION: (6)..(7)
<223> OTHER INFORMATION: The amino acids may be A, F, I, L, M, T, or V.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acids may be A, F, I, L, M, T, or V.
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: The amino acids may be A, G, N, or S.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: The amino acid may be D, E, K, N, M, S, R, or
      Q.
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: The amino acid may be A, F, I, L, M, T, or V.
<220> FEATURE:
<221> NAME/KEY: misc_feature
<222> LOCATION: (19)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: The amino acid may be A, F, I, L, M, T, or V.
<220> FEATURE:
<221> NAME/KEY: misc_feature
<222> LOCATION: (29)..(35)
<223> OTHER INFORMATION: Xaa can be any naturally occurring amino acid
<220> FEATURE:
<221> NAME/KEY: MISC_FEATURE
<222> LOCATION: (36)..(36)
<223> OTHER INFORMATION: The amino acid may be A, F, I, L, M, T, or V.
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: MISC_FEATURE
<222> LOCATION: (40)..(40)
<223> OTHER INFORMATION: The amino acid may be D, E, K, N, M, S, R, or
      Q.
<220> FEATURE:
<221> NAME/KEY: MISC_FEATURE
<222> LOCATION: (41)..(42)
<223> OTHER INFORMATION: The amino acids may be A, F, I, L, M, T, or V.
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: MISC_FEATURE
<222> LOCATION: (44)..(44)
<223> OTHER INFORMATION: The amino acid may be A, F, I, L, M, T, or V.
<220> FEATURE:
```

```
<221> NAME/KEY: misc_feature
<222> LOCATION: (45)..(47)
<223> OTHER INFORMATION: Xaa can be any naturally occurring amino acid
<220> FEATURE:
<221> NAME/KEY: MISC_FEATURE
<222> LOCATION: (48)..(49)
<223> OTHER INFORMATION: The amino acid may be A, G, N, or S.
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: MISC_FEATURE
<222> LOCATION: (51)..(51)
<223> OTHER INFORMATION: The amino acid may be D, E, K, N, M, S, R, or
      Q.
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: MISC_FEATURE
<222> LOCATION: (53)..(53)
<223> OTHER INFORMATION: The amino acid may be A, F, I, L, M, T, or V.
<220> FEATURE:
<221> NAME/KEY: misc_feature
<222> LOCATION: (54)..(62)
<223> OTHER INFORMATION: Xaa can be any naturally occurring amino acid
<220> FEATURE:
<221> NAME/KEY: MISC_FEATURE
<222> LOCATION: (63)..(63)
<223> OTHER INFORMATION: The amino acid may be A, F, I, L, M, T, or V.

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

<210> SEQ ID NO 18
<211> LENGTH: 64
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, or V.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: The amino acid may be D, E, K, N, M, S, R, or
      Q.
<220> FEATURE:
<221> NAME/KEY: MISC_FEATURE
<222> LOCATION: (6)..(7)
<223> OTHER INFORMATION: The amino acids may be A, F, I, L, M, T, or V.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, or V.
```

-continued

```
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: The amino acid may be A, G, N, or S.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: The amino acid may be D, E, K, N, M, S, R, or
      Q.
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: The amino acid may be A, F, I, L, M, T, or V.
<220> FEATURE:
<221> NAME/KEY: misc_feature
<222> LOCATION: (19)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: The amino acid may be A, F, I, L, M, T, or V.
<220> FEATURE:
<221> NAME/KEY: misc_feature
<222> LOCATION: (29)..(36)
<223> OTHER INFORMATION: Xaa can be any naturally occurring amino acid
<220> FEATURE:
<221> NAME/KEY: MISC_FEATURE
<222> LOCATION: (37)..(37)
<223> OTHER INFORMATION: The amino acid may be A, F, I, L, M, T, or V.
<220> FEATURE:
<221> NAME/KEY: misc_feature
<222> LOCATION: (38)..(40)
<223> OTHER INFORMATION: Xaa can be any naturally occurring amino acid
<220> FEATURE:
<221> NAME/KEY: MISC_FEATURE
<222> LOCATION: (41)..(41)
<223> OTHER INFORMATION: The amino acid may be D, E, K, N, M, S, R, or
      Q.
<220> FEATURE:
<221> NAME/KEY: MISC_FEATURE
<222> LOCATION: (42)..(43)
<223> OTHER INFORMATION: The amino acids may be A, F, I, L, M, T, or V.
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: MISC_FEATURE
<222> LOCATION: (45)..(45)
<223> OTHER INFORMATION: The amino acid may be A, F, I, L, M, T, or V.
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: MISC_FEATURE
<222> LOCATION: (49)..(50)
<223> OTHER INFORMATION: The amino acids may be A, G, N, or S.
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: MISC_FEATURE
<222> LOCATION: (52)..(52)
<223> OTHER INFORMATION: The amino acid may be D, E, K, N, M, S, R, or
      Q.
```

```
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (54)..(54)
<223> OTHER INFORMATION: The amino acid may be A, F, I, L, M, T, or V.
<220> FEATURE:
<221> NAME/KEY: misc_feature
<222> LOCATION: (55)..(63)
<223> OTHER INFORMATION: Xaa can be any naturally occurring amino acid
<220> FEATURE:
<221> NAME/KEY: MISC_FEATURE
<222> LOCATION: (64)..(64)
<223> OTHER INFORMATION: The amino acid may be A, F, I, L, M, T, or V.

<400> SEQUENCE: 18

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

<210> SEQ ID NO 19
<211> LENGTH: 28
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, or V.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: The amino acid may be D, E, K, N, M, S, R, or
      Q.
<220> FEATURE:
<221> NAME/KEY: MISC_FEATURE
<222> LOCATION: (6)..(7)
<223> OTHER INFORMATION: The amino acids may be A, F, I, L, M, T, or V.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, or V.
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: The amino acids may be A, G, N, or S.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: The amino acids may be D, E, K, N, M, S, R, or
```

```
                                  Q.
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: The amino acid may be A, F, I, L, M, T, or V.
<220> FEATURE:
<221> NAME/KEY: misc_feature
<222> LOCATION: (19)..(27)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: The amino acid may be A, F, I, L, M, T, or V.

<400> SEQUENCE: 19

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 20
<211> LENGTH: 120
<212> TYPE: PRT
<213> ORGANISM: Artificial sequence
<220> FEATURE:
<223> OTHER INFORMATION: synthetic sequence

<400> SEQUENCE: 20

Asp Ala Thr Asn Asp Asn Ser Gln Ala Ser Ser Ser Tyr Ser Ser Lys
1               5                   10                  15

Ser Ser Pro Ala Ser Ala Asn Ala Arg Lys Arg Thr Ser Arg Lys Glu
            20                  25                  30

Met Ser Gly Pro Pro Ser Lys Glu Pro Ala Asn Thr Lys Ser Arg Arg
        35                  40                  45

Ala Asn Ser Gln Asn Asn Lys Leu Ser Leu Ala Asp Arg Leu Thr Lys
    50                  55                  60

Tyr Asn Ile Asp Glu Glu Phe Tyr Gln Thr Arg Ser Asp Ser Leu Leu
65                  70                  75                  80

Ser Leu Asn Tyr Thr Lys Lys Gln Ile Glu Arg Leu Ile Leu Tyr Lys
                85                  90                  95

Gly Arg Thr Ser Ala Val Gln Gln Leu Leu Cys Lys His Glu Glu Leu
            100                 105                 110

Leu Asn Leu Ile Ser Pro Asp Gly
        115                 120

<210> SEQ ID NO 21
<211> LENGTH: 115
<212> TYPE: PRT
<213> ORGANISM: Artificial sequence
<220> FEATURE:
<223> OTHER INFORMATION: synthetic sequence

<400> SEQUENCE: 21

Asn Ser Gln Ala Ser Ser Ser Tyr Ser Ser Lys Ser Ser Pro Ala Ser
1               5                   10                  15

Ala Asn Ala Arg Lys Arg Thr Ser Arg Lys Glu Met Ser Gly Pro Pro
            20                  25                  30

Ser Lys Glu Pro Ala Asn Thr Lys Ser Arg Arg Ala Asn Ser Gln Asn
        35                  40                  45
```

```
Asn Lys Leu Ser Leu Ala Asp Arg Leu Thr Lys Tyr Asn Ile Asp Glu
    50                  55                  60

Glu Phe Tyr Gln Thr Arg Ser Asp Ser Leu Leu Ser Leu Asn Tyr Thr
65                  70                  75                  80

Lys Lys Gln Ile Glu Arg Leu Ile Leu Tyr Lys Gly Arg Thr Ser Ala
                85                  90                  95

Val Gln Gln Leu Leu Cys Lys His Glu Glu Leu Leu Asn Leu Ile Ser
            100                 105                 110

Pro Asp Gly
        115

<210> SEQ ID NO 22
<211> LENGTH: 63
<212> TYPE: PRT
<213> ORGANISM: Artificial sequence
<220> FEATURE:
<223> OTHER INFORMATION: synthetic sequence
<400> SEQUENCE: 22

Ala Leu Val Lys Glu Tyr Phe Pro Val Phe Ser Ser Phe His Phe Thr
1               5                   10                  15

Ala Asp Gln Ile Val Ala Leu Ile Cys Gln Ser Lys Gln Cys Phe Arg
            20                  25                  30

Asn Leu Lys Lys Asn His Gln Gln Trp Lys Asn Lys Gly Leu Ser Ala
        35                  40                  45

Glu Gln Ile Val Asp Leu Ile Leu Gln Glu Thr Pro Pro Lys Pro
    50                  55                  60

<210> SEQ ID NO 23
<211> LENGTH: 33
<212> TYPE: PRT
<213> ORGANISM: Legionella maceachernii
<400> SEQUENCE: 23

Phe Ser Ala Glu Gln Ile Val Arg Ile Ala Ala His Asp Gly Gly Ser
1               5                   10                  15

Arg Asn Ile Glu Ala Val Gln Gln Ala Gln His Val Leu Lys Glu Leu
            20                  25                  30

Gly

<210> SEQ ID NO 24
<211> LENGTH: 33
<212> TYPE: PRT
<213> ORGANISM: Legionella maceachernii
<400> SEQUENCE: 24

Phe Ser Ala Glu Gln Ile Val Ser Ile Val Ala His Asp Gly Gly Ser
1               5                   10                  15

Arg Asn Ile Glu Ala Val Gln Gln Ala Gln His Ile Leu Lys Glu Leu
            20                  25                  30

Gly

<210> SEQ ID NO 25
<211> LENGTH: 33
<212> TYPE: PRT
<213> ORGANISM: Legionellales bacterium
<400> SEQUENCE: 25

Leu Asp Arg Gln Gln Ile Leu Arg Ile Ala Ser His Asp Gly Gly Ser
1               5                   10                  15
```

```
Lys Asn Ile Ala Ala Val Gln Lys Phe Leu Pro Lys Leu Met Asn Phe
            20                  25                  30
Gly

<210> SEQ ID NO 26
<211> LENGTH: 33
<212> TYPE: PRT
<213> ORGANISM: Legionella maceachernii

<400> SEQUENCE: 26

Phe Ser Ala Glu Gln Ile Val Arg Ile Ala Ala His Asp Gly Gly Ser
1               5                   10                  15

Leu Asn Ile Asp Ala Val Gln Gln Ala Gln Gln Ala Leu Lys Glu Leu
            20                  25                  30

Gly

<210> SEQ ID NO 27
<211> LENGTH: 33
<212> TYPE: PRT
<213> ORGANISM: Legionella maceachernii

<400> SEQUENCE: 27

Phe Ser Thr Glu Gln Ile Val Cys Ile Ala Gly His Gly Gly Gly Ser
1               5                   10                  15

Leu Asn Ile Lys Ala Val Leu Leu Ala Gln Gln Ala Leu Lys Asp Leu
            20                  25                  30

Gly

<210> SEQ ID NO 28
<211> LENGTH: 33
<212> TYPE: PRT
<213> ORGANISM: Legionella maceachernii

<400> SEQUENCE: 28

Tyr Ser Ser Glu Gln Ile Val Arg Val Ala Ala His Gly Gly Gly Ser
1               5                   10                  15

Leu Asn Ile Lys Ala Val Leu Gln Ala His Gln Ala Leu Lys Glu Leu
            20                  25                  30

Asp

<210> SEQ ID NO 29
<211> LENGTH: 33
<212> TYPE: PRT
<213> ORGANISM: Legionella maceachernii

<400> SEQUENCE: 29

Phe Ser Ala Glu Gln Ile Val His Ile Ala Ala His Gly Gly Gly Ser
1               5                   10                  15

Leu Asn Ile Lys Ala Ile Leu Gln Ala His Gln Thr Leu Lys Glu Leu
            20                  25                  30

Asn

<210> SEQ ID NO 30
<211> LENGTH: 33
<212> TYPE: PRT
<213> ORGANISM: Legionella maceachernii

<400> SEQUENCE: 30

Phe Ser Ala Glu Gln Ile Val Arg Ile Ala Ala His Ile Gly Gly Ser
```

-continued

```
1               5                   10                  15

Arg Asn Ile Glu Ala Ile Gln Gln Ala His His Ala Leu Lys Glu Leu
            20                  25                  30

Gly

<210> SEQ ID NO 31
<211> LENGTH: 33
<212> TYPE: PRT
<213> ORGANISM: Legionella maceachernii

<400> SEQUENCE: 31

Phe Ser Ala Glu Gln Ile Val Arg Ile Ala Ala His Ile Gly Gly Ser
1               5                   10                  15
His Asn Leu Lys Ala Val Leu Gln Ala Gln Gln Ala Leu Lys Glu Leu
            20                  25                  30

Asp

<210> SEQ ID NO 32
<211> LENGTH: 33
<212> TYPE: PRT
<213> ORGANISM: Legionella maceachernii

<400> SEQUENCE: 32

Phe Ser Ala Lys His Ile Val Arg Ile Ala Ala His Ile Gly Gly Ser
1               5                   10                  15
Leu Asn Ile Lys Ala Val Gln Gln Ala Gln Gln Ala Leu Lys Glu Leu
            20                  25                  30

Gly

<210> SEQ ID NO 33
<211> LENGTH: 33
<212> TYPE: PRT
<213> ORGANISM: Legionella quateirensis

<400> SEQUENCE: 33

Phe Asn Ala Glu Gln Ile Val Arg Met Val Ser His Lys Gly Gly Ser
1               5                   10                  15

Lys Asn Leu Ala Leu Val Lys Glu Tyr Phe Pro Val Phe Ser Ser Phe
            20                  25                  30

His

<210> SEQ ID NO 34
<211> LENGTH: 33
<212> TYPE: PRT
<213> ORGANISM: Legionella maceachernii

<400> SEQUENCE: 34

Phe Ser Ala Asp Gln Ile Val Arg Ile Ala Ala His Lys Gly Gly Ser
1               5                   10                  15

His Asn Ile Val Ala Val Gln Gln Ala Gln Gln Ala Leu Lys Glu Leu
            20                  25                  30

Asp

<210> SEQ ID NO 35
<211> LENGTH: 33
<212> TYPE: PRT
<213> ORGANISM: Legionella maceachernii

<400> SEQUENCE: 35
```

-continued

Phe Ser Ala Glu Gln Ile Val Ser Ile Ala Ala His Val Gly Gly Ser
1               5                   10                  15

His Asn Ile Glu Ala Val Gln Lys Ala His Gln Ala Leu Lys Glu Leu
            20                  25                  30

Asp

<210> SEQ ID NO 36
<211> LENGTH: 33
<212> TYPE: PRT
<213> ORGANISM: Burkholderia

<400> SEQUENCE: 36

Phe Ser Ser Gly Glu Thr Val Gly Ala Thr Val Gly Ala Gly Gly Thr
1               5                   10                  15

Glu Thr Val Ala Gln Gly Gly Thr Ala Ser Asn Thr Thr Val Ser Ser
            20                  25                  30

Gly

<210> SEQ ID NO 37
<211> LENGTH: 33
<212> TYPE: PRT
<213> ORGANISM: Burkholderia

<400> SEQUENCE: 37

Phe Ser Gly Gly Met Ala Thr Ser Thr Thr Val Gly Ser Gly Gly Thr
1               5                   10                  15

Gln Asp Val Leu Ala Gly Gly Ala Ala Val Gly Gly Thr Val Gly Thr
            20                  25                  30

Gly

<210> SEQ ID NO 38
<211> LENGTH: 33
<212> TYPE: PRT
<213> ORGANISM: Burkholderia

<400> SEQUENCE: 38

Phe Ser Ala Ala Asp Ile Val Lys Ile Ala Gly Lys Ile Gly Gly Ala
1               5                   10                  15

Gln Ala Leu Gln Ala Phe Ile Thr His Arg Ala Ala Leu Ile Gln Ala
            20                  25                  30

Gly

<210> SEQ ID NO 39
<211> LENGTH: 33
<212> TYPE: PRT
<213> ORGANISM: Burkholderia

<400> SEQUENCE: 39

Phe Asn Pro Thr Asp Ile Val Lys Ile Ala Gly Asn Asp Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 40
<211> LENGTH: 33
<212> TYPE: PRT
<213> ORGANISM: Burkholderia

<400> SEQUENCE: 40

```
Phe Asn Pro Thr Asp Ile Val Arg Met Ala Gly Asn Asp Gly Gly Ala
1               5                   10                  15

Gln Ala Leu Gln Ala Val Phe Glu Leu Glu Pro Ala Phe Arg Glu Arg
            20                  25                  30

Ser

<210> SEQ ID NO 41
<211> LENGTH: 33
<212> TYPE: PRT
<213> ORGANISM: Burkholderia

<400> SEQUENCE: 41

Phe Asn Pro Thr Asp Ile Val Arg Met Ala Gly Asn Asp Gly Gly Ala
1               5                   10                  15

Gln Ala Leu Gln Ala Val Leu Glu Leu Glu Pro Ala Phe Arg Glu Arg
            20                  25                  30

Gly

<210> SEQ ID NO 42
<211> LENGTH: 33
<212> TYPE: PRT
<213> ORGANISM: Burkholderia

<400> SEQUENCE: 42

Phe Ser Gln Val Asp Ile Val Lys Ile Ala Ser Asn Asp Gly Gly Ala
1               5                   10                  15

Gln Ala Leu Tyr Ser Val Leu Asp Val Glu Pro Thr Phe Arg Glu Arg
            20                  25                  30

Gly

<210> SEQ ID NO 43
<211> LENGTH: 33
<212> TYPE: PRT
<213> ORGANISM: Burkholderia

<400> SEQUENCE: 43

Phe Ser Arg Ala Asp Ile Val Lys Ile Ala Gly Asn Asp Gly Gly Ala
1               5                   10                  15

Gln Ala Leu Tyr Ser Val Leu Asp Val Glu Pro Pro Leu Arg Glu Arg
            20                  25                  30

Gly

<210> SEQ ID NO 44
<211> LENGTH: 33
<212> TYPE: PRT
<213> ORGANISM: Burkholderia

<400> SEQUENCE: 44

Phe Ser Arg Gly Asp Ile Val Lys Ile Ala Gly Asn Asp Gly Gly Ala
1               5                   10                  15

Gln Ala Leu Tyr Ser Val Leu Asp Val Glu Pro Pro Leu Arg Glu Arg
            20                  25                  30

Gly

<210> SEQ ID NO 45
<211> LENGTH: 33
<212> TYPE: PRT
<213> ORGANISM: Burkholderia
```

<400> SEQUENCE: 45

Phe Asn Arg Ala Asp Ile Val Arg Ile Ala Gly Asn Gly Gly Ala
1               5                   10                  15

Gln Ala Leu Tyr Ser Val Arg Asp Ala Gly Pro Thr Leu Gly Lys Arg
            20                  25                  30

Gly

<210> SEQ ID NO 46
<211> LENGTH: 33
<212> TYPE: PRT
<213> ORGANISM: Burkholderia

<400> SEQUENCE: 46

Phe Arg Gln Ala Asp Ile Val Lys Ile Ala Ser Asn Gly Gly Ser Ala
1               5                   10                  15

Gln Ala Leu Asn Ala Val Ile Lys Leu Gly Pro Thr Leu Arg Gln Arg
            20                  25                  30

Gly

<210> SEQ ID NO 47
<211> LENGTH: 33
<212> TYPE: PRT
<213> ORGANISM: Burkholderia

<400> SEQUENCE: 47

Phe Arg Gln Ala Asp Ile Val Lys Met Ala Ser Asn Gly Gly Ser Ala
1               5                   10                  15

Gln Ala Leu Asn Ala Val Ile Lys Leu Gly Pro Thr Leu Arg Gln Arg
            20                  25                  30

Gly

<210> SEQ ID NO 48
<211> LENGTH: 33
<212> TYPE: PRT
<213> ORGANISM: Burkholderia

<400> SEQUENCE: 48

Phe Ser Arg Ala Asp Ile Val Lys Ile Ala Gly Asn Gly Gly Gly Ala
1               5                   10                  15

Gln Ala Leu Gln Ala Val Leu Glu Leu Glu Pro Thr Phe Arg Glu Arg
            20                  25                  30

Gly

<210> SEQ ID NO 49
<211> LENGTH: 33
<212> TYPE: PRT
<213> ORGANISM: Burkholderia

<400> SEQUENCE: 49

Phe Ser Arg Ala Asp Ile Val Arg Ile Ala Gly Asn Gly Gly Gly Ala
1               5                   10                  15

Gln Ala Leu Tyr Ser Val Leu Asp Val Gly Pro Thr Leu Gly Lys Arg
            20                  25                  30

Gly

<210> SEQ ID NO 50
<211> LENGTH: 33
<212> TYPE: PRT
<213> ORGANISM: Burkholderia

<400> SEQUENCE: 50

Phe Ser Arg Gly Asp Ile Val Arg Ile Ala Gly Asn Gly Gly Ala
1               5                   10                  15

Gln Ala Leu Gln Ala Val Leu Glu Leu Glu Pro Thr Leu Gly Glu Arg
            20                  25                  30

Gly

<210> SEQ ID NO 51
<211> LENGTH: 33
<212> TYPE: PRT
<213> ORGANISM: Burkholderia

<400> SEQUENCE: 51

Phe Ser Arg Ala Asp Ile Val Lys Ile Ala Gly Asn Gly Gly Ala
1               5                   10                  15

Gln Ala Leu Gln Ala Val Ile Thr His Arg Ala Ala Leu Thr Gln Ala
            20                  25                  30

Gly

<210> SEQ ID NO 52
<211> LENGTH: 33
<212> TYPE: PRT
<213> ORGANISM: Burkholderia

<400> SEQUENCE: 52

Phe Ser Arg Gly Asp Thr Val Lys Ile Ala Gly Asn Ile Gly Ala
1               5                   10                  15

Gln Ala Leu Gln Ala Val Leu Glu Leu Glu Pro Thr Leu Arg Glu Arg
            20                  25                  30

Gly

<210> SEQ ID NO 53
<211> LENGTH: 33
<212> TYPE: PRT
<213> ORGANISM: Burkholderia

<400> SEQUENCE: 53

Phe Asn Pro Thr Asp Ile Val Lys Ile Ala Gly Asn Ile Gly Ala
1               5                   10                  15

Gln Ala Leu Gln Ala Val Leu Glu Leu Glu Pro Ala Phe Arg Glu Arg
            20                  25                  30

Gly

<210> SEQ ID NO 54
<211> LENGTH: 33
<212> TYPE: PRT
<213> ORGANISM: Burkholderia

<400> SEQUENCE: 54

Phe Ser Ala Ala Asp Ile Val Lys Ile Ala Gly Asn Ile Gly Ala
1               5                   10                  15

Gln Ala Leu Gln Ala Ile Phe Thr His Arg Ala Ala Leu Ile Gln Ala
            20                  25                  30

Gly

<210> SEQ ID NO 55
<211> LENGTH: 33
<212> TYPE: PRT

-continued

```
<213> ORGANISM: Burkholderia

<400> SEQUENCE: 55

Phe Ser Ala Ala Asp Ile Val Lys Ile Ala Gly Asn Ile Gly Gly Ala
1               5                   10                  15
Gln Ala Leu Gln Ala Val Ile Thr His Arg Ala Thr Leu Thr Gln Ala
            20                  25                  30
Gly

<210> SEQ ID NO 56
<211> LENGTH: 33
<212> TYPE: PRT
<213> ORGANISM: Burkholderia

<400> SEQUENCE: 56

Phe Ser Ala Thr Asp Ile Val Lys Ile Ala Ser Asn Ile Gly Gly Ala
1               5                   10                  15
Gln Ala Leu Gln Ala Val Ile Ser Arg Arg Ala Ala Leu Ile Gln Ala
            20                  25                  30
Gly

<210> SEQ ID NO 57
<211> LENGTH: 33
<212> TYPE: PRT
<213> ORGANISM: Burkholderia

<400> SEQUENCE: 57

Phe Ser Gln Pro Asp Ile Val Lys Ile Ala Gly Asn Ile Gly Gly Ala
1               5                   10                  15
Gln Ala Leu Gln Ala Val Leu Glu Leu Glu Pro Ala Phe Arg Glu Arg
            20                  25                  30
Gly

<210> SEQ ID NO 58
<211> LENGTH: 33
<212> TYPE: PRT
<213> ORGANISM: Burkholderia

<400> SEQUENCE: 58

Phe Ser Arg Ala Asp Ile Val Lys Ile Ala Gly Asn Ile Gly Gly Ala
1               5                   10                  15
Gln Ala Leu Gln Ala Val Leu Glu Leu Glu Ser Thr Phe Arg Glu Arg
            20                  25                  30
Ser

<210> SEQ ID NO 59
<211> LENGTH: 33
<212> TYPE: PRT
<213> ORGANISM: Burkholderia

<400> SEQUENCE: 59

Phe Ser Arg Ala Asp Ile Val Lys Ile Ala Gly Asn Ile Gly Gly Ala
1               5                   10                  15
Gln Ala Leu Gln Ala Val Leu Glu Leu Glu Ser Thr Leu Arg Glu Arg
            20                  25                  30
Ser

<210> SEQ ID NO 60
<211> LENGTH: 33
```

```
<212> TYPE: PRT
<213> ORGANISM: Burkholderia

<400> SEQUENCE: 60

Phe Ser Arg Gly Asp Ile Val Lys Met Ala Gly Asn Ile Gly Gly Ala
1               5                   10                  15

Gln Ala Leu Gln Ala Gly Leu Glu Leu Glu Pro Ala Phe Arg Glu Arg
            20                  25                  30

Gly

<210> SEQ ID NO 61
<211> LENGTH: 33
<212> TYPE: PRT
<213> ORGANISM: Burkholderia

<400> SEQUENCE: 61

Phe Ser Arg Gly Asp Ile Val Lys Met Ala Gly Asn Ile Gly Gly Ala
1               5                   10                  15

Gln Ala Leu Gln Ala Val Leu Glu Leu Glu Pro Ala Phe His Glu Arg
            20                  25                  30

Ser

<210> SEQ ID NO 62
<211> LENGTH: 33
<212> TYPE: PRT
<213> ORGANISM: Burkholderia

<400> SEQUENCE: 62

Phe Thr Leu Thr Asp Ile Val Lys Met Ala Gly Asn Ile Gly Gly Ala
1               5                   10                  15

Gln Ala Leu Lys Ala Val Leu Glu His Gly Pro Thr Leu Arg Gln Arg
            20                  25                  30

Asp

<210> SEQ ID NO 63
<211> LENGTH: 33
<212> TYPE: PRT
<213> ORGANISM: Burkholderia

<400> SEQUENCE: 63

Phe Thr Leu Thr Asp Ile Val Lys Met Ala Gly Asn Ile Gly Gly Ala
1               5                   10                  15

Gln Ala Leu Lys Val Val Leu Glu His Gly Pro Thr Leu Arg Gln Arg
            20                  25                  30

Asp

<210> SEQ ID NO 64
<211> LENGTH: 33
<212> TYPE: PRT
<213> ORGANISM: Burkholderia

<400> SEQUENCE: 64

Phe Asn Pro Thr Asp Ile Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 65
```

```
<211> LENGTH: 33
<212> TYPE: PRT
<213> ORGANISM: Burkholderia

<400> SEQUENCE: 65

Phe Asn Pro Thr Asp Ile Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Ser

<210> SEQ ID NO 66
<211> LENGTH: 33
<212> TYPE: PRT
<213> ORGANISM: Burkholderia

<400> SEQUENCE: 66

Phe Asn Pro Thr Asp Met Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 67
<211> LENGTH: 33
<212> TYPE: PRT
<213> ORGANISM: Burkholderia

<400> SEQUENCE: 67

Phe Ser Ala Ala Asp Ile Val Lys Ile Ala Ser Asn Asn Gly Gly Ala
1               5                   10                  15

Gln Ala Leu Gln Ala Leu Ile Asp His Trp Ser Thr Leu Ser Gly Lys
            20                  25                  30

Thr

<210> SEQ ID NO 68
<211> LENGTH: 33
<212> TYPE: PRT
<213> ORGANISM: Burkholderia

<400> SEQUENCE: 68

Phe Ser Ala Ala Asp Ile Val Lys Ile Ala Ser Asn Asn Gly Gly Ala
1               5                   10                  15

Gln Ala Leu Gln Ala Val Ile Ser Arg Arg Ala Ala Leu Ile Gln Ala
            20                  25                  30

Gly

<210> SEQ ID NO 69
<211> LENGTH: 33
<212> TYPE: PRT
<213> ORGANISM: Burkholderia

<400> SEQUENCE: 69

Phe Ser Ala Ala Asp Ile Val Lys Ile Ala Ser Asn Asn Gly Gly Ala
1               5                   10                  15

Gln Ala Leu Gln Ala Val Ile Thr His Arg Ala Ala Leu Ala Gln Ala
            20                  25                  30

Gly
```

```
<210> SEQ ID NO 70
<211> LENGTH: 33
<212> TYPE: PRT
<213> ORGANISM: Burkholderia

<400> SEQUENCE: 70

Phe Ser Ala Ala Asp Ile Val Lys Ile Ala Ser Asn Asn Gly Gly Ala
1               5                   10                  15

Arg Ala Leu Gln Ala Leu Ile Asp His Trp Ser Thr Leu Ser Gly Lys
            20                  25                  30

Thr

<210> SEQ ID NO 71
<211> LENGTH: 33
<212> TYPE: PRT
<213> ORGANISM: Burkholderia

<400> SEQUENCE: 71

Phe Thr Leu Thr Asp Ile Val Glu Met Ala Gly Asn Asn Gly Gly Ala
1               5                   10                  15

Gln Ala Leu Lys Ala Val Leu Glu His Gly Ser Thr Leu Asp Glu Arg
            20                  25                  30

Gly

<210> SEQ ID NO 72
<211> LENGTH: 33
<212> TYPE: PRT
<213> ORGANISM: Burkholderia

<400> SEQUENCE: 72

Phe Thr Leu Thr Asp Ile Val Lys Met Ala Gly Asn Asn Gly Gly Ala
1               5                   10                  15

Gln Ala Leu Lys Ala Val Leu Glu His Gly Pro Thr Leu Asp Glu Arg
            20                  25                  30

Gly

<210> SEQ ID NO 73
<211> LENGTH: 33
<212> TYPE: PRT
<213> ORGANISM: Burkholderia

<400> SEQUENCE: 73

Phe Thr Leu Thr Asp Ile Val Lys Met Ala Gly Asn Asn Gly Gly Ala
1               5                   10                  15

Gln Ala Leu Lys Val Val Leu Glu His Gly Pro Thr Leu Arg Gln Arg
            20                  25                  30

Gly

<210> SEQ ID NO 74
<211> LENGTH: 33
<212> TYPE: PRT
<213> ORGANISM: Burkholderia

<400> SEQUENCE: 74

Phe Thr Leu Thr Asp Ile Val Lys Met Ala Ser Asn Asn Gly Gly Ala
1               5                   10                  15

Gln Ala Leu Lys Ala Val Leu Glu His Gly Pro Thr Leu Asp Glu Arg
            20                  25                  30

Gly
```

<210> SEQ ID NO 75
<211> LENGTH: 33
<212> TYPE: PRT
<213> ORGANISM: Burkholderia

<400> SEQUENCE: 75

Phe Ser Ala Ala Asp Ile Val Lys Ile Ala Gly Asn Ser Gly Gly Ala
1               5                   10                  15

Gln Ala Leu Gln Ala Val Ile Ser His Arg Ala Ala Leu Thr Gln Ala
            20                  25                  30

Gly

<210> SEQ ID NO 76
<211> LENGTH: 33
<212> TYPE: PRT
<213> ORGANISM: Burkholderia

<400> SEQUENCE: 76

Phe Ser Gly Gly Asp Ala Val Ser Thr Val Arg Ser Gly Gly Ala
1               5                   10                  15

Gln Ser Val Ala Ser Gly Gly Thr Ala Ser Gly Thr Thr Val Ser Ala
            20                  25                  30

Gly

<210> SEQ ID NO 77
<211> LENGTH: 33
<212> TYPE: PRT
<213> ORGANISM: Burkholderia

<400> SEQUENCE: 77

Phe Arg Gln Thr Asp Ile Val Lys Met Ala Gly Ser Gly Gly Ser Ala
1               5                   10                  15

Gln Ala Leu Asn Ala Val Ile Lys His Gly Pro Thr Leu Arg Gln Arg
            20                  25                  30

Gly

<210> SEQ ID NO 78
<211> LENGTH: 33
<212> TYPE: PRT
<213> ORGANISM: Burkholderia

<400> SEQUENCE: 78

Phe Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Thr Gln Ala Gly
            20                  25                  30

Arg

<210> SEQ ID NO 79
<211> LENGTH: 33
<212> TYPE: PRT
<213> ORGANISM: Burkholderia

<400> SEQUENCE: 79

Phe Ser Gly Gly Asp Ala Ala Gly Thr Val Val Ser Ser Gly Gly Ala
1               5                   10                  15

Gln Asn Val Thr Gly Gly Leu Ala Ser Gly Thr Thr Val Ala Ser Gly
            20                  25                  30

Gly

<210> SEQ ID NO 80
<211> LENGTH: 33
<212> TYPE: PRT
<213> ORGANISM: Paraburkholderia

<400> SEQUENCE: 80

Phe Asn Leu Thr Asp Ile Val Glu Met Ala Ala Asn Ser Gly Gly Ala
1               5                   10                  15

Gln Ala Leu Lys Ala Val Leu Glu His Gly Pro Thr Leu Arg Gln Arg
            20                  25                  30

Gly

<210> SEQ ID NO 81
<211> LENGTH: 33
<212> TYPE: PRT
<213> ORGANISM: Paraburkholderia

<400> SEQUENCE: 81

Phe Asn Arg Ala Ser Ile Val Lys Ile Ala Gly Asn Ser Gly Gly Ala
1               5                   10                  15

Gln Ala Leu Gln Ala Val Leu Lys His Gly Pro Thr Leu Asp Glu Arg
            20                  25                  30

Gly

<210> SEQ ID NO 82
<211> LENGTH: 33
<212> TYPE: PRT
<213> ORGANISM: Paraburkholderia

<400> SEQUENCE: 82

Phe Ser Gln Ala Asn Ile Val Lys Met Ala Gly Asn Ser Gly Gly Ala
1               5                   10                  15

Gln Ala Leu Gln Ala Val Leu Asp Leu Glu Leu Val Phe Arg Glu Arg
            20                  25                  30

Gly

<210> SEQ ID NO 83
<211> LENGTH: 33
<212> TYPE: PRT
<213> ORGANISM: Paraburkholderia

<400> SEQUENCE: 83

Phe Ser Gln Pro Asp Ile Val Lys Met Ala Gly Asn Ser Gly Gly Ala
1               5                   10                  15

Gln Ala Leu Gln Ala Val Leu Asp Leu Glu Leu Ala Phe Arg Glu Arg
            20                  25                  30

Gly

<210> SEQ ID NO 84
<211> LENGTH: 33
<212> TYPE: PRT
<213> ORGANISM: Paraburkholderia

<400> SEQUENCE: 84

Phe Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Met Gln Ala Gly
            20                  25                  30

Arg

<210> SEQ ID NO 85
<211> LENGTH: 33
<212> TYPE: PRT
<213> ORGANISM: Francisella

<400> SEQUENCE: 85

Tyr Lys Ser Glu Asp Ile Ile Arg Leu Ala Ser His Asp Gly Gly Ser
1               5                   10                  15

Val Asn Leu Glu Ala Val Leu Arg Leu His Ser Gln Leu Thr Arg Leu
            20                  25                  30

Gly

<210> SEQ ID NO 86
<211> LENGTH: 33
<212> TYPE: PRT
<213> ORGANISM: Francisella

<400> SEQUENCE: 86

Tyr Lys Pro Glu

Gly

<210> SEQ ID NO 90
<211> LENGTH: 19
<212> TYPE: DNA
<213> ORGANISM: Artificial sequence
<220> FEATURE:
<223> OTHER INFORMATION: synthetic sequence

<400> SEQUENCE: 90
gaggaagagg gggcgggag                                              19

<210> SEQ ID NO 91
<211> LENGTH: 20
<212> TYPE: DNA
<213> ORGANISM: Artificial sequence
<220> FEATURE:
<223> OTHER INFORMATION: synthetic sequence

<400> SEQUENCE: 91 gaggggggcgg gagcaagggg                                            20

<210> SEQ ID NO 92
<211> LENGTH: 19
<212> TYPE: DNA
<213> ORGANISM: Artificial sequence
<220> FEATURE:
<223> OTHER INFORMATION: synthetic sequence

<400> SEQUENCE: 92
gagcaagggg cgggcaccc                                              19

<210> SEQ ID NO 93
<211> LENGTH: 20
<212> TYPE: DNA
<213> ORGANISM: Artificial sequence
<220> FEATURE:
<223> OTHER INFORMATION: synthetic sequence

<400> SEQUENCE: 93
gaagggaggg tgcccgcccc                                             20

<210> SEQ ID NO 94
<211> LENGTH: 20
<212> TYPE: DNA
<213> ORGANISM: Artificial sequence
<220> FEATURE:
<223> OTHER INFORMATION: synthetic sequence

<400> SEQUENCE: 94
gacctgggac agtttccctt                                             20

<210> SEQ ID NO 95
<211> LENGTH: 19
<212> TYPE: DNA
<213> ORGANISM: Artificial sequence
<220> FEATURE:
<223> OTHER INFORMATION: synthetic sequence

<400> SEQUENCE: 95
gacagtttcc cttccgctc                                              19

<210> SEQ ID NO 96
<211> LENGTH: 20
<212> TYPE: DNA

<213> ORGANISM: Artificial sequence
<220> FEATURE:
<223> OTHER INFORMATION: synthetic sequence

<400> SEQUENCE: 96
gagcagcccc accagagtgc                                              20

<210> SEQ ID NO 97
<211> LENGTH: 20
<212> TYPE: DNA
<213> ORGANISM: Artificial sequence
<220> FEATURE:
<223> OTHER INFORMATION: synthetic sequence

<400> SEQUENCE: 97
gatctgcatg cctggagcag                                              20

<210> SEQ ID NO 98
<211> LENGTH: 932
<212> TYPE: PRT
<213> ORGANISM: Artificial sequence
<220> FEATURE:
<223> OTHER INFORMATION: synthetic sequence

<400> SEQUENCE: 98

```
Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
    130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Leu Gln Asn Met
        195                 200                 205

Gly Phe Asn Val Glu Gln Ile Val Arg Met Val Ser His Asn Gly Gly
    210                 215                 220

Ser Lys Asn Leu Lys Ala Val Thr Asp Asn His Asp Leu Lys Asn
225                 230                 235                 240

Met Gly Phe Asn Val Glu Gln Ile Val Arg Met Val Ser His Asn Gly
                245                 250                 255

Gly Ser Lys Asn Leu Lys Ala Val Thr Asp Asn His Asp Leu Lys
```

```
                    260             265             270
Asn Met Gly Phe Ser Ser Gln Gln Ile Ile Arg Met Val Ser His Ala
            275             280             285
Gly Gly Ala Asn Asn Leu Lys Ala Val Thr Ala Asn His Asp Asp Leu
            290             295             300
Gln Asn Met Gly Phe Ser Ser Gln Gln Ile Ile Arg Met Val Ser His
305             310             315             320
Ala Gly Gly Ala Asn Asn Leu Lys Ala Val Thr Ala Asn His Asp Asp
            325             330             335
Leu Gln Asn Met Gly Phe Asn Val Glu Gln Ile Val Arg Met Val Ser
            340             345             350
His Asn Gly Gly Ser Lys Asn Leu Lys Ala Val Thr Asp Asn His Asp
            355             360             365
Asp Leu Lys Asn Met Gly Phe Ser Ser Gln Gln Ile Ile Arg Met Val
            370             375             380
Ser His Ala Gly Gly Ala Asn Asn Leu Lys Ala Val Thr Ala Asn His
385             390             395             400
Asp Asp Leu Gln Asn Met Gly Phe Asn Val Glu Gln Ile Val Arg Met
            405             410             415
Val Ser His Asn Gly Gly Ser Lys Asn Leu Lys Ala Val Thr Asp Asn
            420             425             430
His Asp Asp Leu Lys Asn Met Gly Phe Asn Val Glu Gln Ile Val Arg
            435             440             445
Met Val Ser His Asn Gly Gly Ser Lys Asn Leu Lys Ala Val Thr Asp
            450             455             460
Asn His Asp Asp Leu Lys Asn Met Gly Phe Asn Val Glu Gln Ile Val
465             470             475             480
Arg Met Val Ser His Asn Gly Gly Ser Lys Asn Leu Lys Ala Val Thr
            485             490             495
Asp Asn His Asp Asp Leu Lys Asn Met Gly Phe Asn Val Glu Gln Ile
            500             505             510
Val Arg Met Val Ser His Asn Gly Gly Ser Lys Asn Leu Lys Ala Val
            515             520             525
Thr Asp Asn His Asp Asp Leu Lys Asn Met Gly Phe Asn Val Glu Gln
            530             535             540
Ile Val Arg Met Val Ser His Asn Gly Gly Ser Lys Asn Leu Lys Ala
545             550             555             560
Val Thr Asp Asn His Asp Asp Leu Lys Asn Met Gly Phe Asn Thr Glu
            565             570             575
Gln Ile Val Arg Met Val Ser His Asp Gly Gly Ser Leu Asn Leu Lys
            580             585             590
Ala Val Lys Lys Tyr His Asp Ala Leu Arg Glu Arg Lys Phe Asn Val
            595             600             605
Glu Gln Ile Val Arg Met Val Ser His Asn Gly Gly Ser Lys Asn Leu
            610             615             620
Lys Ala Val Thr Asp Asn His Asp Asp Leu Lys Asn Met Gly Phe Asn
625             630             635             640
Val Glu Gln Ile Val Arg Met Val Ser His Asn Gly Gly Ser Lys Asn
            645             650             655
Leu Lys Ala Val Thr Asp Asn His Asp Asp Leu Lys Asn Met Gly Phe
            660             665             670
Asn Val Glu Gln Ile Val Arg Met Val Ser His Asn Gly Gly Ser Lys
            675             680             685
```

```
Asn Leu Lys Ala Val Thr Asp Asn His Asp Leu Lys Asn Met Gly
        690                 695                 700

Phe Ser Ser Gln Gln Ile Ile Arg Met Val Ser His Ala Gly Gly Ala
705                 710                 715                 720

Asn Asn Leu Lys Ala Val Thr Ala Asn His Asp Asp Leu Gln Asn Met
            725                 730                 735

Gly Phe Asn Ala Glu Gln Ile Val Arg Met Val Ser His Lys Gly Gly
            740                 745                 750

Ser Lys Asn Leu Ala Leu Val Lys Glu Tyr Phe Pro Val Phe Ser Ser
            755                 760                 765

Phe His Phe Thr Ala Asp Gln Ile Val Ala Leu Ile Cys Gln Ser Lys
            770                 775                 780

Gln Cys Phe Arg Asn Leu Lys Lys Asn His Gln Gln Trp Lys Asn Lys
785                 790                 795                 800

Gly Leu Ser Ala Glu Gln Ile Val Asp Leu Ile Leu Gln Glu Thr Pro
            805                 810                 815

Pro Lys Pro Asn Phe Asn Asn Thr Ser Ser Thr Pro Ser Pro Ser
            820                 825                 830

Ala Pro Ser Phe Phe Gln Gly Pro Ser Thr Pro Ile Pro Thr Pro Val
            835                 840                 845

Leu Asp Asn Ser Pro Ala Pro Ile Phe Ser Asn Pro Val Cys Phe Phe
            850                 855                 860

Ser Ser Arg Ser Glu Asn Asn Thr Glu Gln Tyr Leu Gln Asp Ser Thr
865                 870                 875                 880

Leu Asp Leu Asp Ser Gln Leu Gly Asp Pro Thr Lys Asn Phe Asn Val
            885                 890                 895

Asn Asn Phe Trp Ser Leu Phe Pro Phe Asp Asp Val Gly Tyr His Pro
            900                 905                 910

His Ser Asn Asp Val Gly Tyr His Leu His Ser Asp Glu Glu Ser Pro
            915                 920                 925

Phe Phe Asp Phe
    930

<210> SEQ ID NO 99
<211> LENGTH: 819
<212> TYPE: PRT
<213> ORGANISM: Artificial sequence
<220> FEATURE:
<223> OTHER INFORMATION: synthetic sequence

<400> SEQUENCE: 99

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Ser Pro Ala Ser Ala Asn Ala Arg
            35                  40                  45

Lys Arg Thr Ser Arg Lys Glu Met Ser Gly Pro Pro Ser Lys Glu Pro
50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
            85                  90                  95

Thr Arg Ser Asp Ser Leu Leu Ser Leu Asn Tyr Thr Lys Lys Gln Ile
            100                 105                 110
```

```
Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
    130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
                180                 185                 190

Asn Asn Leu Lys Ala Val Thr Ala Asn His Asp Asp Leu Gln Asn Met
            195                 200                 205

Gly Phe Asn Val Glu Gln Ile Val Arg Met Val Ser His Asn Gly Gly
        210                 215                 220

Ser Lys Asn Leu Lys Ala Val Thr Asp Asn His Asp Asp Leu Lys Asn
225                 230                 235                 240

Met Gly Phe Asn Val Glu Gln Ile Val Arg Met Val Ser His Asn Gly
                245                 250                 255

Gly Ser Lys Asn Leu Lys Ala Val Thr Asp Asn His Asp Asp Leu Lys
                260                 265                 270

Asn Met Gly Phe Ser Ser Gln Gln Ile Ile Arg Met Val Ser His Ala
            275                 280                 285

Gly Gly Ala Asn Asn Leu Lys Ala Val Thr Ala Asn His Asp Asp Leu
        290                 295                 300

Gln Asn Met Gly Phe Ser Ser Gln Gln Ile Ile Arg Met Val Ser His
305                 310                 315                 320

Ala Gly Gly Ala Asn Asn Leu Lys Ala Val Thr Ala Asn His Asp Asp
                325                 330                 335

Leu Gln Asn Met Gly Phe Asn Val Glu Gln Ile Val Arg Met Val Ser
                340                 345                 350

His Asn Gly Gly Ser Lys Asn Leu Lys Ala Val Thr Asp Asn His Asp
            355                 360                 365

Asp Leu Lys Asn Met Gly Phe Ser Ser Gln Gln Ile Ile Arg Met Val
        370                 375                 380

Ser His Ala Gly Gly Ala Asn Asn Leu Lys Ala Val Thr Ala Asn His
385                 390                 395                 400

Asp Asp Leu Gln Asn Met Gly Phe Asn Val Glu Gln Ile Val Arg Met
                405                 410                 415

Val Ser His Asn Gly Gly Ser Lys Asn Leu Lys Ala Val Thr Asp Asn
                420                 425                 430

His Asp Asp Leu Lys Asn Met Gly Phe Asn Val Glu Gln Ile Val Arg
            435                 440                 445

Met Val Ser His Asn Gly Gly Ser Lys Asn Leu Lys Ala Val Thr Asp
        450                 455                 460

Asn His Asp Asp Leu Lys Asn Met Gly Phe Asn Val Glu Gln Ile Val
465                 470                 475                 480

Arg Met Val Ser His Asn Gly Gly Ser Lys Asn Leu Lys Ala Val Thr
                485                 490                 495

Asp Asn His Asp Asp Leu Lys Asn Met Gly Phe Asn Val Glu Gln Ile
                500                 505                 510

Val Arg Met Val Ser His Asn Gly Gly Ser Lys Asn Leu Lys Ala Val
            515                 520                 525
```

```
Thr Asp Asn His Asp Asp Leu Lys Asn Met Gly Phe Asn Val Glu Gln
            530                 535                 540

Ile Val Arg Met Val Ser His Asn Gly Gly Ser Lys Asn Leu Lys Ala
545                 550                 555                 560

Val Thr Asp Asn His Asp Asp Leu Lys Asn Met Gly Phe Asn Thr Glu
                565                 570                 575

Gln Ile Val Arg Met Val Ser His Asp Gly Ser Leu Asn Leu Lys
            580                 585                 590

Ala Val Lys Lys Tyr His Asp Ala Leu Arg Glu Arg Lys Phe Asn Val
                595                 600                 605

Glu Gln Ile Val Arg Met Val Ser His Asn Gly Gly Ser Lys Asn Leu
610                 615                 620

Lys Ala Val Thr Asp Asn His Asp Asp Leu Lys Asn Met Gly Phe Asn
625                 630                 635                 640

Val Glu Gln Ile Val Arg Met Val Ser His Asn Gly Gly Ser Lys Asn
                645                 650                 655

Leu Lys Ala Val Thr Asp Asn His Asp Asp Leu Lys Asn Met Gly Phe
                660                 665                 670

Asn Val Glu Gln Ile Val Arg Met Val Ser His Asn Gly Gly Ser Lys
                675                 680                 685

Asn Leu Lys Ala Val Thr Asp Asn His Asp Asp Leu Lys Asn Met Gly
690                 695                 700

Phe Ser Ser Gln Gln Ile Ile Arg Met Val Ser His Ala Gly Gly Ala
705                 710                 715                 720

Asn Asn Leu Lys Ala Val Thr Ala Asn His Asp Asp Leu Gln Asn Met
                725                 730                 735

Gly Phe Asn Ala Glu Gln Ile Val Arg Met Val Ser His Lys Gly Gly
            740                 745                 750

Ser Lys Asn Leu Ala Leu Val Lys Glu Tyr Phe Pro Val Phe Ser Ser
            755                 760                 765

Phe His Phe Thr Ala Asp Gln Ile Val Ala Leu Ile Cys Gln Ser Lys
            770                 775                 780

Gln Cys Phe Arg Asn Leu Lys Lys Asn His Gln Gln Trp Lys Asn Lys
785                 790                 795                 800

Gly Leu Ser Ala Glu Gln Ile Val Asp Leu Ile Leu Gln Glu Thr Pro
                805                 810                 815

Pro Lys Pro

<210> SEQ ID NO 100
<211> LENGTH: 965
<212> TYPE: PRT
<213> ORGANISM: Artificial sequence
<220> FEATURE:
<223> OTHER INFORMATION: synthetic sequence

<400> SEQUENCE: 100

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Pro Ala Ser Ala Asn Ala Arg
            35                  40                  45

Lys Arg Thr Ser Arg Lys Glu Met Ser Gly Pro Ser Lys Glu Pro
50                  55                  60

Ala Asn Thr Lys Ser Arg Arg Ala Asn Ser Gln Asn Asn Lys Leu Ser
```

```
                65                  70                  75                  80
Leu Ala Asp Arg Leu Thr Lys Tyr Asn Ile Asp Glu Glu Phe Tyr Gln
                    85                  90                  95

Thr Arg Ser Asp Ser Leu Leu Ser Leu Asn Tyr Thr Lys Lys Gln Ile
                100                 105                 110

Glu Arg Leu Ile Leu Tyr Lys Gly Arg Thr Ser Ala Val Gln Gln Leu
                115                 120                 125

Leu Cys Lys His Glu Glu Leu Leu Asn Leu Ile Ser Pro Asp Gly Leu
            130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
                180                 185                 190

Asn Asn Leu Lys Ala Val Thr Ala Asn His Asp Asp Leu Gln Asn Met
            195                 200                 205

Gly Phe Asn Val Glu Gln Ile Val Arg Met Val Ser His Asn Gly Gly
            210                 215                 220

Ser Lys Asn Leu Lys Ala Val Thr Asp Asn His Asp Asp Leu Lys Asn
225                 230                 235                 240

Met Gly Phe Asn Val Glu Gln Ile Val Arg Met Val Ser His Asn Gly
                245                 250                 255

Gly Ser Lys Asn Leu Lys Ala Val Thr Asp Asn His Asp Asp Leu Lys
            260                 265                 270

Asn Met Gly Phe Asn Val Glu Gln Ile Val Arg Met Val Ser His Asn
            275                 280                 285

Gly Gly Ser Lys Asn Leu Lys Ala Val Thr Asp Asn His Asp Asp Leu
            290                 295                 300

Lys Asn Met Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
                325                 330                 335

Leu Lys Asn Met Gly Phe Asn Val Glu Gln Ile Val Arg Met Val Ser
                340                 345                 350

His Asn Gly Gly Ser Lys Asn Leu Lys Ala Val Thr Asp Asn His Asp
            355                 360                 365

Asp Leu Lys Asn Met Gly Phe Asn Thr Glu Gln Ile Val Arg Met Val
            370                 375                 380

Ser His Asp Gly Gly Ser Leu Asn Leu Lys Ala Val Lys Lys Tyr His
385                 390                 395                 400

Asp Ala Leu Arg Glu Arg Lys Phe Asn Val Glu Gln Ile Val Arg Met
                405                 410                 415

Val Ser His Asn Gly Gly Ser Lys Asn Leu Lys Ala Val Thr Asp Asn
                420                 425                 430

His Asp Asp Leu Lys Asn Met Gly Phe Asn Val Glu Gln Ile Val Arg
            435                 440                 445

Met Val Ser His Asn Gly Gly Ser Lys Asn Leu Lys Ala Val Thr Asp
            450                 455                 460

Asn His Asp Asp Leu Lys Asn Met Gly Phe Asn Val Glu Gln Ile Val
465                 470                 475                 480

Arg Met Val Ser His Asn Gly Gly Ser Lys Asn Leu Lys Ala Val Thr
                485                 490                 495
```

```
Asp Asn His Asp Asp Leu Lys Asn Met Gly Phe Ser Ser Gln Gln Ile
            500                 505                 510

Ile Arg Met Val Ser His Ala Gly Ala Asn Asn Leu Lys Ala Val
            515                 520                 525

Thr Ala Asn His Asp Asp Leu Gln Asn Met Gly Phe Asn Val Glu Gln
            530                 535                 540

Ile Val Arg Met Val Ser His Asn Gly Ser Lys Asn Leu Lys Ala
545                 550                 555                 560

Val Thr Asp Asn His Asp Asp Leu Lys Asn Met Gly Phe Asn Thr Glu
                565                 570                 575

Gln Ile Val Arg Met Val Ser His Asp Gly Gly Ser Leu Asn Leu Lys
                580                 585                 590

Ala Val Lys Lys Tyr His Asp Ala Leu Arg Glu Arg Lys Phe Ser Ser
            595                 600                 605

Gln Gln Ile Ile Arg Met Val Ser His Ala Gly Gly Ala Asn Asn Leu
            610                 615                 620

Lys Ala Val Thr Ala Asn His Asp Asp Leu Gln Asn Met Gly Phe Ser
625                 630                 635                 640

Ser Gln Gln Ile Ile Arg Met Val Ser His Ala Gly Gly Ala Asn Asn
                645                 650                 655

Leu Lys Ala Val Thr Ala Asn His Asp Asp Leu Gln Asn Met Gly Phe
            660                 665                 670

Asn Val Glu Gln Ile Val Arg Met Val Ser His Asn Gly Gly Ser Lys
            675                 680                 685

Asn Leu Lys Ala Val Thr Asp Asn His Asp Asp Leu Lys Asn Met Gly
            690                 695                 700

Phe Asn Val Glu Gln Ile Val Arg Met Val Ser His Asn Gly Gly Ser
705                 710                 715                 720

Lys Asn Leu Lys Ala Val Thr Asp Asn His Asp Asp Leu Lys Asn Met
                725                 730                 735

Gly Phe Asn Val Glu Gln Ile Val Arg Met Val Ser His Asn Gly Gly
                740                 745                 750

Ser Lys Asn Leu Lys Ala Val Thr Asp Asn His Asp Asp Leu Lys Asn
            755                 760                 765

Met Gly Phe Asn Ala Glu Gln Ile Val Arg Met Val Ser His Lys Gly
            770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
                820                 825                 830

Lys Gly Leu Ser Ala Glu Gln Ile Val Asp Leu Ile Leu Gln Glu Thr
            835                 840                 845

Pro Pro Lys Pro Asn Phe Asn Asn Thr Ser Ser Ser Thr Pro Ser Pro
            850                 855                 860

Ser Ala Pro Ser Phe Phe Gln Gly Pro Ser Thr Pro Ile Pro Thr Pro
865                 870                 875                 880

Val Leu Asp Asn Ser Pro Ala Pro Ile Phe Ser Asn Pro Val Cys Phe
                885                 890                 895

Phe Ser Ser Arg Ser Glu Asn Asn Thr Glu Gln Tyr Leu Gln Asp Ser
                900                 905                 910
```

-continued

```
Thr Leu Asp Leu Asp Ser Gln Leu Gly Asp Pro Thr Lys Asn Phe Asn
            915                 920                 925

Val Asn Asn Phe Trp Ser Leu Phe Pro Phe Asp Val Gly Tyr His
        930                 935                 940

Pro His Ser Asn Asp Val Gly Tyr His Leu His Ser Asp Glu Glu Ser
945                 950                 955                 960

Pro Phe Phe Asp Phe
                965

<210> SEQ ID NO 101
<211> LENGTH: 852
<212> TYPE: PRT
<213> ORGANISM: Artificial sequence
<220> FEATURE:
<223> OTHER INFORMATION: synthetic sequence

<400> SEQUENCE: 101

Met Pro Asp Leu Glu Leu Asn Phe Ala Ile Pro Leu His Leu Phe Asp
1               5                  10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
        195                 200                 205

Gly Phe Asn Val Glu Gln Ile Val Arg Met Val Ser His Asn Gly Gly
210                 215                 220

Ser Lys Asn Leu Lys Ala Val Thr Asp Asn His Asp Asp Leu Lys Asn
225                 230                 235                 240

Met Gly Phe Asn Val Glu Gln Ile Val Arg Met Val Ser His Asn Gly
                245                 250                 255

Gly Ser Lys Asn Leu Lys Ala Val Thr Asp Asn His Asp Asp Leu Lys
            260                 265                 270

Asn Met Gly Phe Asn Val Glu Gln Ile Val Arg Met Val Ser His Asn
        275                 280                 285

Gly Gly Ser Lys Asn Leu Lys Ala Val Thr Asp Asn His Asp Asp Leu
290                 295                 300
```

```
Lys Asn Met Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
                325                 330                 335

Leu Lys Asn Met Gly Phe Asn Val Glu Gln Ile Val Arg Met Val Ser
                340                 345                 350

His Asn Gly Gly Ser Lys Asn Leu Lys Ala Val Thr Asp Asn His Asp
                355                 360                 365

Asp Leu Lys Asn Met Gly Phe Asn Thr Glu Gln Ile Val Arg Met Val
        370                 375                 380

Ser His Asp Gly Gly Ser Leu Asn Leu Lys Ala Val Lys Lys Tyr His
385                 390                 395                 400

Asp Ala Leu Arg Glu Arg Lys Phe Asn Val Glu Gln Ile Val Arg Met
                405                 410                 415

Val Ser His Asn Gly Gly Ser Lys Asn Leu Lys Ala Val Thr Asp Asn
                420                 425                 430

His Asp Asp Leu Lys Asn Met Gly Phe Asn Val Glu Gln Ile Val Arg
                435                 440                 445

Met Val Ser His Asn Gly Gly Ser Lys Asn Leu Lys Ala Val Thr Asp
450                 455                 460

Asn His Asp Asp Leu Lys Asn Met Gly Phe Asn Val Glu Gln Ile Val
465                 470                 475                 480

Arg Met Val Ser His Asn Gly Gly Ser Lys Asn Leu Lys Ala Val Thr
                485                 490                 495

Asp Asn His Asp Asp Leu Lys Asn Met Gly Phe Ser Ser Gln Gln Ile
                500                 505                 510

Ile Arg Met Val Ser His Ala Gly Gly Ala Asn Asn Leu Lys Ala Val
        515                 520                 525

Thr Ala Asn His Asp Asp Leu Gln Asn Met Gly Phe Asn Val Glu Gln
        530                 535                 540

Ile Val Arg Met Val Ser His Asn Gly Gly Ser Lys Asn Leu Lys Ala
545                 550                 555                 560

Val Thr Asp Asn His Asp Asp Leu Lys Asn Met Gly Phe Asn Thr Glu
                565                 570                 575

Gln Ile Val Arg Met Val Ser His Asp Gly Gly Ser Leu Asn Leu Lys
                580                 585                 590

Ala Val Lys Lys Tyr His Asp Ala Leu Arg Glu Arg Lys Phe Ser Ser
                595                 600                 605

Gln Gln Ile Ile Arg Met Val Ser His Ala Gly Gly Ala Asn Asn Leu
        610                 615                 620

Lys Ala Val Thr Ala Asn His Asp Asp Leu Gln Asn Met Gly Phe Ser
625                 630                 635                 640

Ser Gln Gln Ile Ile Arg Met Val Ser His Ala Gly Gly Ala Asn Asn
                645                 650                 655

Leu Lys Ala Val Thr Ala Asn His Asp Asp Leu Gln Asn Met Gly Phe
                660                 665                 670

Asn Val Glu Gln Ile Val Arg Met Val Ser His Asn Gly Gly Ser Lys
                675                 680                 685

Asn Leu Lys Ala Val Thr Asp Asn His Asp Asp Leu Lys Asn Met Gly
                690                 695                 700

Phe Asn Val Glu Gln Ile Val Arg Met Val Ser His Asn Gly Gly Ser
705                 710                 715                 720

Lys Asn Leu Lys Ala Val Thr Asp Asn His Asp Asp Leu Lys Asn Met
```

```
                    725                 730                 735
Gly Phe Asn Val Glu Gln Ile Val Arg Met Val Ser His Asn Gly Gly
                740                 745                 750

Ser Lys Asn Leu Lys Ala Val Thr Asp Asn His Asp Asp Leu Lys Asn
            755                 760                 765

Met Gly Phe Asn Ala Glu Gln Ile Val Arg Met Val Ser His Lys Gly
        770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
                820                 825                 830

Lys Gly Leu Ser Ala Glu Gln Ile Val Asp Leu Ile Leu Gln Glu Thr
            835                 840                 845

Pro Pro Lys Pro
    850

<210> SEQ ID NO 102
<211> LENGTH: 932
<212> TYPE: PRT
<213> ORGANISM: Artificial sequence
<220> FEATURE:
<223> OTHER INFORMATION: synthetic sequence

<400> SEQUENCE: 102

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Pro Ala Ser Ala Asn Ala Arg
            35                  40                  45

Lys Arg Thr Ser Arg Lys Glu Met Ser Gly Pro Pro Ser Lys Glu Pro
50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
                100                 105                 110

Glu Arg Leu Ile Leu Tyr Lys Gly Arg Thr Ser Ala Val Gln Gln Leu
            115                 120                 125

Leu Cys Lys His Glu Glu Leu Leu Asn Leu Ile Ser Pro Asp Gly Leu
130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
        195                 200                 205

Gly Phe Asn Val Glu Gln Ile Val Arg Met Val Ser His Asn Gly Gly
    210                 215                 220

Ser Lys Asn Leu Lys Ala Val Thr Asp Asn His Asp Asp Leu Lys Asn
```

```
                225                 230                 235                 240
        Met Gly Phe Asn Thr Glu Gln Ile Val Arg Met Val Ser His Asp Gly
                        245                 250                 255

Gly Ser Leu Asn Leu Lys Ala Val Lys Lys Tyr His Asp Ala Leu Arg
                        260                 265                 270

Glu Arg Lys Phe Ser Ser Gln Ile Ile Arg Met Val Ser His Ala
                        275                 280                 285

Gly Gly Ala Asn Asn Leu Lys Ala Val Thr Ala Asn His Asp Asp Leu
                        290                 295                 300

Gln Asn Met Gly Phe Ser Ser Gln Gln Ile Ile Arg Met Val Ser His
        305                 310                 315                 320

Ala Gly Gly Ala Asn Asn Leu Lys Ala Val Thr Ala Asn His Asp Asp
                        325                 330                 335

Leu Gln Asn Met Gly Phe Asn Val Glu Gln Ile Val Arg Met Val Ser
                        340                 345                 350

His Asn Gly Gly Ser Lys Asn Leu Lys Ala Val Thr Asp Asn His Asp
                        355                 360                 365

Asp Leu Lys Asn Met Gly Phe Asn Val Glu Gln Ile Val Arg Met Val
                        370                 375                 380

Ser His Asn Gly Gly Ser Lys Asn Leu Lys Ala Val Thr Asp Asn His
        385                 390                 395                 400

Asp Asp Leu Lys Asn Met Gly Phe Asn Val Glu Gln Ile Val Arg Met
                        405                 410                 415

Val Ser His Asn Gly Gly Ser Lys Asn Leu Lys Ala Val Thr Asp Asn
                        420                 425                 430

His Asp Asp Leu Lys Asn Met Gly Phe Asn Val Glu Gln Ile Val Arg
                        435                 440                 445

Met Val Ser His Asn Gly Gly Ser Lys Asn Leu Lys Ala Val Thr Asp
                        450                 455                 460

Asn His Asp Asp Leu Lys Asn Met Gly Phe Asn Thr Glu Gln Ile Val
        465                 470                 475                 480

Arg Met Val Ser His Asp Gly Gly Ser Leu Asn Leu Lys Ala Val Lys
                        485                 490                 495

Lys Tyr His Asp Ala Leu Arg Glu Arg Lys Phe Asn Val Glu Gln Ile
                        500                 505                 510

Val Arg Met Val Ser His Asn Gly Gly Ser Lys Asn Leu Lys Ala Val
                        515                 520                 525

Thr Asp Asn His Asp Asp Leu Lys Asn Met Gly Phe Asn Val Glu Gln
        530                 535                 540

Ile Val Arg Met Val Ser His Asn Gly Gly Ser Lys Asn Leu Lys Ala
        545                 550                 555                 560

Val Thr Asp Asn His Asp Asp Leu Lys Asn Met Gly Phe Asn Val Glu
                        565                 570                 575

Gln Ile Val Arg Met Val Ser His Asn Gly Gly Ser Lys Asn Leu Lys
                        580                 585                 590

Ala Val Thr Asp Asn His Asp Asp Leu Lys Asn Met Gly Phe Asn Thr
                        595                 600                 605

Glu Gln Ile Val Arg Met Val Ser His Asp Gly Gly Ser Leu Asn Leu
                        610                 615                 620

Lys Ala Val Lys Lys Tyr His Asp Ala Leu Arg Glu Arg Lys Phe Ser
        625                 630                 635                 640

Ser Gln Gln Ile Ile Arg Met Val Ser His Ala Gly Gly Ala Asn Asn
                        645                 650                 655
```

Leu Lys Ala Val Thr Ala Asn His Asp Asp Leu Gln Asn Met Gly Phe
                660                 665                 670

Asn Thr Glu Gln Ile Val Arg Met Val Ser His Asp Gly Gly Ser Leu
            675                 680                 685

Asn Leu Lys Ala Val Lys Lys Tyr His Asp Ala Leu Arg Glu Arg Lys
        690                 695                 700

Phe Asn Thr Glu Gln Ile Val Arg Met Val Ser His Asp Gly Gly Ser
705                 710                 715                 720

Leu Asn Leu Lys Ala Val Lys Lys Tyr His Asp Ala Leu Arg Glu Arg
                725                 730                 735

Lys Phe Asn Ala Glu Gln Ile Val Arg Met Val Ser His Asp Gly Gly
            740                 745                 750

Ser Lys Asn Leu Ala Leu Val Lys Glu Tyr Phe Pro Val Phe Ser Ser
        755                 760                 765

Phe His Phe Thr Ala Asp Gln Ile Val Ala Leu Ile Cys Gln Ser Lys
770                 775                 780

Gln Cys Phe Arg Asn Leu Lys Lys Asn His Gln Gln Trp Lys Asn Lys
785                 790                 795                 800

Gly Leu Ser Ala Glu Gln Ile Val Asp Leu Ile Leu Gln Glu Thr Pro
                805                 810                 815

Pro Lys Pro Asn Phe Asn Asn Thr Ser Ser Thr Pro Ser Pro Ser
            820                 825                 830

Ala Pro Ser Phe Phe Gln Gly Pro Ser Thr Pro Ile Pro Thr Pro Val
        835                 840                 845

Leu Asp Asn Ser Pro Ala Pro Ile Phe Ser Asn Pro Val Cys Phe Phe
850                 855                 860

Ser Ser Arg Ser Glu Asn Asn Thr Glu Gln Tyr Leu Gln Asp Ser Thr
865                 870                 875                 880

Leu Asp Leu Asp Ser Gln Leu Gly Asp Pro Thr Lys Asn Phe Asn Val
                885                 890                 895

Asn Asn Phe Trp Ser Leu Phe Pro Phe Asp Asp Val Gly Tyr His Pro
            900                 905                 910

His Ser Asn Asp Val Gly Tyr His Leu His Ser Asp Glu Glu Ser Pro
        915                 920                 925

Phe Phe Asp Phe
    930

<210> SEQ ID NO 103
<211> LENGTH: 819
<212> TYPE: PRT
<213> ORGANISM: Artificial sequence
<220> FEATURE:
<223> OTHER INFORMATION: synthetic sequence

<400> SEQUENCE: 103

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
            115                 120                 125

Leu Cys Lys His Glu Glu Leu Leu Asn Leu Ile Ser Pro Asp Gly Leu
            130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
            195                 200                 205

Gly Phe Asn Val Glu Gln Ile Val Arg Met Val Ser His Asn Gly Gly
            210                 215                 220

Ser Lys Asn Leu Lys Ala Val Thr Asp Asn His Asp Asp Leu Lys Asn
225                 230                 235                 240

Met Gly Phe Asn Thr Glu Gln Ile Val Arg Met Val Ser His Asp Gly
                245                 250                 255

Gly Ser Leu Asn Leu Lys Ala Val Lys Lys Tyr His Asp Ala Leu Arg
            260                 265                 270

Glu Arg Lys Phe Ser Ser Gln Gln Ile Ile Arg Met Val Ser His Ala
            275                 280                 285

Gly Gly Ala Asn Asn Leu Lys Ala Val Thr Ala Asn His Asp Asp Leu
            290                 295                 300

Gln Asn Met Gly Phe Ser Ser Gln Gln Ile Ile Arg Met Val Ser His
305                 310                 315                 320

Ala Gly Gly Ala Asn Asn Leu Lys Ala Val Thr Ala Asn His Asp Asp
                325                 330                 335

Leu Gln Asn Met Gly Phe Asn Val Glu Gln Ile Val Arg Met Val Ser
            340                 345                 350

His Asn Gly Gly Ser Lys Asn Leu Lys Ala Val Thr Asp Asn His Asp
            355                 360                 365

Asp Leu Lys Asn Met Gly Phe Asn Val Glu Gln Ile Val Arg Met Val
            370                 375                 380

Ser His Asn Gly Gly Ser Lys Asn Leu Lys Ala Val Thr Asp Asn His
385                 390                 395                 400

Asp Asp Leu Lys Asn Met Gly Phe Asn Val Glu Gln Ile Val Arg Met
                405                 410                 415

Val Ser His Asn Gly Gly Ser Lys Asn Leu Lys Ala Val Thr Asp Asn
            420                 425                 430

His Asp Asp Leu Lys Asn Met Gly Phe Asn Val Glu Gln Ile Val Arg
            435                 440                 445

Met Val Ser His Asn Gly Gly Ser Lys Asn Leu Lys Ala Val Thr Asp
            450                 455                 460

Asn His Asp Asp Leu Lys Asn Met Gly Phe Asn Thr Glu Gln Ile Val
465                 470                 475                 480

Arg Met Val Ser His Asp Gly Gly Ser Leu Asn Leu Lys Ala Val Lys
                485                 490                 495

Lys Tyr His Asp Ala Leu Arg Glu Arg Lys Phe Asn Val Glu Gln Ile
            500                 505                 510

Val Arg Met Val Ser His Asn Gly Gly Ser Lys Asn Leu Lys Ala Val
        515                 520                 525

Thr Asp Asn His Asp Asp Leu Lys Asn Met Gly Phe Asn Val Glu Gln
    530                 535                 540

Ile Val Arg Met Val Ser His Asn Gly Gly Ser Lys Asn Leu Lys Ala
545                 550                 555                 560

Val Thr Asp Asn His Asp Asp Leu Lys Asn Met Gly Phe Asn Val Glu
                565                 570                 575

Gln Ile Val Arg Met Val Ser His Asn Gly Gly Ser Lys Asn Leu Lys
            580                 585                 590

Ala Val Thr Asp Asn His Asp Asp Leu Lys Asn Met Gly Phe Asn Thr
        595                 600                 605

Glu Gln Ile Val Arg Met Val Ser His Asp Gly Gly Ser Leu Asn Leu
    610                 615                 620

Lys Ala Val Lys Lys Tyr His Asp Ala Leu Arg Glu Arg Lys Phe Ser
625                 630                 635                 640

Ser Gln Gln Ile Ile Arg Met Val Ser His Ala Gly Gly Ala Asn Asn
                645                 650                 655

Leu Lys Ala Val Thr Ala Asn His Asp Asp Leu Gln Asn Met Gly Phe
            660                 665                 670

Asn Thr Glu Gln Ile Val Arg Met Val Ser His Asp Gly Gly Ser Leu
        675                 680                 685

Asn Leu Lys Ala Val Lys Lys Tyr His Asp Ala Leu Arg Glu Arg Lys
    690                 695                 700

Phe Asn Thr Glu Gln Ile Val Arg Met Val Ser His Asp Gly Gly Ser
705                 710                 715                 720

Leu Asn Leu Lys Ala Val Lys Lys Tyr His Asp Ala Leu Arg Glu Arg
                725                 730                 735

Lys Phe Asn Ala Glu Gln Ile Val Arg Met Val Ser His Asp Gly Gly
            740                 745                 750

Ser Lys Asn Leu Ala Leu Val Lys Glu Tyr Phe Pro Val Phe Ser Ser
        755                 760                 765

Phe His Phe Thr Ala Asp Gln Ile Val Ala Leu Ile Cys Gln Ser Lys
    770                 775                 780

Gln Cys Phe Arg Asn Leu Lys Lys Asn His Gln Gln Trp Lys Asn Lys
785                 790                 795                 800

Gly Leu Ser Ala Glu Gln Ile Val Asp Leu Ile Leu Gln Glu Thr Pro
                805                 810                 815

Pro Lys Pro

<210> SEQ ID NO 104
<211> LENGTH: 965
<212> TYPE: PRT
<213> ORGANISM: Artificial sequence
<220> FEATURE:
<223> OTHER INFORMATION: synthetic sequence

<400> SEQUENCE: 104

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Ser Pro Ala Ser Ala Asn Ala Arg

-continued

```
            35                  40                  45
Lys Arg Thr Ser Arg Lys Glu Met Ser Gly Pro Pro Ser Lys Glu Pro
 50                  55                  60
Ala Asn Thr Lys Ser Arg Arg Ala Asn Ser Gln Asn Asn Lys Leu Ser
 65                  70                  75                  80
Leu Ala Asp Arg Leu Thr Lys Tyr Asn Ile Asp Glu Glu Phe Tyr Gln
                     85                  90                  95
Thr Arg Ser Asp Ser Leu Leu Ser Leu Asn Tyr Thr Lys Lys Gln Ile
                100                 105                 110
Glu Arg Leu Ile Leu Tyr Lys Gly Arg Thr Ser Ala Val Gln Gln Leu
                115                 120                 125
Leu Cys Lys His Glu Glu Leu Leu Asn Leu Ile Ser Pro Asp Gly Leu
    130                 135                 140
Gly His Lys Glu Leu Ile Lys Ile Ala Ala Arg Asn Gly Gly Gly Asn
145                 150                 155                 160
Asn Leu Ile Ala Val Leu Ser Cys Tyr Ala Lys Leu Lys Glu Met Gly
                    165                 170                 175
Phe Ser Ser Gln Gln Ile Ile Arg Met Val Ser His Ala Gly Gly Ala
                180                 185                 190
Asn Asn Leu Lys Ala Val Thr Ala Asn His Asp Asp Leu Gln Asn Met
    195                 200                 205
Gly Phe Ser Ser Gln Gln Ile Ile Arg Met Val Ser His Ala Gly Gly
    210                 215                 220
Ala Asn Asn Leu Lys Ala Val Thr Ala Asn His Asp Asp Leu Gln Asn
225                 230                 235                 240
Met Gly Phe Asn Val Glu Gln Ile Val Arg Met Val Ser His Asn Gly
                245                 250                 255
Gly Ser Lys Asn Leu Lys Ala Val Thr Asp Asn His Asp Asp Leu Lys
                260                 265                 270
Asn Met Gly Phe Asn Val Glu Gln Ile Val Arg Met Val Ser His Asn
                275                 280                 285
Gly Gly Ser Lys Asn Leu Lys Ala Val Thr Asp Asn His Asp Asp Leu
    290                 295                 300
Lys Asn Met Gly Phe Asn Val Glu Gln Ile Val Arg Met Val Ser His
305                 310                 315                 320
Asn Gly Gly Ser Lys Asn Leu Lys Ala Val Thr Asp Asn His Asp Asp
                325                 330                 335
Leu Lys Asn Met Gly Phe Ser Ser Gln Gln Ile Ile Arg Met Val Ser
                340                 345                 350
His Ala Gly Gly Ala Asn Asn Leu Lys Ala Val Thr Ala Asn His Asp
    355                 360                 365
Asp Leu Gln Asn Met Gly Phe Asn Val Glu Gln Ile Val Arg Met Val
    370                 375                 380
Ser His Asn Gly Gly Ser Lys Asn Leu Lys Ala Val Thr Asp Asn His
385                 390                 395                 400
Asp Asp Leu Lys Asn Met Gly Phe Asn Val Glu Gln Ile Val Arg Met
                405                 410                 415
Val Ser His Asn Gly Gly Ser Lys Asn Leu Lys Ala Val Thr Asp Asn
                420                 425                 430
His Asp Asp Leu Lys Asn Met Gly Phe Asn Val Glu Gln Ile Val Arg
    435                 440                 445
Met Val Ser His Asn Gly Gly Ser Lys Asn Leu Lys Ala Val Thr Asp
    450                 455                 460
```

```
Asn His Asp Asp Leu Lys Asn Met Gly Phe Asn Ala Glu Gln Ile Val
465                 470                 475                 480

Ser Met Val Ser Asn Gly Gly Ser Leu Asn Leu Lys Ala Val Lys
            485                 490                 495

Lys Tyr His Asp Ala Leu Lys Asp Arg Gly Phe Asn Val Glu Gln Ile
            500                 505                 510

Val Arg Met Val Ser His Asn Gly Gly Ser Lys Asn Leu Lys Ala Val
            515                 520                 525

Thr Asp Asn His Asp Asp Leu Lys Asn Met Gly Phe Asn Thr Glu Gln
            530                 535                 540

Ile Val Arg Met Val Ser His Asp Gly Gly Ser Leu Asn Leu Lys Ala
545                 550                 555                 560

Val Lys Lys Tyr His Asp Ala Leu Arg Glu Arg Lys Phe Asn Thr Glu
                565                 570                 575

Gln Ile Val Arg Met Val Ser His Asp Gly Gly Ser Leu Asn Leu Lys
                580                 585                 590

Ala Val Lys Lys Tyr His Asp Ala Leu Arg Glu Arg Lys Phe Asn Thr
            595                 600                 605

Glu Gln Ile Val Arg Met Val Ser His Asp Gly Gly Ser Leu Asn Leu
            610                 615                 620

Lys Ala Val Lys Lys Tyr His Asp Ala Leu Arg Glu Arg Lys Phe Asn
625                 630                 635                 640

Val Glu Gln Ile Val Arg Met Val Ser His Asn Gly Gly Ser Lys Asn
                645                 650                 655

Leu Lys Ala Val Thr Asp Asn His Asp Asp Leu Lys Asn Met Gly Phe
            660                 665                 670

Asn Thr Glu Gln Ile Val Arg Met Val Ser His Asp Gly Gly Ser Leu
            675                 680                 685

Asn Leu Lys Ala Val Lys Lys Tyr His Asp Ala Leu Arg Glu Arg Lys
690                 695                 700

Phe Asn Thr Glu Gln Ile Val Arg Met Val Ser His Asp Gly Gly Ser
705                 710                 715                 720

Leu Asn Leu Lys Ala Val Lys Lys Tyr His Asp Ala Leu Arg Glu Arg
            725                 730                 735

Lys Phe Asn Thr Glu Gln Ile Val Arg Met Val Ser His Asp Gly Gly
            740                 745                 750

Ser Leu Asn Leu Lys Ala Val Lys Lys Tyr His Asp Ala Leu Arg Glu
            755                 760                 765

Arg Lys Phe Asn Ala Glu Gln Ile Val Arg Met Val Ser His Asp Gly
            770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
            820                 825                 830

Lys Gly Leu Ser Ala Glu Gln Ile Val Asp Leu Ile Leu Gln Glu Thr
            835                 840                 845

Pro Pro Lys Pro Asn Phe Asn Asn Thr Ser Ser Ser Thr Pro Ser Pro
850                 855                 860

Ser Ala Pro Ser Phe Phe Gln Gly Pro Ser Thr Pro Ile Pro Thr Pro
865                 870                 875                 880
```

```
Val Leu Asp Asn Ser Pro Ala Pro Ile Phe Ser Asn Pro Val Cys Phe
                885                 890                 895

Phe Ser Ser Arg Ser Glu Asn Asn Thr Glu Gln Tyr Leu Gln Asp Ser
            900                 905                 910

Thr Leu Asp Leu Asp Ser Gln Leu Gly Asp Pro Thr Lys Asn Phe Asn
        915                 920                 925

Val Asn Asn Phe Trp Ser Leu Phe Pro Phe Asp Val Gly Tyr His
    930                 935                 940

Pro His Ser Asn Asp Val Gly Tyr His Leu His Ser Asp Glu Glu Ser
945                 950                 955                 960

Pro Phe Phe Asp Phe
                965

<210> SEQ ID NO 105
<211> LENGTH: 852
<212> TYPE: PRT
<213> ORGANISM: Artificial sequence
<220> FEATURE:
<223> OTHER INFORMATION: synthetic sequence

<400> SEQUENCE: 105

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
        195                 200                 205

Gly Phe Ser Ser Gln Gln Ile Ile Arg Met Val Ser His Ala Gly Gly
210                 215                 220

Ala Asn Asn Leu Lys Ala Val Thr Ala Asn His Asp Asp Leu Gln Asn
225                 230                 235                 240

Met Gly Phe Asn Val Glu Gln Ile Val Arg Met Val Ser His Asn Gly
                245                 250                 255

Gly Ser Lys Asn Leu Lys Ala Val Thr Asp Asn His Asp Asp Leu Lys
            260                 265                 270
```

```
Asn Met Gly Phe Asn Val Glu Gln Ile Val Arg Met Val Ser His Asn
            275                 280                 285

Gly Gly Ser Lys Asn Leu Lys Ala Val Thr Asp Asn His Asp Asp Leu
        290                 295                 300

Lys Asn Met Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
                325                 330                 335

Leu Lys Asn Met Gly Phe Ser Ser Gln Gln Ile Ile Arg Met Val Ser
            340                 345                 350

His Ala Gly Gly Ala Asn Asn Leu Lys Ala Val Thr Ala Asn His Asp
        355                 360                 365

Asp Leu Gln Asn Met Gly Phe Asn Val Glu Gln Ile Val Arg Met Val
370                 375                 380

Ser His Asn Gly Gly Ser Lys Asn Leu Lys Ala Val Thr Asp Asn His
385                 390                 395                 400

Asp Asp Leu Lys Asn Met Gly Phe Asn Val Glu Gln Ile Val Arg Met
                405                 410                 415

Val Ser His Asn Gly Gly Ser Lys Asn Leu Lys Ala Val Thr Asp Asn
            420                 425                 430

His Asp Asp Leu Lys Asn Met Gly Phe Asn Val Glu Gln Ile Val Arg
        435                 440                 445

Met Val Ser His Asn Gly Gly Ser Lys Asn Leu Lys Ala Val Thr Asp
    450                 455                 460

Asn His Asp Asp Leu Lys Asn Met Gly Phe Asn Ala Glu Gln Ile Val
465                 470                 475                 480

Ser Met Val Ser Asn Gly Gly Gly Ser Leu Asn Leu Lys Ala Val Lys
                485                 490                 495

Lys Tyr His Asp Ala Leu Lys Asp Arg Gly Phe Asn Val Glu Gln Ile
            500                 505                 510

Val Arg Met Val Ser His Asn Gly Gly Ser Lys Asn Leu Lys Ala Val
        515                 520                 525

Thr Asp Asn His Asp Asp Leu Lys Asn Met Gly Phe Asn Thr Glu Gln
530                 535                 540

Ile Val Arg Met Val Ser His Asp Gly Gly Ser Leu Asn Leu Lys Ala
545                 550                 555                 560

Val Lys Lys Tyr His Asp Ala Leu Arg Glu Arg Lys Phe Asn Thr Glu
                565                 570                 575

Gln Ile Val Arg Met Val Ser His Asp Gly Gly Ser Leu Asn Leu Lys
            580                 585                 590

Ala Val Lys Lys Tyr His Asp Ala Leu Arg Glu Arg Lys Phe Asn Thr
        595                 600                 605

Glu Gln Ile Val Arg Met Val Ser His Asp Gly Gly Ser Leu Asn Leu
    610                 615                 620

Lys Ala Val Lys Lys Tyr His Asp Ala Leu Arg Glu Arg Lys Phe Asn
625                 630                 635                 640

Val Glu Gln Ile Val Arg Met Val Ser His Asn Gly Gly Ser Lys Asn
                645                 650                 655

Leu Lys Ala Val Thr Asp Asn His Asp Asp Leu Lys Asn Met Gly Phe
            660                 665                 670

Asn Thr Glu Gln Ile Val Arg Met Val Ser His Asp Gly Gly Ser Leu
        675                 680                 685

Asn Leu Lys Ala Val Lys Lys Tyr His Asp Ala Leu Arg Glu Arg Lys
```

```
            690             695             700
Phe Asn Thr Glu Gln Ile Val Arg Met Val Ser His Asp Gly Gly Ser
705             710             715             720

Leu Asn Leu Lys Ala Val Lys Lys Tyr His Asp Ala Leu Arg Glu Arg
                725             730             735

Lys Phe Asn Thr Glu Gln Ile Val Arg Met Val Ser His Asp Gly Gly
            740             745             750

Ser Leu Asn Leu Lys Ala Val Lys Lys Tyr His Asp Ala Leu Arg Glu
        755             760             765

Arg Lys Phe Asn Ala Glu Gln Ile Val Arg Met Val Ser His Asp Gly
    770             775             780

Gly Ser Lys Asn Leu Ala Leu Val Lys Glu Tyr Phe Pro Val Phe Ser
785             790             795             800

Ser Phe His Phe Thr Ala Asp Gln Ile Val Ala Leu Ile Cys Gln Ser
                805             810             815

Lys Gln Cys Phe Arg Asn Leu Lys Lys Asn His Gln Gln Trp Lys Asn
                820             825             830

Lys Gly Leu Ser Ala Glu Gln Ile Val Asp Leu Ile Leu Gln Glu Thr
            835             840             845

Pro Pro Lys Pro
        850

<210> SEQ ID NO 106
<211> LENGTH: 965
<212> TYPE: PRT
<213> ORGANISM: Artificial sequence
<220> FEATURE:
<223> OTHER INFORMATION: synthetic sequence

<400> SEQUENCE: 106

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Pro Ala Ser Ala Asn Ala Arg
            35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
                100                 105                 110

Glu Arg Leu Ile Leu Tyr Lys Gly Arg Thr Ser Ala Val Gln Gln Leu
            115                 120                 125

Leu Cys Lys His Glu Glu Leu Leu Asn Leu Ile Ser Pro Asp Gly Leu
        130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
                180                 185                 190

Asn Asn Leu Lys Ala Val Thr Ala Asn His Asp Asp Leu Gln Asn Met
```

```
            195                 200                 205
Gly Phe Asn Thr Glu Gln Ile Val Arg Met Val Ser His Asp Gly Gly
210                 215                 220

Ser Leu Asn Leu Lys Ala Val Lys Lys Tyr His Asp Ala Leu Arg Glu
225                 230                 235                 240

Arg Lys Phe Asn Thr Glu Gln Ile Val Arg Met Val Ser His Asp Gly
                245                 250                 255

Gly Ser Leu Asn Leu Lys Ala Val Lys Lys Tyr His Asp Ala Leu Arg
            260                 265                 270

Glu Arg Lys Phe Asn Ala Glu Gln Ile Val Ser Met Val Ser Asn Gly
        275                 280                 285

Gly Gly Ser Leu Asn Leu Lys Ala Val Lys Lys Tyr His Asp Ala Leu
    290                 295                 300

Lys Asp Arg Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
                325                 330                 335

Leu Lys Asn Met Gly Phe Asn Val Glu Gln Ile Val Arg Met Val Ser
            340                 345                 350

His Asn Gly Gly Ser Lys Asn Leu Lys Ala Val Thr Asp Asn His Asp
        355                 360                 365

Asp Leu Lys Asn Met Gly Phe Asn Val Glu Gln Ile Val Arg Met Val
    370                 375                 380

Ser His Asn Gly Gly Ser Lys Asn Leu Lys Ala Val Thr Asp Asn His
385                 390                 395                 400

Asp Asp Leu Lys Asn Met Gly Phe Ser Ser Gln Gln Ile Ile Arg Met
                405                 410                 415

Val Ser His Ala Gly Gly Ala Asn Asn Leu Lys Ala Val Thr Ala Asn
            420                 425                 430

His Asp Asp Leu Gln Asn Met Gly Phe Asn Thr Glu Gln Ile Val Arg
        435                 440                 445

Met Val Ser His Asp Gly Gly Ser Leu Asn Leu Lys Ala Val Lys Lys
    450                 455                 460

Tyr His Asp Ala Leu Arg Glu Arg Lys Phe Ser Ser Gln Gln Ile Ile
465                 470                 475                 480

Arg Met Val Ser His Ala Gly Gly Ala Asn Asn Leu Lys Ala Val Thr
                485                 490                 495

Ala Asn His Asp Asp Leu Gln Asn Met Gly Phe Asn Val Glu Gln Ile
            500                 505                 510

Val Arg Met Val Ser His Asn Gly Gly Ser Lys Asn Leu Lys Ala Val
        515                 520                 525

Thr Asp Asn His Asp Asp Leu Lys Asn Met Gly Phe Asn Ala Glu Gln
    530                 535                 540

Ile Val Ser Met Val Ser Asn Gly Gly Gly Ser Leu Asn Leu Lys Ala
545                 550                 555                 560

Val Lys Lys Tyr His Asp Ala Leu Lys Asp Arg Gly Phe Asn Ala Glu
                565                 570                 575

Gln Ile Val Ser Met Val Ser Asn Gly Gly Gly Ser Leu Asn Leu Lys
            580                 585                 590

Ala Val Lys Lys Tyr His Asp Ala Leu Lys Asp Arg Gly Phe Asn Ala
        595                 600                 605

Glu Gln Ile Val Ser Met Val Ser Asn Gly Gly Gly Ser Leu Asn Leu
    610                 615                 620
```

Lys Ala Val Lys Lys Tyr His Asp Ala Leu Lys Asp Arg Gly Phe Asn
625                 630                 635                 640

Thr Glu Gln Ile Val Arg Met Val Ser His Asp Gly Gly Ser Leu Asn
            645                 650                 655

Leu Lys Ala Val Lys Lys Tyr His Asp Ala Leu Arg Glu Arg Lys Phe
        660                 665                 670

Asn Thr Glu Gln Ile Val Arg Met Val Ser His Asp Gly Gly Ser Leu
    675                 680                 685

Asn Leu Lys Ala Val Lys Lys Tyr His Asp Ala Leu Arg Glu Arg Lys
690                 695                 700

Phe Asn Thr Glu Gln Ile Val Arg Met Val Ser His Asp Gly Gly Ser
705                 710                 715                 720

Leu Asn Leu Lys Ala Val Lys Lys Tyr His Asp Ala Leu Arg Glu Arg
            725                 730                 735

Lys Phe Asn Ala Glu Gln Ile Val Ser Met Val Ser Asn Gly Gly Gly
        740                 745                 750

Ser Leu Asn Leu Lys Ala Val Lys Lys Tyr His Asp Ala Leu Lys Asp
    755                 760                 765

Arg Gly Phe Asn Ala Glu Gln Ile Val Arg Met Val Ser Asn Gly Gly
770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
            805                 810                 815

Lys Gln Cys Phe Arg Asn Leu Lys Lys Asn His Gln Gln Trp Lys Asn
        820                 825                 830

Lys Gly Leu Ser Ala Glu Gln Ile Val Asp Leu Ile Leu Gln Glu Thr
    835                 840                 845

Pro Pro Lys Pro Asn Phe Asn Asn Thr Ser Ser Ser Thr Pro Ser Pro
850                 855                 860

Ser Ala Pro Ser Phe Phe Gln Gly Pro Ser Thr Pro Ile Pro Thr Pro
865                 870                 875                 880

Val Leu Asp Asn Ser Pro Ala Pro Ile Phe Ser Asn Pro Val Cys Phe
            885                 890                 895

Phe Ser Ser Arg Ser Glu Asn Asn Thr Glu Gln Tyr Leu Gln Asp Ser
        900                 905                 910

Thr Leu Asp Leu Asp Ser Gln Leu Gly Asp Pro Thr Lys Asn Phe Asn
    915                 920                 925

Val Asn Asn Phe Trp Ser Leu Phe Pro Phe Asp Asp Val Gly Tyr His
930                 935                 940

Pro His Ser Asn Asp Val Gly Tyr His Leu His Ser Asp Glu Glu Ser
945                 950                 955                 960

Pro Phe Phe Asp Phe
            965

<210> SEQ ID NO 107
<211> LENGTH: 852
<212> TYPE: PRT
<213> ORGANISM: Artificial sequence
<220> FEATURE:
<223> OTHER INFORMATION: synthetic sequence

<400> SEQUENCE: 107

Met Pro Asp Leu Glu Leu Asn Phe Ala Ile Pro Leu His Leu Phe Asp
1               5                   10                  15

```
Asp Glu Thr Val Phe Thr His Asp Ala Thr Asn Asp Asn Ser Gln Ala
        20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
 50                  55                  60

Ala Asn Thr Lys Ser Arg Arg Ala Asn Ser Gln Asn Asn Lys Leu Ser
 65                  70                  75                  80

Leu Ala Asp Arg Leu Thr Lys Tyr Asn Ile Asp Glu Glu Phe Tyr Gln
            85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
            115                 120                 125

Leu Cys Lys His Glu Glu Leu Leu Asn Leu Ile Ser Pro Asp Gly Leu
 130                 135                 140

Gly His Lys Glu Leu Ile Lys Ile Ala Ala Arg Asn Gly Gly Gly Asn
 145                 150                 155                 160

Asn Leu Ile Ala Val Leu Ser Cys Tyr Ala Lys Leu Lys Glu Met Gly
            165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
            195                 200                 205

Gly Phe Asn Thr Glu Gln Ile Val Arg Met Val Ser His Asp Gly Gly
            210                 215                 220

Ser Leu Asn Leu Lys Ala Val Lys Lys Tyr His Asp Ala Leu Arg Glu
225                 230                 235                 240

Arg Lys Phe Asn Thr Glu Gln Ile Val Arg Met Val Ser His Asp Gly
            245                 250                 255

Gly Ser Leu Asn Leu Lys Ala Val Lys Lys Tyr His Asp Ala Leu Arg
            260                 265                 270

Glu Arg Lys Phe Asn Ala Glu Gln Ile Val Ser Met Val Ser Asn Gly
            275                 280                 285

Gly Gly Ser Leu Asn Leu Lys Ala Val Lys Lys Tyr His Asp Ala Leu
            290                 295                 300

Lys Asp Arg Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
            325                 330                 335

Leu Lys Asn Met Gly Phe Asn Val Glu Gln Ile Val Arg Met Val Ser
            340                 345                 350

His Asn Gly Gly Ser Lys Asn Leu Lys Ala Val Thr Asp Asn His Asp
            355                 360                 365

Asp Leu Lys Asn Met Gly Phe Asn Val Glu Gln Ile Val Arg Met Val
            370                 375                 380

Ser His Asn Gly Gly Ser Lys Asn Leu Lys Ala Val Thr Asp Asn His
385                 390                 395                 400

Asp Asp Leu Lys Asn Met Gly Phe Ser Ser Gln Gln Ile Ile Arg Met
            405                 410                 415

Val Ser His Ala Gly Gly Ala Asn Asn Leu Lys Ala Val Thr Ala Asn
            420                 425                 430
```

```
His Asp Asp Leu Gln Asn Met Gly Phe Asn Thr Glu Gln Ile Val Arg
            435                 440                 445

Met Val Ser His Asp Gly Gly Ser Leu Asn Leu Lys Ala Val Lys Lys
    450                 455                 460

Tyr His Asp Ala Leu Arg Glu Arg Lys Phe Ser Ser Gln Gln Ile Ile
465                 470                 475                 480

Arg Met Val Ser His Ala Gly Ala Asn Asn Leu Lys Ala Val Thr
                485                 490                 495

Ala Asn His Asp Asp Leu Gln Asn Met Gly Phe Asn Val Glu Gln Ile
            500                 505                 510

Val Arg Met Val Ser His Asn Gly Gly Ser Lys Asn Leu Lys Ala Val
        515                 520                 525

Thr Asp Asn His Asp Asp Leu Lys Asn Met Gly Phe Asn Ala Glu Gln
        530                 535                 540

Ile Val Ser Met Val Ser Asn Gly Gly Gly Ser Leu Asn Leu Lys Ala
545                 550                 555                 560

Val Lys Lys Tyr His Asp Ala Leu Lys Asp Arg Gly Phe Asn Ala Glu
                565                 570                 575

Gln Ile Val Ser Met Val Ser Asn Gly Gly Gly Ser Leu Asn Leu Lys
            580                 585                 590

Ala Val Lys Lys Tyr His Asp Ala Leu Lys Asp Arg Gly Phe Asn Ala
        595                 600                 605

Glu Gln Ile Val Ser Met Val Ser Asn Gly Gly Gly Ser Leu Asn Leu
        610                 615                 620

Lys Ala Val Lys Lys Tyr His Asp Ala Leu Lys Asp Arg Gly Phe Asn
625                 630                 635                 640

Thr Glu Gln Ile Val Arg Met Val Ser His Asp Gly Gly Ser Leu Asn
                645                 650                 655

Leu Lys Ala Val Lys Lys Tyr His Asp Ala Leu Arg Glu Arg Lys Phe
            660                 665                 670

Asn Thr Glu Gln Ile Val Arg Met Val Ser His Asp Gly Gly Ser Leu
        675                 680                 685

Asn Leu Lys Ala Val Lys Lys Tyr His Asp Ala Leu Arg Glu Arg Lys
        690                 695                 700

Phe Asn Thr Glu Gln Ile Val Arg Met Val Ser His Asp Gly Gly Ser
705                 710                 715                 720

Leu Asn Leu Lys Ala Val Lys Lys Tyr His Asp Ala Leu Arg Glu Arg
                725                 730                 735

Lys Phe Asn Ala Glu Gln Ile Val Ser Met Val Ser Asn Gly Gly Gly
            740                 745                 750

Ser Leu Asn Leu Lys Ala Val Lys Lys Tyr His Asp Ala Leu Lys Asp
        755                 760                 765

Arg Gly Phe Asn Ala Glu Gln Ile Val Arg Met Val Ser Asn Gly Gly
        770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
            820                 825                 830

Lys Gly Leu Ser Ala Glu Gln Ile Val Asp Leu Ile Leu Gln Glu Thr
        835                 840                 845

Pro Pro Lys Pro
```

<210> SEQ ID NO 108
<211> LENGTH: 932
<212> TYPE: PRT
<213> ORGANISM: Artificial sequence
<220> FEATURE:
<223> OTHER INFORMATION: synthetic sequence

<400> SEQUENCE: 108

| | | | | | | | | | | | | | | |
|---|---|---|---|---|---|---|---|---|---|---|---|---|---|---|
| Met | Pro | Asp | Leu | Glu | Leu | Asn | Phe | Ala | Ile | Pro | Leu | His | Leu | Phe | Asp |
| 1 | | | | 5 | | | | | 10 | | | | | 15 | |
| Asp | Glu | Thr | Val | Phe | Thr | His | Asp | Ala | Thr | Asn | Asp | Asn | Ser | Gln | Ala |
| | | | 20 | | | | | 25 | | | | | 30 | | |
| Ser | Ser | Ser | Tyr | Ser | Ser | Lys | Ser | Ser | Pro | Ala | Ser | Ala | Asn | Ala | Arg |
| | | 35 | | | | | 40 | | | | | 45 | | | |
| Lys | Arg | Thr | Ser | Arg | Lys | Glu | Met | Ser | Gly | Pro | Pro | Ser | Lys | Glu | Pro |
| | 50 | | | | | 55 | | | | | 60 | | | | |
| Ala | Asn | Thr | Lys | Ser | Arg | Arg | Ala | Asn | Ser | Gln | Asn | Asn | Lys | Leu | Ser |
| 65 | | | | | 70 | | | | | 75 | | | | | 80 |
| Leu | Ala | Asp | Arg | Leu | Thr | Lys | Tyr | Asn | Ile | Asp | Glu | Glu | Phe | Tyr | Gln |
| | | | | 85 | | | | | 90 | | | | | 95 | |
| Thr | Arg | Ser | Asp | Ser | Leu | Leu | Ser | Leu | Asn | Tyr | Thr | Lys | Lys | Gln | Ile |
| | | | 100 | | | | | 105 | | | | | 110 | | |
| Glu | Arg | Leu | Ile | Leu | Tyr | Lys | Gly | Arg | Thr | Ser | Ala | Val | Gln | Gln | Leu |
| | | 115 | | | | | 120 | | | | | 125 | | | |
| Leu | Cys | Lys | His | Glu | Glu | Leu | Leu | Asn | Leu | Ile | Ser | Pro | Asp | Gly | Leu |
| | 130 | | | | | 135 | | | | | 140 | | | | |
| Gly | His | Lys | Glu | Leu | Ile | Lys | Ile | Ala | Ala | Arg | Asn | Gly | Gly | Gly | Asn |
| 145 | | | | | 150 | | | | | 155 | | | | | 160 |
| Asn | Leu | Ile | Ala | Val | Leu | Ser | Cys | Tyr | Ala | Lys | Leu | Lys | Glu | Met | Gly |
| | | | | 165 | | | | | 170 | | | | | 175 | |
| Phe | Ser | Ser | Gln | Gln | Ile | Ile | Arg | Met | Val | Ser | His | Ala | Gly | Gly | Ala |
| | | | 180 | | | | | 185 | | | | | 190 | | |
| Asn | Asn | Leu | Lys | Ala | Val | Thr | Ala | Asn | His | Asp | Asp | Leu | Gln | Asn | Met |
| | | 195 | | | | | 200 | | | | | 205 | | | |
| Gly | Phe | Asn | Thr | Glu | Gln | Ile | Val | Arg | Met | Val | Ser | His | Asp | Gly | Gly |
| | 210 | | | | | 215 | | | | | 220 | | | | |
| Ser | Leu | Asn | Leu | Lys | Ala | Val | Lys | Lys | Tyr | His | Asp | Ala | Leu | Arg | Glu |
| 225 | | | | | 230 | | | | | 235 | | | | | 240 |
| Arg | Lys | Phe | Ser | Ser | Gln | Gln | Ile | Ile | Arg | Met | Val | Ser | His | Ala | Gly |
| | | | | 245 | | | | | 250 | | | | | 255 | |
| Gly | Ala | Asn | Asn | Leu | Lys | Ala | Val | Thr | Ala | Asn | His | Asp | Asp | Leu | Gln |
| | | | 260 | | | | | 265 | | | | | 270 | | |
| Asn | Met | Gly | Phe | Asn | Val | Glu | Gln | Ile | Val | Arg | Met | Val | Ser | His | Asn |
| | | 275 | | | | | 280 | | | | | 285 | | | |
| Gly | Gly | Ser | Lys | Asn | Leu | Lys | Ala | Val | Thr | Asp | Asn | His | Asp | Asp | Leu |
| | 290 | | | | | 295 | | | | | 300 | | | | |
| Lys | Asn | Met | Gly | Phe | Asn | Ala | Glu | Gln | Ile | Val | Ser | Met | Val | Ser | Asn |
| 305 | | | | | 310 | | | | | 315 | | | | | 320 |
| Gly | Gly | Gly | Ser | Leu | Asn | Leu | Lys | Ala | Val | Lys | Lys | Tyr | His | Asp | Ala |
| | | | | 325 | | | | | 330 | | | | | 335 | |
| Leu | Lys | Asp | Arg | Gly | Phe | Asn | Ala | Glu | Gln | Ile | Val | Ser | Met | Val | Ser |
| | | | 340 | | | | | 345 | | | | | 350 | | |
| Asn | Gly | Gly | Gly | Ser | Leu | Asn | Leu | Lys | Ala | Val | Lys | Lys | Tyr | His | Asp |

```
                355                 360                 365
Ala Leu Lys Asp Arg Gly Phe Asn Ala Glu Gln Ile Val Ser Met Val
370                 375                 380

Ser Asn Gly Gly Gly Ser Leu Asn Leu Lys Ala Val Lys Lys Tyr His
385                 390                 395                 400

Asp Ala Leu Lys Asp Arg Gly Phe Asn Thr Glu Gln Ile Val Arg Met
                405                 410                 415

Val Ser His Asp Gly Gly Ser Leu Asn Leu Lys Ala Val Lys Lys Tyr
                420                 425                 430

His Asp Ala Leu Arg Glu Arg Lys Phe Asn Thr Glu Gln Ile Val Arg
                435                 440                 445

Met Val Ser His Asp Gly Gly Ser Leu Asn Leu Lys Ala Val Lys Lys
                450                 455                 460

Tyr His Asp Ala Leu Arg Glu Arg Lys Phe Asn Thr Glu Gln Ile Val
465                 470                 475                 480

Arg Met Val Ser His Asp Gly Gly Ser Leu Asn Leu Lys Ala Val Lys
                485                 490                 495

Lys Tyr His Asp Ala Leu Arg Glu Arg Lys Phe Asn Ala Glu Gln Ile
                500                 505                 510

Val Ser Met Val Ser Asn Gly Gly Gly Ser Leu Asn Leu Lys Ala Val
                515                 520                 525

Lys Lys Tyr His Asp Ala Leu Lys Asp Arg Gly Phe Asn Ala Glu Gln
530                 535                 540

Ile Val Ser Met Val Ser Asn Gly Gly Gly Ser Leu Asn Leu Lys Ala
545                 550                 555                 560

Val Lys Lys Tyr His Asp Ala Leu Lys Asp Arg Gly Phe Asn Thr Glu
                565                 570                 575

Gln Ile Val Arg Met Val Ser His Asp Gly Gly Ser Leu Asn Leu Lys
                580                 585                 590

Ala Val Lys Lys Tyr His Asp Ala Leu Arg Glu Arg Lys Phe Asn Thr
                595                 600                 605

Glu Gln Ile Val Arg Met Val Ser His Asp Gly Gly Ser Leu Asn Leu
610                 615                 620

Lys Ala Val Lys Lys Tyr His Asp Ala Leu Arg Glu Arg Lys Phe Asn
625                 630                 635                 640

Val Glu Gln Ile Val Arg Met Val Ser His Asn Gly Gly Ser Lys Asn
                645                 650                 655

Leu Lys Ala Val Thr Asp Asn His Asp Asp Leu Lys Asn Met Gly Phe
                660                 665                 670

Asn Thr Glu Gln Ile Val Arg Met Val Ser His Asp Gly Gly Ser Leu
                675                 680                 685

Asn Leu Lys Ala Val Lys Lys Tyr His Asp Ala Leu Arg Glu Arg Lys
                690                 695                 700

Phe Asn Ala Glu Gln Ile Val Ser Met Val Ser Asn Gly Gly Gly Ser
705                 710                 715                 720

Leu Asn Leu Lys Ala Val Lys Lys Tyr His Asp Ala Leu Lys Asp Arg
                725                 730                 735

Gly Phe Asn Ala Glu Gln Ile Val Arg Met Val Ser His Asp Gly Gly
                740                 745                 750

Ser Lys Asn Leu Ala Leu Val Lys Glu Tyr Phe Pro Val Phe Ser Ser
                755                 760                 765

Phe His Phe Thr Ala Asp Gln Ile Val Ala Leu Ile Cys Gln Ser Lys
770                 775                 780
```

```
Gln Cys Phe Arg Asn Leu Lys Lys Asn His Gln Gln Trp Lys Asn Lys
785                 790                 795                 800

Gly Leu Ser Ala Glu Gln Ile Val Asp Leu Ile Leu Gln Glu Thr Pro
            805                 810                 815

Pro Lys Pro Asn Phe Asn Asn Thr Ser Ser Thr Pro Ser Pro Ser
        820                 825                 830

Ala Pro Ser Phe Phe Gln Gly Pro Ser Thr Pro Ile Pro Thr Pro Val
        835                 840                 845

Leu Asp Asn Ser Pro Ala Pro Ile Phe Ser Asn Pro Val Cys Phe Phe
    850                 855                 860

Ser Ser Arg Ser Glu Asn Asn Thr Glu Gln Tyr Leu Gln Asp Ser Thr
865                 870                 875                 880

Leu Asp Leu Asp Ser Gln Leu Gly Asp Pro Thr Lys Asn Phe Asn Val
            885                 890                 895

Asn Asn Phe Trp Ser Leu Phe Pro Phe Asp Asp Val Gly Tyr His Pro
                900                 905                 910

His Ser Asn Asp Val Gly Tyr His Leu His Ser Asp Glu Glu Ser Pro
            915                 920                 925

Phe Phe Asp Phe
    930

<210> SEQ ID NO 109
<211> LENGTH: 819
<212> TYPE: PRT
<213> ORGANISM: Artificial sequence
<220> FEATURE:
<223> OTHER INFORMATION: synthetic sequence

<400> SEQUENCE: 109

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Ser Pro Ala Ser Ala Asn Ala Arg
            35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
    115                 120                 125

Leu Cys Lys His Glu Glu Leu Leu Asn Leu Ile Ser Pro Asp Gly Leu
130                 135                 140

Gly His Lys Glu Leu Ile Lys Ile Ala Ala Arg Asn Gly Gly Gly Asn
                150                 155                 160
145

Asn Leu Ile Ala Val Leu Ser Cys Tyr Ala Lys Leu Lys Glu Met Gly
            165                 170                 175

Phe Ser Ser Gln Gln Ile Ile Arg Met Val Ser His Ala Gly Gly Ala
    180                 185                 190

Asn Asn Leu Lys Ala Val Thr Ala Asn His Asp Asp Leu Gln Asn Met
195                 200                 205
```

```
Gly Phe Asn Thr Glu Gln Ile Val Arg Met Val Ser His Asp Gly Gly
    210                 215                 220

Ser Leu Asn Leu Lys Ala Val Lys Lys Tyr His Asp Ala Leu Arg Glu
225                 230                 235                 240

Arg Lys Phe Ser Ser Gln Gln Ile Ile Arg Met Val Ser His Ala Gly
                245                 250                 255

Gly Ala Asn Asn Leu Lys Ala Val Thr Ala Asn His Asp Asp Leu Gln
                260                 265                 270

Asn Met Gly Phe Asn Val Glu Gln Ile Val Arg Met Val Ser His Asn
            275                 280                 285

Gly Gly Ser Lys Asn Leu Lys Ala Val Thr Asp Asn His Asp Asp Leu
    290                 295                 300

Lys Asn Met Gly Phe Asn Ala Glu Gln Ile Val Ser Met Val Ser Asn
305                 310                 315                 320

Gly Gly Gly Ser Leu Asn Leu Lys Ala Val Lys Lys Tyr His Asp Ala
                325                 330                 335

Leu Lys Asp Arg Gly Phe Asn Ala Glu Gln Ile Val Ser Met Val Ser
                340                 345                 350

Asn Gly Gly Gly Ser Leu Asn Leu Lys Ala Val Lys Lys Tyr His Asp
            355                 360                 365

Ala Leu Lys Asp Arg Gly Phe Asn Ala Glu Gln Ile Val Ser Met Val
    370                 375                 380

Ser Asn Gly Gly Gly Ser Leu Asn Leu Lys Ala Val Lys Lys Tyr His
385                 390                 395                 400

Asp Ala Leu Lys Asp Arg Gly Phe Asn Thr Glu Gln Ile Val Arg Met
                405                 410                 415

Val Ser His Asp Gly Gly Ser Leu Asn Leu Lys Ala Val Lys Lys Tyr
                420                 425                 430

His Asp Ala Leu Arg Glu Arg Lys Phe Asn Thr Glu Gln Ile Val Arg
            435                 440                 445

Met Val Ser His Asp Gly Gly Ser Leu Asn Leu Lys Ala Val Lys Lys
    450                 455                 460

Tyr His Asp Ala Leu Arg Glu Arg Lys Phe Asn Thr Glu Gln Ile Val
465                 470                 475                 480

Arg Met Val Ser His Asp Gly Gly Ser Leu Asn Leu Lys Ala Val Lys
                485                 490                 495

Lys Tyr His Asp Ala Leu Arg Glu Arg Lys Phe Asn Ala Glu Gln Ile
                500                 505                 510

Val Ser Met Val Ser Asn Gly Gly Gly Ser Leu Asn Leu Lys Ala Val
            515                 520                 525

Lys Lys Tyr His Asp Ala Leu Lys Asp Arg Gly Phe Asn Ala Glu Gln
    530                 535                 540

Ile Val Ser Met Val Ser Asn Gly Gly Gly Ser Leu Asn Leu Lys Ala
545                 550                 555                 560

Val Lys Lys Tyr His Asp Ala Leu Lys Asp Arg Gly Phe Asn Thr Glu
                565                 570                 575

Gln Ile Val Arg Met Val Ser His Asp Gly Gly Ser Leu Asn Leu Lys
                580                 585                 590

Ala Val Lys Lys Tyr His Asp Ala Leu Arg Glu Arg Lys Phe Asn Thr
            595                 600                 605

Glu Gln Ile Val Arg Met Val Ser His Asp Gly Gly Ser Leu Asn Leu
    610                 615                 620
```

-continued

```
Lys Ala Val Lys Lys Tyr His Asp Ala Leu Arg Glu Arg Lys Phe Asn
625                 630                 635                 640

Val Glu Gln Ile Val Arg Met Val Ser His Asn Gly Gly Ser Lys Asn
            645                 650                 655

Leu Lys Ala Val Thr Asp Asn His Asp Asp Leu Lys Asn Met Gly Phe
            660                 665                 670

Asn Thr Glu Gln Ile Val Arg Met Val Ser His Asp Gly Gly Ser Leu
        675                 680                 685

Asn Leu Lys Ala Val Lys Lys Tyr His Asp Ala Leu Arg Glu Arg Lys
    690                 695                 700

Phe Asn Ala Glu Gln Ile Val Ser Met Val Ser Asn Gly Gly Gly Ser
705                 710                 715                 720

Leu Asn Leu Lys Ala Val Lys Lys Tyr His Asp Ala Leu Lys Asp Arg
            725                 730                 735

Gly Phe Asn Ala Glu Gln Ile Val Arg Met Val Ser His Asp Gly Gly
            740                 745                 750

Ser Lys Asn Leu Ala Leu Val Lys Glu Tyr Phe Pro Val Phe Ser Ser
        755                 760                 765

Phe His Phe Thr Ala Asp Gln Ile Val Ala Leu Ile Cys Gln Ser Lys
    770                 775                 780

Gln Cys Phe Arg Asn Leu Lys Lys Asn His Gln Gln Trp Lys Asn Lys
785                 790                 795                 800

Gly Leu Ser Ala Glu Gln Ile Val Asp Leu Ile Leu Gln Glu Thr Pro
            805                 810                 815

Pro Lys Pro
```

<210> SEQ ID NO 110
<211> LENGTH: 965
<212> TYPE: PRT
<213> ORGANISM: Artificial sequence
<220> FEATURE:
<223> OTHER INFORMATION: synthetic sequence

<400> SEQUENCE: 110

```
Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
            85                  90                  95

Thr Arg Ser Asp Ser Leu Leu Ser Leu Asn Tyr Thr Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
    130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
```

```
                    165                 170                 175
            Phe Ser Ser Gln Gln Ile Ile Arg Met Val Ser His Ala Gly Gly Ala
                        180                 185                 190
            Asn Asn Leu Lys Ala Val Thr Ala Asn His Asp Asp Leu Gln Asn Met
                        195                 200                 205
            Gly Phe Asn Val Glu Gln Ile Val Arg Met Val Ser His Asn Gly Gly
                210                 215                 220
            Ser Lys Asn Leu Lys Ala Val Thr Asp Asn His Asp Asp Leu Lys Asn
            225                 230                 235                 240
            Met Gly Phe Asn Thr Glu Gln Ile Val Arg Met Val Ser His Asp Gly
                            245                 250                 255
            Gly Ser Leu Asn Leu Lys Ala Val Lys Lys Tyr His Asp Ala Leu Arg
                        260                 265                 270
            Glu Arg Lys Phe Ser Ser Gln Gln Ile Ile Arg Met Val Ser His Ala
                        275                 280                 285
            Gly Gly Ala Asn Asn Leu Lys Ala Val Thr Ala Asn His Asp Asp Leu
                        290                 295                 300
            Gln Asn Met Gly Phe Asn Val Glu Gln Ile Val Arg Met Val Ser His
            305                 310                 315                 320
            Asn Gly Gly Ser Lys Asn Leu Lys Ala Val Thr Asp Asn His Asp Asp
                            325                 330                 335
            Leu Lys Asn Met Gly Phe Asn Thr Glu Gln Ile Val Arg Met Val Ser
                        340                 345                 350
            His Asp Gly Gly Ser Leu Asn Leu Lys Ala Val Lys Lys Tyr His Asp
                        355                 360                 365
            Ala Leu Arg Glu Arg Lys Phe Asn Thr Glu Gln Ile Val Arg Met Val
                        370                 375                 380
            Ser His Asp Gly Gly Ser Leu Asn Leu Lys Ala Val Lys Lys Tyr His
            385                 390                 395                 400
            Asp Ala Leu Arg Glu Arg Lys Phe Asn Thr Glu Gln Ile Val Arg Met
                            405                 410                 415
            Val Ser His Asp Gly Gly Ser Leu Asn Leu Lys Ala Val Lys Lys Tyr
                        420                 425                 430
            His Asp Ala Leu Arg Glu Arg Lys Phe Asn Thr Glu Gln Ile Val Arg
                        435                 440                 445
            Met Val Ser His Asp Gly Gly Ser Leu Asn Leu Lys Ala Val Lys Lys
                        450                 455                 460
            Tyr His Asp Ala Leu Arg Glu Arg Lys Phe Ser Ser Gln Gln Ile Ile
            465                 470                 475                 480
            Arg Met Val Ser His Ala Gly Gly Ala Asn Asn Leu Lys Ala Val Thr
                            485                 490                 495
            Ala Asn His Asp Asp Leu Gln Asn Met Gly Phe Asn Thr Glu Gln Ile
                        500                 505                 510
            Val Arg Met Val Ser His Asp Gly Gly Ser Leu Asn Leu Lys Ala Val
                        515                 520                 525
            Lys Lys Tyr His Asp Ala Leu Arg Glu Arg Lys Phe Asn Thr Glu Gln
                        530                 535                 540
            Ile Val Arg Met Val Ser His Asp Gly Gly Ser Leu Asn Leu Lys Ala
            545                 550                 555                 560
            Val Lys Lys Tyr His Asp Ala Leu Arg Glu Arg Lys Phe Ser Ser Gln
                            565                 570                 575
            Gln Ile Ile Arg Met Val Ser His Ala Gly Gly Ala Asn Asn Leu Lys
                        580                 585                 590
```

```
Ala Val Thr Ala Asn His Asp Asp Leu Gln Asn Met Gly Phe Asn Val
        595                 600                 605

Glu Gln Ile Val Arg Met Val Ser His Asn Gly Gly Ser Lys Asn Leu
610                 615                 620

Lys Ala Val Thr Asp Asn His Asp Asp Leu Lys Asn Met Gly Phe Ser
625                 630                 635                 640

Ser Gln Gln Ile Ile Arg Met Val Ser His Ala Gly Gly Ala Asn Asn
            645                 650                 655

Leu Lys Ala Val Thr Ala Asn His Asp Asp Leu Gln Asn Met Gly Phe
                660                 665                 670

Asn Val Glu Gln Ile Val Arg Met Val Ser His Asn Gly Gly Ser Lys
            675                 680                 685

Asn Leu Lys Ala Val Thr Asp Asn His Asp Asp Leu Lys Asn Met Gly
        690                 695                 700

Phe Asn Ala Glu Gln Ile Val Ser Met Val Ser Asn Gly Gly Gly Ser
705                 710                 715                 720

Leu Asn Leu Lys Ala Val Lys Lys Tyr His Asp Ala Leu Lys Asp Arg
                725                 730                 735

Gly Phe Asn Val Glu Gln Ile Val Arg Met Val Ser His Asn Gly Gly
            740                 745                 750

Ser Lys Asn Leu Lys Ala Val Thr Asp Asn His Asp Asp Leu Lys Asn
        755                 760                 765

Met Gly Phe Asn Ala Glu Gln Ile Val Arg Met Val Ser His Asp Gly
770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
                820                 825                 830

Lys Gly Leu Ser Ala Glu Gln Ile Val Asp Leu Ile Leu Gln Glu Thr
            835                 840                 845

Pro Pro Lys Pro Asn Phe Asn Asn Thr Ser Ser Thr Pro Ser Pro
        850                 855                 860

Ser Ala Pro Ser Phe Phe Gln Gly Pro Ser Thr Pro Ile Pro Thr Pro
865                 870                 875                 880

Val Leu Asp Asn Ser Pro Ala Pro Ile Phe Ser Asn Pro Val Cys Phe
                885                 890                 895

Phe Ser Ser Arg Ser Glu Asn Asn Thr Glu Gln Tyr Leu Gln Asp Ser
                900                 905                 910

Thr Leu Asp Leu Asp Ser Gln Leu Gly Asp Pro Thr Lys Asn Phe Asn
            915                 920                 925

Val Asn Asn Phe Trp Ser Leu Phe Pro Phe Asp Asp Val Gly Tyr His
        930                 935                 940

Pro His Ser Asn Asp Val Gly Tyr His Leu His Ser Asp Glu Glu Ser
945                 950                 955                 960

Pro Phe Phe Asp Phe
            965

<210> SEQ ID NO 111
<211> LENGTH: 852
<212> TYPE: PRT
<213> ORGANISM: Artificial sequence
<220> FEATURE:
```

<223> OTHER INFORMATION: synthetic sequence

<400> SEQUENCE: 111

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
    130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
        195                 200                 205

Gly Phe Asn Val Glu Gln Ile Val Arg Met Val Ser His Asn Gly Gly
    210                 215                 220

Ser Lys Asn Leu Lys Ala Val Thr Asp Asn His Asp Asp Leu Lys Asn
225                 230                 235                 240

Met Gly Phe Asn Thr Glu Gln Ile Val Arg Met Val Ser His Asp Gly
                245                 250                 255

Gly Ser Leu Asn Leu Lys Ala Val Lys Lys Tyr His Asp Ala Leu Arg
            260                 265                 270

Glu Arg Lys Phe Ser Ser Gln Gln Ile Ile Arg Met Val Ser His Ala
        275                 280                 285

Gly Gly Ala Asn Asn Leu Lys Ala Val Thr Ala Asn His Asp Asp Leu
    290                 295                 300

Gln Asn Met Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
                325                 330                 335

Leu Lys Asn Met Gly Phe Asn Thr Glu Gln Ile Val Arg Met Val Ser
            340                 345                 350

His Asp Gly Gly Ser Leu Asn Leu Lys Ala Val Lys Lys Tyr His Asp
        355                 360                 365

Ala Leu Arg Glu Arg Lys Phe Asn Thr Glu Gln Ile Val Arg Met Val
    370                 375                 380

Ser His Asp Gly Gly Ser Leu Asn Leu Lys Ala Val Lys Lys Tyr His
385                 390                 395                 400

```
Asp Ala Leu Arg Glu Arg Lys Phe Asn Thr Glu Gln Ile Val Arg Met
                405                 410                 415

Val Ser His Asp Gly Gly Ser Leu Asn Leu Lys Ala Val Lys Lys Tyr
            420                 425                 430

His Asp Ala Leu Arg Glu Arg Lys Phe Asn Thr Glu Gln Ile Val Arg
        435                 440                 445

Met Val Ser His Asp Gly Gly Ser Leu Asn Leu Lys Ala Val Lys Lys
    450                 455                 460

Tyr His Asp Ala Leu Arg Glu Arg Lys Phe Ser Gln Gln Ile Ile
465                 470                 475                 480

Arg Met Val Ser His Ala Gly Ala Asn Asn Leu Lys Ala Val Thr
                485                 490                 495

Ala Asn His Asp Asp Leu Gln Asn Met Gly Phe Asn Thr Glu Gln Ile
            500                 505                 510

Val Arg Met Val Ser His Asp Gly Gly Ser Leu Asn Leu Lys Ala Val
        515                 520                 525

Lys Lys Tyr His Asp Ala Leu Arg Glu Arg Lys Phe Asn Thr Glu Gln
    530                 535                 540

Ile Val Arg Met Val Ser His Asp Gly Gly Ser Leu Asn Leu Lys Ala
545                 550                 555                 560

Val Lys Lys Tyr His Asp Ala Leu Arg Glu Arg Lys Phe Ser Ser Gln
                565                 570                 575

Gln Ile Ile Arg Met Val Ser His Ala Gly Ala Asn Asn Leu Lys
            580                 585                 590

Ala Val Thr Ala Asn His Asp Asp Leu Gln Asn Met Gly Phe Asn Val
        595                 600                 605

Glu Gln Ile Val Arg Met Val Ser His Asn Gly Gly Ser Lys Asn Leu
    610                 615                 620

Lys Ala Val Thr Asp Asn His Asp Asp Leu Lys Asn Met Gly Phe Ser
625                 630                 635                 640

Ser Gln Gln Ile Ile Arg Met Val Ser His Ala Gly Gly Ala Asn Asn
                645                 650                 655

Leu Lys Ala Val Thr Ala Asn His Asp Asp Leu Gln Asn Met Gly Phe
            660                 665                 670

Asn Val Glu Gln Ile Val Arg Met Val Ser His Asn Gly Gly Ser Lys
        675                 680                 685

Asn Leu Lys Ala Val Thr Asp Asn His Asp Asp Leu Lys Asn Met Gly
    690                 695                 700

Phe Asn Ala Glu Gln Ile Val Ser Met Val Ser Asn Gly Gly Gly Ser
705                 710                 715                 720

Leu Asn Leu Lys Ala Val Lys Lys Tyr His Asp Ala Leu Lys Asp Arg
                725                 730                 735

Gly Phe Asn Val Glu Gln Ile Val Arg Met Val Ser His Asn Gly Gly
            740                 745                 750

Ser Lys Asn Leu Lys Ala Val Thr Asp Asn His Asp Asp Leu Lys Asn
        755                 760                 765

Met Gly Phe Asn Ala Glu Gln Ile Val Arg Met Val Ser His Asp Gly
    770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
```

```
                    820                 825                 830
Lys Gly Leu Ser Ala Glu Gln Ile Val Asp Leu Ile Leu Gln Glu Thr
            835                 840                 845

Pro Pro Lys Pro
    850

<210> SEQ ID NO 112
<211> LENGTH: 965
<212> TYPE: PRT
<213> ORGANISM: Artificial sequence
<220> FEATURE:
<223> OTHER INFORMATION: synthetic sequence

<400> SEQUENCE: 112

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
        195                 200                 205

Gly Phe Asn Ala Glu Gln Ile Val Ser Met Val Ser Asn Gly Gly Gly
    210                 215                 220

Ser Leu Asn Leu Lys Ala Val Lys Lys Tyr His Asp Ala Leu Lys Asp
225                 230                 235                 240

Arg Gly Phe Asn Thr Glu Gln Ile Val Arg Met Val Ser His Asp Gly
                245                 250                 255

Gly Ser Leu Asn Leu Lys Ala Val Lys Lys Tyr His Asp Ala Leu Arg
            260                 265                 270

Glu Arg Lys Phe Asn Ala Glu Gln Ile Val Ser Met Val Ser Asn Gly
        275                 280                 285

Gly Gly Ser Leu Asn Leu Lys Ala Val Lys Lys Tyr His Asp Ala Leu
    290                 295                 300

Lys Asp Arg Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
```

-continued

```
                325                 330                 335
Leu Lys Asn Met Gly Phe Asn Thr Glu Gln Ile Val Arg Met Val Ser
                340                 345                 350
His Asp Gly Gly Ser Leu Asn Leu Lys Ala Val Lys Lys Tyr His Asp
                355                 360                 365
Ala Leu Arg Glu Arg Lys Phe Ser Ser Gln Gln Ile Ile Arg Met Val
                370                 375                 380
Ser His Ala Gly Ala Asn Asn Leu Lys Ala Val Thr Ala Asn His
385                 390                 395                 400
Asp Asp Leu Gln Asn Met Gly Phe Asn Ala Glu Gln Ile Val Ser Met
                405                 410                 415
Val Ser Asn Gly Gly Ser Leu Asn Leu Lys Ala Val Lys Lys Tyr
                420                 425                 430
His Asp Ala Leu Lys Asp Arg Gly Phe Asn Val Glu Gln Ile Val Arg
                435                 440                 445
Met Val Ser His Asn Gly Gly Ser Lys Asn Leu Lys Ala Val Thr Asp
                450                 455                 460
Asn His Asp Asp Leu Lys Asn Met Gly Phe Asn Thr Glu Gln Ile Val
465                 470                 475                 480
Arg Met Val Ser His Asp Gly Gly Ser Leu Asn Leu Lys Ala Val Lys
                485                 490                 495
Lys Tyr His Asp Ala Leu Arg Glu Arg Lys Phe Asn Thr Glu Gln Ile
                500                 505                 510
Val Arg Met Val Ser His Asp Gly Gly Ser Leu Asn Leu Lys Ala Val
                515                 520                 525
Lys Lys Tyr His Asp Ala Leu Arg Glu Arg Lys Phe Asn Ala Glu Gln
                530                 535                 540
Ile Val Ser Met Val Ser Asn Gly Gly Ser Leu Asn Leu Lys Ala
545                 550                 555                 560
Val Lys Lys Tyr His Asp Ala Leu Lys Asp Arg Gly Phe Asn Val Glu
                565                 570                 575
Gln Ile Val Arg Met Val Ser His Asn Gly Gly Ser Lys Asn Leu Lys
                580                 585                 590
Ala Val Thr Asp Asn His Asp Asp Leu Lys Asn Met Gly Phe Asn Val
                595                 600                 605
Glu Gln Ile Val Arg Met Val Ser His Gly Gly Ser Lys Asn Leu
                610                 615                 620
Lys Ala Val Thr Asp Asn His Asp Asp Leu Lys Asn Met Gly Phe Ser
625                 630                 635                 640
Ser Gln Gln Ile Ile Arg Met Val Ser His Ala Gly Gly Ala Asn Asn
                645                 650                 655
Leu Lys Ala Val Thr Ala Asn His Asp Asp Leu Gln Asn Met Gly Phe
                660                 665                 670
Asn Val Glu Gln Ile Val Arg Met Val Ser His Gly Gly Ser Lys
                675                 680                 685
Asn Leu Lys Ala Val Thr Asp Asn His Asp Asp Leu Lys Asn Met Gly
                690                 695                 700
Phe Asn Thr Glu Gln Ile Val Arg Met Val Ser His Asp Gly Gly Ser
705                 710                 715                 720
Leu Asn Leu Lys Ala Val Lys Lys Tyr His Asp Ala Leu Arg Glu Arg
                725                 730                 735
Lys Phe Ser Ser Gln Gln Ile Ile Arg Met Val Ser His Ala Gly Gly
                740                 745                 750
```

Ala Asn Asn Leu Lys Ala Val Thr Ala Asn His Asp Asp Leu Gln Asn
            755                 760                 765

Met Gly Phe Asn Ala Glu Gln Ile Val Arg Met Val Ser His Lys Gly
    770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
            820                 825                 830

Lys Gly Leu Ser Ala Glu Gln Ile Val Asp Leu Ile Leu Gln Glu Thr
            835                 840                 845

Pro Pro Lys Pro Asn Phe Asn Asn Thr Ser Ser Ser Thr Pro Ser Pro
            850                 855                 860

Ser Ala Pro Ser Phe Phe Gln Gly Pro Ser Thr Pro Ile Pro Thr Pro
865                 870                 875                 880

Val Leu Asp Asn Ser Pro Ala Pro Ile Phe Ser Asn Pro Val Cys Phe
                885                 890                 895

Phe Ser Arg Ser Glu Asn Asn Thr Glu Gln Tyr Leu Gln Asp Ser
            900                 905                 910

Thr Leu Asp Leu Asp Ser Gln Leu Gly Asp Pro Thr Lys Asn Phe Asn
            915                 920                 925

Val Asn Asn Phe Trp Ser Leu Phe Pro Phe Asp Val Gly Tyr His
    930                 935                 940

Pro His Ser Asn Asp Val Gly Tyr His Leu His Ser Asp Glu Glu Ser
945                 950                 955                 960

Pro Phe Phe Asp Phe
            965

<210> SEQ ID NO 113
<211> LENGTH: 852
<212> TYPE: PRT
<213> ORGANISM: Artificial sequence
<220> FEATURE:
<223> OTHER INFORMATION: synthetic sequence

<400> SEQUENCE: 113

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
                20                  25                  30

Ser Ser Ser Tyr Ser Ser Lys Ser Pro Ala Ser Ala Asn Ala Arg
            35                  40                  45

Lys Arg Thr Ser Arg Lys Glu Met Ser Gly Pro Pro Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Gln Ile
            100                 105                 110

Glu Arg Leu Ile Leu Tyr Lys Gly Arg Thr Ser Ala Val Gln Gln Leu
    115                 120                 125

Leu Cys Lys His Glu Glu Leu Leu Asn Leu Ile Ser Pro Asp Gly Leu
130                 135                 140

```
Gly His Lys Glu Leu Ile Lys Ile Ala Ala Arg Asn Gly Gly Asn
145                 150                 155                 160

Asn Leu Ile Ala Val Leu Ser Cys Tyr Ala Lys Leu Lys Glu Met Gly
                165                 170                 175

Phe Ser Ser Gln Gln Ile Ile Arg Met Val Ser His Ala Gly Gly Ala
            180                 185                 190

Asn Asn Leu Lys Ala Val Thr Ala Asn His Asp Asp Leu Gln Asn Met
                195                 200                 205

Gly Phe Asn Ala Glu Gln Ile Val Ser Met Val Ser Asn Gly Gly Gly
            210                 215                 220

Ser Leu Asn Leu Lys Ala Val Lys Lys Tyr His Asp Ala Leu Lys Asp
225                 230                 235                 240

Arg Gly Phe Asn Thr Glu Gln Ile Val Arg Met Val Ser His Asp Gly
                245                 250                 255

Gly Ser Leu Asn Leu Lys Ala Val Lys Lys Tyr His Asp Ala Leu Arg
            260                 265                 270

Glu Arg Lys Phe Asn Ala Glu Gln Ile Val Ser Met Val Ser Asn Gly
            275                 280                 285

Gly Gly Ser Leu Asn Leu Lys Ala Val Lys Lys Tyr His Asp Ala Leu
290                 295                 300

Lys Asp Arg Gly Phe Asn Val Glu Gln Ile Val Arg Met Val Ser His
305                 310                 315                 320

Asn Gly Gly Ser Lys Asn Leu Lys Ala Val Thr Asp Asn His Asp Asp
                325                 330                 335

Leu Lys Asn Met Gly Phe Asn Thr Glu Gln Ile Val Arg Met Val Ser
                340                 345                 350

His Asp Gly Gly Ser Leu Asn Leu Lys Ala Val Lys Lys Tyr His Asp
                355                 360                 365

Ala Leu Arg Glu Arg Lys Phe Ser Ser Gln Gln Ile Ile Arg Met Val
                370                 375                 380

Ser His Ala Gly Gly Ala Asn Asn Leu Lys Ala Val Thr Ala Asn His
385                 390                 395                 400

Asp Asp Leu Gln Asn Met Gly Phe Asn Ala Glu Gln Ile Val Ser Met
                405                 410                 415

Val Ser Asn Gly Gly Gly Ser Leu Asn Leu Lys Ala Val Lys Lys Tyr
                420                 425                 430

His Asp Ala Leu Lys Asp Arg Gly Phe Asn Val Glu Gln Ile Val Arg
                435                 440                 445

Met Val Ser His Asn Gly Gly Ser Lys Asn Leu Lys Ala Val Thr Asp
                450                 455                 460

Asn His Asp Asp Leu Lys Asn Met Gly Phe Asn Thr Glu Gln Ile Val
465                 470                 475                 480

Arg Met Val Ser His Asp Gly Gly Ser Leu Asn Leu Lys Ala Val Lys
                485                 490                 495

Lys Tyr His Asp Ala Leu Arg Glu Arg Lys Phe Asn Thr Glu Gln Ile
                500                 505                 510

Val Arg Met Val Ser His Asp Gly Gly Ser Leu Asn Leu Lys Ala Val
                515                 520                 525

Lys Lys Tyr His Asp Ala Leu Arg Glu Arg Lys Phe Asn Ala Glu Gln
                530                 535                 540

Ile Val Ser Met Val Ser Asn Gly Gly Gly Ser Leu Asn Leu Lys Ala
545                 550                 555                 560
```

Val Lys Lys Tyr His Asp Ala Leu Lys Asp Arg Gly Phe Asn Val Glu
                565                 570                 575

Gln Ile Val Arg Met Val Ser His Asn Gly Ser Lys Asn Leu Lys
            580                 585                 590

Ala Val Thr Asp Asn His Asp Asp Leu Lys Asn Met Gly Phe Asn Val
                595                 600                 605

Glu Gln Ile Val Arg Met Val Ser His Asn Gly Gly Ser Lys Asn Leu
            610                 615                 620

Lys Ala Val Thr Asp Asn His Asp Asp Leu Lys Asn Met Gly Phe Ser
625                 630                 635                 640

Ser Gln Gln Ile Ile Arg Met Val Ser His Ala Gly Gly Ala Asn Asn
                645                 650                 655

Leu Lys Ala Val Thr Ala Asn His Asp Asp Leu Gln Asn Met Gly Phe
            660                 665                 670

Asn Val Glu Gln Ile Val Arg Met Val Ser His Asn Gly Gly Ser Lys
            675                 680                 685

Asn Leu Lys Ala Val Thr Asp Asn His Asp Asp Leu Lys Asn Met Gly
            690                 695                 700

Phe Asn Thr Glu Gln Ile Val Arg Met Val Ser His Asp Gly Gly Ser
705                 710                 715                 720

Leu Asn Leu Lys Ala Val Lys Lys Tyr His Asp Ala Leu Arg Glu Arg
                725                 730                 735

Lys Phe Ser Ser Gln Gln Ile Ile Arg Met Val Ser His Ala Gly Gly
            740                 745                 750

Ala Asn Asn Leu Lys Ala Val Thr Ala Asn His Asp Asp Leu Gln Asn
            755                 760                 765

Met Gly Phe Asn Ala Glu Gln Ile Val Arg Met Val Ser His Lys Gly
    770                 775                 780

Gly Ser Lys Asn Leu Ala Leu Val Lys Glu Tyr Phe Pro Val Phe Ser
785                 790                 795                 800

Ser Phe His Phe Thr Ala Asp Gln Ile Val Ala Leu Ile Cys Gln Ser
                805                 810                 815

Lys Gln Cys Phe Arg Asn Leu Lys Lys Asn His Gln Gln Trp Lys Asn
            820                 825                 830

Lys Gly Leu Ser Ala Glu Gln Ile Val Asp Leu Ile Leu Gln Glu Thr
            835                 840                 845

Pro Pro Lys Pro
    850

<210> SEQ ID NO 114
<211> LENGTH: 33
<212> TYPE: PRT
<213> ORGANISM: Paraburkholderia

<400> SEQUENCE: 114

Phe Asn Leu Thr Asp Ile Val Glu Met Ala Gly Lys Gly Gly Ala
1               5                   10                  15

Gln Ala Leu Lys Ala Val Leu Glu His Gly Pro Thr Leu Arg Gln Arg
            20                  25                  30

Gly

<210> SEQ ID NO 115
<211> LENGTH: 33
<212> TYPE: PRT
<213> ORGANISM: Paraburkholderia

```
<400> SEQUENCE: 115

Phe Arg Gln Ala Asp Ile Ile Lys Ile Ala Gly Asn Asp Gly Ala
1               5                  10                  15

Gln Ala Leu Gln Ala Val Ile Glu His Gly Pro Thr Leu Arg Gln His
            20                  25                  30

Gly

<210> SEQ ID NO 116
<211> LENGTH: 33
<212> TYPE: PRT
<213> ORGANISM: Paraburkholderia

<400> SEQUENCE: 116

Phe Ser Gln Ala Asp Ile Val Lys Ile Ala Gly Asn Asp Gly Thr
1               5                  10                  15

Gln Ala Leu His Ala Val Leu Asp Leu Glu Arg Met Leu Gly Glu Arg
            20                  25                  30

Gly

<210> SEQ ID NO 117
<211> LENGTH: 33
<212> TYPE: PRT
<213> ORGANISM: Paraburkholderia

<400> SEQUENCE: 117

Phe Ser Arg Ala Asp Ile Val Lys Ile Ala Gly Asn Gly Gly Ala
1               5                  10                  15

Gln Ala Leu Lys Ala Val Leu Glu His Glu Ala Thr Leu Asp Glu Arg
            20                  25                  30

Gly

<210> SEQ ID NO 118
<211> LENGTH: 33
<212> TYPE: PRT
<213> ORGANISM: Paraburkholderia

<400> SEQUENCE: 118

Phe Ser Arg Ala Asp Ile Val Arg Ile Ala Gly Asn Gly Gly Ala
1               5                  10                  15

Gln Ala Leu Tyr Ser Val Leu Asp Val Glu Pro Thr Leu Gly Lys Arg
            20                  25                  30

Gly

<210> SEQ ID NO 119
<211> LENGTH: 33
<212> TYPE: PRT
<213> ORGANISM: Paraburkholderia

<400> SEQUENCE: 119

Phe Ser Gln Pro Asp Ile Val Lys Met Ala Ser Asn Ile Gly Ala
1               5                  10                  15

Gln Ala Leu Gln Ala Val Leu Glu Leu Glu Pro Ala Leu Arg Glu Arg
            20                  25                  30

Gly

<210> SEQ ID NO 120
<211> LENGTH: 33
<212> TYPE: PRT
<213> ORGANISM: Paraburkholderia
```

<400> SEQUENCE: 120

Phe Ser Gln Pro Asp Ile Val Lys Met Ala Gly Asn Ile Gly Gly Ala
1               5                   10                  15

Gln Ala Leu Gln Ala Val Leu Ser Leu Gly Pro Ala Leu Arg Glu Arg
            20                  25                  30

Gly

<210> SEQ ID NO 121
<211> LENGTH: 33
<212> TYPE: PRT
<213> ORGANISM: Paraburkholderia

<400> SEQUENCE: 121

Phe Ser Gln Pro Glu Ile Val Lys Ile Ala Gly Asn Ile Gly Gly Ala
1               5                   10                  15

Gln Ala Leu His Thr Val Leu Glu Leu Glu Pro Thr Leu His Lys Arg
            20                  25                  30

Gly

<210> SEQ ID NO 122
<211> LENGTH: 33
<212> TYPE: PRT
<213> ORGANISM: Paraburkholderia

<400> SEQUENCE: 122

Phe Ser Gln Ser Asp Ile Val Lys Ile Ala Gly Asn Ile Gly Gly Ala
1               5                   10                  15

Gln Ala Leu Gln Ala Val Leu Asp Leu Glu Ser Met Leu Gly Lys Arg
            20                  25                  30

Gly

<210> SEQ ID NO 123
<211> LENGTH: 33
<212> TYPE: PRT
<213> ORGANISM: Paraburkholderia

<400> SEQUENCE: 123

Phe Ser Gln Ser Asp Ile Val Lys Ile Ala Gly Asn Ile Gly Gly Ala
1               5                   10                  15

Gln Ala Leu Gln Ala Val Leu Glu Leu Glu Pro Thr Leu Arg Glu Ser
            20                  25                  30

Asp

<210> SEQ ID NO 124
<211> LENGTH: 33
<212> TYPE: PRT
<213> ORGANISM: Paraburkholderia

<400> SEQUENCE: 124

Phe Asn Pro Thr Asp Ile Val Lys Ile Ala Gly Asn Lys Gly Gly Ala
1               5                   10                  15

Gln Ala Leu Gln Ala Val Leu Glu Leu Glu Pro Ala Leu Arg Glu Arg
            20                  25                  30

Gly

<210> SEQ ID NO 125
<211> LENGTH: 33
<212> TYPE: PRT

<213> ORGANISM: Paraburkholderia

<400> SEQUENCE: 125

Phe Ser Pro Thr Asp Ile Ile Lys Ile Ala Gly Asn Asn Gly Gly Ala
1               5                   10                  15

Gln Ala Leu Gln Ala Val Leu Asp Leu Glu Leu Met Leu Arg Glu Arg
            20                  25                  30

Gly

<210> SEQ ID NO 126
<211> LENGTH: 33
<212> TYPE: PRT
<213> ORGANISM: Paraburkholderia

<400> SEQUENCE: 126

Phe Ser Gln Ala Asp Ile Val Lys Ile Ala Gly Asn Asn Gly Gly Ala
1               5                   10                  15

Gln Ala Leu Tyr Ser Val Leu Asp Val Glu Pro Thr Leu Gly Lys Arg
            20                  25                  30

Gly

<210> SEQ ID NO 127
<211> LENGTH: 33
<212> TYPE: PRT
<213> ORGANISM: Paraburkholderia

<400> SEQUENCE: 127

Phe Ser Arg Gly Asp Ile Val Thr Ile Ala Gly Asn Asn Gly Gly Ala
1               5                   10                  15

Gln Ala Leu Gln Ala Val Leu Glu Leu Glu Pro Thr Leu Arg Glu Arg
            20                  25                  30

Gly

<210> SEQ ID NO 128
<211> LENGTH: 33
<212> TYPE: PRT
<213> ORGANISM: Paraburkholderia

<400> SEQUENCE: 128

Phe Ser Arg Ile Asp Ile Val Lys Ile Ala Ala Asn Asn Gly Gly Ala
1               5                   10                  15

Gln Ala Leu His Ala Val Leu Asp Leu Gly Pro Thr Leu Arg Glu Cys
            20                  25                  30

Gly

<210> SEQ ID NO 129
<211> LENGTH: 33
<212> TYPE: PRT
<213> ORGANISM: Paraburkholderia

<400> SEQUENCE: 129

Phe Ser Gln Ala Asp Ile Val Lys Ile Val Gly Asn Asn Gly Gly Ala
1               5                   10                  15

Gln Ala Leu Gln Ala Val Phe Glu Leu Glu Pro Thr Leu Arg Glu Arg
            20                  25                  30

Gly

<210> SEQ ID NO 130
<211> LENGTH: 33

```
<212> TYPE: PRT
<213> ORGANISM: Paraburkholderia

<400> SEQUENCE: 130

Phe Ser Gln Pro Asp Ile Val Arg Ile Thr Gly Asn Arg Gly Gly Ala
1               5                   10                  15

Gln Ala Leu Gln Ala Val Leu Ala Leu Glu Leu Thr Leu Arg Glu Arg
            20                  25                  30

Gly

<210> SEQ ID NO 131
<211> LENGTH: 33
<212> TYPE: PRT
<213> ORGANISM: Legionellales

<400> SEQUENCE: 131

Phe Lys Ala Asp Asp Ala Val Arg Ile Ala Cys Arg Thr Gly Gly Ser
1               5                   10                  15

His Asn Leu Lys Ala Val His Lys Asn Tyr Glu Arg Leu Arg Ala Arg
            20                  25                  30

Gly

<210> SEQ ID NO 132
<211> LENGTH: 33
<212> TYPE: PRT
<213> ORGANISM: Legionellales

<400> SEQUENCE: 132

Phe Asn Ala Asp Gln Val Ile Lys Ile Val Gly His Asp Gly Gly Ser
1               5                   10                  15

Asn Asn Ile Asp Val Val Gln Gln Phe Phe Pro Glu Leu Lys Ala Phe
            20                  25                  30

Gly

<210> SEQ ID NO 133
<211> LENGTH: 33
<212> TYPE: PRT
<213> ORGANISM: Legionella maceachernii

<400> SEQUENCE: 133

Phe Ser Ala Glu Gln Ile Val Arg Ile Ala Ala His Ile Gly Gly Ser
1               5                   10                  15

Arg Asn Ile Glu Ala Thr Ile Lys His Tyr Ala Met Leu Thr Gln Pro
            20                  25                  30

Pro

<210> SEQ ID NO 134
<211> LENGTH: 33
<212> TYPE: PRT
<213> ORGANISM: Francisella

<400> SEQUENCE: 134

Tyr Lys Ser Glu Asp Ile Ile Arg Leu Ala Ser His Asp Gly Gly Ser
1               5                   10                  15

Val Asn Leu Glu Ala Val Leu Arg Leu Asn Pro Gln Leu Ile Gly Leu
            20                  25                  30

Gly

<210> SEQ ID NO 135
```

```
<211> LENGTH: 33
<212> TYPE: PRT
<213> ORGANISM: Francisella

<400> SEQUENCE: 135

Tyr Lys Ser Gl

Gly Ile Val His Arg Gly Gln Leu Glu Phe Ala Ile Asn Leu Glu Gln
 50                  55                  60

Leu Glu Gln Lys Ile Asn Glu Pro Ala Phe Lys Ala Val Ile Leu Glu
 65                  70                  75                  80

Lys Thr Ser Arg Ala Val Gly Tyr Thr Ile Ser Asn Glu Cys Phe Asn
                 85                  90                  95

Val Glu Leu Asn Ala Leu Ala Lys Ala Gly Phe Asn Asn Leu Asp Ile
                100                 105                 110

Asp Lys Leu Ile Phe Arg Arg Ser Ser Arg Gly Thr Val Gln Thr Val
                115                 120                 125

Leu Asn Ser Tyr Asn Ile Leu Leu Glu Lys Pro Tyr Asn Leu Asp Arg
130                 135                 140

Gln Gln Ile Leu Arg Ile Ala Ser His Asp Gly Gly Ser Lys Asn Ile
145                 150                 155                 160

Ala Ala Val Gln Lys Phe Leu Pro Lys Leu Met Asn Phe Gly Phe Asn
                165                 170                 175

Ala Asp Gln Val Ile Lys Ile Val Gly His Asp Gly Gly Ser Asn Asn
                180                 185                 190

Ile Asp Val Val Gln Gln Phe Phe Pro Glu Leu Lys Ala Phe Gly Phe
                195                 200                 205

Ser Ala Asp Gln Val Val Lys Ile Ala Gly His Ser Gly Gly Ser Asn
210                 215                 220

Asn Ile Ala Val Met Leu Ala Val Phe Pro Arg Leu Arg Asp Phe Gly
225                 230                 235                 240

Phe Lys Ala Asp Asp Ala Val Arg Ile Ala Cys Arg Thr Gly Gly Ser
                245                 250                 255

His Asn Leu Lys Ala Val His Lys Asn Tyr Glu Arg Leu Arg Ala Arg
                260                 265                 270

Gly Tyr Asp Asn Lys Lys Ile Ile Ser Ile Ala Ala Ser Asn Cys Gly
                275                 280                 285

Thr Glu Thr Ile Asn Thr Ile Met Ser Thr Asp Glu Val Glu Glu Ser
                290                 295                 300

Asp Phe Leu Tyr Phe Val Thr Thr Val Ser Thr Pro Val Ala Ser Gln
305                 310                 315                 320

Asn Leu Ser Ser Ala Ser Asn Thr Asn Ile Asn Tyr Ser Asn Arg Phe
                325                 330                 335

Met Thr Ala Arg Lys Lys Thr Ser Asp Asn Thr Asp Glu Val Glu
                340                 345                 350

Glu Asp Gln His Arg Asp Lys Arg Arg Ser Asn Gly Arg
                355                 360                 365

<210> SEQ ID NO 140
<211> LENGTH: 141
<212> TYPE: PRT
<213> ORGANISM: Artificial sequence
<220> FEATURE:
<223> OTHER INFORMATION: synthetic sequence

<400> SEQUENCE: 140

Met Pro Lys Thr Lys Ile Thr Thr Val Ser His Gly Tyr Asp Leu Asp
1               5                   10                  15

Leu Met Ser Ser Leu Pro Asn Gly Asp Pro Asn Gln Ala Lys Gln Gly
                20                  25                  30

Lys Ile Tyr Leu Ser Gly Asn Gly Val Tyr Val Arg Asp Val Ala
                35                  40                  45

```
Gly Ile Val His Arg Gly Gln Leu Glu Phe Ala Ile Asn Leu Glu Gln
    50                  55                  60

Leu Glu Gln Lys Ile Asn Glu Pro Ala Phe Lys Ala Val Ile Leu Glu
65                  70                  75                  80

Lys Thr Ser Arg Ala Val Gly Tyr Thr Ile Ser Asn Glu Cys Phe Asn
                85                  90                  95

Val Glu Leu Asn Ala Leu Ala Lys Ala Gly Phe Asn Asn Leu Asp Ile
            100                 105                 110

Asp Lys Leu Ile Phe Arg Arg Ser Ser Arg Gly Thr Val Gln Thr Val
                115                 120                 125

Leu Asn Ser Tyr Asn Ile Leu Leu Glu Lys Pro Tyr Asn
    130                 135                 140

<210> SEQ ID NO 141
<211> LENGTH: 92
<212> TYPE: PRT
<213> ORGANISM: Artificial sequence
<220> FEATURE:
<223> OTHER INFORMATION: synthetic sequence

<400> SEQUENCE: 141

Tyr Asp Asn Lys Lys Ile Ile Ser Ile Ala Ala Ser Asn Cys Gly Thr
1               5                   10                  15

Glu Thr Ile Asn Thr Ile Met Ser Thr Asp Glu Val Glu Glu Ser Asp
                20                  25                  30

Phe Leu Tyr Phe Val Thr Thr Val Ser Thr Pro Val Ala Ser Gln Asn
            35                  40                  45

Leu Ser Ser Ala Ser Asn Thr Asn Ile Asn Tyr Ser Asn Arg Phe Met
    50                  55                  60

Thr Ala Arg Lys Lys Thr Ser Asp Asp Asn Thr Asp Glu Val Glu Glu
65                  70                  75                  80

Asp Gln His Arg Asp Lys Arg Arg Ser Asn Gly Arg
                85                  90

<210> SEQ ID NO 142
<211> LENGTH: 63
<212> TYPE: PRT
<213> ORGANISM: Artificial sequence
<220> FEATURE:
<223> OTHER INFORMATION: synthetic sequence

<400> SEQUENCE: 142

Tyr Asp Asn Lys Lys Ile Ile Ser Ile Ala Ala Ser Asn Cys Gly Thr
1               5                   10                  15

Glu Thr Ile Asn Thr Ile Met Ser Thr Asp Glu Val Glu Glu Ser Asp
                20                  25                  30

Phe Leu Tyr Phe Val Thr Thr Val Ser Thr Pro Val Ala Ser Gln Asn
            35                  40                  45

Leu Ser Ser Ala Ser Asn Thr Asn Ile Asn Tyr Ser Asn Arg Phe
    50                  55                  60

<210> SEQ ID NO 143
<211> LENGTH: 808
<212> TYPE: PRT
<213> ORGANISM: Legionella maceachernii

<400> SEQUENCE: 143

Met Pro Lys Thr Asn Gln Pro Lys Asn Leu Glu Ala Lys Ser Thr Lys
1               5                   10                  15
```

```
Asn Lys Ile Ser Leu Pro Gln Asp Pro Gln Thr Leu Asn Glu Leu Lys
             20                  25                  30

Ile Lys Gly Tyr Pro Gln Asp Leu Ala Glu Arg Leu Ile Lys Lys Gly
             35                  40                  45

Ser Ser Leu Ala Val Lys Thr Val Leu Lys Asp His Glu Gln Leu Val
 50                  55                  60

Asn Phe Phe Thr His Leu Gln Ile Ile Arg Met Ala Ala Gln Lys Gly
 65                  70                  75                  80

Gly Ala Lys Asn Ile Thr Thr Ala Leu Asn Glu Tyr Asn Ser Leu Thr
                 85                  90                  95

Asn Leu Gly Tyr Ser Ser Glu Gln Ile Val Arg Val Ala Ala His Gly
                100                 105                 110

Gly Gly Ser Leu Asn Ile Lys Ala Val Leu Gln Ala His Gln Ala Leu
            115                 120                 125

Lys Glu Leu Asp Phe Ser Ala Glu Gln Ile Val Arg Ile Ala Ala His
            130                 135                 140

Asp Gly Gly Ser Leu Asn Ile Asp Ala Val Gln Gln Ala Gln Gln Ala
145                 150                 155                 160

Leu Lys Glu Leu Gly Phe Ser Ala Lys His Ile Val Arg Ile Ala Ala
                165                 170                 175

His Ile Gly Gly Ser Leu Asn Ile Lys Ala Val Gln Gln Ala Gln Gln
            180                 185                 190

Ala Leu Lys Glu Leu Gly Phe Ser Ala Asp Gln Ile Val Arg Ile Ala
        195                 200                 205

Ala His Lys Gly Gly Ser His Asn Ile Val Ala Val Gln Gln Ala Gln
210                 215                 220

Gln Ala Leu Lys Glu Leu Asp Phe Ser Ala Glu Gln Ile Val Arg Ile
225                 230                 235                 240

Ala Ala His Ile Gly Gly Ser Arg Asn Ile Glu Ala Ile Gln Gln Ala
                245                 250                 255

His His Ala Leu Lys Glu Leu Gly Phe Ser Ala Glu Gln Ile Val Arg
            260                 265                 270

Ile Ala Ala His Ile Gly Gly Ser His Asn Leu Lys Ala Val Leu Gln
            275                 280                 285

Ala Gln Gln Ala Leu Lys Glu Leu Asp Phe Ser Ala Glu Gln Ile Val
290                 295                 300

Arg Ile Ala Ala His Asp Gly Gly Ser Arg Asn Ile Glu Ala Val Gln
305                 310                 315                 320

Gln Ala Gln His Val Leu Lys Glu Leu Gly Phe Ser Ala Glu Gln Ile
                325                 330                 335

Val His Ile Ala Ala His Gly Gly Gly Ser Leu Asn Ile Lys Ala Ile
            340                 345                 350

Leu Gln Ala His Gln Thr Leu Lys Glu Leu Asn Phe Ser Ala Glu Gln
            355                 360                 365

Ile Val Ser Ile Val Ala His Asp Gly Gly Ser Arg Asn Ile Glu Ala
            370                 375                 380

Val Gln Gln Ala Gln His Ile Leu Lys Glu Leu Gly Phe Ser Thr Glu
385                 390                 395                 400

Gln Ile Val Cys Ile Ala Gly His Gly Gly Gly Ser Leu Asn Ile Lys
                405                 410                 415

Ala Val Leu Leu Ala Gln Gln Ala Leu Lys Asp Leu Gly Phe Ser Ala
            420                 425                 430

Glu Gln Ile Val Ser Ile Ala Ala His Val Gly Gly Ser His Asn Ile
```

```
                435                 440                 445
Glu Ala Val Gln Lys Ala His Gln Ala Leu Lys Glu Leu Asp Phe Ser
450                 455                 460
Ala Glu Gln Ile Val Arg Ile Ala Ala His Ile Gly Gly Ser Arg Asn
465                 470                 475                 480
Ile Glu Ala Thr Ile Lys His Tyr Ala Met Leu Thr Gln Pro Pro Tyr
                485                 490                 495
Met Leu Ser Gln Glu Gln Phe Leu Arg Leu Ile Asp His His Ser Gly
                500                 505                 510
His Leu Asn Leu Ser Ile Leu Leu Asp Glu Gln Gln Trp Gln Ala Ile
                515                 520                 525
Asn Asp Leu Cys Leu Gln Pro His His Phe Gly Arg Gln Asn Ala Leu
530                 535                 540
Glu Lys Phe Leu Gln Gly Gln Arg Lys Tyr Gln Asn Leu Gln Glu
545                 550                 555                 560
Leu Glu Gln Phe Leu Phe Gln Asp Ser Ala Asp Pro Met Leu Leu Gln
                565                 570                 575
Glu Thr Glu Asn Gln His Glu Ala Glu Lys Ile Asn Asp Cys Met Asp
                580                 585                 590
Phe Ile Leu Arg Leu Ile Ser Ala Thr Glu Pro Leu Asp Leu Gln Ile
                595                 600                 605
Glu Ile Glu Gly Ile Gly Leu Phe Ser Pro Ser Met His Phe Asp Ala
                610                 615                 620
Thr Gln Ala Asn Phe Ser Thr Pro Ala Ala Asn Glu Glu Lys Ile Asp
625                 630                 635                 640
Asn Ser Ala Thr Glu Ala Gly Val Asn Ser Arg Lys Arg Lys Ile Ala
                645                 650                 655
Ala Ala His Gln Lys Gln Pro Pro Arg Lys Lys Thr Ala Thr Pro Leu
                660                 665                 670
Ser Ala Thr Phe Ile Ser Thr Leu Thr Thr Leu Ala Gln Ser Asp Asn
                675                 680                 685
Pro Arg Leu Glu Met Ala Ser Ala Glu Ala Leu Met Leu Lys Ala Pro
690                 695                 700
Gln Lys Leu Ala Met Gly Ile Thr Val Arg Lys Lys Thr Lys Cys Glu
705                 710                 715                 720
Gly Ile Ala Ile Ile Thr Val Thr Asp Lys Thr Lys Leu Asn Gly Trp
                725                 730                 735
Leu Ser Ser Ala Ser Glu Ser Thr Tyr Ser Ser Val Glu Ala Gln Gly
                740                 745                 750
Thr Arg Thr Val Asn Asn Thr His Ala Phe Phe Ser Thr Pro Leu Thr
                755                 760                 765
Ser Asp Lys Lys Ser Pro Ser Phe Ser Ser Leu Asp Phe Tyr Glu Asp
770                 775                 780
Ser Gly Leu Gly Phe Asp Glu Glu Ile Thr Asn Pro Pro Tyr Met Pro
785                 790                 795                 800
Glu Leu Glu Pro Glu Phe Ile Leu
                805

<210> SEQ ID NO 144
<211> LENGTH: 99
<212> TYPE: PRT
<213> ORGANISM: Artificial sequence
<220> FEATURE:
<223> OTHER INFORMATION: synthetic sequence
```

<400> SEQUENCE: 144

Met Pro Lys Thr Asn Gln Pro Lys Asn Leu Glu Ala Lys Ser Thr Lys
1               5                   10                  15

Asn Lys Ile Ser Leu Pro Gln Asp Pro Gln Thr Leu Asn Glu Leu Lys
            20                  25                  30

Ile Lys Gly Tyr Pro Gln Asp Leu Ala Glu Arg Leu Ile Lys Lys Gly
        35                  40                  45

Ser Ser Leu Ala Val Lys Thr Val Leu Lys Asp His Glu Gln Leu Val
    50                  55                  60

Asn Phe Phe Thr His Leu Gln Ile Ile Arg Met Ala Ala Gln Lys Gly
65                  70                  75                  80

Gly Ala Lys Asn Ile Thr Thr Ala Leu Asn Glu Tyr Asn Ser Leu Thr
                85                  90                  95

Asn Leu Gly

<210> SEQ ID NO 145
<211> LENGTH: 313
<212> TYPE: PRT
<213> ORGANISM: Artificial sequence
<220> FEATURE:
<223> OTHER INFORMATION: synthetic sequence

<400> SEQUENCE: 145

Tyr Met Leu Ser Gln Glu Gln Phe Leu Arg Leu Ile Asp His His Ser
1               5                   10                  15

Gly His Leu Asn Leu Ser Ile Leu Leu Asp Glu Gln Gln Trp Gln Ala
            20                  25                  30

Ile Asn Asp Leu Cys Leu Gln Pro His His Phe Gly Arg Gln Asn Ala
        35                  40                  45

Leu Glu Lys Phe Leu Gln Gln Gly Gln Arg Lys Tyr Gln Asn Leu Gln
    50                  55                  60

Glu Leu Glu Gln Phe Leu Phe Gln Asp Ser Ala Asp Pro Met Leu Leu
65                  70                  75                  80

Gln Glu Thr Glu Asn Gln His Glu Ala Glu Lys Ile Asn Asp Cys Met
                85                  90                  95

Asp Phe Ile Leu Arg Leu Ile Ser Ala Thr Glu Pro Leu Asp Leu Gln
            100                 105                 110

Ile Glu Ile Glu Gly Ile Gly Leu Phe Ser Pro Ser Met His Phe Asp
        115                 120                 125

Ala Thr Gln Ala Asn Phe Ser Thr Pro Ala Ala Asn Glu Gly Lys Ile
    130                 135                 140

Asp Asn Ser Ala Thr Glu Ala Gly Val Asn Ser Arg Lys Arg Lys Ile
145                 150                 155                 160

Ala Ala Ala His Gln Lys Gln Pro Pro Arg Lys Lys Thr Ala Thr Pro
                165                 170                 175

Leu Ser Ala Thr Phe Ile Ser Thr Leu Thr Thr Leu Ala Gln Ser Asp
            180                 185                 190

Asn Pro Arg Leu Glu Met Ala Ser Ala Glu Ala Leu Met Leu Lys Ala
        195                 200                 205

Pro Gln Lys Leu Ala Met Gly Ile Thr Val Arg Lys Lys Thr Lys Cys
    210                 215                 220

Glu Gly Ile Ala Ile Ile Thr Val Thr Asp Lys Thr Lys Leu Asn Gly
225                 230                 235                 240

Trp Leu Ser Ser Ala Ser Glu Ser Thr Tyr Ser Ser Val Glu Ala Gln
                245                 250                 255

```
Gly Thr Arg Thr Val Asn Asn Thr His Ala Phe Phe Ser Thr Pro Leu
            260                 265                 270

Thr Ser Asp Lys Lys Ser Pro Ser Phe Ser Ser Leu Asp Phe Tyr Glu
        275                 280                 285

Asp Ser Gly Leu Gly Phe Asp Glu Glu Ile Thr Asn Pro Pro Tyr Met
    290                 295                 300

Pro Glu Leu Glu Pro Glu Phe Ile Leu
305             310
```

<210> SEQ ID NO 146
<211> LENGTH: 63
<212> TYPE: PRT
<213> ORGANISM: Artificial sequence
<220> FEATURE:
<223> OTHER INFORMATION: synthetic sequence

<400> SEQUENCE: 146

```
Tyr Met Leu Ser Gln Glu Gln Phe Leu Arg Leu Ile Asp His His Ser
1               5                   10                  15

Gly His Leu Asn Leu Ser Ile Leu Leu Asp Glu Gln Gln Trp Gln Ala
            20                  25                  30

Ile Asn Asp Leu Cys Leu Gln Pro His His Phe Gly Arg Gln Asn Ala
        35                  40                  45

Leu Glu Lys Phe Leu Gln Gln Gly Gln Arg Lys Tyr Gln Asn Leu
    50                  55                  60
```

<210> SEQ ID NO 147
<211> LENGTH: 1356
<212> TYPE: PRT
<213> ORGANISM: Francisella

<400> SEQUENCE: 147

Met Thr Leu Thr Leu Lys Gln Glu Lys Ile Ala Ile Asn Lys Lys Leu
1 5 10 15

Arg Ser Tyr Arg Thr Ser Lys Arg Lys Phe Leu Leu Asp Phe Ser Lys
20 25 30

Met Asn Leu Ser Pro Glu Gly Leu Asn Tyr Ala Gln Glu Glu Leu Ala
35 40 45

Lys Leu Gln Phe Gln Ala Lys Ala Ser Leu Glu Thr Asp Gln Gly Ile
50 55 60

Asn Ile Glu Glu Gln Leu Tyr Gln Leu Gly Tyr Thr Gln Ser His Leu
65 70 75 80

Arg Pro Cys Ala Asp Arg Tyr Asn Cys Ser Ile Leu Leu Asn Thr Leu
85 90 95

Leu Thr Asn Asn Asn Ser Phe Val Thr Gln Glu Ile Ser Leu Glu Asn
100 105 110

Arg Val Asn Leu Val Val Ala Ala Asn Gly Asn Asn Asp Gly Ile Gln
115 120 125

Val Phe Phe Lys Thr Tyr Pro Lys Leu Lys Ser Val Gly Tyr Lys Ile
130 135 140

Asn His Cys Val Asn Leu Leu Lys Leu Asn His Asp Gly Phe Met Leu
145 150 155 160

Lys Asn Leu Ile Pro Tyr Asp Ser Lys Leu Thr Gly Leu Gly Tyr Lys
165 170 175

Pro Glu Asp Ile Ile Arg Leu Ala Ser His Gly Gly Gly Ser Val Asn
180 185 190

-continued

```
Leu Glu Ala Val Leu Arg Leu Asn Pro Gln Leu Ile Gly Leu Gly Tyr
            195                 200                 205
Lys Ser Glu Asp Ile Ile Arg Leu Ala Ser His Asp Gly Gly Ser Val
        210                 215                 220
Asn Leu Glu Ala Val Leu Arg Leu His Ser Gln Leu Thr Arg Leu Gly
225                 230                 235                 240
Tyr Lys Ser Glu Asp Ile Ile Arg Leu Ala Ser His Gly Gly Gly Ser
                245                 250                 255
Val Asn Leu Glu Ala Val Leu Arg Leu His Ser Gln Leu Thr Arg Leu
            260                 265                 270
Gly Tyr Lys Ser Glu Asp Ile Ile Arg Leu Ala Ser His Gly Gly Gly
        275                 280                 285
Ser Val Asn Leu Glu Ala Val Leu Arg Leu Asn Pro Gln Leu Ile Gly
        290                 295                 300
Leu Gly Tyr Lys Ser Glu Asp Ile Ile Arg Leu Ala Ser His Gly Gly
305                 310                 315                 320
Gly Ser Val Asn Leu Glu Ala Val Leu Arg Leu His Ser Gln Leu Thr
                325                 330                 335
Arg Leu Gly Tyr Lys Ser Glu Asp Ile Ile Arg Leu Ala Ser His Gly
            340                 345                 350
Gly Gly Ser Val Asn Leu Glu Ala Val Leu Arg Leu Asn Pro Gln Leu
        355                 360                 365
Ile Gly Leu Gly Tyr Lys Ser Glu Asp Ile Ile Arg Leu Ala Ser His
        370                 375                 380
Gly Gly Gly Ser Val Asn Leu Glu Ala Val Leu Arg Leu His Ser Gln
385                 390                 395                 400
Leu Thr Arg Leu Gly Tyr Lys Ser Glu Asp Ile Ile Arg Leu Ala Ser
                405                 410                 415
His Gly Gly Gly Ser Val Asn Leu Glu Ala Val Leu Arg Leu Asn Pro
            420                 425                 430
Gln Leu Ile Gly Leu Gly Tyr Lys Ser Glu Asp Ile Ile Arg Leu Ala
        435                 440                 445
Ser His Asp Gly Gly Ser Val Asn Leu Glu Ala Val Leu Arg Leu Asn
        450                 455                 460
Pro Gln Leu Ile Gly Leu Gly Tyr Lys Ser Glu Asp Ile Ile Arg Leu
465                 470                 475                 480
Ala Ser His Asp Gly Ser Ile Asn Leu Glu Ala Val Leu Arg Leu
                485                 490                 495
Asn Pro Gln Leu Ile Gly Leu Gly Tyr Lys Ser Glu Asp Ile Ile Arg
            500                 505                 510
Leu Ala Ser Ser Asn Gly Gly Ser Val Asn Leu Glu Ala Val Leu Arg
        515                 520                 525
Leu Asn Pro Gln Leu Ile Gly Leu Gly Tyr Lys Ser Glu Asp Ile Ile
        530                 535                 540
Arg Leu Ala Ser Ser Asn Gly Gly Ser Val Asn Leu Glu Ala Val Leu
545                 550                 555                 560
Arg Leu Asn Pro Gln Leu Ile Gly Leu Gly Tyr Lys Ser Glu Asp Ile
                565                 570                 575
Ile Arg Leu Ala Ser His Asp Gly Gly Ser Val Asn Leu Glu Ala Val
            580                 585                 590
Leu Arg Leu His Ser Gln Leu Thr Arg Leu Gly Tyr Lys Ser Glu Asp
        595                 600                 605
Ile Ile Arg Leu Ala Ser Ser Asn Gly Gly Ser Val Asn Leu Glu Ala
```

-continued

```
                610                 615                 620
Val Ile Ala Val His Lys Ala Leu His Ser Asn Gly Tyr Asn Lys Lys
625                 630                 635                 640

Gln Ile Val Leu Ile Ala Ser Gly Ser Gly Gly Met Arg Leu His
                    645                 650                 655

Ala Leu Asn Asn Tyr His Phe Leu Phe His Ser Ile Glu Asn Ile Gln
                660                 665                 670

Leu Leu Ile Thr Ile Leu Gln Ser His Leu Glu Ala Phe Arg Ile Glu
                675                 680                 685

Gln Tyr Met Ile Ser Gly Val Leu Leu Asn Leu Leu Lys Gln Gly Gln
                690                 695                 700

Val Ile Ser Glu Gln Pro Cys Lys Ile Leu Ile Asp Ser Ser Ile Leu
705                 710                 715                 720

Asn Pro Asn Ile Cys Gln Thr Leu Ser Asn Ile Asn Lys Tyr Gln
                    725                 730                 735

Phe Lys Asn Lys Pro Leu Tyr Phe Asn Pro Thr Thr Ser Ile Ile Thr
                740                 745                 750

Cys Met Leu Ser Thr Gln Glu Cys Tyr Gln Leu Leu Ala Val Trp Glu
                755                 760                 765

Arg Arg Asn Ile Ser Pro Ser Glu Ile Leu Asn Asn Leu Leu Asn Pro
770                 775                 780

Ile Asn Ile Phe Gln Tyr Gln Leu Ile Ser Gln Thr Asn Glu Pro Asp
785                 790                 795                 800

Val Tyr Phe Leu Asp Cys Tyr His Trp His Lys Phe Tyr Pro Asn Met
                    805                 810                 815

Glu Ile Lys Gln Leu Gln Gln Leu Leu Ile Lys Ala Ile Asn Leu Gly
                820                 825                 830

Ile Asn Asn Cys Asp Ile Leu Pro Glu Asp Asn Arg Thr Leu Ile Ile
                835                 840                 845

Glu Pro Tyr Asn Asp Asn Trp Ile Lys Leu Ser Ile Ser Ile Ile Asp
850                 855                 860

Thr Ile Met Asp Asp Ser Phe Asn Asn Leu Thr Arg Glu Leu Phe Phe
865                 870                 875                 880

Cys Gln Leu Ala Pro Asp Ser Ser Asn Leu Ile Asp Asp Ala Ile Tyr
                885                 890                 895

Ile Tyr Lys Thr Gln Gln Thr Ile Glu Phe Leu Val Thr Ser Lys Ser
                900                 905                 910

Arg Ser Ser Glu Arg Phe Ile Leu Asp Thr Ser Thr Ile Tyr Lys Asp
                915                 920                 925

Thr Ile Glu Glu Ile Glu Gln Ala Leu Thr His Lys Leu Gly Ala Leu
930                 935                 940

Lys Gly Ala Thr Tyr His Thr Leu Ile Lys Cys Leu Leu Ala Gln Gly
945                 950                 955                 960

Tyr Gln Val Thr Gly Tyr Phe Ser Met Asn Ile Ile Gly Ala Asp Val
                    965                 970                 975

Met Pro Pro Thr Ile Ile Ala Asp Asp Tyr Pro Glu Tyr Ile Thr Leu
                980                 985                 990

Glu Trp Leu Ser Ser Glu Pro Met  Ser Gln Arg Ser Arg  Leu Arg Thr
                995                  1000                 1005

His Asp  Ile Asn Ser Ile Lys  Thr Leu His Asn Pro  Thr Pro Lys
    1010                 1015                 1020

Ser Gln  Ala Ile His Gln Met  Leu Asn Leu Leu Ala  Leu Pro Asp
    1025                 1030                 1035
```

Ala Ile Ser Pro Leu Asp Ser Ile Gln Asn Asn His Thr Ser Ala
        1040            1045                1050

Asn His Glu Gln Gln Thr Gln Gly Arg Ile Ser Pro Ile Ser Gln
        1055            1060                1065

Gln Leu Asp Ile Thr Leu Met Arg Ser Arg Lys Arg Pro Leu Gln
        1070            1075                1080

Lys Ser Asp Asn Thr Ile Tyr His Asp Lys Arg Tyr Trp Thr Phe
        1085            1090                1095

Ile Gly Glu Gly Ser Tyr Asn Lys Ala Tyr Thr Asp Gly Gln Gly
        1100            1105                1110

Phe Val Val Lys Val Ala Lys Asn Glu Leu Gly Leu Met Asp Lys
        1115            1120                1125

Ser Glu Arg Ser Val Arg Val Phe Asn Glu Ile Asn Pro Thr Leu
        1130            1135                1140

Pro Gln Glu Val Leu Ala His Val Ser Gln Asp Leu Trp Ile Ser
        1145            1150                1155

Pro Leu Ile Glu Asn Glu Thr Leu Ser Pro Ile Glu Gln Ala Ser
        1160            1165                1170

Phe Ile Phe Lys Thr Tyr Ile Glu His Gly Arg Leu Ile Leu Asp
        1175            1180                1185

Gly Tyr Cys Gln Asn Asn Leu Leu Gln Ser Ala Lys Tyr Asn Thr
        1190            1195                1200

Pro Val Cys Ile Asp Pro Gly Asn Val Val Arg Arg Asn Ser Ile
        1205            1210                1215

Ala Ser Gln Glu His Trp Tyr Ala Ala Asn Glu Lys Thr Leu Leu
        1220            1225                1230

Arg Arg Gln Leu Tyr Arg Lys His Met Ile Asp Thr Ile Asp His
        1235            1240                1245

Tyr His Lys Ile Arg His Ile Asp Arg Thr Leu Pro Ile Leu Met
        1250            1255                1260

Ile Leu Ala Leu Asp Phe Ile Asp Arg Lys Met Gln His Leu Gln
        1265            1270                1275

Leu Gln Leu Ile Leu Lys Lys Asn Ile Lys Ser Leu Gly Ile Ala
        1280            1285                1290

Phe Tyr Phe Tyr Lys His Asn Gln Ser Ser Thr Gln Gln Glu
        1295            1300                1305

Phe Ile Leu Ser Ala Asn Ile Ile Asp Lys Ile Leu Tyr Gly Asp
        1310            1315                1320

Gln Tyr Ile Cys Asp Thr Leu Asp Gln Ser Phe Lys Thr Leu Asn
        1325            1330                1335

Lys Ser Arg Val Val Thr Leu Phe Arg Gln Ile Asn Ile Asp Met
        1340            1345                1350

Ser Leu Ile
        1355

<210> SEQ ID NO 148
<211> LENGTH: 141
<212> TYPE: PRT
<213> ORGANISM: Artificial sequence
<220> FEATURE:
<223> OTHER INFORMATION: synthetic sequence

<400> SEQUENCE: 148

Met Thr Leu Thr Leu Lys Gln Glu Lys Ile Ala Ile Asn Lys Lys Leu
1               5                   10                  15

Arg Ser Tyr Arg Thr Ser Lys Arg Lys Phe Leu Leu Asp Phe Ser Lys
            20                  25                  30

Met Asn Leu Ser Pro Glu Gly Leu Asn Tyr Ala Gln Glu Leu Ala
        35                  40                  45

Lys Leu Gln Phe Gln Ala Lys Ala Ser Leu Glu Thr Asp Gln Gly Ile
    50                  55                  60

Asn Ile Glu Glu Gln Leu Tyr Gln Leu Gly Tyr Thr Gln Ser His Leu
65                  70                  75                  80

Arg Pro Cys Ala Asp Arg Tyr Asn Cys Ser Ile Leu Leu Asn Thr Leu
                85                  90                  95

Leu Thr Asn Asn Asn Ser Phe Val Thr Gln Glu Ile Ser Leu Glu Asn
                100                 105                 110

Arg Val Asn Leu Val Val Ala Ala Asn Gly Asn Asn Asp Gly Ile Gln
            115                 120                 125

Val Phe Phe Lys Thr Tyr Pro Lys Leu Lys Ser Val Gly
            130                 135                 140

<210> SEQ ID NO 149
<211> LENGTH: 704
<212> TYPE: PRT
<213> ORGANISM: Artificial sequence
<220> FEATURE:
<223> OTHER INFORMATION: synthetic sequence

<400> SEQUENCE: 149

Met Arg Leu His Ala Leu Asn Asn Tyr His Phe Leu Phe His Ser Ile
1               5                   10                  15

Glu Asn Ile Gln Leu Leu Ile Thr Ile Leu Gln Ser His Leu Glu Ala
            20                  25                  30

Phe Arg Ile Glu Gln Tyr Met Ile Ser Gly Val Leu Leu Asn Leu Leu
        35                  40                  45

Lys Gln Gly Gln Val Ile Ser Glu Gln Pro Cys Lys Ile Leu Ile Asp
    50                  55                  60

Ser Ser Ile Leu Asn Pro Asn Ile Cys Gln Thr Leu Ser Asn Ile Ile
65                  70                  75                  80

Asn Lys Tyr Gln Phe Lys Asn Lys Pro Leu Tyr Phe Asn Pro Thr Thr
                85                  90                  95

Ser Ile Ile Thr Cys Met Leu Ser Thr Gln Glu Cys Tyr Gln Leu Leu
                100                 105                 110

Ala Val Trp Glu Arg Arg Asn Ile Ser Pro Ser Glu Ile Leu Asn Asn
            115                 120                 125

Leu Leu Asn Pro Ile Asn Ile Phe Gln Tyr Gln Leu Ile Ser Gln Thr
    130                 135                 140

Asn Glu Pro Asp Val Tyr Phe Leu Asp Cys Tyr His Trp His Lys Phe
145                 150                 155                 160

Tyr Pro Asn Met Glu Ile Lys Gln Leu Gln Gln Leu Leu Ile Lys Ala
                165                 170                 175

Ile Asn Leu Gly Ile Asn Asn Cys Asp Ile Leu Pro Glu Asp Asn Arg
            180                 185                 190

Thr Leu Ile Ile Glu Pro Tyr Asn Asp Asn Trp Ile Lys Leu Ser Ile
        195                 200                 205

Ser Ile Ile Asp Thr Ile Met Asp Asp Ser Phe Asn Asn Leu Thr Arg
    210                 215                 220

Glu Leu Phe Phe Cys Gln Leu Ala Pro Asp Ser Ser Asn Leu Ile Asp
225                 230                 235                 240

-continued

```
Asp Ala Ile Tyr Ile Tyr Lys Thr Gln Gln Thr Ile Glu Phe Leu Val
                245                 250                 255
Thr Ser Lys Ser Arg Ser Ser Glu Arg Phe Ile Leu Asp Thr Ser Thr
            260                 265                 270
Ile Tyr Lys Asp Thr Ile Glu Glu Ile Glu Gln Ala Leu Thr His Lys
        275                 280                 285
Leu Gly Ala Leu Lys Gly Ala Thr Tyr His Thr Leu Ile Lys Cys Leu
    290                 295                 300
Leu Ala Gln Gly Tyr Gln Val Thr Gly Tyr Phe Ser Met Asn Ile Ile
305                 310                 315                 320
Gly Ala Asp Val Met Pro Pro Thr Ile Ala Asp Asp Tyr Pro Glu
                325                 330                 335
Tyr Ile Thr Leu Glu Trp Leu Ser Ser Glu Pro Met Ser Gln Arg Ser
            340                 345                 350
Arg Leu Arg Thr His Asp Ile Asn Ser Ile Lys Thr Leu His Asn Pro
        355                 360                 365
Thr Pro Lys Ser Gln Ala Ile His Gln Met Leu Asn Leu Leu Ala Leu
    370                 375                 380
Pro Asp Ala Ile Ser Pro Leu Asp Ser Ile Gln Asn Asn His Thr Ser
385                 390                 395                 400
Ala Asn His Glu Gln Gln Thr Gln Gly Arg Ile Ser Pro Ile Ser Gln
                405                 410                 415
Gln Leu Asp Ile Thr Leu Met Arg Ser Arg Lys Arg Pro Leu Gln Lys
            420                 425                 430
Ser Asp Asn Thr Ile Tyr His Asp Lys Arg Tyr Trp Thr Phe Ile Gly
        435                 440                 445
Glu Gly Ser Tyr Asn Lys Ala Tyr Thr Asp Gly Gln Gly Phe Val Val
    450                 455                 460
Lys Val Ala Lys Asn Glu Leu Gly Leu Met Asp Lys Ser Glu Arg Ser
465                 470                 475                 480
Val Arg Val Phe Asn Glu Ile Asn Pro Thr Leu Pro Gln Glu Val Leu
                485                 490                 495
Ala His Val Ser Gln Asp Leu Trp Ile Ser Pro Leu Ile Glu Asn Glu
            500                 505                 510
Thr Leu Ser Pro Ile Glu Gln Ala Ser Phe Ile Phe Lys Thr Tyr Ile
        515                 520                 525
Glu His Gly Arg Leu Ile Leu Asp Gly Tyr Cys Gln Asn Asn Leu Leu
    530                 535                 540
Gln Ser Ala Lys Tyr Asn Thr Pro Val Cys Ile Asp Pro Gly Asn Val
545                 550                 555                 560
Val Arg Arg Asn Ser Ile Ala Ser Gln Glu His Trp Tyr Ala Ala Asn
                565                 570                 575
Glu Lys Thr Leu Leu Arg Arg Gln Leu Tyr Arg Lys His Met Ile Asp
            580                 585                 590
Thr Ile Asp His Tyr His Lys Ile Arg His Ile Asp Arg Thr Leu Pro
        595                 600                 605
Ile Leu Met Ile Leu Ala Leu Asp Phe Ile Asp Arg Lys Met Gln His
    610                 615                 620
Leu Gln Leu Gln Leu Ile Leu Lys Lys Asn Ile Lys Ser Leu Gly Ile
625                 630                 635                 640
Ala Phe Tyr Phe Tyr Tyr Lys His Asn Gln Ser Ser Thr Gln Gln Glu
                645                 650                 655
```

```
Phe Ile Leu Ser Ala Asn Ile Ile Asp Lys Ile Leu Tyr Gly Asp Gln
                660                 665                 670

Tyr Ile Cys Asp Thr Leu Asp Gln Ser Phe Lys Thr Leu Asn Lys Ser
            675                 680                 685

Arg Val Val Thr Leu Phe Arg Gln Ile Asn Ile Asp Met Ser Leu Ile
        690                 695                 700

<210> SEQ ID NO 150
<211> LENGTH: 47
<212> TYPE: PRT
<213> ORGANISM: Artificial sequence
<220> FEATURE:
<223> OTHER INFORMATION: synthetic sequence

<400> SEQUENCE: 150

Met Arg Leu His Ala Leu Asn Asn Tyr His Phe Leu Phe His Ser Ile
1               5                   10                  15

Glu Asn Ile Gln Leu Leu Ile Thr Ile Leu Gln Ser His Leu Glu Ala
            20                  25                  30

Phe Arg Ile Glu Gln Tyr Met Ile Ser Gly Val Leu Leu Asn Leu
        35                  40                  45

<210> SEQ ID NO 151
<211> LENGTH: 33
<212> TYPE: PRT
<213> ORGANISM: Francisella

<400> SEQUENCE: 151

Tyr Lys Ile Asn His Cys Val As

```
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, V, or
      Y.
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: The amino acid may be A, F, I, L, M, T, V, or
      Y. The amino acid may be present or not present. When present, the
      amino acid may be any amino acid.
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (14)..(15)
<223> OTHER INFORMATION: The amino acids may be A, G, N, or S.
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: The amino acid may be A, F, I, L, M, T, V, or
      Y.
<220> FEATURE:
<221> NAME/KEY: misc_feature
<222> LOCATION: (20)..(29)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: The amino acid may be A, F, I, L, M, T, V, or
      Y.
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: The amino acid may be present or not present.
      When present, the amino acid is any amino acid.
<220> FEATURE:
<221> NAME/KEY: MISC_FEATURE
<222> LOCATION: (33)..(33)
<223> OTHER INFORMATION: The amino acid may be present or not present.
      When present, the amino acid is any amino acid.
<220> FEATURE:
<221> NAME/KEY: misc_feature
<222> LOCATION: (34)..(36)
<223> OTHER INFORMATION: Xaa can be any naturally occurring amino acid

<400> SEQUENCE: 153

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa
        35

<210> SEQ ID NO 154
<211> LENGTH: 33
<212> TYPE: PRT
<213> ORGANISM: Artificial sequence
<220> FEATURE:
<223> OTHER INFORMATION: synthetic sequence
```

-continued

```
<220> FEATURE:
<221> NAME/KEY: MISC_FEATURE
<222> LOCATION: (1)..(1)
<223> OTHER INFORMATION: The amino acid may be F, L, or Y.
<220> FEATURE:
<221> NAME/KEY: MISC_FEATURE
<222> LOCATION: (2)..(2)
<223> OTHER INFORMATION: The amino acid may be D, G, N, or S.
<220> FEATURE:
<221> NAME/KEY: MISC_FEATURE
<222> LOCATION: (3)..(3)
<223> OTHER INFORMATION: The amino acid may be A, H, R, S, T, or V.
<220> FEATURE:
<221> NAME/KEY: MISC_FEATURE
<222> LOCATION: (4)..(4)
<223> OTHER INFORMATION: The amino acid may be D, E, K, or Q.
<220> FEATURE:
<221> NAME/KEY: MISC_FEATURE
<222> LOCATION: (5)..(5)
<223> OTHER INFORMATION: The amino acid may be E or H or Q.
<220> FEATURE:
<221> NAME/KEY: MISC_FEATURE
<222> LOCATION: (6)..(6)
<223> OTHER INFORMATION: The amino acid may be I, L, or V.
<220> FEATURE:
<221> NAME/KEY: MISC_FEATURE
<222> LOCATION: (7)..(7)
<223> OTHER INFORMATION: The amino acid may be I, L, or V.
<220> FEATURE:
<221> NAME/KEY: MISC_FEATURE
<222> LOCATION: (8)..(8)
<223> OTHER INFORMATION: The amino acid may be C, H, K, R, or S.
<220> FEATURE:
<221> NAME/KEY: MISC_FEATURE
<222> LOCATION: (9)..(9)
<223> OTHER INFORMATION: The amino acid may be I, M, or V.
<220> FEATURE:
<221> NAME/KEY: MISC_FEATURE
<222> LOCATION: (10)..(10)
<223> OTHER INFORMATION: The amino acid may be A or V.
<220> FEATURE:
<221> NAME/KEY: MISC_FEATURE
<222> LOCATION: (11)..(11)
<223> OTHER INFORMATION: The amino acid may be A, G, or S.
<220> FEATURE:
<221> NAME/KEY: MISC_FEATURE
<222> LOCATION: (12)..(12)
<223> OTHER INFORMATION: The amino acid may be H, N, or R.
<220> FEATURE:
<221> NAME/KEY: MISC_FEATURE
<222> LOCATION: (13)..(13)
<223> OTHER INFORMATION: The amino acid may be A, D, G, I, K, N, S, or
      V.
<220> FEATURE:
<221> NAME/KEY: MISC_FEATURE
<222> LOCATION: (16)..(16)
<223> OTHER INFORMATION: The amino acid may be A, G, or S.
<220> FEATURE:
<221> NAME/KEY: MISC_FEATURE
<222> LOCATION: (17)..(17)
<223> OTHER INFORMATION: The amino acid may be H, K, L, N, or R.
<220> FEATURE:
<221> NAME/KEY: MISC_FEATURE
<222> LOCATION: (19)..(19)
<223> OTHER INFORMATION: The amino acid may be I or L.
<220> FEATURE:
<221> NAME/KEY: MISC_FEATURE
<222> LOCATION: (20)..(20)
<223> OTHER INFORMATION: The amino acid may be A, D, E, I, K, or V.
<220> FEATURE:
<221> NAME/KEY: MISC_FEATURE
<222> LOCATION: (21)..(21)
<223> OTHER INFORMATION: The amino acid may be A, L, or V.
<220> FEATURE:
<221> NAME/KEY: MISC_FEATURE
<222> LOCATION: (22)..(22)
<223> OTHER INFORMATION: The amino acid may be I, M, or V.
<220> FEATURE:
<221> NAME/KEY: MISC_FEATURE
```

```
<222> LOCATION: (23)..(23)
<223> OTHER INFORMATION: The amino acid may be K, L, Q, or T.
<220> FEATURE:
<221> NAME/KEY: MISC_FEATURE
<222> LOCATION: (24)..(24)
<223> OTHER INFORMATION: The amino acid may be A, D, E. K, L, Q, or S.
<220> FEATURE:
<221> NAME/KEY: MISC_FEATURE
<222> LOCATION: (25)..(25)
<223> OTHER INFORMATION: The amino acid may be A, C, F, N, V. or Y.
<220> FEATURE:
<221> NAME/KEY: MISC_FEATURE
<222> LOCATION: (26)..(26)
<223> OTHER INFORMATION: The amino acid may be F, H, L, Q, or Y.
<220> FEATURE:
<221> NAME/KEY: MISC_FEATURE
<222> LOCATION: (27)..(27)
<223> OTHER INFORMATION: The amino acid may be A, D, H, P, or Q.
<220> FEATURE:
<221> NAME/KEY: MISC_FEATURE
<222> LOCATION: (28)..(28)
<223> OTHER INFORMATION: The amino acid may be A, D, I, K, R, T, or V.
<220> FEATURE:
<221> NAME/KEY: MISC_FEATURE
<222> LOCATION: (29)..(29)
<223> OTHER INFORMATION: The amino acid may be F or L.
<220> FEATURE:
<221> NAME/KEY: MISC_FEATURE
<222> LOCATION: (30)..(30)
<223> OTHER INFORMATION: The amino acid may be K, M, Q, R, or S.
<220> FEATURE:
<221> NAME/KEY: MISC_FEATURE
<222> LOCATION: (31)..(31)
<223> OTHER INFORMATION: The amino acid may be D, E, N, or S.
<220> FEATURE:
<221> NAME/KEY: MISC_FEATURE
<222> LOCATION: (32)..(32)
<223> OTHER INFORMATION: The amino acid may be F, L, or M.
<220> FEATURE:
<221> NAME/KEY: MISC_FEATURE
<222> LOCATION: (33)..(33)
<223> OTHER INFORMATION: The amino acid may be D, E, G, H, K, or N.

<400> SEQUENCE: 154

Xaa Xaa Xaa Xaa Xaa Xaa Xaa Xaa Xaa Xaa Xaa Xaa Xaa Gly Gly Xaa
1               5                   10                  15

Xaa Asn Xaa Xaa Xaa Xaa Xaa Xaa Xaa Xaa Xaa Xaa Xaa Xaa Xaa Xaa
            20                  25                  30

Xaa

<210> SEQ ID NO 155
<211> LENGTH: 19
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (12)..(13)
<223> OTHER INFORMATION: The amino acid sequence from position 12 to 13
      may be HK, HD, HA, HN, HG, NN, NG, RN, HI, HV, RT, HD, SN, HS, GS,
      or LN.

<400> SEQUENCE: 155

Phe Asn Ala Glu Gln Ile Val Arg Met Val Ser Xaa Xaa Gly Gly Ser
1               5                   10                  15

Lys Asn Leu

<210> SEQ ID NO 156
<211> LENGTH: 33
<212> TYPE: PRT
<213> ORGANISM: Artificial sequence
```

```
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: The amino acid may be P or S.
<220> FEATURE:
<221> NAME/KEY: MISC_FEATURE
<222> LOCATION: (13)..(13)
<223> OTHER INFORMATION: The amino acid may be D or G.
<220> FEATURE:
<221> NAME/KEY: MISC_FEATURE
<222> LOCATION: (26)..(26)
<223> OTHER INFORMATION: The amino acid may be H or N.
<220> FEATURE:
<221> NAME/KEY: MISC_FEATURE
<222> LOCATION: (27)..(27)
<223> OTHER INFORMATION: The amino acid may be P or S.
<220> FEATURE:
<221> NAME/KEY: MISC_FEATURE
<222> LOCATION: (30)..(30)
<223> OTHER INFORMATION: The amino acid may be I ro T.
<220> FEATURE:
<221> NAME/KEY: MISC_FEATURE
<222> LOCATION: (31)..(31)
<223> OTHER INFORMATION: The amino acid may be G or R.

<400> SEQUENCE: 156

Tyr Lys Xaa Glu Asp Ile Ile Arg Leu Ala Ser His Xaa Gly Gly Ser
1               5                   10                  15

Val Asn Leu Glu Ala Val Leu Arg Leu Xaa Xaa Gln Leu Xaa Xaa Leu
            20                  25                  30

Gly

<210> SEQ ID NO 157
<211> LENGTH: 18
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be A, F, I, L, M, T, V, or
      Y.
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (6)..(7)
<223> OTHER INFORMATION: The amino acids may be A, F, I, L, M, T, V, or
      Y.
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: The amino acid may be A, F, I, L, M, T, V, or
      Y.
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: The amino acid may be present or not present.
      When present, the amino acid may be any amino acid.
<220> FEATURE:
<221> NAME/KEY: misc_feature
<222> LOCATION: (12)..(13)
```

-continued

```
<223> OTHER INFORMATION: Xaa can be any naturally occurring amino acid
<220> FEATURE:
<221> NAME/KEY: MISC_FEATURE
<222> LOCATION: (14)..(15)
<223> OTHER INFORMATION: The amino acid may be A, G, N, or S.
<220> FEATURE:
<221> NAME/KEY: misc_feature
<222> LOCATION: (16)..(18)
<223> OTHER INFORMATION: Xaa can be any naturally occurring amino acid

<400> SEQUENCE: 157

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 158
<211> LENGTH: 33
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: The amino acid may be F or L.
<220> FEATURE:
<221> NAME/KEY: MISC_FEATURE
<222> LOCATION: (2)..(2)
<223> OTHER INFORMATION: The amino acid may be N, S, or G.
<220> FEATURE:
<221> NAME/KEY: MISC_FEATURE
<222> LOCATION: (3)..(3)
<223> OTHER INFORMATION: The amino acid may be S, V, A, T, or H.
<220> FEATURE:
<221> NAME/KEY: MISC_FEATURE
<222> LOCATION: (4)..(4)
<223> OTHER INFORMATION: The amino acid may be E, Q, or K.
<220> FEATURE:
<221> NAME/KEY: MISC_FEATURE
<222> LOCATION: (5)..(5)
<223> OTHER INFORMATION: The amino acid may be Q or E.
<220> FEATURE:
<221> NAME/KEY: MISC_FEATURE
<222> LOCATION: (6)..(6)
<223> OTHER INFORMATION: The amino acid may be I or L.
<220> FEATURE:
<221> NAME/KEY: MISC_FEATURE
<222> LOCATION: (7)..(7)
<223> OTHER INFORMATION: The amino acid may be I or V.
<220> FEATURE:
<221> NAME/KEY: MISC_FEATURE
<222> LOCATION: (8)..(8)
<223> OTHER INFORMATION: The amino acid may be R, S, or K.
<220> FEATURE:
<221> NAME/KEY: MISC_FEATURE
<222> LOCATION: (9)..(9)
<223> OTHER INFORMATION: The amino acid may be M or I.
<220> FEATURE:
<221> NAME/KEY: MISC_FEATURE
<222> LOCATION: (10)..(10)
<223> OTHER INFORMATION: The amino acid may be V or A.
<220> FEATURE:
<221> NAME/KEY: MISC_FEATURE
<222> LOCATION: (11)..(11)
<223> OTHER INFORMATION: The amino acid may be S or A.
<220> FEATURE:
<221> NAME/KEY: MISC_FEATURE
<222> LOCATION: (12)..(13)
<223> OTHER INFORMATION: The amino acid sequence at positions 12 to 13
      may be HK, HD, HA, HN, HG, NN, NG, RN, HI, HV, RT, HD, SN, HS, GS,
      or LN.
<220> FEATURE:
<221> NAME/KEY: MISC_FEATURE
<222> LOCATION: (16)..(16)
<223> OTHER INFORMATION: The amino acid may be G, A, or S.
<220> FEATURE:
```

```
<221> NAME/KEY: MISC_FEATURE
<222> LOCATION: (17)..(17)
<223> OTHER INFORMATION: The amino acid may be L, K, or N.
<220> FEATURE:
<221> NAME/KEY: MISC_FEATURE
<222> LOCATION: (20)..(20)
<223> OTHER INFORMATION: The amino acid may be K or I.
<220> FEATURE:
<221> NAME/KEY: MISC_FEATURE
<222> LOCATION: (23)..(23)
<223> OTHER INFORMATION: The amino acid may be T, K, or L.
<220> FEATURE:
<221> NAME/KEY: MISC_FEATURE
<222> LOCATION: (24)..(24)
<223> OTHER INFORMATION: The amino acid may be A, D, K, or S.
<220> FEATURE:
<221> NAME/KEY: MISC_FEATURE
<222> LOCATION: (25)..(25)
<223> OTHER INFORMATION: The amino acid may be N, Y, or C.
<220> FEATURE:
<221> NAME/KEY: MISC_FEATURE
<222> LOCATION: (26)..(26)
<223> OTHER INFORMATION: The amino acid may be H or Y.
<220> FEATURE:
<221> NAME/KEY: MISC_FEATURE
<222> LOCATION: (27)..(27)
<223> OTHER INFORMATION: The amino acid may be D or K.
<220> FEATURE:
<221> NAME/KEY: MISC_FEATURE
<222> LOCATION: (28)..(28)
<223> OTHER INFORMATION: The amino acid may be D, A, or V.
<220> FEATURE:
<221> NAME/KEY: MISC_FEATURE
<222> LOCATION: (30)..(30)
<223> OTHER INFORMATION: The amino acid may be Q, K, or R.
<220> FEATURE:
<221> NAME/KEY: MISC_FEATURE
<222> LOCATION: (31)..(31)
<223> OTHER INFORMATION: The amino acid may be N, D, or E.
<220> FEATURE:
<221> NAME/KEY: MISC_FEATURE
<222> LOCATION: (32)..(32)
<223> OTHER INFORMATION: The amino acid may be M or R.
<220> FEATURE:
<221> NAME/KEY: MISC_FEATURE
<222> LOCATION: (33)..(33)
<223> OTHER INFORMATION: The amino acid may be G, K, or E.

<400> SEQUENCE: 158

Xaa Xaa Xaa Xaa Xaa Xaa Xaa Xaa Xaa Xaa Xaa Xaa Xaa Gly Gly Xaa
1               5                   10                  15

Xaa Asn Leu Xaa Ala Val Xaa Xaa Xaa Xaa Xaa Leu Xaa Xaa Xaa
            20                  25                  30

Xaa

<210> SEQ ID NO 159
<211> LENGTH: 162
<212> TYPE: PRT
<213> ORGANISM: Artificial sequence
<220> FEATURE:
<223> OTHER INFORMATION: synthetic sequence

<400> SEQUENCE: 159

Phe Thr Ala Asp Gln Ile Val Ala Leu Ile Cys Gln Ser Lys Gln Cys
1               5                   10                  15

Phe Arg Asn Leu Lys Lys Asn His Gln Gln Trp Lys Asn Lys Gly Leu
            20                  25                  30

Ser Ala Glu Gln Ile Val Asp Leu Ile Leu Gln Glu Thr Pro Pro Lys
        35                  40                  45

Pro Asn Phe Asn Asn Thr Ser Ser Ser Thr Pro Ser Pro Ser Ala Pro
    50                  55                  60
```

```
Ser Phe Phe Gln Gly Pro Ser Thr Pro Ile Pro Thr Pro Val Leu Asp
 65              70                  75                  80

Asn Ser Pro Ala Pro Ile Phe Ser Asn Pro Val Cys Phe Phe Ser Ser
             85                  90                  95

Arg Ser Glu Asn Asn Thr Glu Gln Tyr Leu Gln Asp Ser Thr Leu Asp
            100                 105             110

Leu Asp Ser Gln Leu Gly Asp Pro Thr Lys Asn Phe Asn Val Asn Asn
        115                 120                 125

Phe Trp Ser Leu Phe Pro Phe Asp Asp Val Gly Tyr His Pro His Ser
    130                 135             140

Asn Asp Val Gly Tyr His Leu His Ser Asp Glu Glu Ser Pro Phe Phe
145                 150             155             160

Asp Phe
```

# ANIMAL PATHOGEN-DERIVED POLYPEPTIDES AND USES THEREOF FOR GENETIC ENGINEERING

CROSS-REFERENCE TO RELATED APPLICATIONS

This application claims priority pursuant to 35 U.S.C. § 119(e) to U.S. Provisional Application No. 62/659,656, filed Apr. 18, 2018, U.S. Provisional Application No. 62/690,905, filed Jun. 27, 2018, U.S. Provisional Application No. 62/716,223, filed Aug. 8, 2018, U.S. Provisional Application No. 62/738,825, filed Sep. 28, 2018, and U.S. Provisional Application No. 62/819,237, filed Mar. 15, 2019, the disclosures of which are incorporated herein by reference in its entirety.

INCORPORATION BY REFERENCE OF SEQUENCE LISTING PROVIDED AS A TEXT FILE

A Sequence Listing is provided herewith as a text file, "ALTI-720WO Seq List_ST25.txt," created on Apr. 18, 2019 and having a size of 240 KB. The contents of the text file are incorporated by reference herein in their entirety.

INTRODUCTION

Genome editing and gene regulation techniques include the use of nucleic acid binding domains that bind to a target nucleic acid. Nucleic acid binding domains include RNA-guided domains as used in CRISPR-Cas9 mediated-gene editing and protein-only domains such as zinc-finger proteins, TALE proteins, and meganucleases. Due to the importance of genome engineering in applications in a wide variety of areas, including therapeutics, there is a need for nucleic acid binding domains that have desirable features such as ease of production, target specificity, and versatility.

SUMMARY

Provided herein are polypeptides, compositions thereof, and methods for genetic and epigenomic engineering, including, genome editing and gene regulation using the polypeptides and compositions, where polypeptides include a nucleic acid binding domain derived from nucleic acid binding proteins identified in animal pathogens, such as a bacterium from the order Legionellales or the genus *Legionella* or *Francisella*.

In various aspects, the present disclosure provides a composition comprising a non-naturally occurring modular nucleic acid binding domain derived from an animal pathogen protein (MAP-NBD), wherein the MAP-NBD comprises a plurality of repeat units and wherein a repeat unit (RU) of the plurality of repeat units (RUs) recognizes a base in a target nucleic acid. In some aspects, the animal pathogen protein is derived from a bacterium that infects animals. In some aspects, the animal pathogen protein is derived from a bacterium that infects humans. In some aspects, the bacterium is selected from the order Legionellales or the genus of *Legionella* or *Francisella*. In certain aspects, the bacterium is *Legionella quateirensis* (*L. quateirensis*) or *Legionella maceachernii* (*L. maceachernii*). In some aspects, the repeat unit comprises a consensus sequence of 1xxx211x1xxx33x2x1xxxxxxxxx1 (SEQ ID NO: 19).

In some aspects, the target nucleic acid is a single nucleotide or a single base pair. In some aspects, the target nucleic acid is DNA or RNA. In some aspects, the NBD includes at least three RUs, wherein each RU binds to a base in the target nucleic acid and wherein the target nucleic acid is at least three nucleotides in length. In further aspects, the target nucleic acid sequence is DNA or RNA that is at least three nucleotides in length.

In certain aspects, the present disclosure provides a recombinant polypeptide comprising a nucleic acid binding domain (NBD) and a heterologous functional domain, the NBD comprising at least three repeat units (RUs) ordered from N-terminus to C-terminus of the NBD to specifically bind to a target nucleic acid, each of the RUs of the NBD comprising the consensus sequence: 1xxxx11x12xx33xxx1xxxxxxxxxx14xxx (SEQ ID NO:153), where 1=A, F, I, L, M, T, V, or Y; 2=x or xx; 3=A, G, N, or S; 4=x, xx, or xxx; and x=any amino acid, and where each of the RUs independently comprises a 33-36 amino acid long sequence that is at least 70% identical to the amino acid sequence set forth in one of SEQ ID NOs: 2-9, 23-35, 85-89, and 131-137, where SEQ ID NOs: 2-9, 33, and 89 provide amino acid sequences of RUs identified in a *L. quateirensis* bacterium protein (SEQ ID NO:1), where SEQ ID NOs: 23-32, 34-35, and 133 provide amino acid sequences of RUs identified in a *L. maceachernii* bacterium protein (SEQ ID NO: 143), where SEQ ID NOs: 25, 131-132, and 138 provide amino acid sequences of RUs identified in a protein (SEQ ID NO: 139) from a bacterium of the order Legionellales, and where SEQ ID NOs: 85-88, 134-137, and 151 provide amino acid sequences of RUs identified in a protein (SEQ ID NO: 147) from a bacterium of the genus *Francisella*. In certain aspects, the NBD further comprises a half-repeat unit.

In certain aspects, the present disclosure provides a recombinant polypeptide comprising a nucleic acid binding domain (NBD) and a heterologous functional domain, the NBD comprising at least three repeat units (RUs) ordered from N-terminus to C-terminus of the NBD to specifically bind to a target nucleic acid, each of the RUs of the NBD comprising the consensus sequence: (F/L/Y)(D/G/N/S)(A/H/R/S/T/V)(D/E/K/Q)(E/H/Q)(I/L/V)(I/L/V)(C/H/K/R/S)(I/M/V)(A/V)(A/G/S) (H/N/R)(A/D/G/I/K/N/S/V)(G)(G)(A/G/S)(H/K/L/N/R)(N)(I/L)(A/D/E/I/K/V)(A/L/V)(I/M/V)(K/L/Q/T)(A/D/E/K/L/Q/S)(A/C/F/N/V/Y)(F/H/L/Q/Y)(A/D/H/P/Q)(A/D/I/K/R/T/V)(F/L)(K/M/Q/R/S)(D/E/N/S)(F/L/M)(D/E/G/H/K/N) (SEQ ID NO: 154), where the consensus sequence is based upon the amino acid sequences of RUs identified in proteins from a bacterium of the order Legionellales, a *L. quateirensis* bacterium, and a *L. maceachernii* bacterium.

In certain aspects, the present disclosure provides a recombinant polypeptide comprising a nucleic acid binding domain (NBD) and a heterologous functional domain, the NBD comprising at least three repeat units (RUs) ordered from N-terminus to C-terminus of the NBD to specifically bind to a target nucleic acid, each of the RUs of the NBD comprising the consensus sequence: YK(P/S)EDIIRLASH(D/G)GGSVNLEAVLRL(H/N)(P/S)QL(I/T)(G/R)LG (SEQ ID NO:156), where the consensus sequence is based upon the amino acid sequences of RUs identified in a protein from a *Francisella* species bacterium.

In certain aspects, the present disclosure provides a recombinant polypeptide comprising a nucleic acid binding domain (NBD) and a heterologous functional domain, the NBD comprising at least three repeat units (RUs) ordered from N-terminus to C-terminus of the NBD to specifically bind to a target nucleic acid, each of the RUs of the NBD comprising the consensus sequence: (F/L)(N/S/G)(S/V/A/T/

H)(E/Q/K)(Q/E)(I/L)(I/V)(R/S/K)(M/I)(V/A)(S/A) $X_{12}X_{13}$GG(G/A/S)(L/K/N) NL(K/I)AV(T/K/L)(A/D/K/S) (N/Y/C)(H/Y)(D/K)(D/A/V)L(Q/K/R)(N/D/E)(M/R)(G/K/ E) (SEQ ID NO:158), where $X_{12}X_{13}$=HK, HD, HA, HN, HG, NN, NG, RN, HI, HV, RT, HD, SN, HS, GS, or LN and where the consensus sequence is based upon the amino acid sequences of RUs identified in a protein from a *L. quateirensis* bacterium.

In certain aspects, the last RU in the NBD may be a half-repeat that is 15-20 amino acids long and comprises the consensus sequence: 1xxxx11x12xx33x (SEQ ID NO: 157), where 1=A, F, I, L, M, T, V, or Y; 2=x or xx; 3=A, G, N, or S; 4=x, xx, or xxx; and x=any amino acid.

In some aspects, the target nucleic acid is at least three nucleotides in length. In further aspects, the target nucleic acid sequence is DNA or RNA that is at least three nucleotides in length.

In certain aspects, the $12^{th}$ and $13^{th}$ amino acid residues in a repeat unit are designated as base-contacting residues (BCR) that determine the base (A, G, T, or C) to which the repeat unit binds. In certain aspects, the BCR in a repeat unit as provided herein may be replaced with BCR as disclosed herein or by a RVD thereby changing the base to which the repeat unit binds. In certain aspects, the BCR in a repeat unit as provided herein may be replaced with BCR identified in a repeat from a *Legionella* protein (e.g., SEQ ID NO: 1 or 143). In certain aspects, the BCR in a repeat unit as provided herein may be replaced with BCR identified in a repeat from a Legionellales protein (e.g., SEQ ID NO:139). In certain aspects, the BCR in a repeat unit as provided herein may be replaced with BCR identified in a repeat from a *Francisella* protein (e.g., SEQ ID NO:147). In certain aspects, the BCR in a repeat unit as provided herein may be replaced with BCR listed in Table 1 herein.

In some aspects, a naturally occurring or non-naturally occurring linker is positioned between the NBD and the functional domain. In some aspects, the functional domain comprises an enzyme, a transcriptional activation domain, a transcriptional repression domain, a biotinylation reagent, a DNA nucleotide modifier, or a fluorophore. In further aspects, the enzyme is a nuclease, a DNA modifying protein, or a chromatin modifying protein.

In further aspects, the nuclease is a cleavage domain or a half-cleavage domain. In still some aspects, the cleavage domain or half-cleavage domain comprises a type IIS restriction enzyme. In further aspects, the type IIS restriction enzyme comprises FokI or Bfil. In some aspects, FokI has at least 70%, at least 75%, at least 80%, at least 85%, at least 90%, at least 92%, at least 95%, at least 97%, or at least 99% sequence identity to SEQ ID NO: 11. In some aspects, FokI has a sequence of SEQ ID NO: 11.

In some aspects, the chromatin modifying protein is lysine-specific histone demethylase 1 (LSD1). In some aspects, the transcriptional activation domain comprises VP16, VP64, p65, p300 catalytic domain, TET1 catalytic domain, TDG, Ldb1 self-associated domain, SAM activator (VP64, p65, HSF1), VPR (VP64, p65, Rta). In some aspects, the transcriptional repressor domain comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2. In some aspects, the DNA nucleotide modifier is adenosine deaminase.

In some aspects, the functional domain enables genome editing, gene regulation, or imaging at the genomic locus comprising the target nucleic acid bound by the modular nucleic acid binding domain comprising the RUs as described herein. In some aspects, each of the repeat units has at least 70%, at least 75%, at least 80%, at least 85%, at least 90%, at least 92%, at least 94%, at least 95%, at least 96%, at least 98%, or at least 99% sequence identity to any one of SEQ ID NOs: 2-10, 23-35, 85-89, 131-137, and. In further aspects, the repeat unit has the amino acid sequence of any one of SEQ ID NOs: 2-10, 23-35, 85-89, 131-138, and 151-152.

In some aspects, the RU is derived from a wild-type protein from an animal pathogen. In some aspects, the RU comprises a modification of a wild-type protein. In some aspects, the modification enhances specific recognition of a target nucleotide, base pair, or both. In some aspects, the modification comprises 1 to 29 modifications. In further aspects, the animal pathogen protein has at least 70%, at least 75%, at least 80%, at least 85%, at least 90%, at least 92%, at least 95%, at least 97%, or at least 99% sequence identity to SEQ ID NO: 1. In some aspects, the animal pathogen protein is SEQ ID NO: 1.

In further aspects, the NBD includes 3-40 RUs, e.g., 3-35, 3-30, 4-35, 4-30, 5-35, 5-30, 6-30, 7-30, 8-30, 9-30, 10-30, 10-28, or 10-25 RUs. In certain aspects, the NBD binds to a target nucleic acid that is at least 3 nucleotides long, e.g., 3-35, 3-30, 4-35, 4-30, 5-35, 5-30, 6-30, 7-30, 8-30, 9-30, 10-30, 10-28, or 10-25 nucleotides long.

In further aspects, the target nucleic acid is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, an IL2RG gene, or a combination thereof. In other aspects, a chimeric antigen receptor (CAR), alpha-L iduronidase (IDUA), iduronate-2-sulfatase (IDS), or Factor 9 (F9), is inserted upon cleavage of a region of the target nucleic acid sequence.

In various aspects, the present disclosure provides a method of genome editing in a subject, wherein the method comprises: administering a non-naturally occurring modular nucleic acid binding domain comprising a functional domain, wherein the functional domain comprises a cleavage domain or a cleavage half domain; and inducing a double stranded break, wherein the modular nucleic acid binding domain comprises a modular nucleic acid binding domain derived from an animal pathogen protein (MAP-NBD), wherein the MAP-NBD comprises a plurality of repeat units and wherein the plurality of repeat units recognizes a target nucleic acid.

In some aspect, the method further comprises a second MAP-NBD wherein the second MAP-NBD comprises a second plurality of repeat units that recognizes a second target nucleic acid. In some aspects, the MAP-NBD, the second MAP-NBD, or both further comprise a functional domain, e.g., a cleavage domain or a cleavage half domain. In further aspects, the cleavage domain or the cleavage half domain comprises FokI or Bfil. In some aspects, the cleavage domain comprises a meganuclease.

In further aspects, FokI has at least 70%, at least 75%, at least 80%, at least 85%, at least 90%, at least 92%, at least 95%, at least 97%, or at least 99% sequence identity to SEQ ID NO: 11. In still further aspects, FokI has a sequence of SEQ ID NO: 11. In further aspects, the target nucleic acid sequence is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, an IL2RG gene, or a combination thereof. In other aspects, a chimeric antigen receptor (CAR), alpha-L iduronidase (IDUA), iduronate-2-sulfatase (IDS), or Factor 9 (F9), is inserted upon cleavage of a region of the target nucleic acid sequence.

In various aspects, the present disclosure provides a method of gene regulation in a subject, wherein the method comprises: administering a non-naturally occurring modular nucleic acid binding domain; and regulating expression of a gene, wherein the modular nucleic acid binding domain comprises a modular DNA binding domain derived from an animal pathogen protein (MAP-NBD) and wherein the MAP-NBD comprises a plurality of repeat units and wherein a repeat unit of the plurality of repeat units recognizes a target nucleic acid.

In further aspects, the MAP-NBD further comprises a functional domain. In some aspects, the functional domain comprises a transcriptional activation domain or a transcriptional repression domain. In some aspects, the activation domain comprises VP16, VP64, p65, p300 catalytic domain, TET1 catalytic domain, TDG, Ldb1 self-associated domain, SAM activator (VP64, p65, HSF1), VPR (VP64, p65, Rta). In some aspects, the repressor domain comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2.

In some aspects, the target nucleic acid sequence is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, or a combination thereof.

In various aspects, the present disclosure provides a method of imaging a genomic locus in vivo in a subject, wherein the method comprises: administering to the subject a non-naturally occurring modular nucleic acid binding domain conjugated to an imaging agent; and imaging the subject, wherein the modular nucleic acid binding domain comprises a modular DNA binding domain derived from an animal pathogen protein (MAP-NBD) and wherein the MAP-NBD comprises a plurality of repeat units that recognizes a target nucleic acid. In some aspects, the imaging agent is a fluorescent moiety. In some aspects, the fluorescent moiety is GFP or mCHERRY. In some aspects, the target nucleic acid is a single nucleotide, a single base pair, or both. In some aspects, the target nucleic acid is DNA or RNA. In some aspects, the MAP-NBD recognizes a target nucleic acid sequence. In some aspects, the MAP-NBD binds the target nucleic acid sequence. In some aspects, the target nucleic acid sequence is DNA or RNA. In some aspects, the composition further comprises a linker between the MAP-NBD and the functional domain. In some aspects, the animal pathogen protein is derived from a bacterium. In further aspects, the bacterium is selected from the genus of Legionella. In some aspects, the bacterium is L. quateirensis. In some aspects, the repeat unit comprises a consensus sequence of 1xxx211x1xxx33x2x1xxxxxxxxx1 (SEQ ID NO: 19).

In some aspects, the repeat unit has at least 70%, at least 75%, at least 80%, at least 85%, at least 90%, at least 92%, at least 95%, at least 97%, or at least 99% sequence identity to any one of SEQ ID NOs: 2-10, 23-35, 85-89, and 131-137. In some aspects, the repeat unit has the amino acid sequence of any one of SEQ ID NOs: 2-9, 23-35, 85-89, 131-138 or 151.

In some aspects, the repeat unit is derived from a wild-type protein. In some aspects, the repeat unit comprises a modification of a wild-type protein. In some aspects, the modification enhances specific recognition of a target nucleotide. In some aspects, the modification comprises 1 to 29 modifications. In some aspects, the animal pathogen protein has at least 70%, at least 75%, at least 80%, at least 85%, at least 90%, at least 92%, at least 95%, at least 97%, or at least 99% sequence identity to SEQ ID NO: 1. In further aspects, the animal pathogen protein is SEQ ID NO: 1. In some aspects, the genomic locus is in a cell. In some aspects, the cell is in a plurality of cells ex vivo, in a human, or in a non-human animal.

A method for producing a polypeptide that specifically binds to a target DNA sequence is disclosed. The method included synthesizing a polypeptide comprising a DNA binding domain (DBD) that specifically binds to the target sequence, where the DBD comprises repeat units that are selected based on the DNA base bound by the repeat unit and combined in the appropriate order to match the target DNA sequence, where when the target sequence includes an adenine (A), the repeat unit comprises a 33-35 amino acid long sequence that is at least 70% identical to FSSQQIIRMVSHAGGANNLKAVTANHDDLQNMG (SEQ ID NO:2), or LGHKELIKIAARNGGGNNLIA-VLSCYAKLKEMG (SEQ ID NO:89), or comprises the sequence of SEQ ID NO:2 or SEQ ID NO:89 comprising conservative amino acid substitutions; when the target sequence includes a thymine (T), the repeat unit comprises a 33-35 amino acid long sequence that is at least 70% identical to: FNAEQIVRMVSHGGGSKNLKAVTDNHD-DLKNMG (SEQ ID NO:4); FNAEQI-VSMVSNGGGSLNLKAVKKYHDALKDRG (SEQ ID NO:6); or FNVEQIV-SIVSHGGGSLNLKAVKKYHDVLKDRE (SEQ ID NO:8), or comprises the sequence of SEQ ID NOs:4, 6, or 8 comprising conservative amino acid substitutions; when the target sequence includes a cytosine (C), the repeat unit comprises a 33-35 amino acid long sequence that is at least 70% identical to: FNTEQI-VRMVSHDGGSLNLKAVKKYHDALRERK (SEQ ID NO:7); or FNAEQIVRMVSHDGGSLNLKAVTDNHD-DLKNMG (SEQ ID NO:9), or comprises the sequence of SEQ ID NOs:7 or 9 comprising conservative amino acid substitutions; when the target sequence includes a guanine (G), the repeat unit comprises a 33-35 amino acid long sequence that is at least 70% identical to: FNVEQI-VRMVSHNGGSKNLKAVTDNHDDLKNMG (SEQ ID NO:3); FNAEQIVSMVSNNGGSKNLKAVTDNHD-DLKNMG (SEQ ID NO:5); FNAEQIVRMVSHKGGSKN-LALVKEYFPVFSSFH (SEQ ID NO:33); or LGHKELIKI-AARNGGGNNLIAVLSCYAKLKEMG (SEQ ID NO:89), or comprises the sequence of SEQ ID NOs:3, 5, 33, or 89 comprising conservative amino acid substitutions.

An additional method for producing a polypeptide that specifically binds to a target DNA sequence is disclosed. The method includes synthesizing a polypeptide comprising a DNA binding domain (DBD) that specifically binds to the target sequence, wherein the DBD comprises repeat units that are selected based on the DNA base bound by the repeat unit and combined in the appropriate order to match the target DNA sequence, where: when the target sequence includes an adenine (A), the repeat unit comprises a 33-35 amino acid long sequence that is at least 70% identical to FSAKHIVRIAAHIGGSLNIKAVQQAQQALKELG (SEQ ID NO:32), FSAEQIVSIAAHVGGSHNIEAVQKAHQALKELD (SEQ ID NO:35), FSAEQIVRIAAHIGGSHNLKAVLQAQQALKELD (SEQ ID NO:31), or FSAEQIVRIAAHIGGSRNIEATIKHYAMLTQPP (SEQ ID NO:133), or comprises the sequence of SEQ ID NOs:32, 36, 31, or 133 comprising conservative amino acid substitutions; when the target sequence includes a thymine (T), the repeat unit comprises a 33-35 amino acid long sequence that is at least 70% identical to: YSSEQIVRVAAHGGGSLNIKAVLQAHQALKELD (SEQ ID NO:28), FSAEQIVHIAAHGGGSLNIKAILQAHQTLKELN (SEQ ID NO:29), FSTEQIVCIAGHGGGSLNIKAVLLAQQALKDLG (SEQ ID NO:27), FSAEQIVSIAAHVGGSHNIEAVQKAHQALKELD (SEQ ID NO:35), or FSAEQIVRIAAHIGGSRNIEATIKHYAMLTQPP (SEQ ID NO:133), or comprises the sequence of SEQ ID NOs:28, 29, 27, 35, or 133 comprising conservative amino acid substitutions; when the target sequence includes a cytosine (C), the repeat unit comprises a 33-35 amino acid long sequence that is at least 70% identical to: FSAEQIVSIVAHDGGSRNIEAVQQAQHILKELG (SEQ ID NO:24), FSAEQIVRIAAHDGGSLNIDAVQQAQQALKELG (SEQ ID NO:26), or FSAEQIVRIAAHIGGSHNLKAVLQAQQALKELD (SEQ ID NO:31), or comprises the sequence of SEQ ID NOs:24, 26, or 31 comprising conservative amino acid substitutions; when the target sequence includes a guanine (G), the repeat unit comprises a 33-35 amino acid long sequence that is at least 70% identical to: FSAEQIVRIAAHIGGSRNIEAIQQAHHALKELG (SEQ ID NO:30), FSADQIVRIAAHKGGSHNIVAVQQAQQALKELD (SEQ ID NO:34), FSAEQIVSIAAHVGGSHNIEAVQKAHQALKELD (SEQ ID NO:35), or FSAEQIVRIAAHIGGSRNIEATIKHYAMLTQPP (SEQ ID NO:133), or comprises the sequence of SEQ ID NOs:30, 34, 35, or 133 comprising conservative amino acid substitutions.

In certain aspects of the method, the DBD may include any of the repeat units disclosed herein, for example, a DBD may include repeat units derived from different *Legionella* proteins as provided herein. The target sequence may be in a promoter region or the open reading frame of a gene of interest. The DBD may be conjugated to a functional domain, as provided herein.

BRIEF DESCRIPTION OF THE DRAWINGS

FIG. 1 is a schematic of an embodiment of a polypeptide disclosed herein, comprising a nucleic acid binding domain (NBD) made of a plurality of repeat units. Each repeat unit has the consensus sequence 1xxxx11x12xx33xxx1xxxxxxxxxx14xxx (SEQ ID NO:153). The last repeat unit is a half-repeat having a length of 15-20 amino acids. The NBD is flanked by an N-terminal domain and a C-terminal domain.

FIG. 2 illustrates a protein from *L. quateirensis* from which nucleic acid binding repeat domains can be derived. SEQ ID NO: 1 provides the amino acid sequence of the full protein which contains repeats units (RU) having sequences set forth in SEQ ID NOs: 89 and 2-SEQ ID NO: 10. The amino acid sequence set forth in SEQ ID NO: 89 extends from the residue at position 144 to the residue at position 176 of SEQ ID NO:1. The amino acid sequence set forth in SEQ ID NO: 2 extends from the residue at position 177 to the residue at position 209 of SEQ ID NO:1. The amino acid sequence set forth in SEQ ID NO: 3 extends from the residue at position 210 to the residue at position 242 of SEQ ID NO:1. The amino acid sequence set forth in SEQ ID NO: 4 extends from the residue at position 243 to the residue at position 275 of SEQ ID NO:1. The amino acid sequence set forth in SEQ ID NO: 5 extends from the residue at position 276 to the residue at position 308 of SEQ ID NO:1. The amino acid sequence set forth in SEQ ID NO: 6 extends from the residue at position 309 to the residue at position 341 of SEQ ID NO:1. The amino acid sequence set forth in SEQ ID NO: 7 extends from the residue at position 342 to the residue at position 374 of SEQ ID NO:1. The amino acid sequence set forth in SEQ ID NO: 8 extends from the residue at position 375 to the residue at position 407 of SEQ ID NO:1. The amino acid sequence set forth in SEQ ID NO: 9 extends from the residue at position 408 to the residue at position 440 of SEQ ID NO:1. The amino acid sequence set forth in SEQ ID NO: 10 extends from the residue at position 441 to the residue at position 459 of SEQ ID NO:1. The RU having the amino acid sequence of SEQ ID NO:10 is a half-repeat unit.

FIG. 3A shows consensus sequences of SEQ ID NO: 14-SEQ ID NO: 18 that can be present in an animal pathogen-derived protein. Each consensus sequence of SEQ ID NO: 14-SEQ ID NO: 18 includes a repeat motif, followed by a spacer of variable length, and a second repeat motif.

FIG. 3B shows a consensus sequence of SEQ ID NO: 19, which can be present in a repeat domain (e.g., a MAP-NBD) of the present disclosure.

FIG. 4A illustrates the bases to which the repeats (SEQ ID NOs:89 and 2-10 ordered from N-terminus to C-terminus) in a polypeptide having the amino acid sequence set forth in SEQ ID NO:1 can bind. The polypeptide having the amino acid sequence set forth in SEQ ID NO:1 was fused to a His-tag. The larger the size the of the base at a particular position, the higher the relative frequency at which the base is present at that position in a nucleic acid bound by the tested polypeptide.

FIG. 4B illustrates the bases to which the repeats (from N-terminus to C-terminus: SEQ ID NOs:89 and 2-10) in a polypeptide having the amino acid sequence set forth in SEQ ID NO:1 can bind. The polypeptide having the amino acid sequence set forth in SEQ ID NO:1 was fused to a HA-tag. The larger the size the of the base at a particular position, the higher the relative frequency at which the base is present at that position in a nucleic acid bound by the tested polypeptide. Both the His-tagged polypeptide and the HA-tagged polypeptide showed the same binding specificity.

FIG. 5 summarizes the BCR present in repeat units having the amino acid sequence set forth in SEQ ID NOs:89 and 2-10, respectively and the corresponding base to which the repeat unit bind.

FIG. 6 shows that while most of the BCRs in the repeats units derived from *L. quateirensis* show specificity for the same base as RVDs in the repeats from *Xanthomonas* as reported in Miller et al. Nature Methods, 12(5), 465-471, 2015, the BCR "HA" in a *L. quateirensis* derived repeat having the sequence of SEQ ID NO:2 specify binding to "A" rather than binding to "T" as observed for the repeat containing the RVD HA from *Xanthomonas.*

FIG. 7 provides the amino acid sequence (SEQ ID NO:139) of a protein from a Legionellales bacterium. The protein includes four repeat units.

Figure 8A:
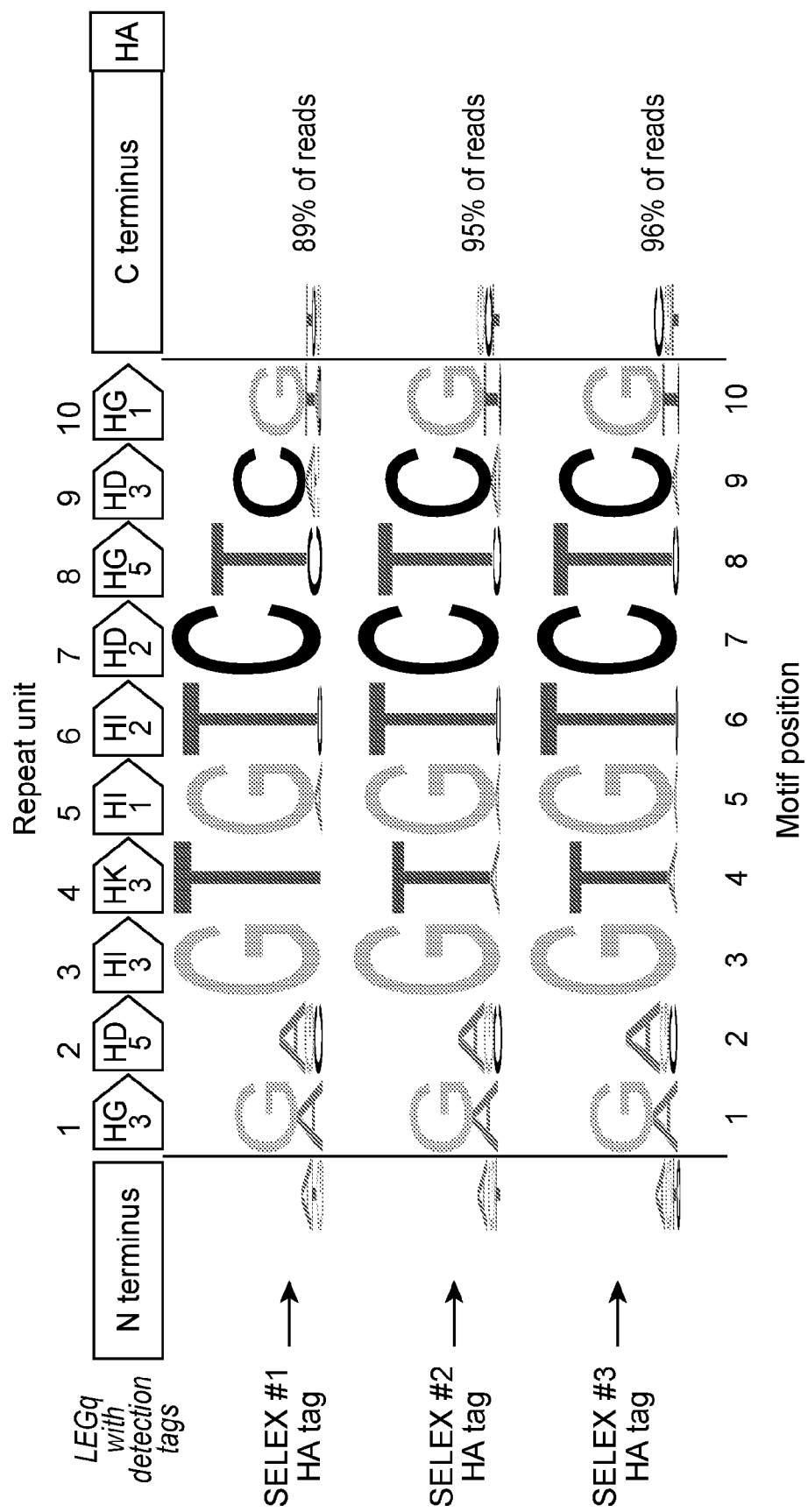

FIG. 8A depicts the bases to which the BCR in repeats (having the amino acid sequence set forth in SEQ ID NOs: 89 and 2-10) ordered from N-terminus to C-terminus in a polypeptide having the amino acid sequence set forth in SEQ ID NO:1 can bind. The larger the size the of the base at a particular position, the higher the relative frequency at which the base is present at that position in a nucleic acid bound by the tested polypeptide. The N-terminus (SEQ ID NO:13) of the protein and the C-terminus (SEQ ID NO:159) of the protein did not show binding to any base.

Figure 8B:
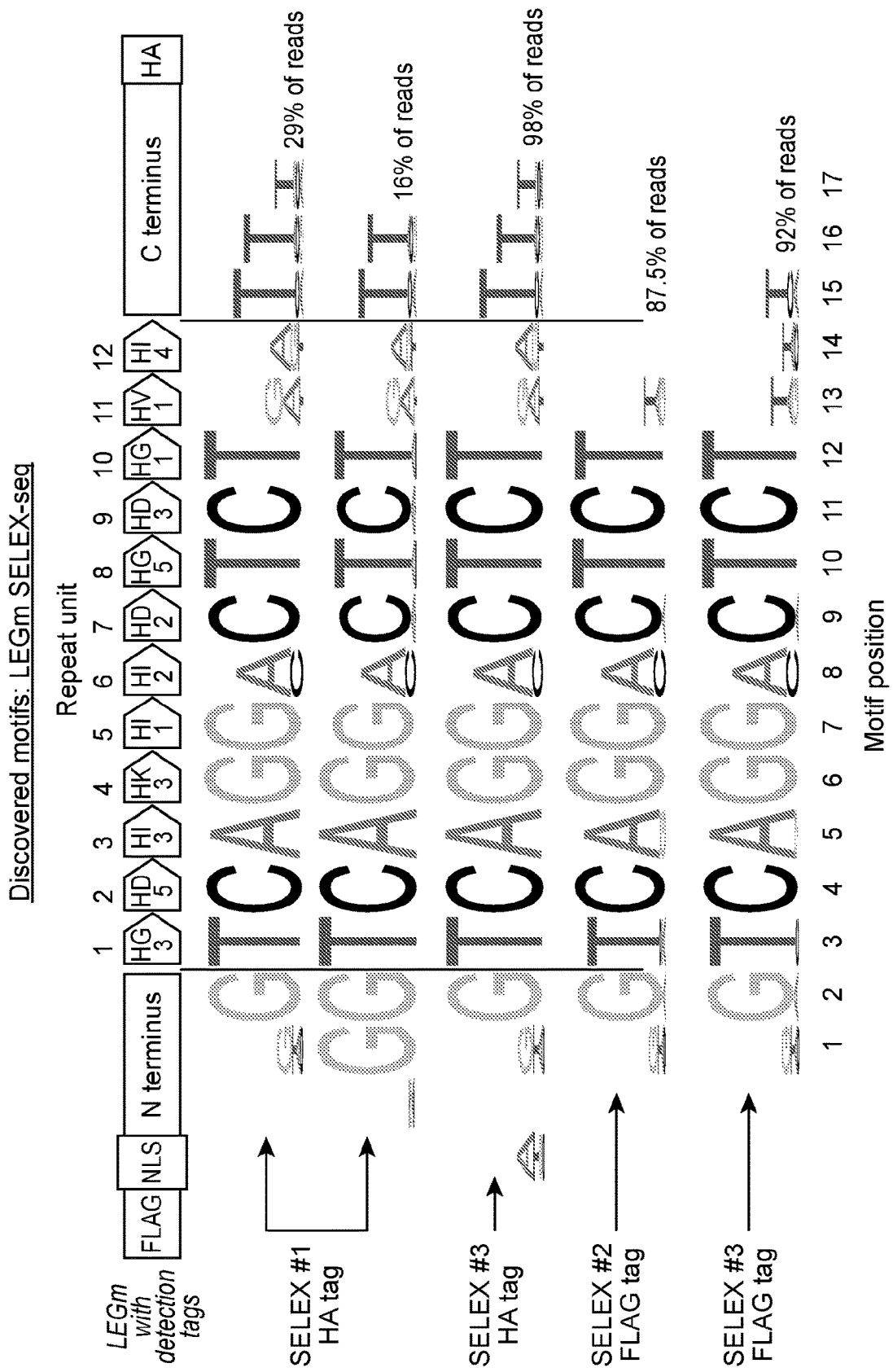

FIG. 8B depicts the bases to which the BCR in repeats (having the amino acid sequence set forth in SEQ ID NOs: 28, 26, 32, 34, 30, 31, 23, 29, 24, 27, 35, and 133) ordered from N-terminus to C-terminus in a polypeptide having the amino acid sequence set forth in SEQ ID NO:143 can bind. The larger the size the of the base at a particular position, the higher the relative frequency at which the base is present at that position in a nucleic acid bound by the tested polypeptide. The N-terminus (SEQ ID NO:144) of the protein mediated binding to either G or the sequence G-G. The C-terminus (SEQ ID NO:145) of the protein potentially mediated binding to the sequence T or T-T.

Figure 9:
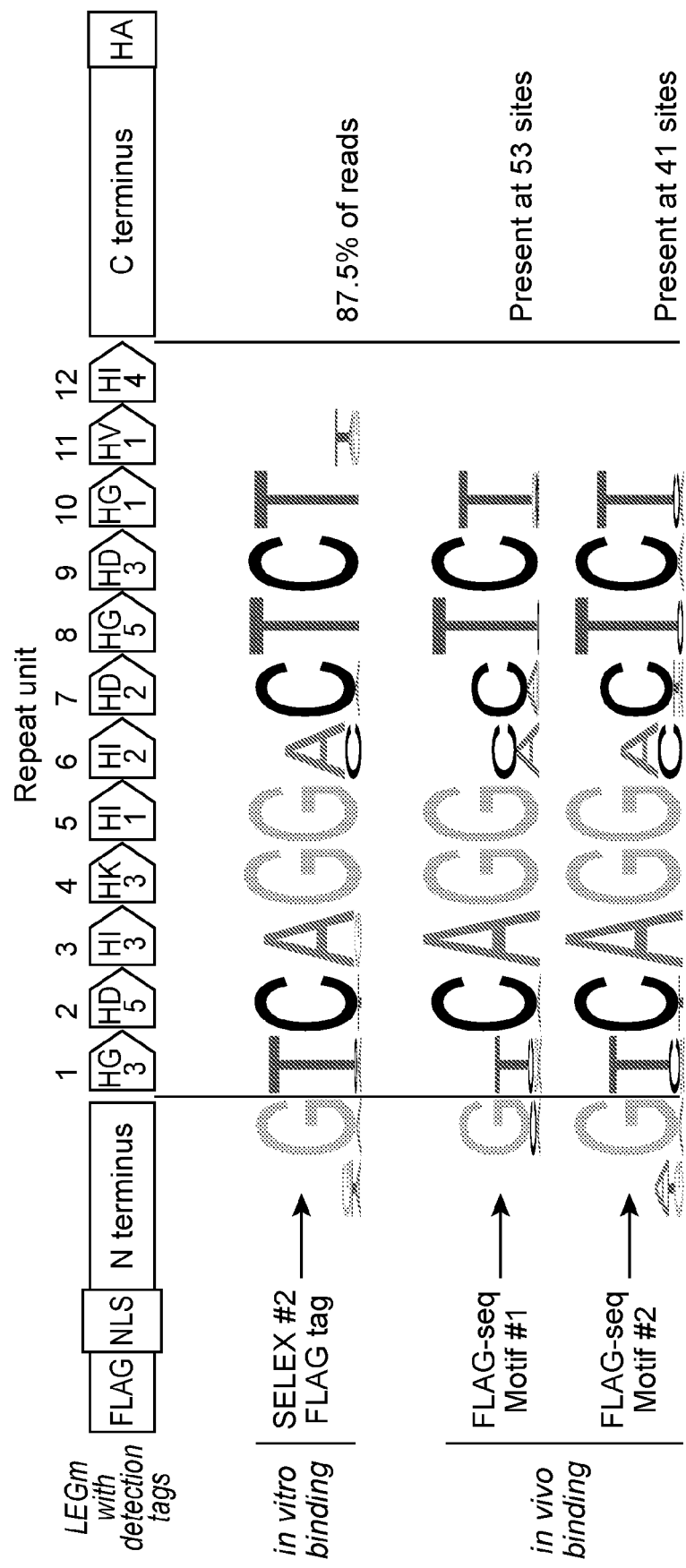

FIG. 9 illustrates that the protein the BCR in repeats (having the amino acid sequence set forth in SEQ ID NOs: 28, 26, 32, 34, 30, 31, 23, 29, 24, 27, 35, and 133) ordered from N-terminus to C-terminus in a polypeptide having the amino acid sequence set forth in SEQ ID NO:143 binds to the same DNA sequence in vivo as discovered by SELEX-seq.

DETAILED DESCRIPTION

Provided herein are polypeptides, compositions, and methods of use thereof for genetic and epigenomic engineering, including, genome editing and gene regulation. These polypeptides and compositions include nucleic acid binding domains that bind to a target nucleic acid of interest. The nucleic acid binding domains include repeat units derived from repeat units identified in proteins from animal pathogens such as bacterium of the order Legionellales and the species *Legionella* and *Francisella*.

Definitions

As used herein, the term "derived" in the context of a polypeptide refers to a polypeptide that has a sequence that is based on that of a protein from a particular source (e.g., an animal pathogen such as *Legionella*). A polypeptide derived from a protein from a particular source may be a variant of the protein from the particular source (e.g., an animal pathogen such as *Legionella*). For example, a polypeptide derived from a protein from a particular source may have a sequence that is modified with respect to the protein's sequence from which it is derived. A polypeptide derived from a protein from a particular source shares at least 30% sequence identity with, at least 40% sequence identity with, at least 50% sequence identity with, at least 60% sequence identity with, at least 70% sequence identity with, at least 80% sequence identity with, or at least 90% sequence identity with the protein from which it is derived.

The term "modular" as used herein in the context of a nucleic acid binding domain, e.g., a modular animal pathogen derived nucleic acid binding domain (MAP-NBD) indicates that the plurality of repeat units present in the NBD can be rearranged and/or replaced with other repeat units and can be arranged in an order such that the NBD binds to the target nucleic acid. For example, any repeat unit in a modular nucleic acid binding domain can be switched with a different repeat unit. In some embodiments, modularity of the nucleic acid binding domains disclosed herein allows for switching the target nucleic acid base for a particular repeat unit by simply switching it out for another repeat unit. In some embodiments, modularity of the nucleic acid binding domains disclosed herein allows for swapping out a particular repeat unit for another repeat unit to increase the affinity of the repeat unit for a particular target nucleic acid. Overall, the modular nature of the nucleic acid binding domains disclosed herein enables the development of genome editing complexes that can precisely target any nucleic acid sequence of interest.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like. In specific embodiments, the terms refer to a polymeric form of amino acids of any length which include genetically coded amino acids. In particular embodiments, the terms refer to a polymeric form of amino acids of any length which include genetically coded amino acids fused to a heterologous amino acid sequence.

The term "heterologous" refers to two components that are defined by structures derived from different sources. For example, in the context of a polypeptide, a "heterologous" polypeptide may include operably linked amino acid sequences that are derived from different polypeptides (e.g., a NBD and a functional domain derived from different sources). Similarly, in the context of a polynucleotide encoding a chimeric polypeptide, a "heterologous" polynucleotide may include operably linked nucleic acid sequences that can be derived from different genes. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) may be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein, the term "cleavage" refers to the breakage of the covalent backbone of a nucleic acid, e.g., a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, the polypeptides provided herein are used for targeted double-stranded DNA cleavage.

A "cleavage half-domain" is a polypeptide sequence which, in conjunction with a second polypeptide (either identical or different) forms a complex having cleavage activity (preferably double-strand cleavage activity).

A "target nucleic acid," "target sequence," or "target site" is a nucleic acid sequence that defines a portion of a nucleic acid to which a binding molecule, such as, the NBD disclosed herein will bind. The target nucleic acid may be present in an isolated form or inside a cell. A target nucleic acid may be present in a region of interest. A "region of interest" may be any region of cellular chromatin, such as, for example, a gene or a non-coding sequence within or adjacent to a gene, in which it is desirable to bind an exogenous molecule. Binding can be for the purposes of targeted DNA cleavage and/or targeted recombination, targeted activated or repression. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, promoter sequences, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

An "exogenous" molecule is a molecule that is not normally present in a cell but can be introduced into a cell by one or more genetic, biochemical or other methods. An exogenous molecule can comprise, for example, a functioning version of a malfunctioning endogenous molecule, e.g. a gene or a gene segment lacking a mutation present in the endogenous gene. An exogenous nucleic acid can be present in an infecting viral genome, a plasmid or episome introduced into a cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control region.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA, shRNA, RNAi, miRNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristylation, and glycosylation.

"Modulation" of gene expression refers to a change in the activity of a gene. Modulation of expression can include, but is not limited to, gene activation and gene repression. Genome editing (e.g., cleavage, alteration, inactivation, donor integration, random mutation) can be used to modulate expression. Gene inactivation refers to any reduction in gene expression as compared to a cell that does not include a polypeptide or has not been modified by a polypeptide as described herein. Thus, gene inactivation may be partial or complete.

The terms "patient" or "subject" are used interchangeably to refer to a human or a non-human animal (e.g., a mammal).

The terms "treat", "treating", treatment" and the like refer to a course of action (such as administering a polypeptide comprising a NBD fused to a heterologous functional domain or a nucleic acid encoding the polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject.

The terms "prevent", "preventing", "prevention" and the like refer to a course of action (such as administering a polypeptide comprising a NBD fused to a heterologous functional domain or a nucleic acid encoding the polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects.

Animal Pathogen Derived Nucleic Acid Binding Domains

The present disclosure provides a modular nucleic acid binding domain (NBD) and methods of using modular NBDs. A modular NBD can be engineered to target and bind to a specific nucleic acid sequence. The nucleic acid sequence can be DNA or RNA. In some embodiments, the modular NBD can comprise a plurality of repeat domains, wherein each repeat domain recognizes and binds to a single nucleotide or base pair. Each repeat domain in the plurality of repeat domains can be specifically selected to target and bind to a specific nucleic acid sequence, thus contributing to the modular nature of the NBD. A non-naturally occurring modular nucleic acid binding domain derived from an animal pathogen protein (MAP-NBD) can comprise a plurality of repeat units, wherein a repeat unit of the plurality of repeat units recognizes a single target nucleotide, base pair, or both.

In some embodiments, the repeat domain can be derived from an animal pathogen and can be referred to as a non-naturally occurring modular nucleic acid binding domain derived from an animal pathogen protein (MAP-NBD), or "modular animal pathogen-nucleic acid binding domain" (MAP-NBD). For example, in some cases, the animal pathogen can be from the Gram-negative bacterium genus, *Legionella*. In other cases, the animal pathogen can be a bacterium from the genus *Burkholderia*. In some cases, the animal pathogen can be a bacterium from the genus *Paraburkholderia*. In other cases, the animal pathogen can be a bacterium from the genus *Francisella*.

In certain aspects, the NBD such as a MAP-NBD comprises RUs derived from the animal pathogen, *L. quateirensis*. In certain aspects, the RUs are derived from RUs identified in a protein from *L. quateirensis*, where the protein has the amino acid sequence set forth in SEQ ID NO:1.

In the context of a repeat unit(s), the terms "repeat(s)," "repeat unit(s)," "repeat motif(s)," "repeat domain(s)," and "repeat sequence(s)" are used interchangeably.

In particular embodiments, the repeat domain can be derived from a Legionellales bacterium, a species of the genus of *Legionella*, such as *L. quateirensis* or *L. maceachernii*, the genus of *Burkholderia*, the genus of *Paraburkholderia*, or the genus of *Francisella*. In some embodiments, the repeat domain can comprise from 19 amino acid residues to 36 amino acid residues, such as, 19-35 amino acids, 20-36 amino acids, 30-36 amino acids, 31-36 amino acids, 32-36 amino acids, 33-35 amino acids, or 33-36 amino acids. In particular embodiments, the repeat domain can comprise 33 amino acid residues. In other embodiments, the repeat unit can comprise 35 amino acid residues. In some embodiments, the MAP-NBD is non-naturally occurring, and comprises a plurality of repeat units ordered from N-terminus to C-terminus of the MAP-NBD to recognize a target nucleic acid.

In some embodiments, a repeat domain can be derived from a *L. quateirensis* protein with the following sequence:

(SEQ ID NO: 1)
MPDLELNFAIPLHLFDDETVFTHDATNDNSQASSSYSSKSSPASANARKR

TSRKEMSGPPSKEPANTKSRRANSQNNKLSLADRLTKYNIDEEFYQTRSD

SLLSLNYTKKQIERLILYKGRTSAVQQLLCKHEELLNLISPDGLGHKELI

KIAARNGGGNNLIAVLSCYAKLKEMGFSSQQIIRMVSHAGGANNLKAVTA

NHDDLQNMGFNVEQIVRMVSHNGGSKNLKAVTDNHDDLKNMGFNAEQIVR

MVSHGGGSKNLKAVTDNHDDLKNMGFNAEQIVSMVSNNGGSKNLKAVTDN

HDDLKNMGFNAEQIVSMVSNGGGSLNLKAVKKYHDALKDRGFNTEQIVRM

VSHDGGSLNLKAVKKYHDALRERKFNVEQIVSIVSHGGGSLNLKAVKKYH

DVLKDREFNAEQIVRMVSHDGGSLNLKAVTDNHDDLKNMGFNAEQIVRMV

-continued
SHKGGSKNLALVKEYFPVFSSFHFTADQIVALICQSKQCFRNLKKNHQQW

KNKGLSAEQIVDLILQETPPKPNFNNTSSSTPSPSAPSFFQGPSTPIPTP

VLDNSPAPIFSNPVCFFSSRSENNTEQYLQDSTLDLDSQLGDPTKNFNVN

NFWSLFPFDDVGYHPHSNDVGYHLHSDEESPFFDF.

As demonstrated in Example 8 herein, repeat units have been identified in this *L. quateirensis* protein. The repeats found in TALE proteins from *Xanthomonas* have highly conserved amino acid sequence other than at positions $12^{th}$ and $13^{th}$. The amino acids present at positions $12^{th}$ and $13^{th}$ in repeats in *Xanthomonas* TALE proteins are referred to as repeat variable di-residues (RVDs) since in most instances only amino acids present at these two positions vary between repeats in *Xanthomonas* TALE proteins. In contrast, the repeat units identified in this *L. quateirensis* protein additionally have sequence variation outside of the $12^{th}$ and $13^{th}$ amino acid positions. However, as demonstrated in Example 8, the amino acids present at $12^{th}$ and $13^{th}$ positions in the RUs disclosed herein mediate binding to a particular base. These residues are herein referred to as base-contacting residues (BCR).

In some embodiments, a repeat from a *L. quateirensis* protein can comprise BCR that have the same sequence of di-residues as that of a RVD in a repeat from a TALE protein from *Xanthomonas*. Such BCR are referred to as canonical BCR. In some embodiments, canonical BCR can comprise the residues NN, NG, or HD. In some embodiments, a repeat from a *L. quateirensis* protein can comprise BCR that have a different sequence of residues than a RVD in a repeat from a TALE protein from *Xanthomonas*. Such BCR are referred to as non-canonical BCR. In some embodiments, non-canonical BCR can comprise the residues RN, HA, HN, HG, or HK.

In some embodiments, a repeat of SEQ ID NO: 89 comprises the BCR RN and recognizes the base guanine (G). In some embodiments, a repeat of SEQ ID NO: 2 comprises the BCR HA and primarily recognizes the base adenine (A). In some embodiments, a repeat of SEQ ID NO: 3 comprises the BCR HN and recognizes the base G. In some embodiments, a repeat of SEQ ID NO: 4 comprises the BCR HG and recognizes the base thymine (T). In some embodiments, a repeat of SEQ ID NO: 5 comprises the BCR NN and recognizes the base G. In some embodiments, a repeat of SEQ ID NO: 6 comprises the BCR NG and recognizes the base T. In some embodiments, a repeat of SEQ ID NO: 7 comprises the BCR HD and recognizes the base cytosine (C). In some embodiments, a repeat of SEQ ID NO: 8 comprises the BCR HG and recognizes the base T. In some embodiments, a repeat of SEQ ID NO: 9 comprises the BCR HD and recognizes the base C. In some embodiments, a half-repeat of SEQ ID NO: 10 comprises the BCR HK and recognizes the base G.

FIG. 2 illustrates a protein from *L. quateirensis* from which nucleic acid binding repeat domains are derived. SEQ ID NO: 1 indicates the full protein and contains repeats of SEQ ID NO: 2-SEQ ID NO: 10 and SEQ ID NO: 89.

TABLE 1 illustrates exemplary repeats from Legionalleles, *L. quateirensis*, *L. maceachernii Burkholderia*, *Paraburkholderia*, or *Francisella* that can make up a MAP-NBD of the present disclosure. The BCR (i.e., the amino acids present at position 12 and 13) of the particular repeat is also indicated. A MAP-NBD of the present disclosure can comprise at least one of the repeats disclosed in TABLE 1. A MAP-NBD of the present disclosure can comprise any combination of repeats disclosed in TABLE 1.

TABLE 1

Animal Pathogen Repeat Domains

| SEQ ID NO | Organism | Repeat Domain Sequence | BCR |
|---|---|---|---|
| 2 | L. quateirensis | FSSQQIIRMVSHAGGANNLKAVTANHDDLQNMG | HA |
| 3 | L. quateirensis | FNVEQIVRMVSHNGGSKNLKAVTDNHDDLKNMG | HN |
| 4 | L. quateirensis | FNAEQIVRMVSHGGGSKNLKAVTDNHDDLKNMG | HG |
| 5 | L. quateirensis | FNAEQIVSMVSNNGGSKNLKAVTDNHDDLKNMG | NN |
| 6 | L. quateirensis | FNAEQIVSMVSNGGGSLNLKAVKKYHDALKDRG | NG |
| 7 | L. quateirensis | FNTEQIVRMVSHDGGSLNLKAVKKYHDALRERK | HD |
| 8 | L. quateirensis | FNVEQIVSIVSHGGGSLNLKAVKKYHDVLKDRE | HG |
| 9 | L. quateirensis | FNAEQIVRMVSHDGGSLNLKAVTDNHDDLKNMG | HD |
| 10 (half-repeat) | L. quateirensis | FNAEQIVRMVSHKGGSKNL | HK |
| 23 | Legionella maceachernii | FSAEQIVRIAAHDGGSRNIEAVQQAQHVLKELG | HD |
| 24 | Legionella maceachernii | FSAEQIVSIVAHDGGSRNIEAVQQAQHILKELG | HD |
| 25 | Legionellales bacterium | LDRQQILRIASHDGGSKNIAAVQKFLPKLMNFG | HD |
| 26 | Legionella maceachernii | FSAEQIVRIAAHDGGSLNIDAVQQAQQALKELG | HD |
| 27 | Legionella maceachernii | FSTEQIVCIAGHGGGSLNIKAVLLAQQALKDLG | HG |
| 28 | Legionella maceachernii | YSSEQIVRVAAHGGGSLNIKAVLQAHQALKELD | HG |
| 29 | Legionella maceachernii | FSAEQIVHIAAHGGGSLNIKAILQAHQTLKELN | HG |
| 30 | Legionella maceachernii | FSAEQIVRIAAHIGGSRNIEAIQQAHHALKELG | HI |
| 31 | Legionella maceachernii | FSAEQIVRIAAHIGGSHNLKAVLQAQQALKELD | HI |
| 32 | Legionella maceachernii | FSAKHIVRIAAHIGGSLNIKAVQQAQQALKELG | HI |
| 33 | L. quateirensis | FNAEQIVRMVSHKGGSKNLALVKEYFPVFSSFH | HK |
| 34 | Legionella maceachernii | FSADQIVRIAAHKGGSHNIVAVQQAQQALKELD | HK |
| 35 | Legionella maceachernii | FSAEQIVSIAAHVGGSHNIEAVQKAHQALKELD | HV |
| 36 | Burkholderia | FSSGETVGATVGAGGTETVAQGGTASNTTVSSG | GA |
| 37 | Burkholderia | FSGGMATSTTVGSGGTQDVLAGGAAVGGTVGTG | GS |
| 38 | Burkholderia | FSAADIVKIAGKIGGAQALQAFITHRAALIQAG | KI |
| 39 | Burkholderia | FNPTDIVKIAGNDGGAQALQAVLELEPALRERG | ND |
| 40 | Burkholderia | FNPTDIVRMAGNDGGAQALQAVFELEPAFRERS | ND |
| 41 | Burkholderia | FNPTDIVRMAGNDGGAQALQAVLELEPAFRERG | ND |
| 42 | Burkholderia | FSQVDIVKIASNDGGAQALYSVLDVEPTFRERG | ND |
| 43 | Burkholderia | FSRADIVKIAGNDGGAQALYSVLDVEPPLRERG | ND |
| 44 | Burkholderia | FSRGDIVKIAGNDGGAQALYSVLDVEPPLRERG | ND |

TABLE 1-continued

Animal Pathogen Repeat Domains

| SEQ ID NO | Organism | Repeat Domain Sequence | BCR |
|---|---|---|---|
| 45 | Burkholderia | FNRADIVRIAGNGGGAQALYSVRDAGPTLGKRG | NG |
| 46 | Burkholderia | FRQADIVKIASNGGSAQALNAVIKLGPTLRQRG | NG |
| 47 | Burkholderia | FRQADIVKMASNGGSAQALNAVIKLGPTLRQRG | NG |
| 48 | Burkholderia | FSRADIVKIAGNGGGAQALQAVLELEPTFRERG | NG |
| 49 | Burkholderia | FSRADIVRIAGNGGGAQALYSVLDVGPTLGKRG | NG |
| 50 | Burkholderia | FSRGDIVRIAGNGGGAQALQAVLELEPTLGERG | NG |
| 51 | Burkholderia | FSRADIVKIAGNGGGAQALQAVITHRAALTQAG | NG |
| 52 | Burkholderia | FSRGDTVKIAGNIGGAQALQAVLELEPTLRERG | NI |
| 53 | Burkholderia | FNPTDIVKIAGNIGGAQALQAVLELEPAFRERG | NI |
| 54 | Burkholderia | FSAADIVKIAGNIGGAQALQAIFTHRAALIQAG | NI |
| 55 | Burkholderia | FSAADIVKIAGNIGGAQALQAVITHRATLTQAG | NI |
| 56 | Burkholderia | FSATDIVKIASNIGGAQALQAVISRRAALIQAG | NI |
| 57 | Burkholderia | FSQPDIVKIAGNIGGAQALQAVLELEPAFRERG | NI |
| 58 | Burkholderia | FSRADIVKIAGNIGGAQALQAVLELESTFRERS | NI |
| 59 | Burkholderia | FSRADIVKIAGNIGGAQALQAVLELESTLRERS | NI |
| 60 | Burkholderia | FSRGDIVKMAGNIGGAQALQAGLELEPAFRERG | NI |
| 61 | Burkholderia | FSRGDIVKMAGNIGGAQALQAVLELEPAFHERS | NI |
| 62 | Burkholderia | FTLTDIVKMAGNIGGAQALKAVLEHGPTLRQRD | NI |
| 63 | Burkholderia | FTLTDIVKMAGNIGGAQALKVVLEHGPTLRQRD | NI |
| 64 | Burkholderia | FNPTDIVKIAGNNGGAQALQAVLELEPALRERG | NN |
| 65 | Burkholderia | FNPTDIVKIAGNNGGAQALQAVLELEPALRERS | NN |
| 66 | Burkholderia | FNPTDMVKIAGNNGGAQALQAVLELEPALRERG | NN |
| 67 | Burkholderia | FSAADIVKIASNNGGAQALQALIDHWSTLSGKT | NN |
| 68 | Burkholderia | FSAADIVKIASNNGGAQALQAVISRRAALIQAG | NN |
| 69 | Burkholderia | FSAADIVKIASNNGGAQALQAVITHRAALAQAG | NN |
| 70 | Burkholderia | FSAADIVKIASNNGGARALQALIDHWSTLSGKT | NN |
| 71 | Burkholderia | FTLTDIVEMAGNNGGAQALKAVLEHGSTLDERG | NN |
| 72 | Burkholderia | FTLTDIVKMAGNNGGAQALKAVLEHGPTLDERG | NN |
| 73 | Burkholderia | FTLTDIVKMAGNNGGAQALKVVLEHGPTLRQRG | NN |
| 74 | Burkholderia | FTLTDIVKMASNNGGAQALKAVLEHGPTLDERG | NN |
| 75 | Burkholderia | FSAADIVKIAGNSGGAQALQAVISHRAALTQAG | NS |
| 76 | Burkholderia | FSGGDAVSTVVRSGGAQSVASGGTASGTTVSAG | RS |
| 77 | Burkholderia | FRQTDIVKMAGSGGSAQALNAVIKHGPTLRQRG | SG |
| 78 | Burkholderia | FSLIDIVEIASNGGAQALKAVLKYGPVLTQAGR | SN |
| 79 | Burkholderia | FSGGDAAGTVVSSGGAQNVTGGLASGTTVASGG | SS |
| 80 | Paraburkholderia | FNLTDIVEMAANSGGAQALKAVLEHGPTLRQRG | NS |
| 81 | Paraburkholderia | FNRASIVKIAGNSGGAQALQAVLKHGPTLDERG | NS |

TABLE 1-continued

Animal Pathogen Repeat Domains

| SEQ ID NO | Organism | Repeat Domain Sequence | BCR |
|---|---|---|---|
| 82 | *Paraburkholderia* | FSQANIVKMAGNSGGAQALQAVLDLELVFRERG | NS |
| 83 | *Paraburkholderia* | FSQPDIVKMAGNSGGAQALQAVLDLELAFRERG | NS |
| 84 | *Paraburkholderia* | FSLIDIVEIASNGGAQALKAVLKYGPVLMQAGR | SN |
| 85 | *Francisella* | YKSEDIIRLASHDGGSVNLEAVLRLHSQLTRLG | HD |
| 86 | *Francisella* | YKPEDIIRLASHGGGSVNLEAVLRLNPQLIGLG | HG |
| 87 | *Francisella* | YKSEDIIRLASHGGGSVNLEAVLRLHSQLTRLG | HG |
| 88 | *Francisella* | YKSEDIIRLASHGGGSVNLEAVLRLNPQLIGLG | HG |
| 89 | *L. quateirensis* | LGHKELIKIAARNGGGNNLIAVLSCYAKLKEMG | RN |
| 114 | *Paraburkholderia* | FNLTDIVEMAGKGGGAQALKAVLEHGPTLRQRG | KG |
| 115 | *Paraburkholderia* | FRQADIIKIAGNDGGAQALQAVIEHGPTLRQHG | ND |
| 116 | *Paraburkholderia* | FSQADIVKIAGNDGGTQALHAVLDLERMLGERG | ND |
| 117 | *Paraburkholderia* | FSRADIVKIAGNGGAQALKAVLEHEATLDERG | NG |
| 118 | *Paraburkholderia* | FSRADIVRIAGNGGGAQALYSVLDVEPTLGKRG | NG |
| 119 | *Paraburkholderia* | FSQPDIVKMASNIGGAQALQAVLELEPALRERG | NI |
| 120 | *Paraburkholderia* | FSQPDIVKMAGNIGGAQALQAVLSLGPALRERG | NI |
| 121 | *Paraburkholderia* | FSQPEIVKIAGNIGGAQALHTVLELEPTLHKRG | NI |
| 122 | *Paraburkholderia* | FSQSDIVKIAGNIGGAQALQAVLDLESMLGKRG | NI |
| 123 | *Paraburkholderia* | FSQSDIVKIAGNIGGAQALQAVLELEPTLRESD | NI |
| 124 | *Paraburkholderia* | FNPTDIVKIAGNKGGAQALQAVLELEPALRERG | NK |
| 125 | *Paraburkholderia* | FSPTDIIKIAGNNGGAQALQAVLDLELMLRERG | NN |
| 126 | *Paraburkholderia* | FSQADIVKIAGNNGGAQALYSVLDVEPTLGKRG | NN |
| 127 | *Paraburkholderia* | FSRGDIVTIAGNNGGAQALQAVLELEPTLRERG | NN |
| 128 | *Paraburkholderia* | FSRIDIVKIAANNGGAQALHAVLDLGPTLRECG | NN |
| 129 | *Paraburkholderia* | FSQADIVKIVGNNGGAQALQAVFELEPTLRERG | NN |
| 130 | *Paraburkholderia* | FSQPDIVRITGNRGGAQALQAVLALELTLRERG | NR |
| 131 | *Legionellales* | FKADDAVRIACRTGGSHNLKAVHKNYERLRARG | RT |
| 132 | *Legionellales* | FNADQVIKIVGHDGGSNNIDVVQQFFPELKAFG | HD |
| 133 | *Legionella maceachernii* | FSAEQIVRIAAHIGGSRNIEATIKHYAMLTQPP | HI |
| 134 | *Francisella* | YKSEDIIRLASHDGGSVNLEAVLRLNPQLIGLG | HD |
| 135 | *Francisella* | YKSEDIIRLASHDGGSINLEAVLRLNPQLIGLG | HD |
| 136 | *Francisella* | YKSEDIIRLASSNGGSVNLEAVLRLNPQLIGLG | SN |
| 137 | *Francisella* | YKSEDIIRLASSNGGSVNLEAVIAVHKALHSNG | SN |
| 138 | *Legionellales* | FSADQVVKIAGHSGGSNNIAVMLAVFPRLRDFG | HS |
| 151 | *Francisella* | YKINHCVNLLKLNHDGFMLKNLIPYDSKLTGLG | LN |
| 152 | *Francisella* (half-repeat) | YNKKQIVLIASGSSGG | GS |

In any one of the animal pathogen-derived repeat domains of SEQ ID NOs: 2-10, 23-89, and 114-137 there can be considerable sequence divergence between repeats of a MAP-NBD in addition to the sequence variation of the BCR.

This lack of conservation of sequence outside of the 12th and 13th amino acid positions in the RUs described herein contrasts with TALE proteins that include repeats in which the sequence outside of the 12th and 13th amino acid positions is mostly conserved.

In some embodiments, a MAP-NBD of the present disclosure can comprise between 1 to 50 animal pathogen-derived repeat domains, e.g., between 9 and 36, between 12 and 30, between 5 to 10, between 10 to 15, between 15 to 20, between 20 to 25, between 25 to 30, between 30 to 35 animal pathogen-derived repeat domains, or between 35 to 40 animal pathogen-derived repeat domains. In certain aspects, a MAP-NBD described herein can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 animal pathogen-derived repeat domains.

An animal pathogen-derived repeat domain can be derived from a wild-type repeat domain, such as any one of SEQ ID NOs:2-10, 23-89, 114-138, and 151-152. An animal pathogen-derived repeat domain can also comprise a modified animal pathogen-derived repeat domain enhanced for specific recognition of a nucleotide or base pair. A MAP-NBD described herein can comprise one or more wild-type animal pathogen-derived repeat domains, one or more modified animal pathogen-derived repeat domains, or a combination thereof. In some embodiments, a modified animal pathogen-derived repeat domain can comprise 1, 2, 3, 4, 5, 6, 7, 8, 9, 10, 11, 12, 13, 14, 15, 16, 17, 18, 19, 20, 21, 22, 23, 24, 25, 26, 27, 28, or 29 mutations that can enhance recognition of a specific nucleobase or base pair. In some embodiments, a modified animal pathogen-derived repeat domain can comprise more than 1 modification, for example 1 to 5 modifications, 5 to 10 modifications, 10 to 15 modifications, 15 to 20 modifications, 20 to 25 modifications, or 25-29 modifications. In some embodiments, a MAP-NBD can comprise more than one modified animal pathogen-derived repeat domains, wherein each of the modified animal pathogen-derived repeat domains can have a different number of modifications.

In some embodiments, a MAP-NBD of the present disclosure can have the full length naturally occurring N-terminus of a naturally occurring *L. quateirensis*-derived protein, such as the N-terminus of SEQ ID NO: 1. An N-terminus can be the full-length N-terminus sequence and can have a sequence: MPDLELNFAIPLHLFDDETVFTH-DATNDNSQASSSYS-SKSSPASANARKRTSRKEMSGPPSK EPANTKSR-RANSQNNKLSLADRLTKYNIDEEFYQTRSDSLLSLN YTKKQIERLILYKGRTSA VQQLLCKHEELLNLISPDG (SEQ ID NO: 13). In some embodiments, any truncation of SEQ ID NO: 13 can be used as the N-terminus in a MAP-NBD of the present disclosure. For example, in some embodiments, a MAP-NBD comprises a truncated N-terminus including amino acid residues at position 15 (D) to position 143 (G) of the naturally occurring *L. quateirensis* N-terminus as follows: DATNDNSQASSSYS-SKSSPASANARKRTSRKEMSGPPSKEPANTKSR-RANSQNNKLSLADR LTKYNIDEEFYQTRSD-SLLSLNYTKKQIERLILYKGRTSAVQQLLCKHEELLN LISPDG (SEQ ID NO: 20). In some embodiments, a MAP-NBD comprises a truncated N-terminus including amino acid residues at position 29 (N) to position 143 (G) of the naturally occurring *L. quateirensis* N-terminus as follows: NSQASSSYS-SKSSPASANARKRTSRKEMSGPPSKEPANTKSR-RANSQNNKLSLADRLTKYNI DEEFYQTRSD-SLLSLNYTKKQIERLILYKGRTSAVQQLLCKHEELLN LISPDG (SEQ ID NO: 21). In some embodiments, any truncation of the naturally occurring *L. quateirensis* N-terminus can be used at the N-terminus of a NBD disclosed herein. The naturally occurring N-terminus of *L. quateirensis* can be truncated to amino acid residues at positions 1 to 50, 1 to 70, 1 to 100, 1 to 120, 1 to 130, 10 to 40, 60 to 100, or 100 to 120 and used at the N-terminus of the MAP-NBD.

In some embodiments, the present disclosure provides methods for identifying an animal pathogen-derived repeat domain. For example, a consensus sequence can be defined comprising a first repeat motif, a spacer, and a second repeat motif. The consensus sequence can be (SEQ ID NO: 14)
1xxx211x1xxx33x2x1xxxxxxxxx1xxxx1xxx211x1xxx33x2x1
xxxxxxxxx1, (SEQ ID NO: 15)
1xxx211x1xxx33x2x1xxxxxxxxx1xxxxx1xxx211x1xxx33x2x
1xxxxxxxxx1, (SEQ ID NO: 16)
1xxx211x1xxx33x2x1xxxxxxxxx1xxxxxx1xxx211x1xxx33x2
x1xxxxxxxxx1, (SEQ ID NO: 17)
1xxx211x1xxx33x2x1xxxxxxxxx1xxxxxxx1xxx211x1xxx33x
2x1xxxxxxxxx1, (SEQ ID NO: 18)
1xxx211x1xxx33x2x1xxxxxxxxx1xxxxxxxx1xxx211x1xxx33
x2x1xxxxxxxxx1.

For any one of SEQ ID NO: 14-SEQ ID NO: 18, x can be any amino acid residue, 1, 2, and 3 are flexible residues that are defined as follows: 1 can be selected from any one of A, F, I, L, M, T, or V, 2 can be selected from any one of D, E, K, N, M, S, R, or Q, and 3 can be selected from any one of A, G, N, or S. Thus, in some embodiments, a MAP-NBD can be derived from an animal pathogen comprising the consensus sequence of SEQ ID NO: 14, SEQ ID NO: 15, SEQ ID NO: 16, SEQ ID NO: 17, or SEQ ID NO: 18. Any one of consensus sequences of SEQ ID NO: 14-SEQ ID NO: 18 can be compared against all sequences in databases such as NCBI, MGRast, JGI, and EBI to identify matches corresponding to animal pathogen proteins containing repeat units of a DNA-binding repeat domain.

In some embodiments, a MAP-NBD repeat domain can itself have a consensus sequence of 1xxx211x1xxx33x2x1xxxxxxxxx1 (SEQ ID NO: 19), wherein x can be any amino acid residue, 1, 2, and 3 are flexible residues that are defined as follows: 1 can be selected from any one of A, F, I, L, M, T, or V, 2 can be selected from any one of D, E, K, N, M, S, R, or Q, and 3 can be selected from any one of A, G, N, or S. FIGS. 3A and 3B show consensus sequences of SEQ ID NO: 14-SEQ ID NO: 18 present in an animal pathogen protein of the present disclosure and a consensus sequence of SEQ ID NO: 19 in a MAP-NBD of the present disclosure. FIG. 3A shows consensus sequences of SEQ ID NO: 14-SEQ ID NO: 18 that can be present in an animal pathogen-derived protein from which a MAP-NBD of the present disclosure is provided. Each consensus sequence of SEQ ID NO: 14-SEQ ID NO: 18 includes a repeat motif, followed by a spacer of variable length, and a second repeat motif. FIG. 3B shows a consensus sequence of SEQ ID NO: 19, which can be present in a repeat domain (e.g., a MAP-NBD) of the present disclosure.

The terms "MAP-NBD" and "NBD" are used herein interchangeably to refer to NBDs that include RUs having sequences derived from RUs identified in proteins from animal pathogens, such as, bacterium of the order Legionellales or the species *Legionella* or *Francisella*.

In certain aspects, the present disclosure provides a recombinant polypeptide comprising a nucleic acid binding domain (NBD) and a heterologous functional domain, the NBD comprising at least three repeat units (RUs) ordered from N-terminus to C-terminus of the NBD to specifically bind to a target nucleic acid, each of the RUs of the NBD comprising the consensus sequence: 1xxxx11x12xx33xxx1xxxxxxxxxx14xxx, where 1=A, F, I, L, M, T, V, or Y; 2=x or xx; 3=A, G, N, or S; 4=x, xx, or xxx; and x=any amino acid, and where each of the RUs independently comprises a 33-36 amino acid long sequence that is at least 70% (e.g., at least 75%, 80%, 85%, 90%, 95%, or 99%, or a 100%) identical to the amino acid sequence set forth in one of SEQ ID NOs: 2-9, 23-35, 85-89, and 131-137, where SEQ ID NOs: 2-9, 33, and 89 provide amino acid sequences of repeat units identified in a protein (SEQ ID NO:1) from a *L. quateirensis* bacterium, where SEQ ID NOs: 23-32, 34-35, and 133 provide amino acid sequences of repeat units identified in a protein (SEQ ID NO: 143) from a *L. maceachernii* bacterium, where SEQ ID NOs: 25, 131-132, and 138 provide amino acid sequences of repeat units identified in a protein (SEQ ID NO: 139) from a bacterium of the order Legionellales, and where SEQ ID NOs: 85-88, 134-137 provide amino acid sequences of repeat units identified in a protein (SEQ ID NO: 147) from a bacterium of the genus *Francisella*. In certain aspects, a half-RU is present at the C-terminus of the NBD (i.e., following the last RU), wherein the half-RU comprises a 15-20 amino acid long sequence that is at least 70% (e.g., at least 75%, 80%, 85%, 90%, 95%, or 99%, or a 100%) identical to FNAEQIVRMVSHKGGSKNL (SEQ ID NO:10) and wherein the BCR (i.e., the amino acids at positions 12 and 13) present in the half-RU may be HK, HD, HA, HN, HG, NN, NG, RN, HI, HV, RT, HD, SN, HS, GS, or LN.

In certain aspects, the present disclosure provides a recombinant polypeptide comprising a nucleic acid binding domain (NBD) and a heterologous functional domain, the NBD comprising at least three repeat units (RUs) ordered from N-terminus to C-terminus of the NBD to specifically bind to a target nucleic acid, each of the RUs of the NBD comprising the consensus sequence: (F/L/Y)(D/G/N/S)(A/H/R/S/T/V)(D/E/K/Q)(E/H/Q)(I/L/V)(I/L/V)(C/H/K/R/S)(I/M/V)(A/V)(A/G/S) (H/N/R)(A/D/G/I/K/N/S/V)(G)(G)(A/G/S)(H/K/L/N/R)(N)(I/L)(A/D/E/I/K/V)(A/L/V)(I/M/V)(K/L/Q/T)(A/D/E/K/L/Q/S)(A/C/F/N/V/Y)(F/H/L/Q/Y)(A/D/H/P/Q)(A/D/I/K/R/T/V)(F/L)(K/M/Q/R/S)(D/E/N/S)(F/L/M)(D/E/G/H/K/N) (SEQ ID NO: 154), where the consensus sequence is based upon the amino acid sequences of repeat units identified in proteins from a bacterium of the order Legionellales, a *L. quateirensis* bacterium, and a *L. maceachernii* bacterium and having the sequences set forth in SEQ ID NOs: 2-10, 23-35, 85-89, and 131-137.

In certain aspects, the NBD provided herein may additionally include a half-RU at the C-terminus, where the half-RU comprises a 15-20 amino acid long sequence that is at least 70% (e.g., at least 75%, 80%, 85%, 90%, or 99%, or a 100%) identical to FNAEQIVRMVSX$_{12}$X$_{13}$GGSKNL (SEQ ID NO:155) and comprises a sequence having the sequence of SEQ ID NO:155 with one or more conservative amino acid substitutions thereto, and where X$_{12}$X$_{13}$=HK, HD, HA, HN, HG, NN, NG, RN, HI, HV, RT, HD, SN, HS, GS, or LN.

In certain aspects, each of the at least three RUs present in the NBD provided herein independently comprises a 33-36 amino acid long sequence that is at least 70% identical (e.g., at least 75%, 80%, 85%, 90%, 95%, or 99%, or a 100% identical) to

```
                                       (SEQ ID NO: 2)
    FSSQQIIRMVSHAGGANNLKAVTANHDDLQNMG;

(SEQ ID NO: 3)
    FNVEQIVRMVSHNGGSKNLKAVTDNHDDLKNMG;

(SEQ ID NO: 4)
    FNAEQIVRMVSHGGGSKNLKAVTDNHDDLKNMG;

(SEQ ID NO: 5)
    FNAEQIVSMVSNNGGSKNLKAVTDNHDDLKNMG;

(SEQ ID NO: 6)
    FNAEQIVSMVSNGGGSLNLKAVKKYHDALKDRG;

(SEQ ID NO: 7)
    FNTEQIVRMVSHDGGSLNLKAVKKYHDALRERK;

(SEQ ID NO: 8)
    FNVEQIVSIVSHGGGSLNLKAVKKYHDVLKDRE;

(SEQ ID NO: 9)
    FNAEQIVRMVSHDGGSLNLKAVTDNHDDLKNMG;

(SEQ ID NO: 33)
    FNAEQIVRMVSHKGGSKNLALVKEYFPVFSSFH;
    or (SEQ ID NO: 89)
    LGHKELIKIAARNGGGNNLIAVLSCYAKLKEMG;
``` and comprises BCR selected from HK, HD, HA, HN, HG, NN, NG, RN, HI, HV, RT, HD, SN, HS, GS, or LN, at amino acid positions 12 and 13, respectively, numbered relative to one of SEQ ID NOs:2-9, 33, and 89. In certain aspects, the RUs present in the NBD may have an amino acid sequence of any one of SEQ ID NOs: 2-9, 33, and 89 with one or more conservative amino acid substitutions thereto. In certain aspects, the BCR present at amino acid positions 12 and 13 of a RU disclosed herein can be substituted with another BCR or a RVD to change the base to which the RU binds.

In certain aspects, the NBD may comprise at least three of the RUs and a half-repeat unit as disclosed herein. In certain aspects, the half-repeat unit may be present as the last repeat (i.e., the last RU that binds to the last base of the target nucleic acid sequence) in the NBD. In certain aspects, a half-RU is present at the C-terminus of the NBD (i.e., following the last RU), wherein the half-RU comprises a 15-20 amino acid long sequence that is at least 70% (e.g., at least 75%, 80%, 85%, 90%, 95%, or 99%, or a 100%) identical to FNAEQIVRMVSHKGGSKNL (SEQ ID NO:10) and wherein the BCR (i.e., the amino acids at positions 12 and 13) present in the half-RU may be HK, HD, HA, HN, HG, NN, NG, RN, HI, HV, RT, HD, SN, HS, GS, or LN.

In certain aspects, the NBD may include at least one RU that binds to adenine and comprises a 33-36 amino acid long sequence that is at least 70% (e.g., at least 75%, 80%, 85%, 90%, 95%, or 99%, or a 100%) identical to FSSQQIIRMVSX$_{12}$X$_{13}$GGANNLKAVTANHDDLQNMG (SEQ ID NO:2) or comprises an amino acid sequence of SEQ ID NO:2 with one or more conservative amino acid substitutions thereto, and where X$_{12}$X$_{13}$=HA.

In certain aspects, the first RU in the NBD (i.e., the first RU that binds to the first base of the target nucleic acid sequence) may be 33-36 amino acid long sequence that is at least 70% identical (e.g., at least 75%, 80%, 85%, 90%, 95%, or 99%, or a 100% identical) to LGHKELIKI-AARNGGGNNLIAVLSCYAKLKEMG (SEQ ID NO:89). In certain aspects, the BCR (i.e., the amino acids at position 12 and 13, numbered relative to SEQ ID NO:89) in the first RU of the NBD may be one of HK, HD, HA, HN, HG, NN, NG, RN, HI, HV, RT, HD, SN, HS, GS, or LN.

In certain aspects, the polypeptide comprises an N-terminal domain, where the C-terminus (i.e., the last amino acid) of the N-terminal domain is covalently linked to the N-terminus (i.e., the first amino acid) of the first RU of the NBD either directly or via a linker. In certain aspects, the N-terminal domain is the N-terminus of *L. quateirensis* protein having the amino acid sequence set forth in SEQ ID NO:1 and may have the amino acid sequence set forth in SEQ ID NO: 13. In certain aspects, the N-terminal domain comprises a fragment of SEQ ID NO:13, such as a fragment having the amino acid sequence set forth in SEQ ID NO: 20 or 21. In certain aspects, the N-terminal domain is a polypeptide that includes the amino acid sequence of SEQ ID NOs:13, 20, or 21 with one or more conservative amino acid substitutions thereto. In certain aspects, the N-terminal domain is a polypeptide that includes an amino acid sequence at least 85% (e.g., at least 90%, 95%, or 99%, or a 100%) identical to the amino acid sequence of any one of SEQ ID NOs:13, 20, or 21. In certain aspects, the N-terminal domain is a N-cap domain or a fragment thereof from TALE proteins like those expressed in *Burkholderia, Paraburkholderia*, or *Xanthomonas.*

In certain aspects, the polypeptide comprises a C-terminal domain, where the N-terminus (i.e., the first amino acid) of the C-terminal domain is covalently linked to the C-terminus (i.e., the last amino acid) of the last RU or the half-repeat unit, if present, in the NBD either directly or via a linker. In certain aspects, the C-terminal domain is the C-terminus of *L. quateirensis* protein having the amino acid sequence set forth in SEQ ID NO:1 and may have the amino acid sequence set forth in SEQ ID NO:12 or SEQ ID NO: 159. In certain aspects, the C-terminal domain comprises a fragment of SEQ ID NO:12, such as a fragment having the amino acid sequence set forth in SEQ ID NO: 22. In certain aspects, the C-terminal domain is a polypeptide that includes the amino acid sequence of SEQ ID NO:12, 159, or 22 with one or more conservative amino acid substitutions thereto. In certain aspects, the C-terminal domain is a polypeptide that includes an amino acid sequence at least 85% (e.g., at least 90%, 95%, or 99%, or a 100%) identical to the amino acid sequence of any one of SEQ ID NO: 12, 159, or 22. In certain aspects, the C-terminal domain is a C-cap domain or a fragment thereof from TALE proteins like those expressed in *Burkholderia, Paraburkholderia*, or *Xanthomonas.*

In certain aspects, each of the three or more RUs present in the NBD of the polypeptides disclosed herein independently comprises a 33-36 amino acid long sequence that is at least 70% (e.g., at least 75%, 80%, 85%, 90%, 95%, or 99%, or a 100%) identical to:

```
                                  (SEQ ID NO: 131)
FKADDAVRIACRTGGSHNLKAVHKNYERLRARG;

(SEQ ID NO: 132)
FNADQVIKIVGHDGGSNNIDVVQQFFPELKAFG;
```

-continued

```
                                  (SEQ ID NO: 138)
FSADQVVKIAGHSGGSNNIAVMLAVFPRLRDFG;
or (SEQ ID NO: 25)
LDRQQILRIASHDGGSKNIAAVQKFLPKLMNFG,
``` and may include BCR selected from HK, HD, HA, HN, HG, NN, NG, RN, HI, HV, RT, HD, SN, HS, GS, or LN, at amino acid positions 12 and 13, respectively, numbered relative to one of SEQ ID NOs:25, 131, 132, and 138. In certain aspects, each of the three or more RUs may independently have the sequence of one of SEQ ID NOs:25, 131, 132, and 138 with one or more conservative amino acid substitutions thereto. As indicated in Table 1, SEQ ID NOs:25, 131, 132, and 138 are repeat units identified in a protein from a bacterium of the order Legionellales. This Legionellales bacterium protein has the amino acid sequence:

```
                                                  (SEQ ID NO: 139)
MPKTKITTVSHGYDLDLMSSLPNGDPNQAKQGKIYLSGNGVYVVRDVAG

IVHRGQLEFAINLEQLEQKINEPAFKAVILEKTSRAVGYTISNECFNVE

LNALAKAGFNNLDIDKLIFRRSSRGTVQTVLNSYNILLEKPYNLDRQQI

LRIASHDGGSKNIAAVQKFLPKLMNFGFNADQVIKIVGHDGGSNNIDVV

QQFFPELKAFGFSADQVVKIAGHSGGSNNIAVMLAVFPRLRDFGFKADD

AVRIACRTGGSHNLKAVHKNYERLRARGYDNKKIISIAASNCGTETINT

IMSTDEVEESDFLYFVTTVSTPVASQNLSSASNTNINYSNRFMTARKKT

SDDNTDEVEEDQHRDKRRSNGR
```

The RUs identified in this protein are indicated by SEQ ID NOs: 25, 131, 132, and 138 in FIG. 7.

In certain aspects, the polypeptide comprises an N-terminal domain, where the C-terminus (i.e., the last amino acid) of the N-terminal domain is covalently linked to the N-terminus (i.e., the first amino acid) of the first RU of the NBD either directly or via a linker. In certain aspects, the N-terminal domain comprises an amino acid sequence at least 85% (e.g., at least 90%, 95%, or 99%, or a 100%) identical to the amino acid sequence set forth in SEQ ID NO:140 or a fragment thereof. SEQ ID NO:140 sets forth the amino acid sequence N-terminal to the repeat of SEQ ID NO: 25 as shown in FIG. 7. A fragment of SEQ ID NO:140 may exclude about 10, 20, or 30 amino acids from the N-terminus of SEQ ID NO:140. In certain aspects, the N-terminal domain is a polypeptide that includes the amino acid sequence of SEQ ID NOs:13, 20, 21, 140 with one or more conservative amino acid substitutions thereto. In certain aspects, the N-terminal domain is a polypeptide that includes an amino acid sequence at least 85% (e.g., at least 90%, 95%, or 99%, or a 100%) identical to the amino acid sequence of any one of SEQ ID NOs:13, 20, 21, or 140. In certain aspects, the N-terminal domain is a N-cap domain or a fragment thereof from TALE proteins like those expressed in *Burkholderia, Paraburkholderia*, or *Xanthomonas.*

In certain aspects, the polypeptide comprises a C-terminal domain, where the N-terminus (i.e., the first amino acid) of the C-terminal domain is fused to the C-terminus (i.e., the last amino acid) of the last RU or the half-repeat unit, if present, in the NBD either directly or via a linker. In certain aspects, the C-terminal domain is the C-terminus of the Legionellales bacterium protein having the amino acid sequence set forth in SEQ ID NO:139 and may have the amino acid sequence set forth in SEQ ID NO:141. SEQ ID NO:141 sets forth the amino acid sequence C-terminal to the last repeat of SEQ ID NO: 131 as shown in FIG. 7. A fragment of SEQ ID NO:141 may exclude about 10, 20, or 25 amino acids from the C-terminus of SEQ ID NO:141. In certain aspects, the C-terminal domain comprises a fragment of SEQ ID NO:141, such as a fragment having the amino acid sequence set forth in SEQ ID NO: 142. In certain aspects, the C-terminal domain is a polypeptide that includes the amino acid sequence of SEQ ID NO:141 or 142 with one or more conservative amino acid substitutions thereto. In certain aspects, the C-terminal domain is a polypeptide that includes an amino acid sequence at least 85% (e.g., at least 90%, 95%, or 99%, or a 100%) identical to the amino acid sequence of any one of SEQ ID NO:141 or 142. In certain aspects, the C-terminal domain is a C-cap domain or a fragment thereof from TALE proteins like those expressed in *Burkholderia, Paraburkholderia*, or *Xanthomonas.*

In certain aspects, the C-terminal domain is a polypeptide that includes the amino acid sequence of SEQ ID NO:12, 159, 22, 141, or 142 with one or more conservative amino acid substitutions thereto. In certain aspects, the C-terminal domain is a polypeptide that includes an amino acid sequence at least 85% (e.g., at least 90%, 95%, or 99%, or a 100%) identical to the amino acid sequence of any one of SEQ ID NO:12, 159, 22, 141, or 142. In certain aspects, the C-terminal domain is a C-cap domain or a fragment thereof from TALE proteins like those expressed in *Burkholderia, Paraburkholderia*, or *Xanthomonas.*

In certain aspects, each of the three or more RUs present in the NBD of the polypeptides disclosed herein independently comprises a 33-36 amino acid long sequence that is at least 70% (e.g., at least 75%, 80%, 85%, 90%, 95%, or 99%, or a 100%) identical to:

(SEQ ID NO: 23)
FSAEQIVRIAAHDGGSRNIEAVQQAQHVLKELG;

(SEQ ID NO: 24)
FSAEQIVSIVAHDGGSRNIEAVQQAQHILKELG;

(SEQ ID NO: 26)
FSAEQIVRIAAHDGGSLNIDAVQQAQQALKELG;

(SEQ ID NO: 27)
FSTEQIVCIAGHGGGSLNIKAVLLAQQALKDLG;

(SEQ ID NO: 28)
YSSEQIVRVAAHGGGSLNIKAVLQAHQALKELD;

(SEQ ID NO: 29)
FSAEQIVHIAAHGGGSLNIKAILQAHQTLKELN;

(SEQ ID NO: 30)
FSAEQIVRIAAHIGGSRNIEAIQQAHHALKELG;

(SEQ ID NO: 31)
FSAEQIVRIAAHIGGSHNLKAVLQAQQALKELD;

(SEQ ID NO: 32)
FSAKHIVRIAAHIGGSLNIKAVQQAQQALKELG;

(SEQ ID NO: 34)
FSADQIVRIAAHKGGSHNIVAVQQAQQALKELD;

(SEQ ID NO: 35)
FSAEQIVSIAAHVGGSHNIEAVQKAHQALKELD;
or (SEQ ID NO: 133)
FSAEQIVRIAAHIGGSRNIEATIKHYAMLTQPP, and comprises BCR selected from HK, HD, HA, HN, HG, NN, NG, RN, HI, HV, RT, HD, SN, HS, GS, or LN at amino acid positions 12 and 13, respectively, numbered relative to one of SEQ ID NOs:23-24, 26-32, 34-35, and 133. In certain aspects, each of the three or more RUs may independently have the sequence of one of SEQ ID NOs: 23-24, 26-32, 34-35, and 133 with one or more conservative amino acid substitutions thereto.

The RUs listed in SEQ ID NOs:23-24, 26-32, 34-35, and 133 were identified in a protein from *L. maceachernii*. The amino acid sequence for this protein is set forth in SEQ ID NO:143:

```
MPKTNQPKNLEAKSTKNKISLPQDPQTLNELKIKGYPQDLAERLIKKGS
SLAVKTVLKDHEQLVNFFTHLQIIRMAAQKGGAKNITTALNEYNSLTNL
GYSSEQIVRVAAHGGGSLNIKAVLQAHQALKELDFSAEQIVRIAAHDGG
SLNIDAVQQAQQALKELGFSAKHIVRIAAHIGGSLNIKAVQQAQQALKE
LGFSADQIVRIAAHKGGSHNIVAVQQAQQALKELDFSAEQIVRIAAHIG
GSRNIEAIQQAHHALKELGFSAEQIVRIAAHIGGSHNLKAVLQAQQALK
ELDFSAEQIVRIAAHDGGSRNIEAVQQAQHVLKELGFSAEQIVHIAAHG
GGSLNIKAILQAHQTLKELNFSAEQIVSIVAHDGGSRNIEAVQQAQHIL
KELGESTEQIVCIAGHGGGSLNIKAVLLAQQALKDLGFSAEQIVSIAAH
VGGSHNIEAVQKAHQALKELDFSAEQIVRIAAHIGGSRNIEATIKHYAM
LTQPPYMLSQEQFLRLIDHHSGHLNLSILLDEQQWQAINDLCLQPHHFG
RQNALEKFLQQGQRKYQNLQELEQFLFQDSADPMLLQETENQHEAEKIN
DCMDFILRLISATEPLDLQIEIEGIGLFSPSMHFDATQANFSTPAANEE
KIDNSATEAGVNSRKRKIAAAHQKQPPRKKTATPLSATFISTLTTLAQS
DNPRLEMASAEALMLKAPQKLAMGITVRKKTKCEGIAIITVTDKTKLNG
WLSSASESTYSSVEAQGTRTVNNTHAFFSTPLTSDKKSPSFSSLDFYED
SGLGFDEEITNPPYMPELEPEFIL
```

The 12 RUs identified in the protein from *L. maceachernii* are indicated by underlining and include the amino acid sequences set forth in SEQ ID NOs: 28, 26, 32, 34, 30, 31, 23, 29, 24, 27, 35, and 133, respectively.

In certain aspects, the polypeptide comprises an N-terminal domain, where the C-terminus of the N-terminal domain is fused to the N-terminus of the first RU of the NBD either directly or via a linker. In certain aspects, the N-terminal domain comprises an amino acid sequence at least 85% (e.g., at least 90%, 95%, or 99%, or a 100%) identical to the amino acid sequence set forth in SEQ ID NO:144 or a fragment thereof. SEQ ID NO:144 sets forth the amino acid sequence N-terminal to the repeat of SEQ ID NO: 28 in SEQ ID NO:143 and has the following sequence:

(SEQ ID NO: 144)
MPKTNQPKNLEAKSTKNKISLPQDPQTLNELKIKGYPQDLAERLIKKGSSL
AVKTVLKDHEQLVNFFTHLQIIRMAAQKGGAKNITTALNEYNSLTNLG

A fragment of SEQ ID NO:144 may exclude about 10, 20, or 30 amino acids from the N-terminus of SEQ ID NO:144. In certain aspects, the N-terminal domain is a polypeptide that includes the amino acid sequence of SEQ ID NOs:13, 20, 21, 140, or 144 with one or more conservative amino acid substitutions thereto. In certain aspects, the N-terminal domain is a polypeptide that includes an amino acid sequence at least 85% (e.g., at least 90%, 95%, or 99%, or a 100%) identical to the amino acid sequence of any one of SEQ ID NOs:13, 20, 21, 140, or 144. In certain aspects, the N-terminal domain is a N-cap domain or a fragment thereof from TALE proteins like those expressed in *Burkholderia, Paraburkholderia*, or *Xanthomonas*.

In certain aspects, the polypeptide comprises a C-terminal domain, where the N-terminus of the C-terminal domain is fused to the C-terminus of the last RU or the half-repeat unit, if present, in the NBD either directly or via a linker. In certain aspects, the C-terminal domain is the C-terminus of the *L. maceachernii* protein having the amino acid sequence set forth in SEQ ID NO:143 and may have the amino acid sequence set forth in SEQ ID NO:145. SEQ ID NO:145 sets forth the amino acid sequence C-terminal to the last repeat of SEQ ID NO: 133 in SEQ ID NO:143 and has the following sequence:

(SEQ ID NO: 145)
YMLSQEQFLRLIDHHSGHLNLSILLDEQQWQAINDLCLQPHHFGRQNALE

KFLQQGQRKYQNLQELEQFLFQDSADPMLLQETENQHEAEKINDCMDFIL

RLISATEPLDLQIEIEGIGLFSPSMHFDATQANFSTPAANEEKIDNSATE

AGVNSRKRKIAAAHQKQPPRKKTATPLSATFISTLTTLAQSDNPRLEMAS

AEALMLKAPQKLAMGITVRKKTKCEGIAIITVTDKTKLNGWLSSASESTY

SSVEAQGTRTVNNTHAFFSTPLTSDKKSPSFSSLDFYEDSGLGFDEEITN

PPYMPELEPEFIL.

A fragment of SEQ ID NO:145 may exclude about 10, 20, or 25 amino acids from the C-terminus of SEQ ID NO:145. In certain aspects, the C-terminal domain comprises a fragment of SEQ ID NO:145, such as a fragment having the amino acid sequence set forth in SEQ ID NO: 146. In certain aspects, the C-terminal domain is a polypeptide that includes the amino acid sequence of SEQ ID NO:145 or 146 with one or more conservative amino acid substitutions thereto. In certain aspects, the C-terminal domain is a polypeptide that includes an amino acid sequence at least 85% identical to the amino acid sequence of any one of SEQ ID NO:145 or 146. In certain aspects, the C-terminal domain is a C-cap domain or a fragment thereof from TALE proteins like those expressed in *Burkholderia, Paraburkholderia*, or *Xanthomonas*.

In certain aspects, an N-terminus domain or a C-terminus domain derived from the *L. maceachernii* protein having the sequence set forth in SEQ ID NO:143 may be used to construct a polypeptide comprising a NBD, wherein the N-terminus domain mediates binding to the sequence G or G-G. In addition to including one or both of the N-terminus domain and the C-terminus domain derived from the *L. maceachernii* protein having the sequence set forth in SEQ ID NO:143, the polypeptide may include a plurality of repeats, where each repeat has a sequence derived independently from one or more of SEQ ID NOs: 28, 26, 32, 34, 30, 31, 23, 29, 24, 27, 35, and 133, for binding the bases T, C, A, G, G, A or C, C, T, C, T, G or A, and A or G, respectively.

In certain aspects, a recombinant polypeptide comprising a NBD and a heterologous functional domain, the NBD comprising at least three repeat units (RUs) ordered from N-terminus to C-terminus of the NBD to specifically bind to a target nucleic acid, where each of the RUs comprises the consensus sequence: YK(P/S)EDIIRLASH(D/G)GGSVNLEAVLRL(H/N)(P/S)QL(I/T)(G/R)LG (SEQ ID NO:156) is provided. This consensus sequence is based on the repeats identified in a *Francisella* bacterium protein having the amino acid sequence:

(SEQ ID NO: 147)
MTLTLKQEKIAINKKLRSYRISKRKFLLDFSKMNLSPEGLNYAQEELAK

LQFQAKASLETDQGINIEEQLYQLGYTQSHLRPCADRYNCSILLNTLLI

NNNSFVTQEISLENRVNLVVAANGNNDGIQVFFKTYPKLKSVGYKINHC

VNLLKLNHDGFMLKNLIPYDSKLTGLGYKPEDIIRLASHGGGSVNLEAV

LRLNPQLIGLGYKSEDIIRLASHDGGSVNLEAVLRLHSQLTRLGYKSED

IIRLASHGGGSVNLEAVLRLHSQLTRLGYKSEDIIRLASHGGGSVNLEA

VLRLNPQLIGLGYKSEDIIRLASHGGGSVNLEAVLRLHSQLTRLGYKSE

DIIRLASHGGGSVNLEAVLRLNPQLIGLGYKSEDIIRLASHGGGSVNLE

AVLRLHSQLTRLGYKSEDIIRLASHGGGSVNLEAVLRLNPQLIGLGYKS

EDIIRLASHDGGSVNLEAVLRLNPQLIGLGYKSEDIIRLASHDGGSINL

EAVLRLNPQLIGLGYKSEDIIRLASSNGGSVNLEAVLRLNPQLIGLGYK

SEDIIRLASSNGGSVNLEAVLRLNPQLIGLGYKSEDIIRLASHDGGSVN

LEAVLRLHSQLTRLGYKSEDIIRLASSNGGSVNLEAVIAVHKALHSNGY

NKKQIVLIASGSSGGMRLHALNNYHFLFHSIENIQLLITILQSHLEAFR

IEQYMISGVLLNLLKQGQVISEQPCKILIDSSILNPNICQTLSNIINKY

QFKNKPLYFNPTTSIITCMLSTQECYQLLAVWERRNISPSEILNNLLNP

INIFQYQLISQTNEPDVYFLDCYHWHKFYPNMEIKQLQQLLIKAINLGI

NNCDILPEDNRTLIIEPYNDNWIKLSISIIDTIMDDSFNNLTRELFFCQ

LAPDSSNLIDDAIYIYKTQQTIEFLVTSKSRSSERFILDTSTIYKDTIE

EIEQALTHKLGALKGATYHTLIKCLLAQGYQVTGYFSMNIIGADVMPPT

IIADDYPEYITLEWLSSEPMSQRSRLRTHDINSIKTLHNPTPKSQAIHQ

MLNLLALPDAISPLDSIQNNHTSANHEQQTQGRISPISQQLDITLMRSR

KRPLQKSDNTIYHDKRYWTFIGEGSYNKAYTDGQGFVVKVAKNELGLMD

KSERSVRVFNEINPTLPQEVLAHVSQDLWISPLIENETLSPIEQASFIF

KTYIEHGRLILDGYCQNNLLQSAKYNTPVCIDPGNVVRRNSIASQEHWY

AANEKTLLRRQLYRKHMIDTIDHYHKIRHIDRTLPILMILALDFIDRKM

QHLQLQLILKKNIKSLGIAFYFYYKHNQSSTQQEFILSANIIDKILYGD

QYICDTLDQSFKTLNKSRVVTLFRQINIDMSLI

The RUs present in SEQ ID NO:147 have amino acid sequences as set forth in SEQ ID NOs:85-87, 134-137, and 151 and the half-RU present in SEQ ID NO:147 has an amino acid sequence as set forth in SEQ ID NO:152. These RUs are indicated by underlining in SEQ ID NO:147 above. The RU having the amino acid sequence set forth in SEQ ID NO:151 occurs once in SEQ ID NO:147. The RU having the amino acid sequence set forth in SEQ ID NO:86 occurs once in SEQ ID NO:147. SEQ ID NO: 85 occurs twice in SEQ ID NO:147. The RU having the amino acid sequence set forth in SEQ ID NO: 87 occurs thrice in SEQ ID NO:147. The RU having the amino acid sequence set forth in SEQ ID NO: 88 occurs thrice in SEQ ID NO:147. The RU having the amino acid sequence set forth in SEQ ID NO:134 occurs once in SEQ ID NO:147. The RU having the amino acid sequence set forth in SEQ ID NO:135 occurs twice in SEQ ID NO:147. The RU having the amino acid sequence set forth in SEQ ID NO: 136 occurs twice in SEQ ID NO:147.

In certain aspects, the NBD of the recombinant polypeptide disclosed herein may include at three RUs, where each RU independently comprises a 33-36 amino acid long sequence that is at least 70% (e.g., at least 75%, 80%, 85%, 90%, 95%, or 99%, or a 100%) identical to:

```
                                        (SEQ ID NO: 85)
YKSEDIIRLASHDGGSVNLEAVLRLHSQLTRLG;

(SEQ ID NO: 86)
YKPEDIIRLASHGGGSVNLEAVLRLNPQLIGLG;

(SEQ ID NO: 87)
YKSEDIIRLASHGGGSVNLEAVLRLHSQLTRLG;

(SEQ ID NO: 88)
YKSEDIIRLASHGGGSVNLEAVLRLNPQLIGLG;

(SEQ ID NO: 134)
YKSEDIIRLASHDGGSVNLEAVLRLNPQLIGLG;

(SEQ ID NO: 135)
YKSEDIIRLASHDGGSINLEAVLRLNPQLIGLG;

(SEQ ID NO: 136)
YKSEDIIRLASSNGGSVNLEAVLRLNPQLIGLG;

(SEQ ID NO: 137)
YKSEDIIRLASSNGGSVNLEAVIAVHKALHSNG,
or (SEQ ID NO: 151)
YKINHCVNLLKLNHDGFMLKNLIPYDSKLTGLG;
``` and comprises BCR selected from HK, HD, HA, HN, HG, NN, NG, RN, HI, HV, RT, HD, SN, HS, GS, or LN at amino acid positions 12 and 13, respectively, numbered relative to one of SEQ ID NOs:85-88, 134-137, and 151. In certain aspects, each of the RUs may independently have an amino acid sequence of any one of SEQ ID NOs:85-88, 134-137, and 151 with one or more conservative amino acid substitutions thereto.

In certain aspects, the polypeptide comprises a half-RU comprises a 15-20 amino acid long sequence that is at least 70% (e.g., at least 75%, 80%, 85%, 90%, 95%, or 99%, or a 100%) identical to the amino acid sequence set forth in SEQ ID NO: 152 (YNKKQIVLIASGSSGG). In certain aspects, the half-RU may include BCR selected from HK, HD, HA, HN, HG, NN, NG, RN, HI, HV, RT, HD, SN, HS, GS, or LN at amino acid positions 12 and 13, respectively, numbered relative to SEQ ID NO: 152.

In certain aspects, the polypeptide comprises an N-terminal domain, wherein the C-terminus of the N-terminal domain is fused to the N-terminus of the first RU of the NBD directly or via a linker. In certain aspects, the N-terminal domain comprises an amino acid sequence at least 85% identical to the amino acid sequence set forth in SEQ ID NO:148 or a fragment thereof. SEQ ID NO:148 is the amino acid sequence N-terminus to the first RU of SEQ ID NO:86 present in SEQ ID NO: 147. In certain aspects, the N-terminal domain comprises an amino acid sequence at least 85% (e.g., at least 90%, 95%, or 99%, or a 100%) identical to the amino acid sequence set forth in SEQ ID NOs: 13, 20, 21, 140, or 144.

In certain aspects, the polypeptide comprises C-terminal domain, wherein the N-terminus of the C-terminal domain is fused to the C-terminus of the last RU of the NBD directly or via a linker. In certain aspects, the C-terminal domain comprises an amino acid sequence at least 85% (e.g., at least 90%, 95%, or 99%, or a 100%) identical to the amino acid sequence set forth in SEQ ID NO:149 or a fragment thereof, e.g., SEQ ID NO:147. In certain aspects, the C-terminal domain is a polypeptide that includes an amino acid sequence at least 85% (e.g., at least 90%, 95%, or 99%, or a 100%) identical to the amino acid sequence of any one of SEQ ID NO:12, 159, 22, 141, 142, 145, or 146. In certain aspects, the C-terminal domain is a C-cap domain or a fragment thereof from TALE proteins like those expressed in *Burkholderia, Paraburkholderia*, or *Xanthomonas*.

In certain aspects, the N-terminal domains may be derived from the N-terminal regions, e.g., N-cap domain used in conjunction with DNA binding domains disclosed in US20180010152. In certain aspects, the N-terminal domains may be derived from the N-terminal regions disclosed in US20150225465, e.g., SEQ ID NOs.:7, 8, or 9 disclosed therein.

In certain aspects, the RUs present in a NBD of the present disclosure can be independently selected from the RUs provided herein. In certain aspects, the individual RUs listed in Table 1 can be used to generate a NBD without any amino acid modification (e.g., deletion, insertion, and/or substitution). In certain aspects, the individual RUs listed in Table 1 can be modified via deletion, insertion, and/or substitution and used to generate a NBD. As noted herein, RUs identified herein from different animal pathogen proteins can be mixed and matched to create a NBD. In other aspects, a NBD may include RUs from only one genus of bacteria as disclosed herein. In certain aspects, the NBD provided herein does not include the RUs in an order that occurs in the naturally occurring protein from which it is derived, for example, in a protein from a *Legionella* species bacterium, a *Francisella* species bacterium, or a Legionellales order bacterium. In certain aspects, the NBD disclosed herein include a half-repeat at the C-terminus of the NBD, where the half-repeat forms the last RU in the NBD before the start of a linker and/or a C-domain as provided herein.

In certain aspects, one or more RUs in a NBD provided herein may be at least 70%, 75%, 80%, 85%, 90%, 91%, 92%, 93%, 94%, 95%, 96%, 97%, 98%, or 99%, or a 100% identical to a RU provided herein. Percent identity between a pair of sequences may be calculated by multiplying the number of matches in the pair by 100 and dividing by the length of the aligned region, including gaps. Identity scoring only counts perfect matches and does not consider the degree of similarity of amino acids to one another. Only internal gaps are included in the length, not gaps at the sequence ends.

$$\text{Percent Identity}=(\text{Matches}\times 100)/\text{Length of aligned region(with gaps)}$$

The phrase "conservative amino acid substitution" refers to substitution of amino acid residues within the following groups: 1) L, I, M, V, F; 2)R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain.

Guidance for substitutions, insertions, or deletions may be based on alignments of amino acid sequences of proteins from different species or from a consensus sequence based on a plurality of proteins having the same or similar function.

In certain aspects, the N-terminal domain or the C-terminal domain included in the disclosed NBD may include a nuclear localization sequence (NLS) to facilitate entry into the nucleus of a cell, e.g., an animal or a plant cell. In certain aspects, the polypeptide may be produced in a host cell and expressed with a translocation signal at the N-terminus which translocation signal may be cleaved during translocation.

In certain aspects, the RUs may be linked C-terminus to N-terminus with no additional amino acids separating immediately adjacent RUs. In certain aspects, immediately adjacent RUs may be separated by a spacer sequence of at least one amino acid. In certain aspects, the spacer sequence includes at least 2, 3, 4, 5, 6, or 7 amino acids, or up to 5, or up to 10 amino acids. The spacer sequence may include amino acids that have small side chains. In certain aspects, the spacer sequence is a flexible linker.

Linkers

Any functional domain, such as a nuclease domain, a gene regulation domain, or a fluorophore can be linked to a NBD as provided herein, e.g., a MAP-NBD (e.g., a *L. quateirensis, Burkholderia, Paraburkholderia,* or *Francisella*-derived) either directly or through a linker. The linker can be naturally occurring or non-naturally occurring (e.g., synthetic). In some embodiments, a MAP-NBD (e.g., a *L. quateirensis, Burkholderia, Paraburkholderia,* or *Francisella*-derived) can be produced with a "molecular velcro" at its N or C-terminus. For example, the MAP-NBD (e.g., a *L. quateirensis,* Legionellales, *Burkholderia, Paraburkholderia,* or *Francisella*-derived) can be produced with a first peptide sequence. Separately, a nuclease of interest (e.g., a half cleavage domain such as FokI) can be engineered with a second peptide sequence that is complementary and binds to the first peptide sequence, thereby allowing the formation of a MAP-NBD-nuclease after administration in cells.

In other embodiments, a MAP-NBD (e.g., a *L. quateirensis, Burkholderia, Paraburkholderia,* or *Francisella*-derived) can be produced with a linker at its N- or C-terminus and subsequently directly conjugated to a functional domain (e.g., gene editing domain, gene regulator domain, or fluorescent domain).

In certain aspects, a linker can be encoded by a nucleic acid sequence that is 3 to 540 nucleotides in length, e.g., 3 to 18, 18 to 33, 33 to 48, 48 to 63, 63 to 78, 78 to 93, 93 to 108, 108 to 123, 123 to 138, 138 to 153, 153 to 168, 168 to 183, 183 to 198, 198 to 213, 213 to 228, 228 to 243, 243 to 258, 258 to 273, 273 to 288, 288 to 303, 303 to 318, 318 to 333, 333 to 348, 348 to 363, 363 to 378, 378 to 393, 393 to 408, 408 to 423, 423 to 438, 438 to 453, 453 to 468, 468 to 483, 483 to 498, 498 to 513, 513 to 528, 528 to 543, 3, 18, 33, 48, 63, 78, 93, 108, 123, 138, 153, 168, 183, 198, 213, 228, 243, 258, 273, 288, 303, 318, 333, 348, 363, 378, 393, 408, 423, 438, 453, 468, 483, 498, 513, 528, or 543 nucleotides in length. In certain aspects, a linker can be encoded by a nucleic acid sequence that is 3, 18, 33, 48, 63, 78, 93, 108, 123, 138, 153, 168, 183, 198, 213, 228, 243, 258, 273, 288, 303, 318, 333, 348, 363, 378, 393, 408, 423, 438, 453, 468, 483, 498, 513, 528, or 543 nucleotides in length.

In certain aspects, a linker can be from 1 to 180, from 1 to 20, from 20 to 40, from 40 to 60, from 60 to 80, from 80 to 100, from 100 to 120, from 120 to 140, from 140 to 160, or from 160 to 180 amino acid residues in length.

A linker for linking a nuclease domain to a MAP-NBD (e.g., *L. quateirensis, Burkholderia, Paraburkholderia,* or *Francisella*-derived) can be 1, 10, 20, 30, 40, 50, 60, 70, 80, 90, 100, 110, 120, 130, 140, 150, 160, 170, or 180 amino acid residues in length. A linker can be 1, 10, 20, 30, 40, 50, 60, 70, 80, 90, 100, 110, 120, 130, 140, 150, 160, 170, or 180 amino acid residues in length.

In certain aspects, the linker can be the C-terminus of a naturally occurring *L. quateirensis*-derived protein, such as the C-terminus of SEQ ID NO: 1. A C-terminus can be the full-length C-terminus sequence and can have a sequence of ALVKEYFPVFSSFHFTADQIVALICQSKQCFRNLK-KNHQQWKNKGLSAEQIVDLILQETPPK PNFNNTSSSTPSPSAPSFFQGPST-PIPTPVLDNSPAPIFSNPVCFFSSRSENNTEQYLQD-STLDLD SQLGDPT-KNFNVNNFWSLFPFDDVGYHPHSNDVGYHLHSDEE SPFFDF (SEQ ID NO: 12). In some embodiments, any truncation of SEQ ID NO: 12 can be used as a linker. In some embodiments, a linker can be a C-terminus with amino acid residues at position 1 (A) to position 63 (P) of the naturally occurring *L. quateirensis*-derived protein as follows:

```
                                              (SEQ ID NO: 22)
ALVKEYFPVFSSFHFTADQIVALICQSKQCFRNLKKNHQQWKNKGLSAEQ

IVDLILQETPPKP.
```

In certain aspects, the linker can be the C-terminus of a naturally occurring *L. quateirensis*-derived protein, such as the C-terminus of SEQ ID NO: 1. A C-terminus can be the full-length C-terminus sequence and can have a sequence of

```
                                              (SEQ ID NO: 12)
ALVKEYFPVFSSFHFTADQIVALICQSKQCFRNLKKNHQQWKNKGLSAEQ

IVDLILQETPPKPNFNNTSSSTPSPSAPSFFQGPSTPIPTPVLDNSPAPI

FSNPVCFFSSRSENNTEQYLQDSTLDLDSQLGDPTKNFNVNNFWSLFPFD

DVGYHPHSNDVGYHLHSDEESPFFDF.
```

In certain aspects, the linker may be a C-terminal domain as disclosed herein.

In certain aspects, the C-terminal domains that can be present in the polypeptides disclosed herein may be derived from the C-terminal regions, e.g., C-cap domain used in conjunction with DNA binding domains disclosed in US20180010152. In certain aspects, the C-terminal domains may be derived from the C-terminal regions disclosed in US20150225465, e.g., SEQ ID NOs: 64, 65, or 66 disclosed therein.

Functional Domains

A NBD as disclosed herein or a MAP-NBD (e.g., *L. quateirensis, Burkholderia, Paraburkholderia*, or *Francisella*-derived) can be linked to a functional domain. The functional domain can provide different types of activity, such as genome editing, gene regulation (e.g., activation or repression), or visualization of a genomic locus via imaging. In certain aspects, the functional domain is heterologous to the NBD. Heterologous in the context of a functional domain and a NBD as used herein indicates that these domains are derived from different sources and do not exist together in nature.

In certain aspects, a method of modulating expression of an endogenous gene in a cell is disclosed. The method may include introducing into the cell a polypeptide comprising a NBD and a heterologous functional domain, where the endogenous gene comprises the target nucleic acid sequence bound by the NBD of the polypeptide and the heterologous functional domain modulates expression of the endogenous gene. In some embodiments, the polypeptide can be introduced as a nucleic acid encoding the polypeptide. In certain aspects, the nucleic acid is a DNA or a RNA, e.g., a mRNA. In certain aspects, the cell is a human cell and the sequence of the nucleic acid is codon optimized for expression in a human cell. In certain aspects, the functional domain is a transcriptional activator and the target nucleic acid sequence is present in an expression control region of the gene, where the polypeptide increases expression of the gene. In certain aspects, the functional domain is a transcriptional repressor and the target nucleic acid sequence is present in an expression control region of the gene, wherein the polypeptide decreases expression of the gene. In certain aspects, the expression control region of the gene comprises a promoter region of the gene.

In some aspects, the functional domain is a nuclease comprising a cleavage domain or a half-cleavage domain and the endogenous gene is inactivated by cleavage. In some aspects, the inactivation occurs via non-homologous end joining (NHEJ). In some aspects, the inactivation occurs by deletion or insertion of base pairs, introduction of a single nucleotide polymorphism (SNP), or introduction of a longer stretch of heterologous DNA. In some aspects, the inactivation occurs by generation of a premature stop codon by cleavage, as taught herein. In some aspects, the polypeptide is a first polypeptide that binds to a first target nucleic acid sequence in the gene and comprises a half-cleavage domain and the method comprises introducing a second polypeptide that is a polypeptide comprising a NBD that binds to a second target nucleic acid sequence in the gene and comprises a half-cleavage domain. In some aspects, the first target nucleic acid sequence and the second target sequence are spaced apart in the gene and the two half-cleavage domains mediate a cleavage of the gene sequence at a location in between the first and second target nucleic acid sequences.

Also provided herein is a method of introducing an exogenous nucleic acid into a region of interest in the genome of a cell, the method comprising: introducing into the cell: (i) a polypeptide comprising a NBD as disclosed and a cleavage domain or a half cleavage domain, where NBD of the polypeptide binds to a target nucleic acid sequence present adjacent the region of interest, and (ii) the exogenous nucleic acid, where the cleavage domain or the half-cleavage domain introduces a cleavage in the region of interest and where the exogenous nucleic acid in integrated into the cleaved region of interest by homologous recombination.

Further aspects of the polypeptides and methods are described below.

A. Genome Editing Domains

A NBD as disclosed herein or a MAP-NBD (e.g., *L. quateirensis, Burkholderia, Paraburkholderia,* or *Francisella*-derived) can be linked to a nuclease, wherein the MAP-NBD provides specificity and targeting and the nuclease provides genome editing functionality. In some embodiments, the nuclease can be a cleavage half domain, which dimerizes to form an active full domain capable of cleaving DNA. In other embodiments, the nuclease can be a cleavage domain, which is capable of cleaving DNA without needing to dimerize. For example, a nuclease comprising a cleavage half domain can be an endonuclease, such as FokI or Bfil. In some embodiments, two cleavage half domains (e.g., FokI or Bfil) can be fused together to form a fully functional single cleavage domain. When half cleavage domains are used as the nuclease, two MAP-NBDs can be engineered, the first MAP-NBD binding to a top strand of a target nucleic acid sequence and comprising a first FokI cleavage half domain and a second MAP-NBD binding to a bottom strand of a target nucleic acid sequence and comprising a second FokI half cleavage domain. In some embodiments, the nuclease can be a type IIS restriction enzyme, such as FokI or Bfil.

In some embodiments, a cleavage domain capable of cleaving DNA without need to dimerize may be a meganuclease. Meganucleases are also referred to as homing endonucleases. In some embodiments, the meganuclease may be I-AniI or I-OnuI.

A nuclease domain fused to a MAP-NBD (e.g., *L. quateirensis, Burkholderia, Paraburkholderia,* or *Francisella*-derived) can be an endonuclease or an exonuclease. An endonuclease can include restriction endonucleases and homing endonucleases. An endonuclease can also include Si Nuclease, mung bean nuclease, pancreatic DNase I, micrococcal nuclease, or yeast HO endonuclease. An exonuclease can include a 3'-5' exonuclease or a 5'-3' exonuclease. An exonuclease can also include a DNA exonuclease or an RNA exonuclease. Examples of exonuclease includes exonucleases I, II, III, IV, V, and VIII; DNA polymerase I, RNA exonuclease 2, and the like.

A nuclease domain fused to a NBD as disclosed herein or a MAP-NBD (e.g., *L. quateirensis, Burkholderia, Paraburkholderia,* or *Francisella*-derived) can be a restriction endonuclease (or restriction enzyme). In some instances, a restriction enzyme cleaves DNA at a site removed from the recognition site and has a separate binding and cleavage domains. In some instances, such a restriction enzyme is a Type IIS restriction enzyme.

A nuclease domain fused to a NBD as disclosed herein or a MAP-NBD (e.g., *L. quateirensis, Burkholderia, Paraburkholderia,* or *Francisella*-derived) can be a Type IIS nuclease. A Type IIS nuclease can be FokI or Bfil. In some cases, a nuclease domain fused to a MAP-NBD (e.g., *L. quateirensis, Burkholderia, Paraburkholderia,* or *Francisella*-derived) is FokI. In other cases, a nuclease domain fused to a MAP-NBD (e.g., *L. quateirensis, Burkholderia, Paraburkholderia,* or *Francisella*-derived) is Bfil.

FokI can be a wild-type FokI or can comprise one or more mutations. In some cases, FokI can comprise 1, 2, 3, 4, 5, 6, 7, 8, 9, 10, or more mutations. A mutation can enhance cleavage efficiency. A mutation can abolish cleavage activity. In some cases, a mutation can modulate homodimerization. For example, FokI can have a mutation at one or more amino acid residue positions 446, 447, 479, 483, 484, 486, 487, 490, 491, 496, 498, 499, 500, 531, 534, 537, and 538 to modulate homodimerization.

In some instances, a FokI cleavage domain is, for example, as described in Kim et al. "Hybrid restriction enzymes: Zinc finger fusions to Fok I cleavage domain," PNAS 93: 1156-1160 (1996). In some cases, a FokI cleavage domain described herein is a FokI of SEQ ID NO: 11 (TABLE 2). In other instances, a FokI cleavage domain described herein is a FokI, for example, as described in U.S. Pat. No. 8,586,526.

TABLE 2 illustrates an exemplary FokI sequence that can be used herein with a method or system described herein.

TABLE 2

| SEQ ID NO | FokI Sequence |
|---|---|
| SEQ ID NO: 11 | QLVKSELEEKKSELRHKLKYVPHEYIELIEIARNST QDRILEMKVMEFFMKVYGYRGKHLGGSRKPDGAIYT VGSPIDYGVIVDTKAYSGGYNLPIGQADEMQRYVEE NQTRNKHINPNEWWKVYPSSVTEFKFLFVSGHFKGN |

TABLE 2-continued

| SEQ ID NO | FokI Sequence |
|---|---|
| | YKAQLTRLNHITNCNGAVLSVEELLIGGEMIKAGTL TLEEVRRKFNNGEINF |

A MAP-NBD (e.g., *L. quateirensis, Burkholderia, Paraburkholderia,* or *Francisella*-derived) can be linked to a functional group that modifies DNA nucleotides, for example an adenosine deaminase.

B. Regulatory Domains

As another example, NBD as disclosed herein or a MAP-NBD (e.g., *L. quateirensis, Burkholderia, Paraburkholderia,* or *Francisella*-derived) can be linked to a gene regulating domain. A gene regulation domain can be an activator or a repressor. For example, a NBD as disclosed herein or a MAP-NBD (e.g., *L. quateirensis, Burkholderia, Paraburkholderia,* or *Francisella*-derived) can be linked to an activation domain, such as VP16, VP64, p65, p300 catalytic domain, TET1 catalytic domain, TDG, Ldb1 self-associated domain, SAM activator (VP64, p65, HSF1), or VPR (VP64, p65, Rta). The terms "activator," "activation domain" and "transcriptional activator" are used interchangeably to refer to a polypeptide that increases expression of a gene. Alternatively, a MAP-NBD (e.g., *L. quateirensis, Burkholderia, Paraburkholderia,* or *Francisella*-derived) can be linked to a repressor, such as KRAB, Sin3a, LSD1, SUV39H1, G9A (EHMT2), DNMT1, DNMT3A-DNMT3L, DNMT3B, KOX, TGF-beta-inducible early gene (TIEG), v-erbA, MBD2, MBD3, Rb, or MeCP2. The terms "repressor," "repressor domain," and "transcriptional repressor" are used herein interchangeably to refer to a polypeptide that decreases expression of a gene.

In some embodiments, a NBD as disclosed herein or a MAP-NBD (e.g., *L. quateirensis, Burkholderia, Paraburkholderia,* or *Francisella*-derived) can be linked to a DNA modifying protein, such as DNMT3a. A MAP-NBD (e.g., *L. quateirensis, Burkholderia, Paraburkholderia,* or *Francisella*-derived) can be linked to a chromatin-modifying protein, such as lysine-specific histone demethylase 1 (LSD1). A MAP-NBD (e.g., *L. quateirensis, Burkholderia, Paraburkholderia,* or *Francisella*-derived) can be linked to a protein that is capable of recruiting other proteins, such as KRAB. The DNA modifying protein (e.g., DNMT3a) and proteins capable of recruiting other proteins (e.g., KRAB) can serve as repressors of transcription. Thus, MAP-NBDs (e.g., *L. quateirensis, Burkholderia, Paraburkholderia,* or *Francisella*-derived) linked to a DNA modifying protein (e.g., DNMT3a) or a domain capable of recruiting other proteins (e.g., KRAB, a domain found in transcriptional repressors, such as Kox1) can provide gene repression functionality, can serve as transcription factors, wherein the MAP-NBD (e.g., *L. quateirensis, Burkholderia, Paraburkholderia,* or *Francisella*-derived) provides specificity and targeting and the DNA modifying protein and the protein capable of recruiting other proteins provides gene repression functionality, which can be referred to as an engineered genomic regulatory complex or a MAP-NBD-gene regulator (MAP-NBD-GR) and, more specifically, as a MAP-NBD-transcription factor (MAP-NBD-TF).

In some embodiments, expression of the target gene can be reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 92%, at least 95%, at least 97%, or at least 99% by using a DNA binding domain fused to a repression domain (e.g., a MAP-NBD-TF) of the present disclosure as compared to non-treated cells. In some embodiments, expression of a checkpoint gene can be reduced by over 90% by using a MAP-NBD-TF of the present disclosure as compared to non-treated cells.

In some embodiments, repression of the target gene with a DNA binding domain fused to a repression domain (e.g., a MAP-NBD-TF) of the present disclosure and subsequent reduced expression of the target gene can last for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, or at least 28 days. In some embodiments, repression of the target gene with a MAP-NBD-TF of the present disclosure and subsequent reduced expression of the target gene can last for 1 days to 3 days, 3 days to 5 days, 5 days to 7 days, 7 days to 9 days, 9 days to 11 days, 11 days to 13 days, 13 days to 15 days, 15 days to 17 days, 17 days to 19 days, 19 days to 21 days, 21 days to 23 days, 23 days to 25 days, or 25 days to 28 days.

In various aspects, the present disclosure provides a method of identifying a target binding site in a target gene of a cell, the method comprising: (a) contacting a cell with an engineered transcriptional repressor comprising a DNA binding domain, a repressor domain, and a linker; (b) measuring expression of the target gene; and (c) determining expression of the target gene is repressed by at least 50%, at least 60%, at least 70%, at least 80%, at least 85%, at least 90%, at least 92%, at least 95%, at least 97%, or at least 99% for at least 3 days, wherein the target gene is selected from: a checkpoint gene and a T cell surface receptor.

In some aspects, expression of the target gene is repressed in at least 75%, at least 80%, at least 85%, at least 90%, at least 95%, or at least 99% of a plurality of the cells. In some aspects, the engineered genomic regulatory complex is undetectable after at least 3 days. In some aspects, determining the engineered genomic regulatory complex is undetectable is measured by qPCR, imaging of a FLAG-tag, or a combination thereof. In some aspects, the measuring expression of the target gene comprises flow cytometry quantification of expression of the target gene.

In some embodiments, repression of the target gene with a DNA binding domain fused to a repression domain (e.g., a MAP-NBD-TF) of the present disclosure can last even after the DNA binding domain-TF becomes undetectable. The DNA binding domain fused to a repression domain (e.g., a MAP-NBD-TF) can become undetectable after at least 3 days. In some embodiments, the DNA binding domain fused to a repression domain (e.g., a MAP-NBD-TF) can become undetectable after at least 1 day, at least 2 days, at least 3 days, at least 4 days, at least 5 days, at least 6 days, at least 1 week, at least 2 weeks, at least 3 weeks, or at least 4 weeks. In some embodiments, qPCR or imaging via the FLAG-tag can be used to confirm that the DNA binding domain fused to a repression domain (e.g., a MAP-NBD-TF) is no longer detectable.

In some embodiments, repression of the PDCD1 gene can be achieved using the MAP-NBDs comprising repeat units derived from *L. quateirensis*. The sequence of the target DNA present in the promoter region of human PDCD1 gene, the amino acid sequences of a NBD capable of binding to the target DNA and comprising either a full-length C-terminal domain from SEQ ID NO:1 or a C-terminal domain from SEQ ID NO:1 truncated at amino acid position 63 are shown in TABLE 3.

TABLE 3

MAP-NBDs Targeting the PDCD1 Gene

| Target DNA Sequence in PDCD1 (5' -> 3') | Full Length MAP-NBD | MAP-NBD with C-terminal truncation to C63 |
|---|---|---|
| GAGGAAGAGGG GGCGGGAG (SEQ ID NO: 90) | MPDLELNFAIPLHLFDDETVFTHDAT NDNSQASSSYSSKSSPASANARKRTSR KEMSGPPSKEPANTKSRRANSQNNKL SLADRLTKYNIDEEFYQTRSDSLLSLN YTKKQIERLILYKGRTSAVQQLLCKH EELLNLISPDGLGHKELIKIAARNGGG NNLIAVLSCYAKLKEMGFSSQQIIRM VSHAGGANNLKAVTANHDDLQNMG FNVEQIVRMVSHNGGSKNLKAVTDN HDDLKNMGFNVEQIVRMVSHNGGSK NLKAVTDNHDDLKNMGFSSQQIIRM VSHAGGANNLKAVTANHDDLQNMG FSSQQIIRMVSHAGGANNLKAVTANH DDLQNMGFNVEQIVRMVSHNGGSKN LKAVTDNHDDLKNMGFSSQQIIRMVS HAGGANNLKAVTANHDDLQNMGFN VEQIVRMVSHNGGSKNLKAVTDNHD DLKNMGFNVEQIVRMVSHNGGSKNL KAVTDNHDDLKNMGFNVEQIVRMVS HNGGSKNLKAVTDNHDDLKNMGFN VEQIVRMVSHNGGSKNLKAVTDNHD DLKNMGFNVEQIVRMVSHNGGSKNL KAVTDNHDDLKNMGFNTEQIVRMVS HDGGSLNLKAVKKYHDALRERKFNV EQIVRMVSHNGGSKNLKAVTDNHDD LKNMGFNVEQIVRMVSHNGGSKNLK AVTDNHDDLKNMGFNVEQIVRMVSH NGGSKNLKAVTDNHDDLKNMGFSSQ QIIRMVSHAGGANNLKAVTANHDDL QNMGFNAEQIVRMVSHKGGSKNLAL VKEYFPVFSSFHFTADQIVALICQSKQ CFRNLKKNHQQWKNKGLSAEQIVDLI LQETPPKPNFNNTSSSTPSPSAPSFFQG PSTPIPTPVLDNSPAPIFSNPVCFFSSRS ENNTEQYLQDSTLDLDSQLGDPTKNF NVNNFWSLFPFDDVGYHPHSNDVGY HLHSDEESPFFDF (SEQ ID NO: 98) | MPDLELNFAIPLHLFDDETVFTHDA TNDNSQASSSYSSKSSPASANARKR TSRKEMSGPPSKEPANTKSRRANS QNNKLSLADRLTKYNIDEEFYQTRS DSLLSLNYTKKQIERLILYKGRTSA VQQLLCKHEELLNLISPDGLGHKEL IKIAARNGGGNNLIAVLSCYAKLKE MGFSSQQIIRMVSHAGGANNLKAV TANHDDLQNMGFNVEQIVRMVSH NGGSKNLKAVTDNHDDLKNMGFN VEQIVRMVSHNGGSKNLKAVTDN HDDLKNMGFSSQQIIRMVSHAGGA NNLKAVTANHDDLQNMGFSSQQII RMVSHAGGANNLKAVTANHDDLQ NMGFNVEQIVRMVSHNGGSKNLK AVTDNHDDLKNMGFSSQQIIRMVS HAGGANNLKAVTANHDDLQNMGF NVEQIVRMVSHNGGSKNLKAVTD NHDDLKNMGFNVEQIVRMVSHNG GSKNLKAVTDNHDDLKNMGFNVE QIVRMVSHNGGSKNLKAVTDNHD DLKNMGFNVEQIVRMVSHNGGSK NLKAVTDNHDDLKNMGFNVEQIV RMVSHNGGSKNLKAVTDNHDDLK NMGFNTEQIVRMVSHDGGSLNLKA VKKYHDALRERKFNVEQIVRMVSH NGGSKNLKAVTDNHDDLKNMGFN VEQIVRMVSHNGGSKNLKAVTDN HDDLKNMGFNVEQIVRMVSHNGG SKNLKAVTDNHDDLKNMGFSSQQI IRMVSHAGGANNLKAVTANHDDL QNMGFNAEQIVRMVSHKGGSKNL ALVKEYFPVFSSFHFTADQIVALIC QSKQCFRNLKKNHQQWKNKGLSA EQIVDLILQETPPKP (SEQ ID NO: 99) |
| GAGGGGGCGGG AGCAAGGGG (SEQ ID NO: 91) | MPDLELNFAIPLHLFDDETVFTHDAT NDNSQASSSYSSKSSPASANARKRTSR KEMSGPPSKEPANTKSRRANSQNNKL SLADRLTKYNIDEEFYQTRSDSLLSLN YTKKQIERLILYKGRTSAVQQLLCKH EELLNLISPDGLGHKELIKIAARNGGG NNLIAVLSCYAKLKEMGFSSQQIIRM VSHAGGANNLKAVTANHDDLQNMG FNVEQIVRMVSHNGGSKNLKAVTDN HDDLKNMGFNVEQIVRMVSHNGGSK NLKAVTDNHDDLKNMGFNVEQIVRM VSHNGGSKNLKAVTDNHDDLKNMGF NVEQIVRMVSHNGGSKNLKAVTDNH DDLKNMGFNVEQIVRMVSHNGGSKN LKAVTDNHDDLKNMGFNTEQIVRMV SHDGGSLNLKAVKKYFIDALRERKFN VEQIVRMVSHNGGSKNLKAVTDNHD DLKNMGFNVEQIVRMVSHNGGSKNL KAVTDNHDDLKNMGFNVEQIVRMVS HNGGSKNLKAVTDNHDDLKNMGFSS QQIIRMVSHAGGANNLKAVTANHDD LQNMGFNVEQIVRMVSHNGGSKNLK AVTDNHDDLKNMGFNTEQIVRMVSH DGGSLNLKAVKKYHDALRERKFSSQ QIIRMVSHAGGANNLKAVTANHDDL QNMGFSSQQIIRMVSHAGGANNLKA VTANHDDLQNMGFNVEQIVRMVSHN GGSKNLKAVTDNHDDLKNMGFNVE QIVRMVSHNGGSKNLKAVTDNHDDL KNMGFNVEQIVRMVSHNGGSKNLKA VTDNHDDLKNMGFNAEQIVRMVSHK GGSKNLALVKEYFPVFSSFHFTADQIV ALICQSKQCFRNLKKNHQQWKNKGL SAEQIVDLILQETPPKPNFNNTSSSTPS PSAPSFFQGPSTPIPTPVLDNSPAPIFSN | MPDLELNFAIPLHLFDDETVFTHDA TNDNSQASSSYSSKSSPASANARKR TSRKEMSGPPSKEPANTKSRRANS QNNKLSLADRLTKYNIDEEFYQTRS DSLLSLNYTKKQIERLILYKGRTSA VQQLLCKHEELLNLISPDGLGHKEL IKIAARNGGGNNLIAVLSCYAKLKE MGFSSQQIIRMVSHAGGANNLKAV TANHDDLQNMGFNVEQIVRMVSH NGGSKNLKAVTDNHDDLKNMGFN VEQIVRMVSHNGGSKNLKAVTDN HDDLKNMGFNVEQIVRMVSHNGG SKNLKAVTDNHDDLKNMGFNVEQ IVRMVSHNGGSKNLKAVTDNHDD LKNMGFNVEQIVRMVSHNGGSKN LKAVTDNHDDLKNMGFNTEQIVR MVSHDGGSLNLKAVKKYHDALRE RKFNVEQIVRMVSHNGGSKNLKAV TDNHDDLKNMGFNVEQIVRMVSH NGGSKNLKAVTDNHDDLKNMGFN VEQIVRMVSHNGGSKNLKAVTDN HDDLKNMGFSSQQIIRMVSHAGGA NNLKAVTANHDDLQNMGFNVEQI VRMVSHNGGSKNLKAVTDNHDDL KNMGFNTEQIVRMVSHDGGSLNLK AVKKYHDALRERKFSSQQIIRMVS HAGGANNLKAVTANHDDLQNMGF SSQQIIRMVSHAGGANNLKAVTAN HDDLQNMGFNVEQIVRMVSHNGG SKNLKAVTDNHDDLKNMGFNVEQ IVRMVSHNGGSKNLKAVTDNHDD LKNMGFNVEQIVRMVSHNGGSKN LKAVTDNHDDLKNMGFNAEQIVR MVSHKGGSKNLALVKEYFPVFSSF HFTADQIVALICQSKQCFRNLKKNH |

TABLE 3-continued

MAP-NBDs Targeting the PDCD1 Gene

| Target DNA Sequence in PDCD1 (5' -> 3') | Full Length MAP-NBD | MAP-NBD with C-terminal truncation to C63 |
|---|---|---|
| | PVCFFSSRSENNTEQYLQDSTLDLDSQ LGDPTKNFNVNNFWSLFPPDDVGYHP HSNDVGYHLHSDEESPFFDF (SEQ ID NO: 100) | QQWKNKGLSAEQIVDLILQETPPKP (SEQ ID NO: 101) |
| GAGCAAGGGGC GGGCACCC (SEQ ID NO: 92) | MPDLELNFAIPLHLFDDETVFTHDAT NDNSQASSSYSSKSSPASANARKRTSR KEMSGPPSKEPANTKSRRANSQNNKL SLADRLTKYNIDEEFYQTRSDSLLSLN YTKKQIERLILYKGRTSAVQQLLCKH EELLNLISPDGLGHKELIKIAARNGGG NNLIAVLSCYAKLKEMGFSSQQIIRM VSHAGGANNLKAVTANHDDLQNMG FNVEQIVRMVSHNGGSKNLKAVTDN HDDLKNMGFNTEQIVRMVSHDGGSL NLKAVKKYHDALRERKFSSQQIIRMV SHAGGANNLKAVTANHDDLQNMGFS SQQIIRMVSHAGGANNLKAVTANHD DLQNMGFNVEQIVRMVSHNGGSKNL KAVTDNHDDLKNMGFNVEQIVRMVS HNGGSKNLKAVTDNHDDLKNMGFN VEQIVRMVSHNGGSKNLKAVTDNHD DLKNMGFNVEQIVRMVSHNGGSKNL KAVTDNHDDLKNMGFNTEQIVRMVS HDGGSLNLKAVKKYHDALRERKFNV EQIVRMVSHNGGSKNLKAVTDNHDD LKNMGFNVEQIVRMVSHNGGSKNLK AVTDNHDDLKNMGFNVEQIVRMVSH NGGSKNLKAVTDNHDDLKNMGFNTE QIVRMVSHDGGSLNLKAVKKYHDAL RERKFSSQQIIRMVSHAGGANNLKAV TANHDDLQNMGFNTEQIVRMVSHDG GSLNLKAVKKYHDALRERKFNTEQIV RMVSHDGGSLNLKAVKKYHDALRER KFNAEQIVRMVSHDGGSKNLALVK EYFPVFSSFHFTADQIVALICQSKQCF RNLKKNHQQWKNKGLSAEQIVDLIL QETPPKPNFNNTSSSTPSPSAPSFFQGP STPIPTPVLDNSPAPIFSNPVCFFSSRSE NNTEQYLQDSTLDLDSQLGDPTKNFN VNNFWSLFPPDDVGYHPSNDVGYH LHSDEESPFFDF (SEQ ID NO: 102) Sequence shown in bold is based on the sequence of SEQ ID NO: 10 in which the BCR HK have been replaced with the BCR HD. | MPDLELNFAIPLHLFDDETVFTHDA TNDNSQASSSYSSKSSPASANARKR TSRKEMSGPPSKEPANTKSRRANS QNNKLSLADRLTKYNIDEEFYQTRS DSLLSLNYTKKQIERLILYKGRTSA VQQLLCKHEELLNLISPDGLGHKEL IKIAARNGGGNNLIAVLSCYAKLKE MGFSSQQIIRMVSHAGGANNLKAV TANHDDLQNMGFNVEQIVRMVSH NGGSKNLKAVTDNHDDLKNMGFN TEQIVRMVSHDGGSLNLKAVKKYH DALRERKFSSQQIIRMVSHAGGAN NLKAVTANHDDLQNMGFSSQQIIR MVSHAGGANNLKAVTANHDDLQN MGFNVEQIVRMVSHNGGSKNLKA VTDNHDDLKNMGFNVEQIVRMVS HNGGSKNLKAVTDNHDDLKNMGF NVEQIVRMVSHNGGSKNLKAVTD NHDDLKNMGFNVEQIVRMVSHNG GSKNLKAVTDNHDDLKNMGFNTE QIVRMVSHDGGSLNLKAVKKYHD ALRERKFNVEQIVRMVSHNGGSKN LKAVTDNHDDLKNMGFNVEQIVR MVSHNGGSKNLKAVTDNHDDLKN MGFNVEQIVRMVSHNGGSKNLKA VTDNHDDLKNMGFNTEQIVRMVS HDGGSLNLKAVKKYHDALRERKFS SQQIIRMVSHAGGANNLKAVTANH DDLQNMGFNTEQIVRMVSHDGGSL NLKAVKKYHDALRERKFNTEQIVR MVSHDGGSLNLKAVKKYHDALRE RKFNAEQIVRMVSHDGGSKNLAL VKEYFPVFSSFHFTADQIVALICQSK QCFRNLKKNHQQWKNKGLSAEQI VDLILQETPPKP (SEQ ID NO: 103) Sequence shown in bold is based on the sequence of SEQ ID NO: 10 in which the BCR HK have been replaced with the BCR HD. |
| GAAGGGAGGGT GCCCGCCCC (SEQ ID NO: 93) | MPDLELNFAIPLHLFDDETVFTHDA NDNSQASSSYSSKSSPASANARKRTSR KEMSGPPSKEPANTKSRRANSQNNKL SLADRLTKYNIDEEFYQTRSDSLLSLN YTKKQIERLILYKGRTSAVQQLLCKH EELLNLISPDGLGHKELIKIAARNGGG NNLIAVLSCYAKLKEMGFSSQQIIRM VSHAGGANNLKAVTANHDDLQNMG FSSQQIIRMVSHAGGANNLKAVTANH DDLQNMGFNVEQIVRMVSHNGGSKN LKAVTDNHDDLKNMGFNVEQIVRMV SHNGGSKNLKAVTDNHDDLKNMGFN VEQIVRMVSHNGGSKNLKAVTDNHD DLKNMGFSSQQIIRMVSHAGGANNLK AVTANHDDLQNMGFNVEQIVRMVSH NGGSKNLKAVTDNHDDLKNMGFNV EQIVRMVSHNGGSKNLKAVTDNHDD LKNMGFNVEQIVRMVSHNGGSKNLK AVTDNHDDLKNMGFNAEQIVSMVSN GGGSLNLKAVKKYHDALKDRGFNVE QIVRMVSHNGGSKNLKAVTDNHDDL KNMGFNTEQIVRMVSHDGGSLNLKA VKKYHDALRERKFNTEQIVRMVSHD GGSLNLKAVKKYHDALRERKFNTEQI VRMVSHDGGSLNLKAVKKYHDALRE RKFNVEQIVRMVSHNGGSKNLKAVT | MPDLELNFAIPLHLFDDETVFTHDAT TNDNSQASSSYSSKSSPASANARKR TSRKEMSGPPSKEPANTKSRRANS QNNKLSLADRLTKYNIDEEFYQTRS DSLLSLNYTKKQIERLILYKGRTSA VQQLLCKHEELLNLISPDGLGHKEL IKIAARNGGGNNLIAVLSCYAKLKE MGFSSQQIIRMVSHAGGANNLKAV TANHDDLQNMGFSSQQIIRMVSHA GGANNLKAVTANHDDLQNMGFNV EQIVRMVSHNGGSKNLKAVTDNH DDLKNMGFNVEQIVRMVSHNGGS KNLKAVTDNHDDLKNMGFNVEQI VRMVSHNGGSKNLKAVTDNHDDL KNMGFSSQQIIRMVSHAGGANNLK AVTANHDDLQNMGFNVEQIVRMV SHNGGSKNLKAVTDNHDDLKNMG FNVEQIVRMVSHNGGSKNLKAVTD NHDDLKNMGFNVEQIVRMVSHNG GSKNLKAVTDNHDDLKNMGFNAE QIVSMVSNGGGSLNLKAVKKYHD ALKDRGFNVEQIVRMVSHNGGSKN LKAVTDNHDDLKNMGFNTEQIVR MVSHDGGSLNLKAVKKYHDALRE RKFNTEQIVRMVSHDGGSLNLKAV KKYHDALRERKFNTEQIVRMVSHD |

TABLE 3-continued

MAP-NBDs Targeting the PDCD1 Gene

| Target DNA Sequence in PDCD1 (5' -> 3') | Full Length MAP-NBD | MAP-NBD with C-terminal truncation to C63 |
|---|---|---|
| | DNHDDLKNMGFNTEQIVRMVSHDGG<br>SLNLKAVKKYHDALRERKFNTEQIVR<br>MVSHDGGSLNLKAVKKYHDALRERK<br>FNTEQIVRMVSHDGGSLNLKAVKKY<br>HDALRERKFNAEQIVRMVSHDGGSK<br>NLALVKEYFPVFSSFHFTADQIVALIC<br>QSKQCFRNLKKNHQQWKNKGLSAEQ<br>IVDLILQETPPKPNFNNTSSTPSPSAPS<br>FFQGPSTPIPTPVLDNSPAPIFSNPVCFF<br>SSRSENNTEQYLQDSTLDLDSQLGDP<br>TKNFNVNNFWSLFPFDDVGYHPHSN<br>DVGYHLHSDEESPFFDF<br>(SEQ ID NO: 104)<br>Sequence shown in bold is based on the sequence of SEQ ID NO: 10 in which the BCR HK have been replaced with the BCR HD. | GGSLNLKAVKKYHDALRERKFNV<br>EQIVRMVSHNGGSKNLKAVTDNH<br>DDLKNMGFNTEQIVRMVSHDGGSL<br>NLKAVKKYHDALRERKFNTEQIVR<br>MVSHDGGSLNLKAVKKYHDALRE<br>RKFNTEQIVRMVSHDGGSLNLKAV<br>KKYHDALRERKFNAEQIVRMVSH<br>DGGSKNLALVKEYFPVFSSFHFTA<br>DQIVALICQSKQCFRNLKKNHQQW<br>KNKGLSAEQIVDLILQETPPKP<br>(SEQ ID NO: 105)<br>Sequence shown in bold is based on the sequence of SEQ ID NO: 10 in which the BCR HK have been replaced with the BCR HD. |
| GACCTGGGACAG<br>TTTCCCTT<br>(SEQ ID NO: 94) | MPDLELNFAIPLHLFDDETVFTHDAT<br>NDNSQASSSYSSKSSPASANARKRTSR<br>KEMSGPPSKEPANTKSRRANSQNNKL<br>SLADRLTKYNIDEEFYQTRSDSLLSLN<br>YTKKQIERLILYKGRTSAVQQLLCKH<br>EELLNLISPDGLGHKELIKIAARNGGG<br>NNLIAVLSCYAKLKEMGFSSQQIIRM<br>VSHAGGANNLKAVTANHDDLQNMG<br>FNTEQIVRMVSHDGGSLNLKAVKKY<br>HDALRERKFNTEQIVRMVSHDGGSLN<br>LKAVKKYHDALRERKFNAEQIVSMV<br>SNGGGSLNLKAVKKYFIDALKDRGFN<br>VEQIVRMVSHNGGSKNLKAVTDNHD<br>DLKNMGFNVEQIVRMVSHNGGSKNL<br>KAVTDNHDDLKNMGFNVEQIVRMVS<br>HNGGSKNLKAVTDNHDDLKNMGFSS<br>QQIIRMVSHAGGANNLKAVTANHDD<br>LQNMGFNTEQIVRMVSHDGGSLNLK<br>AVKKYHDALRERKFSSQQIIRMVSHA<br>GGANNLKAVTANHDDLQNMGFNVE<br>QIVRMVSHNGGSKNLKAVTDNHDDL<br>KNMGFNAEQIVSMVSNGGGSLNLKA<br>VKKYHDALKDRGFNAEQIVSMVSNG<br>GGSLNLKAVKKYHDALKDRGFNAEQ<br>IVSMVSNGGGSLNLKAVKKYHDALK<br>DRGFNTEQIVRMVSHDGGSLNLKAV<br>KKYHDALRERKFNTEQIVRMVSHDG<br>GSLNLKAVKKYHDALRERKFNTEQIV<br>RMVSHDGGSLNLKAVKKYHDALRER<br>KFNAEQIVSMVSNGGGSLNLKAVKK<br>YHDALKDRGFNAEQIVRMVSNGGGS<br>KNLALVKEYFPVFSSFHFTADQIVALI<br>CQSKQCFRNLKKNHQQWKNKGLSAE<br>QIVDLILQETPPKPNFNNTSSTPSPSA<br>PSFFQGPSTPIPTPVLDNSPAPIFSNPVC<br>FFSSRSENNTEQYLQDSTLDLDSQLGD<br>PTKNFNVNNFWSLFPFDDVGYHPHSN<br>DVGYHLHSDEE SPFFDF<br>(SEQ ID NO: 106) | MPDLELNFAIPLHLFDDETVFTHDA<br>TNDNSQASSSYSSKSSPASANARKR<br>TSRKEMSGPPSKEPANTKSRRANS<br>QNNKLSLADRLTKYNIDEEFYQTRS<br>DSLLSLNYTKKQIERLILYKGRTSA<br>VQQLLCKHEELLNLISPDGLGHKEL<br>IKIAARNGGGNNLIAVLSCYAKLKE<br>MGFSSQQIIRMVSHAGGANNLKAV<br>TANHDDLQNMGFNTEQIVRMVSH<br>DGGSLNLKAVKKYHDALRERKFN<br>TEQIVRMVSHDGGSLNLKAVKKYH<br>DALRERKFNAEQIVSMVSNGGGSL<br>NLKAVKKYHDALKDRGFNVEQIV<br>RMVSHNGGSKNLKAVTDNHDDLK<br>NMGFNVEQIVRMVSHNGGSKNLK<br>AVTDNHDDLKNMGFNVEQIVRMV<br>SHNGGSKNLKAVTDNHDDLKNMG<br>FSSQQIIRMVSHAGGANNLKAVTA<br>NHDDLQNMGFNTEQIVRMVSHDG<br>GSLNLKAVKKYHDALRERKFSSQQ<br>IIRMVSHAGGANNLKAVTANHDDL<br>QNMGFNVEQIVRMVSHNGGSKNL<br>KAVTDNHDDLKNMGFNAEQIVSM<br>VSNGGGSLNLKAVKKYHDALKDR<br>GFNAEQIVSMVSNGGGSLNLKAVK<br>KYHDALKDRGFNAEQIVSMVSNG<br>GGSLNLKAVKKYHDALKDRGFNT<br>EQIVRMVSHDGGSLNLKAVKKYH<br>DALRERKFNTEQIVRMVSHDGGSL<br>NLKAVKKYHDALRERKFNTEQIVR<br>MVSHDGGSLNLKAVKKYHDALRE<br>RKFNAEQIVSMVSNGGGSLNLKAV<br>KKYHDALKDRGFNAEQIVRMVSN<br>GGGSKNLALVKEYFPVFSSFHFTAD<br>QIVALICQSKQCFRNLKKNHQQWK<br>NKGLSAEQIVDLILQETPPKP<br>(SEQ ID NO: 107) |
| GACAGTTTCCCT<br>TCCGCTC<br>(SEQ ID NO: 95) | MPDLELNFAIPLHLFDDETVFTHDAT<br>NDNSQASSSYSSKSSPASANARKRTSR<br>KEMSGPPSKEPANTKSRRANSQNNKL<br>SLADRLTKYNIDEEFYQTRSDSLLSLN<br>YTKKQIERLILYKGRTSAVQQLLCKH<br>EELLNLISPDGLGHKELIKIAARNGGG<br>NNLIAVLSCYAKLKEMGFSSQQIIRM<br>VSHAGGANNLKAVTANHDDLQNMG<br>FNTEQIVRMVSHDGGSLNLKAVKKY<br>HDALRERKFSSQQIIRMVSHAGGANN<br>LKAVTANHDDLQNMGFNVEQIVRMV<br>SHNGGSKNLKAVTDNHDDLKNMGFN<br>AEQIVSMVSNGGGSLNLKAVKKYHD<br>ALKDRGFNAEQIVSMVSNGGGSLNLK<br>AVKKYHDALKDRGFNAEQIVSMVSN<br>GGGSLNLKAVKKYHDALKDRGFNTE | MPDLELNFAIPLHLFDDETVFTHDA<br>TNDNSQASSSYSSKSSPASANARKR<br>TSRKEMSGPPSKEPANTKSRRANS<br>QNNKLSLADRLTKYNIDEEFYQTRS<br>DSLLSLNYTKKQIERLILYKGRTSA<br>VQQLLCKHEELLNLISPDGLGHKEL<br>IKIAARNGGGNNLIAVLSCYAKLKE<br>MGFSSQQIIRMVSHAGGANNLKAV<br>TANHDDLQNMGFNTEQIVRMVSH<br>DGGSLNLKAVKKYHDALRERKFSS<br>QQIIRMVSHAGGANNLKAVTANHD<br>DLQNMGFNVEQIVRMVSHNGGSK<br>NLKAVTDNHDDLKNMGFNAEQIV<br>SMVSNGGGSLNLKAVKKYHDALK<br>DRGFNAEQIVSMVSNGGGSLNLKA<br>VKKYHDALKDRGFNAEQIVSMVS |

TABLE 3-continued

MAP-NBDs Targeting the PDCD1 Gene

| Target DNA Sequence in PDCD1 (5' -> 3') | Full Length MAP-NBD | MAP-NBD with C-terminal truncation to C63 |
|---|---|---|
| | QIVRMVSHDGGSLNLKAVKKYHDAL RERKFNTEQIVRMVSHDGGSLNLKAV KKYHDALRERKFNTEQIVRMVSHDG GSLNLKAVKKYHDALRERKFNAEQIV SMVSNGGGSLNLKAVKKYHDALKDR GFNAEQIVSMVSNGGGSLNLKAVKK YHDALKDRGFNTEQIVRMVSHDGGS LNLKAVKKYHDALRERKFNTEQIVR MVSHDGGSLNLKAVKKYHDALRERK FNVEQIVRMVSHNGGSKNLKAVTDN HDDLKNMGFNTEQIVRMVSHDGGSL NLKAVKKYHDALRERKFNAEQIVSM VSNGGGSLNLKAVKKYHDALKDRGF NAEQIVRMVSHDGGSKNLALVKEYF PVFSSFHFTADQIVALICQSKQCFRNL KKNHQQWKNKGLSAEQIVDLILQETP PKPNFNNTSSSTPSPSAPSFFQGPSTPIP TPVLDNSPAPIFSNPVCFFSSRSENNTE QYLQDSTLDLDSQLGDPTKNFNVNNF WSLFPFDDVGYHPHSNDVGYHLHSD EESP

TABLE 3-continued

MAP-NBDs Targeting the PDCD1 Gene

| Target DNA Sequence in PDCD1 (5' -> 3') | Full Length MAP-NBD | MAP-NBD with C-terminal truncation to C63 |
|---|---|---|
| | SLADRLTKYNIDEEFYQTRSDSLLSLN YTKKQIERLILYKGRTSAVQQLLCKH EELLNLISPDGLGHKELIKIAAR cell already having a mutation can be repaired with a MAP-NBD of the present disclosure.

In some instances, a target cell is a cell comprising one or more single nucleotide polymorphism (SNP). In some instances, a MAP-NBD-nuclease described herein is designed to target and edit a target cell comprising a SNP.

In some cases, a target cell is a cell that does not contain a modification. For example, a target cell can comprise a genome without genetic defect (e.g., without genetic mutation) and a MAP-NBD-nuclease described herein can be used to introduce a modification (e.g., a mutation) within the genome.

In some cases, a target cell is a cancerous cell. Cancer can be a solid tumor or a hematologic malignancy. The solid tumor can include a sarcoma or a carcinoma. Exemplary sarcoma target cell can include, but are not limited to, cell obtained from alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

Exemplary carcinoma target cell can include, but are not limited to, cell obtained from anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

Alternatively, the cancerous cell can comprise cells obtained from a hematologic malignancy. Hematologic malignancy can comprise a leukemia, a lymphoma, a myeloma, a non-Hodgkin's lymphoma, or a Hodgkin's lymphoma. In some cases, the hematologic malignancy can be a T-cell based hematologic malignancy. Other times, the hematologic malignancy can be a B-cell based hematologic malignancy. Exemplary B-cell based hematologic malignancy can include, but are not limited to, chronic lymphocytic leukemia (CLL), small lymphocytic lymphoma (SLL), high-risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. Exemplary T-cell based hematologic malignancy can include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some cases, a cell can be a tumor cell line. Exemplary tumor cell line can include, but are not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly1 0, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, described herein include methods of modifying a target gene utilizing a MAP-NBD described herein. In some embodiments, genome editing can be performed by fusing a nuclease of the present disclosure with a DNA binding domain for a particular genomic locus of interest. Genetic modification can involve introducing a functional gene for therapeutic purposes, knocking out a gene for therapeutic gene, or engineering a cell ex vivo (e.g., HSCs or CAR T cells) to be administered back into a subject in need thereof. For example, the genome editing complex can have a target site within PDCD1, CTLA4, LAG3, TET2, BTLA, HAVCR2, CCR5, CXCR4, TRA, TRB, B2M, albumin, HBB, HBA1, TTR, NR3C1, CD52, erythroid specific enhancer of the BCL11A gene, CBLB, TGFBR1, SERPINA1, HBV genomic DNA in infected cells, CEP290, DMD, CFTR, IL2RG, CS-1, or any combination thereof. In some embodiments, a genome editing complex can cleave double stranded DNA at a target site in order to insert a chimeric antigen receptor (CAR), alpha-L iduronidase (IDUA), iduronate-2-sulfatase (IDS), or Factor 9 (F9). Cells, such as hematopoietic stem cells (HSCs) and T cells, can be engineered ex vivo with the genome editing complex. Alternatively, genome editing complexes can be directly administered to a subject in need thereof.

Methods of Production of Polypeptides

In certain embodiments, the polypeptides disclosed herein, such as, the MAP-NBD is produced using a suitable method including recombinant and non-recombinant methods (e.g., chemical synthesis).

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

B. Recombinant Production

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., E. coli) or a yeast host cell, respectively. In certain aspects, eukaryotic cells that are used as host cells for production of the polypeptides include insect cells, mammalian cells, and/or plant cells. In certain aspects, mammalian host cells are used and may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells). In specific embodiments, the polypeptide disclosed herein are produced in CHO cells.

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Also provided herein are nucleic acids encoding the polypeptides disclosed herein. In certain aspects, a nucleic acid encoding the polypeptides disclosed herein is operably linked to a promoter sequence that confers expression of the polypeptide. In certain aspects, the sequence of the nucleic acid is codon optimized for expression of the polypeptide in a human cell. In certain aspects, the nucleic acid is a deoxyribonucleic acid (DNA). In certain aspects, the nucleic acid is a ribonucleic acid (RNA). Also provided herein is a vector comprising the nucleic acid encoding the polypeptides for binding a target nucleic acid as described herein. In certain aspects, the vector is a viral vector.

In certain aspects, a host cell comprising the nucleic acid or the vector encoding the polypeptides disclosed herein is provided. In certain aspects, a host cell comprising the polypeptides disclosed herein is provided. In certain aspects, a host cell that expresses the polypeptide is also disclosed.

Delivery

The polypeptides disclosed herein, compositions comprising the disclosed polypeptides, and nucleic acids encoding the disclosed polypeptides can be delivered into a target cell by any suitable means, including, for example, by injection, infection, transfection, and vesicle or liposome mediated delivery.

In certain aspects, a mRNA or a vector encoding the polypeptides disclosed herein may be injected, transfected, or introduced via viral infection into a target cell, where the cell is ex vivo or in vivo. Any vector systems may be used including, but not limited to, plasmid vectors, retroviral vectors, lentiviral vectors, adenovirus vectors, poxvirus vectors; herpesvirus vectors and adeno-associated virus vectors, etc. When two or more polypeptides according to present disclosure are introduced into the cell, the nucleic acids encoding the polypeptides may be carried on the same vector or on different vectors. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. Vectors suitable for introduction of polynucleotides as described herein include described herein include non-integrating lentivirus vectors (IDLV).

Non-viral vector delivery systems include electroporation, lipofection, microinjection, biolistics, virosomes, liposomes, immunoliposomes, polycation or lipid:nucleic acid conjugates, naked DNA, artificial virions, and agent-enhanced uptake of DNA.

Primary cells may be isolated and used ex vivo for reintroduction into the subject to be treated. Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells, neuronal stem cells, mesenchymal stem cells, muscle stem cells and skin stem cells. In certain aspects, the stem cells may be isolated from a subject to be treated or may be derived from a somatic cell of a subject to be treated using the polypeptides disclosed herein.

In certain aspects, the cells into which the polypeptides of the present disclosure or a nucleic acid encoding a polypeptide of the present disclosure may be an animal cell, e.g., from a human needing treatment. In other aspects, the cell may be a plant cell. DNA constructs may be introduced into (e.g., into the genome of) a desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment.

In certain aspects, the polypeptide of the present disclosure is only transiently present in a target cell. For example, the polypeptide is expressed from a nucleic acid that expressed the polypeptide for a short period of time, e.g., for up to 1 day, 3 days, 1 week, 3 weeks, or 1 month. In applications where transient expression of the polypeptide of the present disclosure is desired, adenoviral based systems may be used. Adeno-associated virus ("AAV") vectors can also be used to transduce cells with nucleic acids encoding the polypeptide of the present disclosure, e.g., in the in vitro production of nucleic acids and peptides, and for in vivo and ex vivo gene therapy procedures. In certain aspects, recombinant adeno-associated virus vectors (rAAV) such as replication-deficient recombinant adenoviral vectors may be used for introduction of nucleic acids encoding the polypeptides disclosed herein.

In certain aspects, nucleic acids encoding the polypeptides disclosed herein can be delivered using a gene therapy vector with a high degree of specificity to a particular tissue type or cell type. A viral vector is typically modified to have specificity for a given cell type by including a sequence encoding a ligand expressed as a fusion protein with a viral coat protein on the viruses' outer surface. The ligand is chosen to have affinity for a receptor known to be present on the cell type of interest.

In certain aspects, gene therapy vectors can be delivered in vivo by administration to an individual patient. In certain aspects, administration involves systemic administration (e.g., intravenous, intraperitoneal, intramuscular, subdermal, or intracranial infusion), direct injection (e.g., intrathecal), or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector or which have been modified by expression of the polypeptide of the present disclosure encoded by the vector.

In certain aspects, the nucleic acid encoding the polypeptides provided herein may be codon optimized to enhance expression of the polypeptide in the target cell. For example, the sequence of the nucleic acid can be varied to provide codons that are known to be highly used in animal cells, such as, human cells to enhance production of the polypeptide in a human cell. For example, silent mutations may be made in the nucleotide sequence encoding a polypeptide disclosed herein for codon optimization in mammalian cells. Similar codon optimization can be used for optimal expression in other host cell systems (e.g. plant, fungal, etc.).

Compositions

In certain aspects, the polypeptides and the nucleic acids described herein may be present in a pharmaceutical composition comprising a pharmaceutically acceptable excipient. In certain aspects, the polypeptides and the nucleic acids are present in a therapeutically effective amount in the pharmaceutical composition. A therapeutically effective amount can be determined based on an observed effectiveness of the composition. A therapeutically effective amount can be determined using assays that measure the desired effect in a cell, e.g., in a reporter cell line in which expression of a reporter is modulated in response to the polypeptides of the present disclosure. The pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Suitable pharmaceutically acceptable or physiologically acceptable diluents, carriers or excipients include, but are not limited to, nuclease inhibitors, protease inhibitors, a suitable vehicle such as physiological saline solution or citrate buffered saline.

Sequences

Sequences of additional polypeptides described herein are as follows:

| SEQ ID NO | SEQUENCE |
|---|---|
| 1 | MPDLELNFAIPLHLFDDETVFTHDATNDNSQASSSYSSKSSPASANARKRTSRKEMSGPPSKEPA NTKSRRANSQNNKLSLADRLTKYNIDEEFYQTRSDSLLSLNYTKKQIERLILYKGRTSAVQQLLC KHEELLNLISPDGLGHKELIKIAARNGGGNNLIAVLSCYAKLKEMGFSSQQIIRMVSHAGGANNL KAVTANHDDLQNMGFNVEQIVRMVSHNGGSKNLKAVTDNHDDLKNMGFNAEQIVRMVSHGGGSKN LKAVTDNHDDLKNMGFNAEQIVSMVSNNGGSKNLKAVTDNHDDLKNMGFNAEQIVSMVSNGGGSL NLKAVKKYHDALKDRGFNTEQIVRMVSHDGGSLNLKAVKKYHDALRERKFNVEQIVSIVSHGGGS LNLKAVKKYHDVLKDREFNAEQIVRMVSHDGGSLNLKAVTDNHDDLKNMGFNAEQIVRMVSHKGG SKNLALVKEYFPVFSSFPHFTADQIVALICQSKQCFRNLKKNHQQWKNKGLSAEQIVDLILQETPP KPNFNNTSSSTPSPSAPSFFQGPSTPIPTPVLDNSPAPIFSNPVCFFSSRSENNTEQYLQDSTLD LDSQLGDPTKNFNVNNFWSLFPFDDVGYHPHSNDVGYHLHSDEESPFFDF |
| 140 | MPKTKITTVSHGYDLDLMSSLPNGDPNQAKQGKIYLSGNGVYVVRDVAGIVHRGQLEFAINLEQL EQKINEPAFKAVILEKTSRAVGYTISNECFNVELNALAKAGFNNLDIDKLIFRRSSRGTVQTVLN SYNILLEKPYN |
| 141 | YDNKKIISIAASNCGTETINTIMSTDEVEESDFLYFVTTVSTPVASQNLSSASNTNINYSNRFMT ARKKTSDDNTDEVEEDQHRDKRRSNGR |
| 142 | YDNKKIISIAASNCGTETINTIMSTDEVEESDFLYFVTTVSTPVASQNLSSASNTNINYSNRF |
| 144 | MPKTNQPKNLEAKSTKNKISLPQDPQTLNELKIKGYPQDLAERLIKKGSSLAVKTVLKDHEQLVN FFTHLQIIRMAAQKGGAKNITTALNEYNSLTNLG |
| 145 | YMLSQEQFLRLIDHHSGHLNLSILLDEQQWQAINDLCLQPHHFGRQNALEKFLQQGQRKYQNLQE LEQFLFQDSADPMLLQETENQHEAEKINDCMDFILRLISATEPLDLQIEIEGIGLFSPSMHFDAT QANFSTPAANEEKIDNSATEAGVNSRKRKIAAAHQKQPPRKKTATPLSATFISTLTTLAQSDNPR LEMASAEALMLKAPQKLAMGITVRKKTKCEGIAIITVTDKTKLNGWLSSASESTYSSVEAQGTRT VNNTHAFFSTPLTSDKKSPSFSSLDFYEDSGLGFDEEITNPPYMPELEPEFIL |
| 146 | YMLSQEQFLRLIDHHSGHLNLSILLDEQQWQAINDLCLQPHHFGRQNALEKFLQQGQRKYQNL |

-continued

| SEQ ID NO | SEQUENCE |
|---|---|
| 148 | MTLTLKQEKIAINKKLRSYRTSKRKFLLDFSKMNLSPEGLNYAQEELAKLQFQAKASLETDQGIN IEEQLYQLGYTQSHLRPCADRYNCSILLNTLLTNNNSFVTQEISLENRVNLVVAANGNNDGIQVF FKTYPKLKSVG |
| 149 | MRLHALNNYHFLFHSIENIQLLITILQSHLEAFRIEQYMISGVLLNLLKQGQVISEQPCKILIDS SILNPNICQTLSNIINKYQFKNKPLYFNPTTSIITCMLSTQECYQLLAVWERRNISPSEILNNLL NPINIFQYQLISQTNEPDVYFLDCYHWHKFYPNMEIKQLQQLLIKAINLGINNCDILPEDNRTLI IEPYNDNWIKLSISIIDTIMDDSFNNLTRELFFCQLAPDSSNLIDDAIYIYKTQQTIEFLVTSKS RSSERFILDTSTIYKDTIEEIEQALTHKLGALKGATYHTLIKCLLAQGYQVTGYFSMNIIGADVM PPTIIADDYPEYITLEWLSSEPMSQRSRLRTHDINSIKTLHNPTPKSQAIHQMLNLLALPDAISP LDSIQNNHTSANHEQQTQGRISPISQQLDITLMRSRKRPLQKSDNTIYHDKRYWTFIGEGSYNKA YTDGQGFVVKVAKNELGLMDKSERSVRVFNEINPTLPQEVLAHVSQDLWISPLIENETLSPIEQA SFIFKTYIEHGRLILDGYCQNNLLQSAKYNTPVCIDPGNVVRRNSIASQEHWYAANEKTLLRRQL YRKHMIDTIDHYHKIRHIDRTLPILMILALDFIDRKMQHLQLQLILKKNIKSLGIAFYFYYKHNQ SSTQQEFILSANIIDKILYGDQYICDTLDQSFKILNKSRVVTLFRQINIDMSLI |
| 150 | MRLHALNNYHFLFHSIENIQLLITILQSHLEAFRIEQYMISGVLLNL |
| 159 | FTADQIVALICQSKQCFRNLKKNHQQWKNKGLSAEQIVDLILQETPPKPNFNNTSSSTP SPSAPSFFQGPSTPIPTPVLDNSPAPIFSNPVCFFSSRSENNTEQYLQDSTLDLDSQLG DPTKNFNVNNFWSLFPFDDVGYHPHSNDVGYHLHSDEESPFFDF |

EXAMPLES

These examples are provided for illustrative purposes only and not to limit the scope of the claims provided herein.

Example 1

Manufacture of a Modular Animal Pathogen-Nucleic Acid Binding Domain (MAP-NBD)

This example illustrates the manufacture of a modular animal pathogen-nucleic acid binding domain (MAP-NBD). The MAP-NBD is derived from *L. quateirensis*. The MAP-NBD comprises a plurality of repeat domains from *L. quateirensis*, such as any one of SEQ ID NO: 2-SEQ ID NO: 10 or SEQ ID NO: 89, wherein each repeat domain is selected to recognize and bind to a particular nucleotide or base pair, thereby providing a MAP-NBD that targets and binds a nucleic acid sequence of interest. The nucleic acid is DNA or RNA. The MAP-NBD is recombinantly expressed or synthetically constructed.

Example 2

Manufacture of a Modular Animal Pathogen-Nucleic Acid Binding Domain (MAP-NBD)-Nuclease This example illustrates the manufacture of a modular animal pathogen-nucleic acid binding domain (MAP-NBD)-nuclease. The MAP-NBD is derived from *L. quateirensis*. The MAP-NBD comprises a plurality of repeat domains from *L. quateirensis*, such as any one of SEQ ID NO: 2-SEQ ID NO: 10, SEQ ID NO: 89, or SEQ ID NO: 33, where each repeat domain is selected to recognize and bind to a particular nucleotide or base pair, thereby providing a MAP-NBD that targets and binds a nucleic acid sequence of interest. The MAP-NBD-nuclease is recombinantly expressed or synthetically constructed. The MAP-NBD is linked to a nuclease via an optional linker. The linker is a synthetic linker, the full length C-terminus of the naturally occurring *L. quateirensis* protein set forth in SEQ ID NO: 1, or a fragment of the C-terminus of the naturally occurring *L. quateirensis* protein set forth in SEQ ID NO: 1. The nuclease is a cleavage domain (e.g., meganucleases such as I-Anil or I-OnuI) or a cleavage half domain (e.g., FokI nuclease, for example SEQ ID NO: 11, or BfiI).

Example 3

Manufacture of a Modular Animal Pathogen-Nucleic Acid Binding Domain (MAP-NBD)-Gene Regulator (MAP-NBD-GR)

This example illustrates the manufacture of a modular animal pathogen-nucleic acid binding domain (MAP-NBD)-gene regulator (MAP-NBD-GR). The MAP-NBD is derived from *L. quateirensis*. The MAP-NBD comprises a plurality of repeat domains from *L. quateirensis*, such as any one of SEQ ID NO: 2-SEQ ID NO: 10, SEQ ID NO: 89, or SEQ ID NO: 33, wherein each repeat domain is selected to recognize and bind to a particular nucleotide or base pair, thereby providing a MAP-NBD that targets and binds a nucleic acid sequence of interest. The MAP-NBD-GR is recombinantly expressed or synthetically constructed. The MAP-NBD is linked to a gene regulatory domain via an optional linker. The linker is a synthetic linker, the full length C-terminus of the naturally occurring *L. quateirensis* protein set forth in SEQ ID NO: 1, or a fragment of the C-terminus of the naturally occurring *L. quateirensis* protein set forth in SEQ ID NO: 1. The gene regulator is a gene activator (e.g., VP16, VP64, p65, p300 catalytic domain, TET1 catalytic domain, TDG, Ldb1 self-associated domain, SAM activator (VP64, p65, HSF1), or VPR (VP64, p65, Rta)) or a gene repressor (KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2).

Example 4

Manufacture of a Modular Animal Pathogen-Nucleic Acid Binding Domain (MAP-NBD)-Fluorophore This example illustrates the manufacture of a modular animal pathogen-nucleic acid binding domain (MAP-NBD)-fluorophore. The MAP-NBD is derived from L. quateirensis. The MAP-NBD comprises a plurality of repeat domains from L. quateirensis, such as any one of SEQ ID NO: 2-SEQ ID NO: 10, SEQ ID NO: 89, or SEQ ID NO: 33, wherein each repeat domain is selected to recognize and bind to a particular nucleotide or base pair, thereby providing a MAP-NBD that targets and binds a nucleic acid sequence of interest. The MAP-NBD-fluorophore is recombinantly expressed or synthetically constructed. The MAP-NBD is linked to a fluorophore via an optional linker. The linker is a synthetic linker, the full-length C-terminus of the naturally occurring L. quateirensis protein set forth in SEQ ID NO: 1, or a fragment of the C-terminus of the naturally occurring L. quateirensis protein set forth in SEQ ID NO: 1. The fluorophore is a fluorescent moiety, such as green fluorescent protein or mCHERRY.

Example 5

Genome Editing with a Modular Animal Pathogen-Nucleic Acid Binding Domain (MAP-NBD)-Nuclease This example illustrates genome editing with a modular animal pathogen-nucleic acid binding domain (MAP-NBD)-nuclease. The MAP-NBD-nuclease is manufactured as set forth in EXAMPLE 1 and EXAMPLE 2. The MAP-NBD is engineered to comprise a plurality of repeat sequences that will target a nucleic acid sequence of interest. When using a cleavage half-domain as the nuclease (e.g., FokI), two MAP-NBDs are engineered and administered, each with a FokI cleavage half-domain. A first MAP-NBD covalently linked to a FokI cleavage half domain is engineered to bind to first target nucleic acid sequence and a second MAP-NBD covalently linked to another FokI cleavage half domain is engineered to bind to a second target nucleic acid sequence, where the first and second target nucleic acid sequences are suitably spaced apart to provide for dimerization of the FokI cleavage half domains upon binding of the first and second MAP-NBDs to their respective target nucleic acid sequences. Upon administration to a subject, MAP-NBDs bind to their target nucleic acid sequences. Dimerization of two FokI cleavage half domains results in enzyme activity and inducement of a double stranded break (DSB). When using a cleavage domain (e.g., meganucleases such as I-AniI or I-OnuI or a fusion of two FokI domains), a single MAP-NBD bound to the cleavage domain induces a DSB in a target nucleic acid sequence after administration to a subject. The subject is a cell, a plurality of cells, or an animal, such as a human or non-human primate. The nuclease induces a double stranded break in the target sequence resulting in non-homologous end joining or homology directed repair, thereby providing genome editing functionality.

Example 6

Gene Regulation with a Modular Animal Pathogen-Nucleic Acid Binding Domain (MAP-NBD)-Gene Regulator (MAP-NBD-GR)

This example illustrates gene regulation with a modular animal pathogen-nucleic acid binding domain (MAP-NBD)-gene regulator (MAP-NBD-GR). The MAP-NBD-GR is manufactured as set forth in EXAMPLE 1 and EXAMPLE 3. The MAP-NBD is engineered to comprise a plurality of repeat sequences that will target a nucleic acid sequence of interest. The MAP-NBD-GR is administered to a subject. The subject is a cell, a plurality of cells, or an animal, such as a human or non-human primate. The MAP-NBD-GR then regulates gene expression (e.g., an activating or repressing domain), as set forth in EXAMPLE 3.

Example 7

Imaging with a Modular Animal Pathogen-Nucleic Acid Binding Domain (MAP-NBD)-Fluorophore This example illustrates imaging a genomic locus in a cell with a modular animal pathogen-nucleic acid binding domain (MAP-NBD)-fluorophore. The MAP-NBD-fluorophore is manufactured as set forth in EXAMPLE 1 and 4. The MAP-NBD is engineered to comprise a plurality of repeat sequences that will target a nucleic acid sequence of interest. The MAP-NBD-fluorophore is administered to a cell. The cell is in a plurality of cells ex vivo, or is in an animal, such as a human or non-human primate. The MAP-NBD-fluorophore hybridizes to a target nucleic acid sequence, thereby labeling said target nucleic acid sequence. Imaging allows for visualization of labeled target cells, wherein labeled target cells indicate that the target genomic locus is present.

Example 8

Base Specificity of Repeats from *L. quateirensis*

This example illustrates determining the base specificity of repeats from *L. quateirensis*. A polypeptide comprising a *L. quateirensis* protein of sequence set forth in SEQ ID NO: 1 fused to a purification tag was constructed. Base specificity of each of the repeats of SEQ ID NO: 89 and SEQ ID NO: 2-SEQ ID NO: 10 was determined by SELEX.

In vitro transcription and translation (IVTT) of target polypeptides was carried out using the Thermo Fisher 1-Step Human Coupled IVT Kit. The following reagents were added into a nuclease-free tube and mixed: Hela lysate (15 μl), accessory proteins (3 μl), reaction mix (6 μl), plasmid DNA (0.2-0.5 μg/μl) (2.4 μl), and nuclease-free $H_2O$ (3.6 μl). Reactions are carried for 120 minutes to 6 hours at 30° C.

Protein expression was detected by Western blot using appropriate primary antibodies and HRP-conjugated secondary antibodies.

Oligonucleotide target libraries were chemically synthesized at random with a mixture of all 4 phophoramidites. Each oligonucleotide sequence is flanked by discrete 20 base pair sequences as follows: ACACGACGCTCTTCC-GATCTNNNNNNNNNNNNNNNNNNNNNNNNNA-GATCGGAAGAG CACACGTC, where N is any one of the 4 phophoramidites. Oligonucleotide sequences in the library were converted to double-stranded duplexes by annealing each sequence with the 3' library primer (5'-GACGTGTGCTCTTCCGATCT) and incubating at following conditions:

TABLE 4

Conditions for Generation of Library of Double-Stranded Duplexes

| Component | Stock | Final | Amount (100 μl) |
|---|---|---|---|
| N-mer oligo target library | 250 μM | 20 μM | 8 μl |
| Primer | 500 μM | 60 μM | 12 μl |
| Thermo Pol buffer | 10 x | 1 x | 10 μl |
| dNTP | 100 mM each | 1.25 mM each | 1.25 μl each |
| MgSO4 | 100 mM | 3 mM | 3 μl |
| Vent (exo-) | | | 3 μl |
| ddH2O | | | 59 μl |

95° C. 3 min -> 62° C. 10 hour -> 4° C.

The oligonucleotide library was digested with ExoI to remove ssDNA at 37° C. for 2.5 hours as follows.

TABLE 5

Digestion Conditions

| Component | Amount (120 μl) |
|---|---|
| Primer extension reaction | 100 μl |
| Exo I buffer | 12 μl |
| Exo I | 4 μl |
| ddH2O | 4 μl |

DNA was cleaned up with phenol:chloroform:iso-amyl alcohol and EtOH precipitation (–70° C. for 1.5 hours). Duplex libraries were resuspended in QIAGEN EB buffer.

SELEX was carried out using the following SELEX buffers.

TABLE 6

SELEX buffer (for binding)

| Component | Stock | Final | Amount (10 ml) |
|---|---|---|---|
| Tween 20 | 10% | 0.1% | 0.1 ml |
| ZnCl2 | 0.1M | 10 μM | 1 μl |
| MgCl2 | 1M | 0.5 mM | 5 μl |
| poly dIdC | 2 μg/μl | 0.02 μg/μl | 0.1 ml |
| BSA | 0.5% | 0.01% | 0.2 ml |
| DPBS, Ca2+ free | | 1 x | 9.394 ml |
| Proteinase inhibitor cocktail | 50 x | 1 x | 0.2 ml |

TABLE 7

SELEX wash buffer I (same as SELEX binding buffer, but without poly dIdC)

| Component | Stock | Final | Amount (50 ml) |
|---|---|---|---|
| Tween 20 | 10% | 0.1% | 0.5 ml |
| ZnCl2 | 0.1 M | 10 μM | 5 μl |
| MgCl2 | 1 M | 0.5 mM | 0.025 ml |
| BSA | 0.5% | 0.01% | 1 ml |
| DPBS, Ca2 + free | | 1 x | 47.47 ml |
| Proteinase inhibitor cocktail | 50 x | 1 x | 1 ml |

*In DPBS, [NaCl] = 137 mM

TABLE 8

SELEX wash buffer II (without poly dIdC, with additional 75 mM NaCl)

| Component | Stock | Final | Amount (50 ml) |
|---|---|---|---|
| Tween 20 | 10% | 0.1% | 0.5 ml |
| DTT | 1 M | 5 mM | 0.25 ml |
| ZnCl2 | 0.1 M | 10 μM | 5 μl |
| MgCl2 | 1 M | 5 mM | 0.025 ml |
| NaCl | 5 M | 75 mM | 0.75 ml |
| BSA | 0.5% | 0.01% | 1 ml |
| DPBS, Ca2 + free | | 1 x | 46.47 ml |
| Proteinase inhibitor cocktail | 50 x | 1 x | 1 ml |

*In DPBS, [NaCl] = 137 mM

For each polypeptide tested, 25 μl Dynabeads®His-Tag or Pierce™ anti-HA magnetic beads were washed once with 200 μl SELEX binding buffer. Beads were resuspended in 25 μl SELEX binding buffer and left on ice.

SELEX Cycle 1. Bead-protein complexes were mixed with 200 pmol of the oligonucleotide duplex library in a total volume of 100 μl SELEX buffer. The reaction product of the in vitro transcription and translation reaction was pre-incubated with SELEX buffer for 10 min and then added to the library duplex.

TABLE 9

Ratios of IVTT protein, SELEX buffer and Library duplex

| Component | Stock | Final | Amount (100 μl) |
|---|---|---|---|
| IVTT protein | | | 8 μl |
| SELEX buffer | | | 82 μl |
| Library duplex | 40 μM | 4 μM | 10 μl |

Tubes were placed at a low angle on the rotator and incubated at room temperature for 50 minutes. 8 μl of washed beads (in SELEX binding buffer) was added to the complexes and incubated on the rotator for 20 minutes. Tubes were placed on a magnet for 2 min and the supernatant was discarded. Beads were washed 6 times with the SELEX wash buffer. The bound DNA target (with beads) were PCR amplified using the 5'/3' library primers: fwd: ACACGACGCTCTTCCGATCT rev: GACGTGTGCTCTTCCGATCT

TABLE 10

PCR Parameters

| Component | Stock | Final | Amount (50 μl) |
|---|---|---|---|
| Jumpstart buffer | 10 x | 1 x | 5 μl |
| 10 mM dNTP | | | 1 μl |
| Forward primer | 10 μM | 0.5 μM | 2.5 μl |
| Reverse primer | 10 μM | 0.5 μM | 2.5 μl |
| Jump Start Taq DNA Pol | | | 1 μl |
| Template | | | Bead bound DNA |
| PCR-grade H2O | | | 38 μL |

95° C. 2 min -> 25 x [95° C. 10 s -> 64° C. 20 s -> 72° C. 15 s] -> 72° C. 3 min PCR-1 reaction was separated from the beads on the magnet. 5 μl of PCR-1 reaction was used for PCR-2 amplification and μl PCR-2 in SELEX Cycle 2.

TABLE 11

PCR Parameters

| Component | Stock | Final | Amount (30 µl) |
|---|---|---|---|
| Jumpstart buffer | 10 x | 1 x | 3 µl |
| 10 mM dNTP | | | 0.6 µl |
| Forward primer | 10 µM | 0.5 µM | 1.5 µl |
| Reverse primer | 10 µM | 0.5 µM | 1.5 µl |
| Jump Start Taq DNA Pol | | | 0.6 µl |
| PCR-1 from 1st SELEX cycle | | | 5 µl |
| PCR-grade H2O | | | 17.8 µl |

95° C. 2 min -> 3 x [95° C. 10 s -> 64° C. 20 s -> 72° C. 15 s] -> 72° C. 3 min

SELEX Cycle 2. Bead-protein complex were mixed with the PCR product from the 1$^{st}$ cycle in a total volume of 100 µl SELEX buffer. The in vitro transcription and translation (IVTT) reaction was pre-incubated with SELEX buffer for 10 min.

TABLE 12

Ratios of IVTT protein, SELEX buffer and Library duplex

| Component | Stock | Final | Amount (100 µl) |
|---|---|---|---|
| IVTT protein | | | 8 µl |
| SELEX buffer | | | 67 µl |
| PCR-2 from 1$^{st}$ SELEX | | | 25 µl |

Tubes were placed at a low angle on the rotator and incubate at room temperature for 50 minutes. 8 µl of washed beads (in SELEX binding buffer) was added to the complexes and incubated on the rotator for 20 minutes. Tubes were placed on a magnet for 2 min and the supernatant was discarded. Beads were washed 6 times with SELEX was buffer. The bound DNA target (with beads) was PCR amplified using the 5'/3' library primers: fwd: ACACGACGCTCTTCCGATCT and rev: GACGTGTGCTCTTCCGATCT.

TABLE 13

PCR Parameters

| Component | Stock | Final | Amount (50 µl) |
|---|---|---|---|
| Jumpstart buffer | 10 x | 1 x | 5 µl |
| 10 mM dNTP | | | 1 µl |
| Forward primer | 10 µM | 0.5 µM | 2.5 µl |
| Reverse primer | 10 µM | 0.5 µM | 2.5 µl |
| Jump Start Taq DNA Pol | | | 1 µl |
| Template | | | Bead bound DNA |
| PCR-grade H2O | | | 38 µl |

95° C. 2 min -> 25 x [95° C. 10 s -> 64° C. 20 s -> 72° C. 15 s] -> 72° C. 3 min PCR-1 reaction was separated from the beads on the magnet. 5 µl of PCR-1 reaction was used for PCR-2 amplification and 25 µl of PCR-2 in the 3$^{rd}$ SELEX cycle.

TABLE 14

PCR Parameters

| Component | Stock | Final | Amount (30 µl) |
|---|---|---|---|
| Jumpstart buffer | 10 x | 1 x | 3 µl |
| 10 mM dNTP | | | 0.6 µl |
| Forward primer | 10 µM | 0.5 µM | 1.5 µl |
| Reverse primer | 10 µM | 0.5 µM | 1.5 µl |
| Jump Start Taq DNA Pol | | | 0.6 µl |
| PCR-1 from 2$^{nd}$ SELEX cycle | | | 5 µl |
| PCR-grade H2O | | | 17.8 µl |

95° C. 2 min -> 3 x [95° C. 10 s -> 64° C. 20 s -> 72° C. 15 s] -> 72° C. 3 min

SELEX Cycle 3. Mix IVTT protein with PCR product from 1st cycle in a total volume of 100 µl SELEX buffer. The in vitro transcription and translation (IVTT) reaction was pre-incubated with SELEX buffer for 10 min.

TABLE 15

Ratios of IVTT protein, SELEX buffer and Library duplex

| Component | Stock | Final | Amount (100 µl) |
|---|---|---|---|
| IVTT protein | | | 8 µl |
| SELEX buffer | | | 67 µl |
| PCR-2 from 2$^{nd}$ SELEX | | | 25 µl |

Tubes were placed at a low angle on the rotator and incubate at room temperature for 50 minutes. 8 µl of washed beads (in SELEX binding buffer) were added to the complexes and incubated on the rotator for 20 minutes. Tubes were placed on a magnet for 2 min and the supernatant was discarded. Beads were washed 6 times with the SELEX wash buffer. The bound DNA target (with the beads) were PCR amplified using the 5'/3' library primers: fwd: ACACGACGCTCTTCCGATCT, rev: GACGTGTGCTCTTCCGATCT.

TABLE 16

PCR Parameters

| Component | Stock | Final | Amount (50 µl) |
|---|---|---|---|
| Jumpstart buffer | 10 x | 1 x | 5 µl |
| 10 mM dNTP | | | 1 µl |
| Forward primer | 10 µM | 0.5 µM | 2.5 µl |
| Reverse primer | 10 µM | 0.5 µM | 2.5 µl |
| Jump Start Taq DNA Pol | | | 1 µl |
| Template | | | Bead bound DNA |
| PCR-grade H2O | | | 38 µl |

95° C. 2 min -> 25 x [95° C. 10 s -> 64° C. 20 s -> 72° C. 15 s] -> 72° C. 3 min The PCR-1 reaction was separated from the beads on the magnet. 5 µl of PCR-1 reaction was used for PCR-2 amplification.

TABLE 17

PCR Parameters

| Component | Stock | Final | Amount (30 μl) |
|---|---|---|---|
| Jumpstart buffer | 10 x | 1 x | 3 μl |
| 10 mM dNTP | | | 0.6 μl |
| Forward primer | 10 μM | 0.5 μM | 1.5 μl |
| Reverse primer | 10 μM | 0.5 μM | 1.5 μl |
| Jump Start Taq DNA Pol | | | 0.6 μl |
| PCR-1from 3$^{rd}$ SELEX cycle | | | 5 μl |
| PCR-grade H2O | | | 17.8 μl |

95° C. 2 min -> 3 x [95° C. 10 s -> 64°C. 20 s -> 72° C. 15 s] -> 72° C. 3 min

PCR-1 reactions from the 3$^{rd}$ SELEX cycle were separated from the beads on the magnet. PCR-1 reactions from the 1$^{st}$, 2$^{nd}$, and 3$^{rd}$ SELEX cycles were analyzed by MiniSeq.

Paired-end reads were merged with BBmerge. A 25-base pair variable-region sequence was extracted from between recognized constant regions. 5000 sequences were drawn at random from the full set, including duplicates, and given as an input to the GADEM motif discovery program with parameters: '-maskR 1-fullScan 1-gen 3'. Sequence logos in FIGS. 4A and 4B were drawn using the 'ceqlogo' tool in the MEME suite, from the GADEM MEME-format motif files.

Figure 4B:
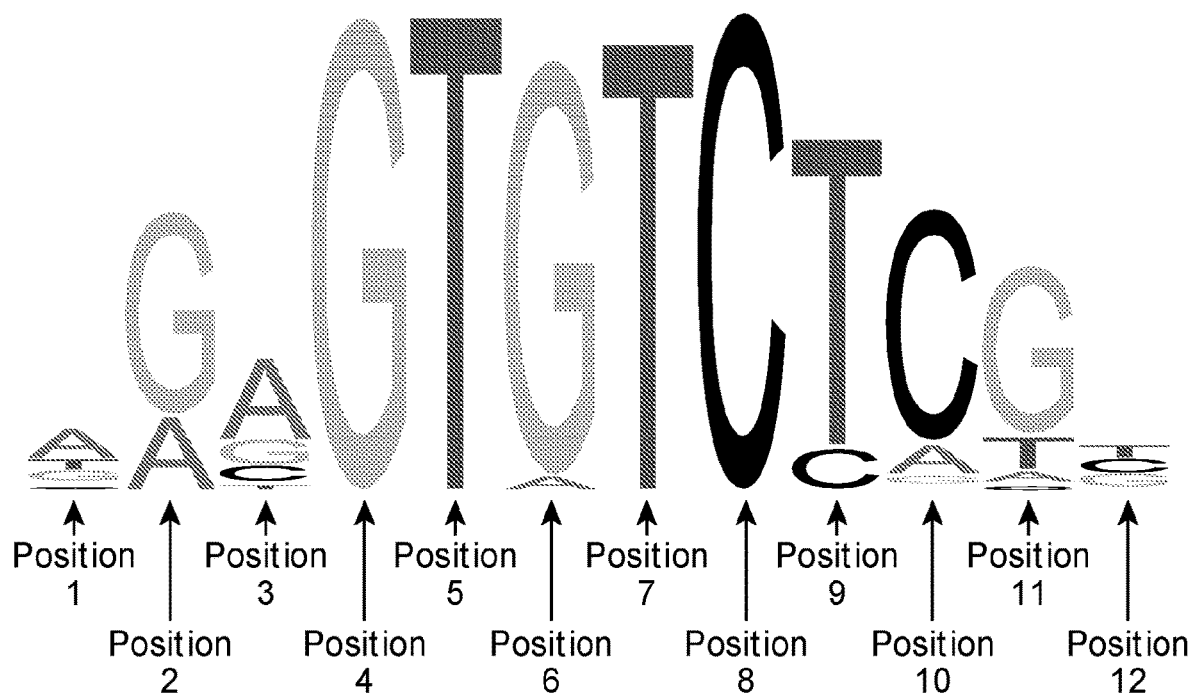

FIGS. 4A and 4B illustrate the binding motifs determined for a polypeptide of SEQ ID NO:1 and comprising the sequence LGHKELIKIAARNGGGNNLIAVLSCYAK-LKEMG (SEQ ID NO: 89) present in an N-terminus of L. quateirensis followed by each of the repeats of SEQ ID NO: 2-SEQ ID NO: 10. The larger the size the of the base at a particular position, the higher the relative frequency at which the base is present at that position in a nucleic acid bound by the tested polypeptide.

FIG. 4A illustrates the bases to which the repeats (SEQ ID NOs:89 and 2-10 ordered from N-terminus to C-terminus) in a polypeptide having the amino acid sequence set forth in SEQ ID NO:1 bind. The polypeptide having the amino acid sequence set forth in SEQ ID NO:1 was fused to a His-tag.

FIG. 4B illustrates the bases to which the repeats (from N-terminus to C-terminus: SEQ ID NOs:89 and 2-10) in a polypeptide having the amino acid sequence set forth in SEQ ID NO:1 bind. The polypeptide having the amino acid sequence set forth in SEQ ID NO:1 was fused to a HA-tag. Both the His-tagged polypeptide and the HA-tagged polypeptide showed the same binding specificity.

A numerical representation of position weight matrices (PWMs) of FIG. 4A and FIG. 4B is shown in the tables below. Background letter frequencies from a uniform background were as follows: A—0.25000; C—0.25000; G—0.25000; and T—0.25000.

TABLE 18

MEME Data Expressing the Position Weight Matrix (PWM) for His-Tagged Protein after 3 Rounds of SELEX

| Binding Motif: rGAGTGTCTCGb | A | C | G | T |
|---|---|---|---|---|
| Position 1 of FIG. 4A | 0.493 | 0.049 | 0.260 | 0.198 |
| Position 2 of FIG. 4A corresponding to the base specificity of a repeat from L. quateirensis of SEQ ID NO: 96 | 0.229 | 0.000 | 0.769 | 0.002 |
| Position 3 of FIG. 4A corresponding to the base specificity of a repeat from L. quateirensis of SEQ ID NO: 2 | 0.665 | 0.108 | 0.224 | 0.003 |
| Position 4 of FIG. 4A corresponding to the base specificity of a repeat from L. quateirensis of SEQ ID NO: 3 | 0.000 | 0.000 | 1.000 | 0.000 |
| Position 5 of FIG. 4A corresponding to the base specificity of a repeat from L. quateirensis of SEQ ID NO: 4 | 0.069 | 0.003 | 0.004 | 0.924 |
| Position 6 of FIG. 4A corresponding to the base specificity of a repeat from L. quateirensis of SEQ ID NO: 5 | 0.006 | 0.000 | 0.994 | 0.000 |
| Position 7 of FIG. 4A corresponding to the base specificity of a repeat from L. quateirensis of SEQ ID NO: 6 | 0.001 | 0.006 | 0.000 | 0.992 |
| Position 8 of FIG. 4A corresponding to the base specificity of a repeat from L. quateirensis of SEQ ID NO: 7 | 0.001 | 0.992 | 0.006 | 0.000 |
| Position 9 of FIG. 4A corresponding to the base specificity of a repeat from L. quateirensis of SEQ ID NO: 8 | 0.003 | 0.018 | 0.000 | 0.979 |
| Position 10 of FIG. 4A corresponding to the base specificity of a repeat from L. quateirensis of SEQ ID NO: 9 | 0.025 | 0.973 | 0.001 | 0.001 |
| Position 11 of FIG. 4A corresponding to the base specificity of a repeat from L. quateirensis of SEQ ID NO: 10 | 0.007 | 0.000 | 0.886 | 0.107 |
| Position 12 of FIG. 4A | 0.009 | 0.293 | 0.370 | 0.328 |

TABLE 19

MEME Data Expressing the Position Weight Matrix (PWM) for HA-Tagged Protein after 3 Rounds of SELEX

| Binding Motif: wGAGTGTCTCGv | A | C | G | T |
|---|---|---|---|---|
| Position 1 of FIG. 4B | 0.492 | 0.067 | 0.200 | 0.240 |
| Position 2 of FIG. 4B corresponding to the base specificity of a repeat from L. quateirensis of SEQ ID NO: 96 | 0.280 | 0.000 | 0.708 | 0.012 |
| Position 3 of FIG. 4B corresponding to the base specificity of a repeat from L. quateirensis of SEQ ID NO: 2 | 0.655 | 0.130 | 0.186 | 0.030 |
| Position 4 of FIG. 4B corresponding to the base specificity of a repeat from | 0.005 | 0.000 | 0.998 | 0.000 |

TABLE 19-continued

MEME Data Expressing the Position Weight Matrix (PWM) for HA-Tagged Protein after 3 Rounds of SELEX

| Binding Motif: wGAGTGTCTCGv | A | C | G | T |
|---|---|---|---|---|
| *L. quateirensis* of SEQ ID NO: 3 Position 5 of FIG. 4B corresponding to the base specificity of a repeat from *L. quateirensis* of SEQ ID NO: 4 | 0.107 | 0.013 | 0.015 | 0.865 |
| Position 6 of FIG. 4B corresponding to the base specificity of a repeat from *L. quateirensis* of SEQ ID NO: 5 | 0.041 | 0.002 | 0.956 | 0.000 |
| Position 7 of FIG. 4B corresponding to the base specificity of a repeat from *L. quateirensis* of SEQ ID NO: 6 | 0.023 | 0.021 | 0.001 | 0.956 |
| Position 8 of FIG. 4B corresponding to the base specificity of a repeat from *L. quateirensis* of SEQ ID NO: 7 | 0.028 | 0.968 | 0.003 | 0.000 |
| Position 9 of FIG. 4B corresponding to the base specificity of a repeat from *L. quateirensis* of SEQ ID NO: 8 | 0.009 | 0.082 | 0.001 | 0.908 |
| Position 10 of FIG. 4B corresponding to the base specificity of a repeat from *L. quateirensis* of SEQ ID NO: 9 | 0.093 | 0.898 | 0.026 | 0.002 |
| Position 11 of FIG. 4B corresponding to the base specificity of a repeat from *L. quateirensis* of SEQ ID NO: 10 | 0.032 | 0.008 | 0.802 | 0.158 |
| Position 12 of FIG. 4B | 0.034 | 0.325 | 0.296 | 0.345 |

Example 9

Manufacture of a Modular Animal Pathogen-Nucleic Acid Binding Domain (MAP-NBD)

This example illustrates the manufacture of a modular animal pathogen-nucleic acid binding domain (MAP-NBD). The MAP-NBD is derived from *L. quateirensis, Burkholderia, Paraburkholderia, Francisella*, or any combination thereof. The MAP-NBD comprises a plurality of repeat domains from *L. quateirensis, Burkholderia, Paraburkholderia, Francisella*, or any combination thereof, such as any one of the repeats in Table 1, wherein each repeat domain is selected to recognize and bind to a particular nucleotide or base pair, thereby providing a MAP-NBD that targets and binds a nucleic acid sequence of interest. The nucleic acid is DNA or RNA. The MAP-NBD is recombinantly expressed or synthetically constructed.

Example 10

Manufacture of a Modular Animal Pathogen-Nucleic Acid Binding Domain (MAP-NBD)-Nuclease This example illustrates the manufacture of a modular animal pathogen-nucleic acid binding domain (MAP-NBD)-nuclease. The MAP-NBD is derived from *L. quateirensis, Burkholderia, Paraburkholderia, Francisella*, or any combination thereof. The MAP-NBD comprises a plurality of repeat domains from *L. quateirensis, Burkholderia, Paraburkholderia, Francisella*, or any combination thereof, such as any one of SEQ ID NO: 2-SEQ ID NO: 95, wherein each repeat domain is selected to recognize and bind to a particular nucleotide or base pair, thereby providing a MAP-NBD that targets and binds a nucleic acid sequence of interest. The MAP-NBD-nuclease is recombinantly expressed or synthetically constructed. The MAP-NBD is linked to a nuclease via an optional linker. The linker is a synthetic linker, the full-length C-terminus or a truncation thereof of the naturally occurring *L. quateirensis, Burkholderia, Paraburkholderia*, or *Francisella* protein. The nuclease is a cleavage domain (e.g., meganucleases such as I-AniI or I-OnuI) or a cleavage half domain (e.g., FokI nuclease, for example SEQ ID NO: 11, or BfiI).

Example 11

Manufacture of a Modular Animal Pathogen-Nucleic Acid Binding Domain (MAP-NBD)-Gene Regulator (MAP-NBD-GR)

This example illustrates the manufacture of a modular animal pathogen-nucleic acid binding domain (MAP-NBD)-gene regulator (MAP-NBD-GR). The MAP-NBD is derived from *L. quateirensis, Burkholderia, Paraburkholderia, Francisella*, or any combination thereof. The MAP-NBD comprises a plurality of repeat domains from *L. quateirensis, Burkholderia, Paraburkholderia, Francisella*, or any combination thereof, such as any one of the repeats listed in Table 1, wherein each repeat domain is selected to recognize and bind to a particular nucleotide or base pair, thereby providing a MAP-NBD that targets and binds a nucleic acid sequence of interest. The MAP-NBD-GR is recombinantly expressed or synthetically constructed. The MAP-NBD is linked to a gene regulatory domain via an optional linker. The linker is a synthetic linker, the full-length C-terminus or a truncation of the C-terminus of the naturally occurring *L. quateirensis, Burkholderia, Paraburkholderia*, or *Francisella* protein. The gene regulator is a gene activator (e.g., VP16, VP64, p65, p300 catalytic domain, TET1 catalytic domain, TDG, Ldb1 self-associated domain, SAM activator (VP64, p65, HSF1), or VPR (VP64, p65, Rta)) or a gene repressor (KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2).

Example 12

Manufacture of a Modular Animal Pathogen-Nucleic Acid Binding Domain (MAP-NBD)-Fluorophore This example illustrates the manufacture of a modular animal pathogen-nucleic acid binding domain (MAP-NBD)-fluorophore. The MAP-NBD is derived from *L. quateirensis, Burkholderia, Paraburkholderia, Francisella*, or any combination thereof. The MAP-NBD comprises a plurality of repeat domains from *L. quateirensis, Burkholderia, Paraburkholderia, Francisella*, or any combination thereof, such as any one of the repeats listed in Table 1, wherein each repeat domain is selected to recognize and bind to a particular nucleotide or base pair, thereby providing a MAP- NBD that targets and binds a nucleic acid sequence of interest. The MAP-NBD-fluorophore is recombinantly expressed or synthetically constructed. The MAP-NBD is linked to a fluorophore via an optional linker. The linker is a synthetic linker, the full-length C-terminus or a truncation of the C-terminus of the naturally occurring *L. quateirensis, Burkholderia, Paraburkholderia*, or *Francisella* protein. The fluorophore is a fluorescent moiety, such as green fluorescent protein or mCHERRY.

Example 13

Genome Editing with a Modular Animal Pathogen-Nucleic Acid Binding Domain (MAP-NBD)-Nuclease This example illustrates genome editing with a modular animal pathogen-nucleic acid binding domain (MAP-NBD)-nuclease. The MAP-NBD-nuclease is manufactured as set forth in EXAMPLE 9 and EXAMPLE 10. The MAP-NBD is engineered to comprise a plurality of repeat sequences that will target a nucleic acid sequence of interest. When using a cleavage half-domain as the nuclease (e.g., FokI), two MAP-NBDs are engineered and administered, each with a FokI cleavage half-domain. A first MAP-NBD covalently linked to a FokI cleavage half domain is engineered to bind to first target nucleic acid sequence and a second MAP-NBD covalently linked to another FokI cleavage half domain is engineered to bind to a second target nucleic acid sequence, where the first and second target nucleic acid sequences are suitably spaced apart to provide for dimerization of the FokI cleavage half domains upon binding of the first and second MAP-NBDs to their respective target nucleic acid sequences. Upon administration to a subject, MAP-NBDs bind to their target nucleic acid sequences. Dimerization of two FokI cleavage half domains results in enzyme activity and inducement of a double stranded break (DSB). When using a cleavage domain (e.g., meganucleases such as I-AniI or I-OnuI or a fusion of two FokI domains), a single MAP-NBD bound to the cleavage domain induces a DSB in a target nucleic acid sequence after administration to a subject. The subject is a cell, a plurality of cells, or an animal, such as a human or non-human primate. The nuclease induces a double stranded break in the target sequence resulting in non-homologous end joining or homology directed repair, thereby providing genome editing functionality.

Example 14

Gene Regulation with a Modular Animal Pathogen-Nucleic Acid Binding Domain (MAP-NBD)-Gene Regulator (MAP-NBD-GR)

This example illustrates gene regulation with a modular animal pathogen-nucleic acid binding domain (MAP-NBD)-gene regulator (MAP-NBD-GR). The MAP-NBD-GR is manufactured as set forth in EXAMPLE 9 and EXAMPLE 11. The MAP-NBD is engineered to comprise a plurality of repeat sequences that will target a nucleic acid sequence of interest. The MAP-NBD-GR is administered to a subject. The subject is a cell, a plurality of cells, or an animal, such as a human or non-human primate. The MAP-NBD-GR then regulates gene expression (ie via its activating or repressing domain).

Example 15

Imaging with a Modular Animal Pathogen-Nucleic Acid Binding Domain (MAP-NBD)-Fluorophore This example illustrates imaging a genomic locus in a cell with a modular animal pathogen-nucleic acid binding domain (MAP-NBD)-fluorophore. The MAP-NBD-fluorophore is manufactured as set forth in EXAMPLE 9 and 12. The MAP-NBD is engineered to comprise a plurality of repeat sequences that will target a nucleic acid sequence of interest. The MAP-NBD-fluorophore is administered to a cell. The cell is in a plurality of cells ex vivo, or is in an animal, such as a human or non-human primate. The MAP-NBD-fluorophore hybridizes to a target nucleic acid sequence, thereby labeling said target nucleic acid sequence. Imaging allows for visualization of labeled target cells, wherein labeled target cells indicate that the target genomic locus is present.

Example 16

In Vitro Base Specificity of Repeats from *L. maceachernii*

In order to determine the base specificity of repeats identified in the hypothetical protein WP_058451450 from *L. maceachernii* "LEGm," DNA constructs to encode the full-length protein was engineered and produced. The full-length protein (having the sequence set forth in SEQ ID NO:143) was synthesized by in vitro transcription and translation reactions and characterized using the SELEX-seq method. The identified sequence motifs were compared with the module structure of each protein to assign a DNA base preference to each repeat as well as the N-terminus and C-terminus. The base specificity of repeats identified in the hypothetical protein WP_WP_058473422 (SEQ ID NO:1) from *L. quateirensis* "LEGq" and described in Example 8, was further confirmed.

Constructs

The LEGq and LEGm proteins were divided into modules based on their domain structure: N terminus, individual repeat units, and C terminus. DNA modules encoding these modules were engineered with flanking restriction sites and synthesized (Integrated DNA Technologies, Coralville, Iowa). These DNA modules were ligated together using a modified protocol from Reyon et al. 2013, (*Current Protocols in Molecular Biology*, 12.16.1) to produce a DNA construct encoding the full-length protein. In the case of the LEGq protein, a DNA construct encoding the entire full-length protein was synthesized. The LEGm construct was engineered to encode an N-terminal FLAG tag and a C-terminal HA tag to enable protein retention during SELEX, and the fully-assembled construct was cloned into the pVax_NG_63aa, propagated in *E. coli* and purified using standard methods. The LEGq construct was cloned into the pT7CFE1-CHA vector (Thermo Scientific), which added C-terminal HA tag to the protein, propagated in *E. coli* and purified using standard methods. Purified plasmid constructs were subjected to Sanger sequencing to verify the expected DNA sequence. The SEQ ID NOs for the individual modules are below:

| Motif position | *L. quateirensis* Protein modules | SEQ ID NO | Motif position | *L. maceachernii* Protein modules | SEQ ID NO |
|---|---|---|---|---|---|
|  | LEGq N-terminus | 13 | 1-2 | LEGm N-terminus | 144 |
| 1 | LEG.RN.001 | 89 | 3 | LEG.HG.003 | 28 |
| 2 | LEG.HA.001 | 2 | 4 | LEG.HD.005 | 26 |
| 3 | LEG.HN.001 | 3 | 5 | LEG.H1.003 | 32 |
| 4 | LEG.HG.002 | 4 | 6 | LEG.HK.003 | 34 |
| 5 | LEG.NN.001 | 5 | 7 | LEG.H1.001 | 30 |

| Motif position | *L. quateirensis* Protein modules | SEQ ID NO | Motif position | *L. maceachernii* Protein modules | SEQ ID NO |
|---|---|---|---|---|---|
| 6 | LEG.NG.001 | 6 | 8 | LEG.H1.002 | 31 |
| 7 | LEG.HD.006 | 7 | 9 | LEG.HD.002 | 23 |
| 8 | LEG.HG.004 | 8 | 10 | LEG.HG.005 | 29 |
| 9 | LEG.HD.001 | 9 | 11 | LEG.HD.003 | 24 |
| 10 | LEG.HK.001 | 33 | 12 | LEG.HG.001 | 27 |
|  | LEGq C-terminus | 159 | 13 | LEG.HV.001 | 35 |
|  |  |  | 14 | LEG.H1.004 | 133 |
|  |  |  | 15-17 | LEGm C-terminus | 159 |

SELEX-Seq

In vitro transcription/translation (IVTT) kits were used to produce full-length protein from our plasmid constructs for LEGq (1-Step human Coupled IVT, Promega) and LEGm (TnT Quick Coupled Transcription/Translation kit, Thermo Scientific) using the manufacturer's protocols. The SELEX-seq protocol was adapted from Miller et al. 2011 (supra). Briefly, a library of random sequences 25 nucleotides (nt) in length, flanked by common 20-nt adapter sequences and ordered as single-stranded DNA oligonucleotides was created. A double-stranded DNA library was created using primer extension.

The IVTT proteins were subjected to three SELEX cycles of: allowing proteins to bind to double-stranded DNA; immobilization of protein:DNA complexes on anti-HA magnetic beads and washing off unbound DNA; PCR amplification of bound DNA. In this way, the DNA molecules bound by the proteins were used as input for successive rounds of binding to the LEGq and LEGq proteins, enriching the preferred binding sequence of these proteins within the pool of DNA molecules at each cycle.

PCR samples from each SELEX cycle were diluted 1:50 and amplified using indexed primers recognizing the common adapters flanking the 25-nt random sequences. PCRs were pooled, purified, and sequenced on an Illumina MiniSeq instrument.

SELEX Seq Data Analysis

Sequence reads from the MiniSeq were de-multiplexed using the index sequences of the primers to assign sequence reads to individual SELEX samples. These reads were then filtered to require constant sequences matching the common adapters flanking a variable region of 25 nucleotides. A random sample of 5,000 reads from each sample was used as input to the GADEM motif finder (Li et al. 2009, *Journal of Computational Biology*, 16(2):317-29). Discovered motifs were visualized using the "ceqlogo" function of the MEME suite (Bailey et al. 2015, *Nucleic Acids Research*, 43(W1):W39-49).

Results

The binding motifs for the LEGq and LEGm proteins as discovered by SELEX-seq are shown in FIGS. 8A and 8B, respectively and the DNA base recognized are listed below:

| Discovered motif: LEGq SELEX DNA recognition by each protein domain | | | Discovered motif: LEGm SELEX DNA recognition by each protein domain | | |
|---|---|---|---|---|---|
| Motif position | Protein domain | DNA base recognized | Motif position | Protein domain | DNA base recognized |
| | LEGq N-terminus | none | 1-2 | LEGm N-terminus | G or GG |
| 1 | LEG.RN (SEQ ID NO:89) | G/A | 3 | LEG.HG.003 (SEQ ID NO:28) | T |
| 2 | LEG.HA.001 (SEQ ID NO:2) | A | 4 | LEG.HD.005 (SEQ ID NO:26) | C |
| 3 | LEG.HN.001 (SEQ ID NO:3) | G | 5 | LEG.HI.003 (SEQ ID NO:32) | A |
| 4 | LEG.HG.002 (SEQ ID NO:4) | T | 6 | LEG.HK.003 (SEQ ID NO:34) | G |
| 5 | LEG.NN.001 (SEQ ID NO:5) | G | 7 | LEG.HI.001 (SEQ ID NO:30) | G |
| 6 | LEG.NG.001 (SEQ ID NO:6) | T | 8 | LEG.HI.002 (SEQ ID NO:31) | A/C |
| 7 | LEG.HD.006 (SEQ ID NO:7) | C | 9 | LEG.HD.002 (SEQ ID NO:23) | C |
| 8 | LEG.HG.004 (SEQ ID NO:8) | T | 10 | LEG.HG.005 (SEQ ID NO:29) | T |
| 9 | LEG.HD.001 (SEQ ID NO:9) | C | 11 | LEG.HD.003 (SEQ ID NO:24) | C |
| 10 | LEG.HK.001 (SEQ ID NO:33) | G | 12 | LEG.HG.001 (SEQ ID NO:27) | T |
| | LEGq C-terminus (SEQ ID NO:159) | none | 13 | LEG.HV.001 (SEQ ID NO:35) | G/A/T |
| | | | 14 | LEG.HI.004 (SEQ ID NO:133) | A/G/T |
| | | | 15-17 | LEGm C-terminus (SEQ ID NO:159) | Potentially T or TT |

Example 17

In Vivo Base Specificity of Repeats from *L. maceachernii*

DNA binding preferences of the LEGm protein (SEQ ID NO:143) to DNA in the chromatin context was assessed by expressing it in vivo and detecting its binding locations in the human genome using the FLAG-seq method.

FLAG-Seq

In vivo binding of LEGm was detected using the CUT&RUN-seq method (Skene and Henikoff 2017) for detection of FLAG-tagged proteins, an approach refered to as "FLAG-seq." Briefly, the LEGm construct described above was linearized by restriction digestion and subjected to in vitro transcription using the T7 mScript™ Standard mRNA Production System (CellScript) according to the manufacturer's protocol. One microgram of this LEGm-encoding mRNA was transfected into 500,000 CD3+ T cells using the BTX ECM-830 nucleofection device (Harvard Apparatus) according to the manufacturer's instructions for the specific cell type. Cells were incubated at 37° C. for six hours and subjected to the CUT&RUN-seq protocol using the FLAG tag for detection of the LEGm protein. Isolated DNA fragments from control and LEGm-transfected cells were end-repaired and ligated to sequencing adapters using the SMARTer ThruPLEX DNA-seq kit (Takara) according to the manufacturer's protocol and sequenced on an Illumina NextSeq instrument using standard protocols.

FLAG-Seq Data Analysis

Sequence reads from the NextSeq were de-multiplexed to assign sequences to individual FLAG-seq samples and aligned to the reference human genome using the BWA algorithm (Li and Durbin 2009). Locations of LEGm binding were discovered by using the MACS peak-calling algorithm (Zhang et al. 2008) to compare FLAG-seq signals from control and LEGm-transfected cells, and then mined for enriched sequence motifs using the MEME suite of tools (Bailey et al. 2015). This analysis recovered the same binding motif for LEGm that was observed in multiple SELEX-seq experiments (FIG. 9).

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

For reasons of completeness, certain aspects of the polypeptides, composition, and methods of the present disclosure are set out in the following numbered clauses:

1. A composition comprising a non-naturally occurring modular nucleic acid binding domain derived from an animal pathogen protein (MAP-NBD), wherein the MAP-NBD comprises a plurality of repeat units and wherein a repeat unit of the plurality of repeat units recognizes a target nucleic acid.

2. The composition of clause 1, wherein the animal pathogen protein is derived from a bacterium.

3. The composition of clause 2, wherein the bacterium is selected from the genus of *Legionella*.

4. The composition of any one of clauses 2-3, wherein the bacterium is *L. quateirensis*.

5. The composition of any one of clauses 1-4, wherein the repeat unit comprises a consensus sequence of 1xxx211x1xxx33x2x1xxxxxxxxx1 (SEQ ID NO: 19).

6. The composition of any one of clauses 1-5, wherein the target nucleic acid is a single nucleotide, a single base pair, or both.

7. The composition of any one of clauses 1-6, wherein the target nucleic acid is DNA or RNA.

8. The composition of any one of clauses 1-7, wherein the MAP-NBD binds a target nucleic acid sequence.

9. The composition of clause 8, wherein the target nucleic acid sequence is DNA or RNA.

10. The composition of any one of clauses 1-9, further comprising a functional domain.

11. The composition of clause 10, further comprising a naturally occurring or non-naturally occurring linker between the MAP-NBD and the functional domain.

12. The composition of any one of clauses 10-11, wherein the functional domain comprises an enzyme, an activation domain, a repression domain, a biotinylation reagent, a DNA nucleotide modifier, or a fluorophore.

13. The composition of clause 12, wherein the enzyme is a nuclease, a DNA modifying protein, or a chromatin modifying protein.

14. The composition of clause 13, wherein the nuclease is a cleavage domain or a half-cleavage domain.

15. The composition of clause 14, wherein the cleavage domain or half-cleavage domain comprises a type IIS restriction enzyme.

16. The composition of clause 15, wherein the type IIS restriction enzyme comprises FokI or Bfil.

17. The composition of clause 16, wherein FokI has at least 70%, at least 75%, at least 80%, at least 85%, at least 90%, at least 92%, at least 95%, at least 97%, or at least 99% sequence identity to SEQ ID NO: 11.

18. The composition of any one of clauses 16-17, wherein FokI has a sequence of SEQ ID NO: 11.

19. The composition of clause 13, wherein the chromatin modifying protein is lysine-specific histone demethylase 1 (LSD1).

20. The composition of clause 12, wherein the activation domain comprises VP16, VP64, p65, p300 catalytic domain, TET1 catalytic domain, TDG, Ldb1 self-associated domain, SAM activator (VP64, p65, HSF1), VPR (VP64, p65, Rta).

21. The composition of clause 12, wherein the repressor domain comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2.

22. The composition of clause 12, wherein the DNA nucleotide modifier is adenosine deaminase.

23. The composition of any one of clauses 10-22, wherein the functional domain enables genome editing, gene regulation, or imaging at the genomic locus specified by the modular nucleic acid binding domain.

24. The composition of any one of clauses 1-23, wherein the repeat unit has at least 70%, at least 75%, at least 80%, at least 85%, at least 90%, at least 92%, at least 95%, at least 97%, or at least 99% sequence identity to any one of SEQ ID NO: 2-SEQ ID NO: 10.

25. The composition of any one of clauses 1-24, wherein the repeat unit is any one of SEQ ID NO: 2-SEQ ID NO: 10.

26. The composition of any one of clauses 1-25, wherein the repeat unit is derived from a wild-type protein.

27. The composition of any one of clauses 1-25, wherein the repeat unit comprises a modification of a wild-type protein.

28. The composition of clause 27, wherein the modification enhances specific recognition of a target nucleotide, base pair, or both.

29. The composition of any one of clauses 27-28, wherein the modification comprises 1 to 29 modifications.

30. The composition of any one of clauses 1-29, wherein the animal pathogen protein has at least 70%, at least 75%, at least 80%, at least 85%, at least 90%, at least 92%, at least 95%, at least 97%, or at least 99% sequence identity to SEQ ID NO: 1.

31. The composition of any one of clauses 1-30, wherein the animal pathogen protein is SEQ ID NO: 1.

32. The composition of clauses 1-31, wherein the target nucleic acid sequence is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, an IL2RG gene, or a combination thereof.

33. The composition of any one of clauses 1-32, wherein a chimeric antigen receptor (CAR), alpha-L iduronidase (IDUA), iduronate-2-sulfatase (IDS), or Factor 9 (F9), is inserted upon cleavage of a region of the target nucleic acid sequence.

34. A method of genome editing in a subject, wherein the method comprises:
    administering a non-naturally occurring modular nucleic acid binding domain; and inducing a double stranded break,
    wherein the modular nucleic acid binding domain comprises a modular nucleic acid binding domain derived from an animal pathogen protein (MAP-NBD), wherein the MAP-NBD comprises a plurality of repeat units and wherein a repeat unit of the plurality of repeat units recognizes a target nucleic acid.

35. The method of clause 34, further comprising a second MAP-NBD wherein the second MAP-NBD comprises a second plurality of repeat units and wherein a repeat unit of the second plurality of repeat units recognizes a second target nucleic acid.

36. The method of any one of clauses 34-35, wherein the MAP-NBD, the second MAP-NBD, or both further comprise a functional domain.

37. The method of clause 36, wherein the functional domain comprises a cleavage domain or a cleavage half domain.

38. The method of clause 35, wherein the cleavage domain or the cleavage half domain comprises FokI or Bfil.

39. The method of clause 38, wherein the cleavage domain comprises a meganuclease.

40. The method of clause 38, wherein FokI has at least 70%, at least 75%, at least 80%, at least 85%, at least 90%, at least 92%, at least 95%, at least 97%, or at least 99% sequence identity to SEQ ID NO: 11.

41. The method of any one of clauses 38 or 40, wherein FokI has a sequence of SEQ ID NO: 11.

42. The method of clauses 34-41, wherein the target nucleic acid sequence is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, an IL2RG gene, or a combination thereof.

43. The method of any one of clauses 34-42, wherein a chimeric antigen receptor (CAR), alpha-L iduronidase (IDUA), iduronate-2-sulfatase (IDS), or Factor 9 (F9), is inserted upon cleavage of a region of the target nucleic acid sequence.

44. A method of gene regulation in a subject, wherein the method comprises:
    administering a non-naturally occurring modular nucleic acid binding domain; and
    regulating expression of a gene,
    wherein the modular nucleic acid binding domain comprises a modular DNA binding domain derived from an animal pathogen protein (MAP-NBD) and wherein the MAP-NBD comprises a plurality of repeat units and wherein a repeat unit of the plurality of repeat units recognizes a target nucleic acid.

45. The method of clause 44, wherein the MAP-NBD further comprises a functional domain.

46. The method of clause 45, wherein the functional domain comprises an activation domain or a repression domain.

47. The method of clause 46, wherein the activation domain comprises VP16, VP64, p65, p300 catalytic domain, TET1 catalytic domain, TDG, Ldb1 self-associated domain, SAM activator (VP64, p65, HSF1), VPR (VP64, p65, Rta).

48. The method of clause 46, wherein the repressor domain comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2.

49. The method of clauses 44-48, wherein the target nucleic acid sequence is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, an IL2RG gene, or a combination thereof.

50. The method of any one of clauses 44-49, wherein a chimeric antigen receptor (CAR), alpha-L iduronidase (IDUA), iduronate-2-sulfatase (IDS), or Factor 9 (F9), is inserted upon cleavage of a region of the target nucleic acid sequence.

51. A method of imaging a genomic locus, wherein the method comprises:
    administering a non-naturally occurring modular nucleic acid binding domain; and imaging the subject,
    wherein the modular nucleic acid binding domain comprises a modular DNA binding domain derived from an animal pathogen protein (MAP-NBD) and wherein the MAP-NBD comprises a plurality of repeat units and wherein a repeat unit of the plurality of repeat units recognizes a target nucleic acid.

52. The method of clause 51, wherein the MAP-NBD further comprises a functional domain.

53. The method of clause 52, wherein the functional domain is an imaging agent.

54. The method of clause 53, wherein the imaging agent is a fluorescent moiety.

55. The method of clause 54, wherein the fluorescent moiety is GFP or mCHERRY.

56. The method of any one of clauses 38-55, wherein the target nucleic acid is a single nucleotide, a single base pair, or both.

57. The method of any one of clauses 38-56, wherein the target nucleic acid is DNA or RNA.

58. The method of any one of clauses 38-57, wherein the MAP-NBD recognizes a target nucleic acid sequence.

59. The method of clause 58, wherein the MAP-NBD binds the target nucleic acid sequence.

60. The method of any one of clauses 58-59, wherein the target nucleic acid sequence is DNA or RNA.

61. The method of any one of clauses 34-43, 44-50, or 51-60, further comprising a linker between the MAP-NBD and the functional domain.

62. The method of any one of clauses 32-61, wherein the animal pathogen protein is derived from a bacterium.

63. The method of clause 62, wherein the bacterium is selected from the genus of *Legionella*.

64. The method of any one of clauses 62-63, wherein the bacterium is *L. quateirensis*.

65. The method of any one of clauses 32-64, wherein the repeat unit comprises a consensus sequence of 1xxx211x1xxx33x2x1xxxxxxxxx1 (SEQ ID NO: 19).

66. The method of any one of clauses 32-65, wherein the repeat unit has at least 70%, at least 75%, at least 80%, at least 85%, at least 90%, at least 92%, at least 95%, at least 97%, or at least 99% sequence identity to any one of SEQ ID NO: 2-SEQ ID NO: 10.

67. The method of any one of clauses 32-66, wherein the repeat unit is any one of SEQ ID NO: 2-SEQ ID NO: 10.

68. The method of any one of clauses 32-67, wherein the repeat unit is derived from a wild-type protein.

69. The method of any one of clauses 32-68, wherein the repeat unit comprises a modification of a wild-type protein.

70. The method of clause 69, wherein the modification enhances specific recognition of a target nucleotide.

71. The method of any one of clauses 69-70, wherein the modification comprises 1 to 29 modifications.

72. The method of any one of clauses 32-71, wherein the animal pathogen protein has at least 70%, at least 75%, at least 80%, at least 85%, at least 90%, at least 92%, at least 95%, at least 97%, or at least 99% sequence identity to SEQ ID NO: 1.

73. The method of any one of clauses 32-66, wherein the animal pathogen protein is SEQ ID NO: 1.

74. The method of any one of clauses 32-73, wherein the genomic locus is in a cell.

75. The method of clause 68, wherein the cell is in a plurality of cells ex vivo, in a human, or in a non-human animal.

76. The method of any one of clauses 51-75, wherein the target nucleic acid sequence is within a PDCD1 gene, a CTLA4 gene, a LAG3 gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, an IL2RG gene, or a combination thereof.

77. The method of any one of clauses 51-76, wherein a chimeric antigen receptor (CAR), alpha-L iduronidase (IDUA), iduronate-2-sulfatase (IDS), or Factor 9 (F9), is inserted upon cleavage of a region of the target nucleic acid sequence.

What is claimed is:

1. A recombinant polypeptide comprising a nucleic acid binding domain (NBD) and a heterologous functional domain, the NBD comprising a plurality of repeat units (RUs), wherein each RU comprises a 33-36 amino acid long sequence that is at least 85% identical to:

```
                                              (SEQ ID NO: 9)
     FNAEQIVRMVSHDGGSLNLKAVIDNHDDLKNMG
``` and
comprises base-contacting residues (BCR) at amino acid positions 12 and 13 ($X_{12}X_{13}$) numbered relative to SEQ ID NO:9, wherein $X_{12}X_{13}$=HK, HD, HA, HN, HG, NN, NG, RN, HI, HV, RT, SN, HS, GS, or LN,
wherein the RUs are ordered from N-terminus to C-terminus of the NBD to bind to a target sequence, and
wherein the polypeptide comprises an N-terminal domain and a C-terminal domain, wherein the C-terminus of the N-terminal domain is fused to the N-terminus of the first RU of the NBD and wherein the N-terminus of the C-terminal domain is fused to the C-terminus of the last RU of the NBD.

2. The recombinant polypeptide of claim 1, further comprising a half-RU at the C-terminus of the NBD, wherein the half-RU comprises a 15-20 amino acid long sequence that is at least 80% identical to

```
                                              (SEQ ID NO: 155)
     FNAEQIVRMVSX₁₂X₁₃GGSKNL,
``` or comprises a sequence having the sequence of SEQ ID NO:155 with one or more conservative amino acid substitutions thereto,
wherein $X_{12}X_{13}$=HK, HD, HA, HN, HG, NN, NG, RN, HI, HV, RT, SN, HS, GS, or LN.

3. The recombinant polypeptide of claim 1, comprising a linker amino acid sequence between the C-terminus of the N-terminal domain and the N-terminus of the first RU of the NBD and/or a linker amino acid sequence between the N-terminus of the C-terminal domain and the C-terminus of the last RU of the NBD.

4. The recombinant polypeptide of claim 1, wherein the N-terminal domain comprises an amino acid sequence at least 85% identical to the amino acid sequence set forth in one of SEQ ID NOs:13, 20, 21, or a fragment thereof and/or wherein the C-terminal domain comprises an amino acid sequence at least 85% identical to the amino acid sequence set forth in one of SEQ ID NOs:12, 159, or 22 or a fragment thereof.

5. The recombinant polypeptide of claim 1, comprising a linker amino acid sequence positioned between two or more adjacent RUs.

6. The recombinant polypeptide of claim 1, wherein the heterologous functional domain is a polypeptide positioned N-terminal or C-terminal to the NBD.

7. The recombinant polypeptide of claim 6, wherein the functional domain comprises an enzyme, a transcriptional activator, a transcriptional repressor, or a DNA nucleotide modifier.

8. The recombinant polypeptide of claim 7, wherein the enzyme is a nuclease, a DNA modifying protein, or a chromatin modifying protein, wherein the transcriptional activator comprises VP16, VP64, p65, p300 catalytic domain, TET1 catalytic domain, TDG, Ldb1 self-associated domain, SAM activator (VP64, p65, HSF1), or VPR (VP64, p65, Rta), wherein the transcriptional repressor comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2, or wherein the DNA nucleotide modifier is adenosine deaminase.

9. The recombinant polypeptide of claim 1, wherein the target sequence is within a PDCD 1 gene, a CTLA4 gene, a LAG3 gene, a TET2 gene, a ETLA gene, a HAVCR2 gene, a CCR5 gene, a CXCR4 gene, a TRA gene, a TRE gene, a E2M gene, an albumin gene, a HEE gene, a HEA1 gene, a TTR gene, a NR3C1 gene, a CD52 gene, an erythroid specific enhancer of the ECL11A gene, a CELE gene, a TGFER1 gene, a SERPINA1 gene, a HEV genomic DNA in infected cells, a CEP290 gene, a DMD gene, a CFTR gene, or an IL2RG gene.

10. The recombinant polypeptide of claim 1, wherein the heterologous functional domain comprises a fluorophore or a detectable tag.

11. A composition comprising the polypeptide of claim 1 or a nucleic acid encoding the polypeptide of claim 4; and a pharmaceutically acceptable excipient.

12. A method of modulating expression of an endogenous gene in a cell, the method comprising:
introducing into the cell the polypeptide of claim 7 or a nucleic acid encoding the polypeptide of claim 7, wherein the NBD of the polypeptide binds to a target nucleic acid sequence present in the endogenous gene and the heterologous functional domain modulates expression of the endogenous gene.

13. The method of claim 12, wherein the polypeptide is introduced as a nucleic acid encoding the polypeptide and wherein the nucleic acid is a deoxyribonucleic acid (DNA) or a ribonucleic acid (RNA), wherein optionally the sequence of the nucleic acid is codon optimized for expression in a human cell.

14. The method of claim 12, wherein the functional domain is a transcriptional activator and the target nucleic acid sequence is present in an expression control region of the gene, wherein the polypeptide increases expression of the gene, and optionally, wherein the transcriptional activator comprises VP16, VP64, p65, p300 catalytic domain, TET1 catalytic domain, TDG, Ldb1 self-associated domain, SAM activator (VP64, p65, HSF1), or VPR (VP64, p65, Rta) or wherein the functional domain is a transcriptional repressor and the target nucleic acid sequence is present in an expression control region of the gene, wherein the polypeptide decreases expression of the gene, and optionally, wherein the transcriptional repressor comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2.

15. The method of claim 12, wherein the gene is a PDCD 1 gene, a CTLA4 gene, a LAG3 gene, a TET2 gene, a ETLA gene, a HA VCR2 gene, a CCR5 gene, a CXCR4 gene, a TRA gene, a TRE gene, a E2M gene, an albumin gene, a HEE gene, a HEA1 gene, a TTR gene, a NR3C1 gene, a CD52 gene, an erythroid specific enhancer of the ECL11A gene, a CELE gene, a TGFER1 gene, a SERPINA1 gene, a HEV genomic DNA in infected cells, a CEP290 gene, a DMD gene, a CFTR gene, or an IL2RG gene.

16. The recombinant polypeptide of claim 1, wherein the plurality of RUs comprise 6-40 repeat units.

17. The recombinant polypeptide of claim 1, wherein the plurality of RUs comprise 9-36 repeat units.

18. The recombinant polypeptide of claim 1, wherein the sequence that is at least 85% identical to SEQ ID NO: 9 includes one or more conservative amino acid substitutions relative to the sequence of SEQ ID NO: 9.

19. The recombinant polypeptide of claim 1, wherein each RU comprises a 33-36 amino acid long sequence that is at least 90% identical to SEQ ID NO: 9; the N-terminal domain comprises an amino acid sequence at least 90% identical to SEQ ID NO: 13; and the C-terminal domain comprises an amino acid sequence at least 90% identical to SEQ ID NO: 159.

20. The recombinant polypeptide of claim 1, wherein each RU comprises the sequence of SEQ ID NO: 9 other than at amino acid positions 12 and 13 ($X_{12}X_{13}$) numbered relative to SEQ ID NO:9, wherein the amino acids at positions $X_{12}X_{13}$ are selected from HK, HD, HA, HN, HG, NN, NG, RN, HI, HV, RT, SN, HS, GS, or LN; the N-terminal domain comprises the amino acid sequence of SEQ ID NO: 13; and the C-terminal domain comprises the amino acid sequence of SEQ ID NO: 159.

* * * * *

UNITED STATES PATENT AND TRADEMARK OFFICE
CERTIFICATE OF CORRECTION

PATENT NO. : 12,312,383 B2
APPLICATION NO. : 17/047373
DATED : May 27, 2025
INVENTOR(S) : Fyodor Urnov et al.

Page 1 of 2

It is certified that error appears in the above-identified patent and that said Letters Patent is hereby corrected as shown below:

In the Specification

In Column 8, Line 41, after "size" delete "the".

In Column 8, Line 50, after "size" delete "the".

In Column 9, Line 8, after "size" delete "the".

In Column 9, Line 19, after "size" delete "the".

In Column 14, Lines 59-60, delete "Legionalleles," and insert -- Legionellales, --.

In Column 26, Line 32, after "SDDNTDEVEEDQHRDKRRSNGR" insert -- . --.

In Column 28, Line 40, after "SGLGFDEEITNPPYMPELEPEFIL" insert -- . --.

In Column 28, Line 59, after "AVKTVLKDHEQLVNFFTHLQIIRMAAQKGGAKNITTALNEYNSLTNLG" insert -- . --.

In Column 30, Line 50, after "QYICDTLDQSFKTLNKSRVVTLFRQINIDMSLI" insert -- . --.

In Column 49, Line 34, delete "epitheioid" and insert -- epithelioid --.

In Column 49, Line 35-36, delete "epitheioid" and insert -- epithelioid --.

In Column 58, Line 58, delete "phophoramidites." and insert -- phosphoramidites. --.

In Column 58, Line 63, delete "phophoramidites." and insert -- phosphoramidites. --.

Signed and Sealed this
Fourteenth Day of October, 2025

John A. Squires
*Director of the United States Patent and Trademark Office*

CERTIFICATE OF CORRECTION (continued)
U.S. Pat. No. 12,312,383 B2

In Column 60, Line 48, after "GACGTGTGCTCTTCCGATCT" insert -- . --.

In Column 61, Lines 66-67, delete "PCR-2 amplification and 25 µl of PCR-2 in the 3rd SELEX cycle." and insert the same on Column 61, Line 65 (approx.), as a continuation of the same paragraph.

In Column 63, Line 33, after "size" delete "the".

In Column 70, Line 59, delete "refered" and insert -- referred --.

In the Claims

In Column 257, Line 31, in Claim 1, delete "FNAEQIVRMVSHDGGSLNLKAVIDNHDDLKNMG" and insert -- FNAEQIVRMVSHDGGSLNLKAVTDNHDDLKNMG --.